United States Patent
Mulvihill et al.

(10) Patent No.: US 12,331,054 B2
(45) Date of Patent: Jun. 17, 2025

(54) PERK INHIBITING IMIDAZOLOPYRAZINE COMPOUNDS

(71) Applicant: HiberCell, Inc., New York, NY (US)

(72) Inventors: Mark J. Mulvihill, New York, NY (US); An-Hu Li, New York, NY (US); Matthew David Surman, Albany, NY (US)

(73) Assignee: HiberCell, Inc., New York, NY (US)

( * ) Notice: Subject to any disclaimer, the term of this patent is extended or adjusted under 35 U.S.C. 154(b) by 765 days.

(21) Appl. No.: 17/639,183

(22) PCT Filed: Aug. 28, 2020

(86) PCT No.: PCT/US2020/048614
§ 371 (c)(1),
(2) Date: Feb. 28, 2022

(87) PCT Pub. No.: WO2021/041970
PCT Pub. Date: Mar. 4, 2021

(65) Prior Publication Data
US 2022/0348583 A1     Nov. 3, 2022

Related U.S. Application Data

(60) Provisional application No. 62/893,519, filed on Aug. 29, 2019.

(51) Int. Cl.
*C07D 487/04* (2006.01)

(52) U.S. Cl.
CPC ........ *C07D 487/04* (2013.01); *C07B 2200/05* (2013.01)

(58) Field of Classification Search
CPC .......................... C07D 487/04; C07B 2200/05
See application file for complete search history.

(56) References Cited

U.S. PATENT DOCUMENTS 10,822,340 B2 * 11/2020 Backes ................... A61P 25/14

FOREIGN PATENT DOCUMENTS

WO     WO-2016004254 A1 *  1/2016  ............. A61K 31/37

* cited by examiner

*Primary Examiner* — Joseph K McKane
*Assistant Examiner* — Jalisa Holmes Ferguson
(74) *Attorney, Agent, or Firm* — Scully, Scott, Murphy & Presser, P.C.

(57) ABSTRACT

Provided herein are compounds, compositions, and methods useful for inhibiting PERK and for treating related conditions, diseases, and disorders.

36 Claims, No Drawings

PERK INHIBITING IMIDAZOLOPYRAZINE COMPOUNDS

CROSS-REFERENCE TO RELATED APPLICATIONS

This application is a U.S. national stage patent application under 35 U.S.C. § 371 of International Application No. PCT/US2020/048614, filed on Aug. 28, 2020, which application claims the benefit of and priority to U.S. Provisional Patent Application No. 62/893,519, filed on Aug. 29, 2019, each of which is incorporated herein by reference in its entirety.

BACKGROUND OF THE INVENTION

Embodiments of the present invention relate to novel imidazolopyrazine compounds, to pharmaceutical compositions comprising the compounds, to methods of using the compounds to treat physiological disorders, and to intermediates and processes useful in the synthesis of the compounds. The present invention is in the field of treatment of cancer and, other diseases and disorders involving protein kinase R (PKR)-like endoplasmic reticulum kinase (PERK).

PERK, an eIF2 kinase involved in the unfolded protein response (UPR) regulates protein synthesis, aids cells to alleviate the impact of endoplasmic reticulum stress and has been implicated in tumor genesis and cancer cell survival.

Tumor cells thrive in a hostile microenvironment caused mainly by nutrient and oxygen limitation, high metabolic demand, and oxidative stress. These stresses are known to disrupt the protein folding capacity of the endoplasmic reticulum (ER) eliciting a cellular remediation response known as the UPR. The UPR serves as a mechanism for cellular survival whereby cells are able to adapt to cope with ER stress, but under extreme stress the UPR switches the cellular machinery toward apoptosis, contributing to greater tumorigenic potential of cancer cells, tumor metastasis, tumor drug resistance, and the ability of cancer cells to avoid effective immune responses. Tumors are believed to utilize the UPR for survival under stressed conditions such as nutrient deprivation or treatment with chemotherapy. Other stress stimuli that activate UPR include hypoxia, disruption of protein glycosylation, depletion of luminal ER calcium, or changes in ER redox status.

There are three major ER transmembrane sensors of the UPR: 1) inositol requiring enzyme (IREla/IREip, encoded by ERN1 and ERN2, respectively); 2) PKR-like ER kinase (PERK, also known as PEK, encoded by EIF2AK3); and 3) the activating transcription factor 6a (encoded by ATF6). Each of these three sensors is regulated similarly through binding of the ER luminal chaperone protein GRP78 or BiP (encoded by HSPA5). When protein folding demands of the ER exceed capacity, reduced BiP binding results in activation of these ER sensor proteins resulting in the induction of coordinated signaling pathways to increase the folding capacity of the ER and alleviate the underlying stress. Effective responses lead to cell adaptation and survival while irreparable ER stress triggers cell death and apoptosis.

PERK is a type I transmembrane serine/threonine kinase and a member of a family of kinases that phosphorylate the eukaryotic translation initiation factor 2a (eIF2-a) and regulate translation initiation. Other family members include HRI (EIF2AK1), PKR (EIF2AK2), and GCN2 (EIF2AK4). Each eIF2 kinase responds to different cellular stress signals to regulate general translation and gene specific translational control.

PERK is an ER transmembrane protein with a stress-sensing domain inside the ER lumen and a cytosolic kinase domain. Upon sensing misfolded proteins, PERK is activated by autophosphorylation and oligomerization through release of BiP/Grp78 from the stress-sensing domain. Activated PERK phosphorylates and activates its downstream substrate, eukaryotic initiation factor 2a (eIF2a), which inhibits the ribosome translation initiation complex in order to attenuate protein synthesis. This serves to prevent exacerbation of ER stress by preventing the accumulation of additional misfolded proteins. Although it inhibits general protein synthesis, activated eIF2a causes the translation of specific mRNAs involved in restoring ER homeostasis including activating transcription factor 4 (ATF4). ATF4 mediates the transcription of certain UPR target genes including those for the endoplasmic-reticulum-associated proteindegradation (ERAD) pathway proteins which target misfolded proteins for ubiquitination and degradation by the proteasome. ATF4 also causes the expression of the transcription factor C/EBP homologous protein (CHoP), which sensitizes cells to ER stress-mediated apoptosis, providing a pathway for regulated removal of severely stressed cells by the organism.

Phosphorylation of eIF2 results in reduced initiation of general translation due to a reduction in eIF2B exchange factor activity decreasing the amount of protein entering the ER (and thus the protein folding burden) and translational demand for ATP.

Phosphorylation of eIF2 also increases translation of some mRNAs in a gene specific manner including the transcription factor ATF4. ATF4 transcriptional targets include numerous genes involved in cell adaptation and survival including several involved in protein folding, nutrient uptake, amino acid metabolism, redox homeostasis, and autophagy.

Selective inhibition of the PERK arm of the UPR is expected to profoundly affect tumor cell growth and survival. As such, compounds which inhibit PERK are believed to be useful in treating cancer.

SUMMARY OF THE INVENTION

Embodiments of the present invention provide a compound having the structure (I):

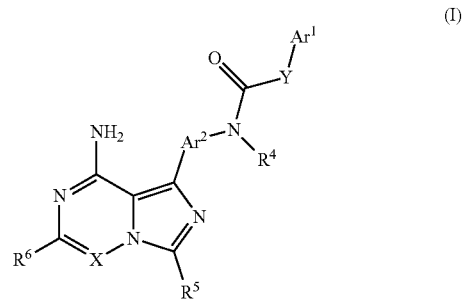

wherein:
Ar$^1$ is aryl, heteroaryl, or cycloalkyl, optionally substituted by one or more independent R$^1$ substituents;
Ar$^2$ is aryl or heteroaryl, optionally substituted by one or more independent R$^2$ substituents;
Y is CR$^{3a}$R$^{3b}$, C(O), CF$_2$, or CNOR$^{3bb}$;
R$^{3a}$ is H, alkyl, or cycloalkyl;
R$^{3b}$ is H, alkyl, OR$^{3c}$, or NR$^{3d}$R$^{3e}$;

$R^{3bb}$ is H or alkyl;
$R^4$ is H, alkyl, or OH;
X is $CR^7$ or N;
$R^1$ is one or more independent H, deuterium, halo, CN, $NO_2$, alkyl, cycloalkyl, $C_{0-6}$alkyl-O—$C_{1-12}$alkyl, $C_{0-6}$alkyl-OH, $C_{0-6}$alkyl-O—$C_{3-12}$cycloalkyl, or $C_{0-6}$alkyl-O—$C_{3-12}$heterocycloalkyl, optionally substituted by one or more independent $G^1$ substituents;
$R^2$ is one or more independent H, deuterium, halo, CN, $NO_2$, alkyl, $C_{0-6}$alkylcycloalkyl, $C_{0-6}$alkyl-O—$C_{1-12}$alkyl, $C_{0-6}$alkyl-OH, or $C_{0-6}$alkyl-O—$C_{3-12}$cycloalkyl, optionally substituted by one or more independent $G^2$ substituents;
$R^{3c}$, $R^{3d}$ and $R^{3e}$ are each independently H, alkyl, or cycloalkyl, optionally substituted by one or more independent $G^3$ substituents;
$R^5$ is H, deuterium, halo, alkyl, cycloalkyl, or heterocycloalkyl, optionally substituted by one or more independent $G^4$ substituents;
$R^6$ is H, alkyl, $CD_3$, or $CF_3$;
$R^7$ is H, deuterium, halo, CN, alkyl, cycloalkyl, heterocycloalkyl, aryl, or heteroaryl, optionally substituted by one or more independent H, deuterium or halo;
$G^1$, $G^2$, $G^3$, or $G^4$ are each independently H, deuterium, halo, CN, $NO_2$, $C_{1-12}$alkyl, $C_{0-12}$alkyl$C_{3-12}$cycloalkyl, $C_{0-12}$alkyl$C_{3-12}$heterocycloalkyl, $OR^8$, $NR^8R^9$, $C(O)R^8$, $C(O)OR^8$, $C(O)NR^8R^9$, $OC(O)R^8$, $OC(O)OR^8$, $OC(O)NR^8R^9$, $N(R^{10})C(O)R^8$, $N(R^{10})C(O)OR^8$, $N(R^{10})C(O)NR^8R^9$, $S(O)_nR^8$, $S(O)_nOR^8$, $S(O)_nNR^8R^9$, $N(R^{10})S(O)_nR^8$, $N(R^{10})S(O)_nOR^8$, or $N(R^{10})S(O)_nNR^8R^9$, optionally substituted by one or more independent H, deuterium, halo, OH, CN, or $NO_2$;
$R^8$, $R^9$, or $R^{10}$ are each independently selected from H, deuterium, halo, CN, $NO_2$, alkyl, cycloalkyl or heterocycloalkyl, optionally substituted by one or more independent H, deuterium, halo, OH, CN, or $NO_2$;
n is 0, 1, or 2;
or a pharmaceutically acceptable salt thereof.

DETAILED DESCRIPTION OF THE INVENTION

With the current state of medical treatment, patients developing cancer often have a poor prognosis even if the disease is detected early. As such, there remains a significant need for new and effective therapies to treat cancer. The compounds of the present invention are inhibitors of PERK, and are believed to be useful in treating cancer.

The present invention provides a compound having the structure (I):

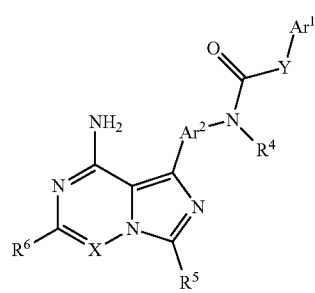

wherein:
$Ar^1$ is aryl, heteroaryl, or cycloalkyl, optionally substituted by one or more independent $R^1$ substituents;
$Ar^2$ is aryl or heteroaryl, optionally substituted by one or more independent $R^2$ substituents;
Y is $CR^{3a}R^{3b}$, C(O), $CF_2$, or $CNOR^{3bb}$;
$R^{3a}$ is H, alkyl, or cycloalkyl;
$R^{3b}$ is H, alkyl, $OR^{3c}$, or $NR^{3d}R^{3e}$;
$R^{3bb}$ is H or alkyl;
$R^4$ is H, alkyl, or OH;
X is $CR^7$ or N;
$R^1$ is one or more independent H, deuterium, halo, CN, $NO_2$, alkyl, cycloalkyl, $C_{0-6}$alkyl-O—$C_{1-12}$alkyl, $C_{0-6}$alkyl-OH, $C_{0-6}$alkyl-O—$C_{3-12}$cycloalkyl, or $C_{0-6}$alkyl-O—$C_{3-12}$heterocycloalkyl, optionally substituted by one or more independent $G^1$ substituents;
$R^2$ is one or more independent H, deuterium, halo, CN, $NO_2$, alkyl, $C_{0-6}$alkylcycloalkyl, $C_{0-6}$alkyl-O—$C_{1-12}$alkyl, $C_{0-6}$alkyl-OH, or $C_{0-6}$alkyl-O—$C_{3-12}$cycloalkyl, optionally substituted by one or more independent $G^2$ substituents;
$R^{3c}$, $R^{3d}$ and $R^{3e}$ are each independently H, alkyl, or cycloalkyl, optionally substituted by one or more independent $G^3$ substituents;
$R^5$ is H, deuterium, halo, alkyl, cycloalkyl, or heterocycloalkyl, optionally substituted by one or more independent $G^4$ substituents;
$R^6$ is H, alkyl, $CD_3$, or $CF_3$;
$R^7$ is H, deuterium, halo, CN, alkyl, cycloalkyl, heterocycloalkyl, aryl, or heteroaryl, optionally substituted by one or more independent H, deuterium or halo;
$G^1$, $G^2$, $G^3$, or $G^4$ are each independently H, deuterium, halo, CN, $NO_2$, $C_{1-12}$alkyl, $C_{0-12}$alkyl$C_{3-12}$cycloalkyl, $C_{0-12}$alkyl$C_{3-12}$heterocycloalkyl, $OR^8$, $NR^8R^9$, $C(O)R^8$, $C(O)OR^8$, $C(O)NR^8R^9$, $OC(O)R^8$, $OC(O)OR^8$, $OC(O)NR^8R^9$, $N(R^{10})C(O)R^8$, $N(R^{10})C(O)OR^8$, $N(R^{10})C(O)NR^8R^9$, $S(O)_nR^8$, $S(O)_nOR^8$, $S(O)_nNR^8R^9$, $N(R^{10})S(O)_nR^8$, $N(R^{10})S(O)_nOR^8$, or $N(R^{10})S(O)_nNR^8R^9$, optionally substituted by one or more independent H, deuterium, halo, OH, CN, or $NO_2$;
$R^8$, $R^9$, or $R^{10}$ are each independently selected from H, deuterium, halo, CN, $NO_2$, alkyl, cycloalkyl or heterocycloalkyl, optionally substituted by one or more independent H, deuterium, halo, OH, CN, or $NO_2$;
n is 0, 1, or 2;
or a pharmaceutically acceptable salt thereof.

In some embodiments, a pharmaceutical composition comprising the compound of the present invention and a pharmaceutically acceptable carrier.

In some embodiments, a pharmaceutical composition comprising the compound of the present invention, an anti-cancer agent and a pharmaceutically acceptable carrier.

The present invention provides a method of inhibiting the growth of a tumor comprising contacting a tumor cell with an effective amount of the compound of the present invention or a pharmaceutically acceptable salt, so as to thereby inhibit the growth of the tumor.

The present invention further provides a method of inhibiting the growth of a tumor comprising contacting a tumor cell with an effective amount of the compound of the present invention or a pharmaceutically acceptable salt, in combination with an anti-cancer agent, so as to thereby inhibit the growth and/or metastasis of the tumor.

The present invention also provides a method of inhibiting PERK comprising contacting the tumor cell with an effective amount of the compound of the present invention or a pharmaceutically acceptable salt.

In some embodiments of the method, further comprising contacting the tumor cell with an effective amount of an anti-cancer agent.

In some embodiments of the method, further comprising administering to the mammal an effective amount of an anti-cancer agent.

The present invention yet further provides a compound having the following structure (Ia):

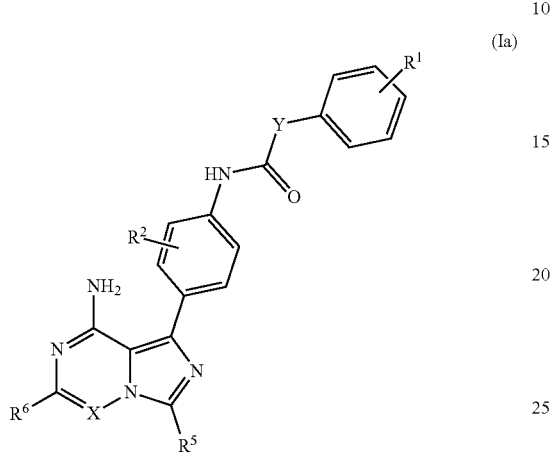

wherein:
Y is $CR^{3a}R^{3b}$;
$R^{3a}$ is H or alkyl;
$R^{3b}$ is $OR^{3c}$ or $NR^{3d}R^{3e}$:
$R^1$ is one or more independent H, deuterium, halo, alkyl, cycloalkyl, $C_{0-6}$alkyl-O—$C_{1-12}$alkyl, $C_{0-6}$alkyl-OH, or $C_{0-6}$alkyl-O—$C_{3-12}$cycloalkyl, optionally substituted by one or more independent $G^1$ substituents;
$R^2$ is one or more independent H, deuterium, halo, alkyl, $C_{0-6}$alkylcycloalkyl, $C_{0-6}$alkyl-O—$C_{1-12}$alkyl, $C_{0-6}$alkyl-OH, or $C_{0-6}$alkyl-O—$C_{3-12}$cycloalkyl, optionally substituted by one or more independent $G^2$ substituents;
$R^{3c}$, $R^{3d}$ and $R^{3e}$ are each independently H or alkyl, optionally substituted by one or more independent $G^3$ substituents;
X is $CR^7$ or N;
$R^5$ is H, deuterium, halo, alkyl, cycloalkyl, or heterocycloalkyl, optionally substituted by one or more independent $G^4$ substituents;
$R^6$ is H, alkyl, $CD_3$, or $CF_3$;
$R^7$ is H, deuterium, halo, CN, alkyl, cycloalkyl, heterocycloalkyl, aryl, or heteroaryl, optionally substituted by one or more independent H, deuterium or halo;
$G^1$, $G^2$, $G^3$, or $G^4$ are each independently H, deuterium, halo, CN, $NO_2$, $C_{1-12}$alkyl, $C_{0-12}$alkyl$C_{3-12}$cycloalkyl, $C_{0-12}$alkyl$C_{3-12}$heterocycloalkyl, $OR^8$, $NR^8R^9$, $C(O)R^8$, $C(O)OR^8$, $C(O)NR^8R^9$, $OC(O)R^8$, $OC(O)OR^8$, $OC(O)NR^8R^9$, $N(R^{10})C(O)R^8$, $N(R^{10})C(O)OR^8$, $N(R^{10})C(O)NR^8R^9$, $S(O)_nR^8$, $S(O)_nOR^8$, $S(O)_nNR^8R^9$, $N(R^{10})S(O)_nOR^8$, or $N(R^{10})S(O)_nNR^8R^9$, optionally substituted by one or more independent H, deuterium, halo, OH, CN, or $NO_2$;
$R^8$, $R^9$, or $R^{10}$ are each independently selected from H, deuterium, halo, CN, $NO_2$, alkyl, cycloalkyl or heterocycloalkyl, optionally substituted by one or more independent H, deuterium, halo, OH, CN, or $NO_2$;
n is 0, 1, or 2;
or a pharmaceutically acceptable salt thereof.

The present invention yet further provides a compound having the following structure (Ib):

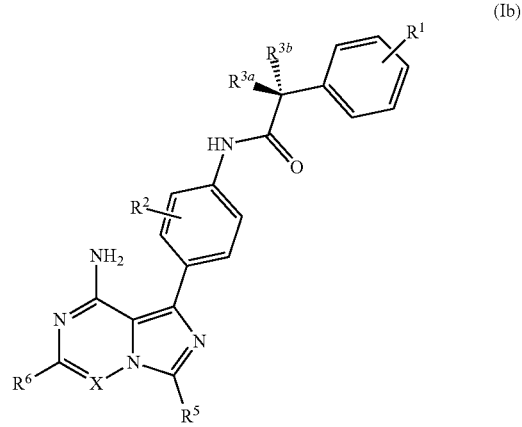

wherein:
X is $CR^7$ or N;
$R^1$ is one or more independent H, deuterium, halo, alkyl, cycloalkyl, $C_{0-6}$alkyl-O—$C_{1-12}$alkyl, $C_{0-6}$alkyl-OH, or $C_{0-6}$alkyl-O—$C_{3-12}$cycloalkyl, optionally substituted by one or more independent $G^1$ substituents;
$R^2$ is one or more independent H, deuterium, halo, alkyl, cycloalkyl, $C_{0-6}$alkyl-O—$C_{1-12}$alkyl, $C_{0-6}$alkyl-OH, or $C_{0-6}$alkyl-O—$C_{3-12}$cycloalkyl, optionally substituted by one or more independent $G^2$ substituents;
$R^{3a}$ is H or alkyl;
$R^{3b}$ is $OR^{3c}$ or $NR^{3d}R^{3e}$;
$R^{3c}$, $R^{3d}$ and $R^{3e}$ are each independently H or alkyl, optionally substituted by one or more independent $G^3$ substituents;
$R^5$ is H, deuterium, halo, alkyl, cycloalkyl, or heterocycloalkyl, optionally substituted by one or more independent $G^4$ substituents;
$R^6$ is H, alkyl, $CD_3$, or $CF_3$;
$R^7$ is H, deuterium, halo, CN, alkyl, cycloalkyl, heterocycloalkyl, aryl, or heteroaryl, optionally substituted by one or more independent H, deuterium or halo;
$G^1$, $G^2$, $G^3$, or $G^4$ are each independently H, deuterium, halo, CN, $NO_2$, $C_{1-12}$alkyl, $C_{0-12}$alkyl$C_{3-12}$cycloalkyl, $C_{0-12}$alkyl$C_{3-12}$heterocycloalkyl, $OR^8$, $NR^8R^9$, $C(O)R^8$, $C(O)OR^8$, $C(O)NR^8R^9$, $OC(O)R^8$, $OC(O)OR^8$, $OC(O)NR^8R^9$, $N(R^{10})C(O)R^8$, $N(R^{10})C(O)OR^8$, $N(R^{10})C(O)NR^8R^9$, $S(O)_nR^8$, $S(O)_nOR^8$, $S(O)_nNR^8R^9$, $N(R^{10})S(O)_nR^8$, $N(R^{10})S(O)_nOR^8$, or $N(R^{10})S(O)_nNR^8R^9$, optionally substituted by one or more independent H, deuterium, halo, OH, CN, or $NO_2$;
$R^8$, $R^9$, or $R^{10}$ are each independently selected from H, deuterium, halo, CN, $NO_2$, alkyl, cycloalkyl or heterocycloalkyl, optionally substituted by one or more independent H, deuterium, halo, OH, CN, or $NO_2$,
n is 0, 1, or 2;
or a pharmaceutically acceptable salt thereof.

The present invention yet further provides a compound having the following structure (Ic):

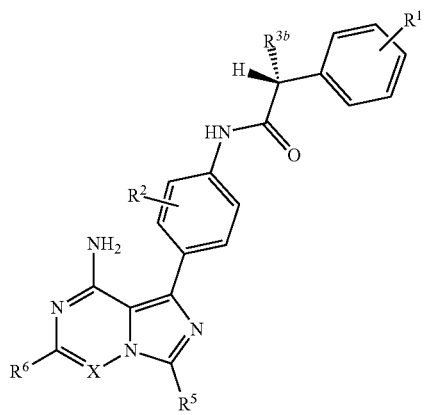

wherein:

X is $CR^7$;

$R^1$ is one or more independent H, deuterium, halo, alkyl, $C_{0-6}$alkyl-OH, or $C_{0-6}$alkyl-O—$C_{1-12}$alkyl, optionally substituted by one or more independent $G^1$ substituents;

$R^2$ is one or more independent H, deuterium, halo, alkyl, $C_{0-6}$alkyl-OH, or $C_{0-6}$alkyl-O—$C_{1-12}$alkyl, optionally substituted by one or more independent $G^2$ substituents;

$R^{3b}$ is $OR^{3c}$, $R^{3c}$ is H or alkyl, optionally substituted by one or more independent $G^3$ substituents;

$R^5$ is H, deuterium, halo, alkyl, cycloalkyl, or heterocycloalkyl, optionally substituted by one or more independent $G^4$ substituents;

$R^6$ is H, alkyl, $CD_3$, or $CF_3$;

$R^7$ is H, deuterium, halo, heteroaryl or alkyl, optionally substituted by one or more independent H, deuterium or halo;

$G^1$, $G^2$, $G^3$, or $G^4$ are each independently H, deuterium, halo, CN, $NO_2$, $C_{1-12}$alkyl, $C_{0-12}$alkyl$C_{3-12}$cycloalkyl, $C_{0-12}$alkyl$C_{3-12}$heterocycloalkyl, $OR^8$, $NR^8R^9$, C(O)$R^8$, C(O)O$R^8$, C(O)N$R^8R^9$, OC(O)$R^8$, OC(O)O$R^8$, OC(O)N$R^8R^9$, N($R^{10}$)C(O)$R^8$, N($R^{10}$)C(O)O$R^8$, N($R^{10}$)C(O)N$R^8R^9$, S(O)$_n R^8$, S(O)$_n$O$R^8$, S(O)$_n$N$R^8R^9$, N($R^{10}$)S(O)$_n R^8$, N($R^{10}$)S(O)$_n$O$R^8$, or N($R^{10}$)S(O)$_n$N$R^8R^9$, optionally substituted by one or more independent H, deuterium, halo, OH, CN, or $NO_2$;

$R^8$, $R^9$, or $R^{10}$ are each independently selected from H, deuterium, halo, CN, $NO_2$, alkyl, cycloalkyl or heterocycloalkyl, optionally substituted by one or more independent H, deuterium, halo, OH, CN, or $NO_2$;

n is 0, 1, or 2;

or a pharmaceutically acceptable salt thereof.

The present invention yet further provides a compound having the following structure (Id):

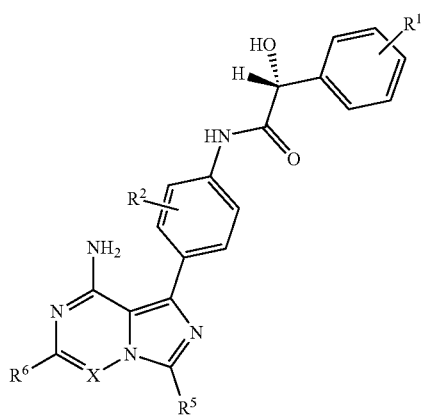

wherein:

X is $CR^7$;

$R^1$ is one or more independent H, deuterium, halo, alkyl, $C_{0-6}$alkyl-OH, or $C_{0-6}$alkyl-O—$C_{1-12}$alkyl, optionally substituted by one or more independent H, deuterium, or halo;

$R^2$ is one or more independent H, deuterium, halo, alkyl, $C_{0-6}$alkyl-OH, or $C_{0-6}$alkyl-O—$C_{1-12}$alkyl, optionally substituted by one or more independent H, deuterium or halo;

$R^5$ is H, deuterium, halo, alkyl, cycloalkyl, or heterocycloalkyl, optionally substituted by one or more independent H, deuterium, halo, OH, or CN;

$R^6$ is H, alkyl, $CD_3$, or $CF_3$;

$R^7$ is H, deuterium, halo, alkyl, heteroaryl, or $CD_3$, wherein the alkyl may be optionally substituted by one or more halo substituents;

or a pharmaceutically acceptable salt thereof.

The present invention yet further provides a compound having the following structure (Ie):

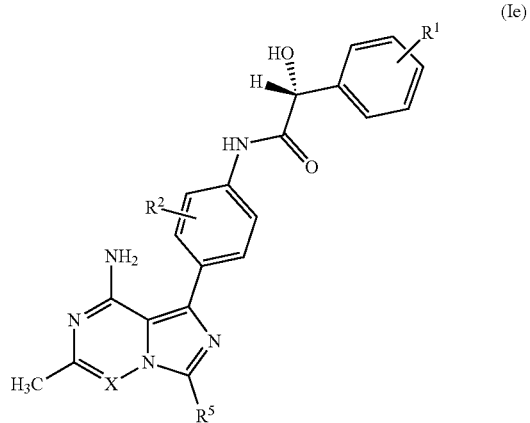

wherein:

X is CH;

$R^1$ is one or more independent H, deuterium, halo, alkyl, $C_{0-6}$alkyl-OH, or $C_{0-6}$alkyl-O—$C_{1-12}$alkyl, optionally substituted by one or more independent H, deuterium, or halo;

$R^2$ is one or more independent H, deuterium, halo, alkyl, $C_{0-6}$alkyl-OH, or $C_{0-6}$alkyl-O—$C_{1-12}$alkyl, optionally substituted by one or more independent H, deuterium or halo;

R⁵ is H, deuterium halo, methyl, ethyl, isopropyl,

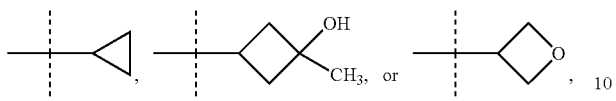

optionally substituted by one or more independent H, deuterium, C₁₋₆alkyl, halo, OH, or CN;
or a pharmaceutically acceptable salt thereof.

In some embodiments, R7 is H, chloro, methyl, ethyl, trifluoromethyl, heteroaryl, or CD3.

In some embodiments, R1, for each occurrence, is H, trifluoromethyl, trifluoromethoxy, methyl, ethyl, isopropyl, methoxy, ethoxy, propoxy, isopropoxy, deuterium, fluoro, or chloro.

In some embodiments, R2 is H, methyl, ethyl, propyl, isopropyl, methoxy, ethoxy, propoxy, isopropoxy, trifluoromethoxy, fluoro, chloro, CF3 or OCF3.

In some embodiments, R5 is H, chloro, methyl, or CD3, ethyl, isopropyl,

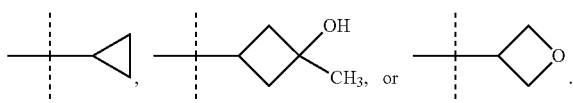

In some embodiments, R6 is H, methyl, ethyl, propyl, isopropyl, CD3, or CF3.

In some embodiments, R6 is other than H.

In some embodiments, G1, G2, G3, or G4 are each independently H, deuterium, halo, CN, NO2, C1-6alkyl, C3-8cycloalkyl, C3-8heterocycloalkyl, OR8, NR8R9, C(O)R8, C(O)OR8, C(O)NR8R9, OC(O)R8, OC(O)OR8, OC(O)NR8R9, N(R10)C(O)R8, N(R10)C(O)OR8, N(R10)C(O)NR8R9, S(O)nR8, S(O)nOR8, S(O)nNR8R9, N(R10)S(O)nR8, N(R10)S(O)nOR8, or N(R10)S(O)nNR8R9, optionally substituted by one or more independent H, deuterium, halo, OH, CN, or NO2.

In some embodiments, G1, G2, G3, or G4 are each independently H, deuterium, halo, CN, NO2, C1-3alkyl, C3-6cycloalkyl, C3-6heterocycloalkyl, OR8, NR8R9, C(O)R8, C(O)OR8, C(O)NR8R9, OC(O)R8, OC(O)OR8, OC(O)NR8R9, N(R10)C(O)R8, N(R10)C(O)OR8, N(R10)C(O)NR8R9, S(O)nR8, S(O)nOR8, S(O)nNR8R9, N(R10)S(O)nR8, N(R10)S(O)nOR8, or N(R10)S(O)nNR8R9, optionally substituted by one or more independent H, deuterium, halo, OH, CN, or NO2.

In some embodiments, Ar1 is phenyl.

In some embodiments, Ar2 is phenyl or pyridyl.

The present invention yet further provides a compound having the following structure (If):

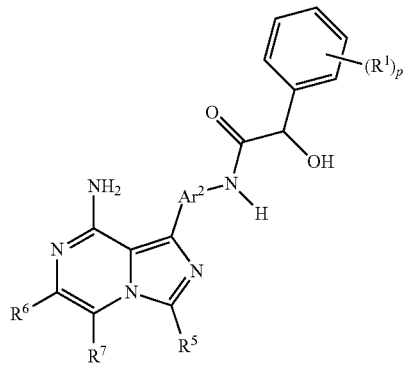

(If)

wherein:
Ar² is aryl or heteroaryl, optionally substituted by one or more independent R² substituents;
R¹ is each independently halo or alkyl, optionally substituted by one or more halogen substituents;
R² is each independently halo, alkyl, or C₀₋₆alkyl-O—C₁₋₁₂alkyl, optionally substituted by one or more halogen substituents;
R⁵ is alkyl or cycloalkyl, optionally substituted by one or more deuterium, hydroxyl, or methyl substituents;
R⁶ is H or alkyl;
R⁷ is H, halo, or alkyl, optionally substituted by one or more halogen substituents; and
p is 1 or 2;
or a pharmaceutically acceptable salt thereof.

In some embodiments, p is 1.

In some embodiments, R1 is chloro, fluoro, methyl, or trifluoromethyl.

In some embodiments, p is 2.

In some embodiments, R1, for each occurrence, is fluoro, methyl, or trifluoromethyl.

In some embodiments, Ar2 is phenyl.

In some embodiments, Ar2 is phenyl, optionally substituted by one substituent selected from R2.

In some embodiments, R2 is methyl, ethyl, fluoro, or trifluoromethoxy.

In some embodiments, Ar2 is phenyl, optionally substituted by two substituents each independently selected from R2.

In some embodiments, R2, for each occurrence, is fluoro or methyl.

In some embodiments, Ar2 is pyridyl, optionally substituted by one substituent selected from R2.

In some embodiments, R2 is methyl.

In some embodiments, R5 is methyl, CD3, or

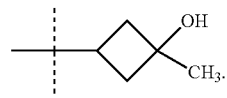

In some embodiments, R6 is H or methyl.

In some embodiments, R7 is H, chloro, methyl, or trifluoromethyl.

In some embodiments, the compound is selected from:
N-(4-(8-amino-3-methylimidazo[1,5-α]pyrazin-1-yl)-3-methylphenyl)-2-(3-fluorophenyl)-2-hydroxyacetamide;
(R)—N-(4-(8-amino-3-methylimidazo[1,5-α]pyrazin-1-yl)-3-methylphenyl)-2-(3-fluorophenyl)-2-hydroxyacetamide, (S)—N-(4-(8-amino-3-methylimidazo[1,5-α]pyrazin-1-yl)-3-methylphenyl)-2-(3-fluorophenyl)-2-hydroxyacetamide, N-(4-(8-amino-3,6-dimethylimidazo[1,5-α]pyrazin-1-yl)-3-methylphenyl)-2-(3-fluorophenyl)-2-hydroxyacetamide;

(R)—N-(4-(8-amino-3,6-dimethylimidazo[1,5-α]pyrazin-1-yl)-3-methylphenyl)-2-(3-fluorophenyl)-2-hydroxyacetamide;

(S)—N-(4-(8-amino-3,6-dimethylimidazo[1,5-α]pyrazin-1-yl)-3-methylphenyl)-2-(3-fluorophenyl)-2-hydroxyacetamide, N-(4-(8-amino-6-methyl-3-(trideuteriomethyl)imidazo[1,5-α]pyrazin-1-yl)-3-methylphenyl)-2-(3-fluorophenyl)-2-hydroxyacetamide;

(R)—N-(4-(8-amino-6-methyl-3-(trideuteriomethyl)imidazo[1,5-α]pyrazin-1-yl)-3-methylphenyl)-2-(3-fluorophenyl)-2-hydroxyacetamide;

(S)—N-(4-(8-amino-6-methyl-3-(trideuteriomethyl)imidazo[1,5-α]pyrazin-1-yl)-3-methylphenyl)-2-(3-fluorophenyl)-2-hydroxyacetamide;

N-(4-(8-amino-3,5-dimethylimidazo[1,5-a]pyrazin-1-yl)-3-methylphenyl)-2-(3-fluorophenyl)-2-hydroxyacetamide;

(R)—N-(4-(8-amino-3,5-dimethylimidazo[1,5-a]pyrazin-1-yl)-3-methylphenyl)-2-(3-fluorophenyl)-2-hydroxyacetamide;

(S)—N-(4-(8-amino-3,5-dimethylimidazo[1,5-a]pyrazin-1-yl)-3-methylphenyl)-2-(3-fluorophenyl)-2-hydroxyacetamide;

N-(4-(8-amino-5-methyl-3-(trideuteriomethyl)imidazo[1,5-a]pyrazin-1-yl)-3-methylphenyl)-2-(3-fluorophenyl)-2-hydroxyacetamide, (R)—N-(4-(8-amino-5-methyl-3-(trideuteriomethyl)imidazo[1,5-α]pyrazin-1-yl)-3-methylphenyl)-2-(3-fluorophenyl)-2-hydroxyacetamide;

(S)—N-(4-(8-amino-5-methyl-3-(trideuteriomethyl)imidazo[1,5-α]pyrazin-1-yl)-3-methylphenyl)-2-(3-fluorophenyl)-2-hydroxyacetamide;

N-(4-(8-amino-3,6-dimethylimidazo[1,5-a]pyrazin-1-yl)-3-methylphenyl)-2-(3-fluorophenyl)-2-hydroxyacetamide;

(R)—N-(4-(8-amino-3,6-dimethylimidazo[1,5-a]pyrazin-1-yl)-3-methylphenyl)-2-(3-fluorophenyl)-2-hydroxyacetamide, (S)—N-(4-(8-amino-3,6-dimethylimidazo[1,5-a]pyrazin-1-yl)-3-methylphenyl)-2-(3-fluorophenyl)-2-hydroxyacetamide;

N-[4-[8-amino-6-methyl-3-(trideuteriomethyl)imidazo[1,5-a]pyrazin-1-yl]-3-methyl-phenyl]-2-hydroxy-2-[3-(trifluoromethyl)phenyl]acetamide;

(R)—N-[4-[8-amino-6-methyl-3-(trideuteriomethyl)imidazo[1,5-a]pyrazin-1-yl]-3-methyl-phenyl]-2-hydroxy-2-[3-(trifluoromethyl)phenyl]acetamide;

(S)—N-[4-[8-amino-6-methyl-3-(trideuteriomethyl)imidazo[1,5-a]pyrazin-1-yl]-3-methyl-phenyl]-2-hydroxy-2-[3-(trifluoromethyl)phenyl]acetamide;

N-[4-[8-amino-5-methyl-3-(trideuteriomethyl)imidazo[1,5-a]pyrazin-1-yl]-3-methyl-phenyl]-2-hydroxy-2-[3-(trifluoromethyl)phenyl]acetamide;

(R)—N-[4-[8-amino-5-methyl-3-(trideuteriomethyl)imidazo[1,5-a]pyrazin-1-yl]-3-methyl-phenyl]-2-hydroxy-2-[3-(trifluoromethyl)phenyl]acetamide;

(S)—N-[4-[8-amino-5-methyl-3-(trideuteriomethyl)imidazo[1,5-a]pyrazin-1-yl]-3-methyl-phenyl]-2-hydroxy-2-[3-(trifluoromethyl)phenyl]acetamide;

N-[4-[8-amino-5-chloro-3-(trideuteriomethyl)imidazo[1,5-a]pyrazin-1-yl]-3-methyl-phenyl]-2-hydroxy-2-[3-(trifluoromethyl)phenyl]acetamide;

(R)—N-[4-[8-amino-5-chloro-3-(trideuteriomethyl)imidazo[1,5-a]pyrazin-1-yl]-3-methyl-phenyl]-2-hydroxy-2-[3-(trifluoromethyl)phenyl]acetamide;

(S)—N-[4-[8-amino-5-chloro-3-(trideuteriomethyl)imidazo[1,5-a]pyrazin-1-yl]-3-methyl-phenyl]-2-hydroxy-2-[3-(trifluoromethyl)phenyl]acetamide, N-[4-[8-amino-3-(trideuteriomethyl)-5-(trifluoromethyl)imidazo[1,5-a]pyrazin-1-yl]-3-methyl-phenyl]-2-hydroxy-2-[3-(trifluoromethyl)phenyl]acetamide;

(R)—N-[4-[8-amino-3-(trideuteriomethyl)-5-(trifluoromethyl)imidazo[1,5-a]pyrazin-1-yl]-3-methyl-phenyl]-2-hydroxy-2-[3-(trifluoromethyl)phenyl]acetamide;

(S)—N-[4-[8-amino-3-(trideuteriomethyl)-5-(trifluoromethyl)imidazo[1,5-a]pyrazin-1-yl]-3-methyl-phenyl]-2-hydroxy-2-[3-(trifluoromethyl)phenyl]acetamide;

N-(4-(8-amino-3,5,6-trimethylimidazo[1,5-a]pyrazin-1-yl)-3-methylphenyl)-2-(3-fluorophenyl)-2-hydroxyacetamide, (R)—N-(4-(8-amino-3,5,6-trimethylimidazo[1,5-a]pyrazin-1-yl)-3-methylphenyl)-2-(3-fluorophenyl)-2-hydroxyacetamide;

(S)—N-(4-(8-amino-3,5,6-trimethylimidazo[1,5-a]pyrazin-1-yl)-3-methylphenyl)-2-(3-fluorophenyl)-2-hydroxyacetamide;

N-(4-(8-amino-3-(3-hydroxy-3-methylcyclobutyl)-6-methylimidazo[1,5-a]pyrazin-1-yl)-3-methylphenyl)-2-(3-fluorophenyl)-2-hydroxyacetamide, (R)—N-(4-(8-amino-3-(3-hydroxy-3-methylcyclobutyl)-6-methylimidazo[1,5-a]pyrazin-1-yl)-3-methylphenyl)-2-(3-fluorophenyl)-2-hydroxyacetamide;

(S)—N-(4-(8-amino-3-(3-hydroxy-3-methylcyclobutyl)-6-methylimidazo[1,5-a]pyrazin-1-yl)-3-methylphenyl)-2-(3-fluorophenyl)-2-hydroxyacetamide;

N-(4-(8-amino-3-methyl-5-(trifluoromethyl)imidazo[1,5-a]pyrazin-1-yl)-3-methylphenyl)-2-(3-fluorophenyl)-2-hydroxyacetamide;

(R)—N-(4-(8-amino-3-methyl-5-(trifluoromethyl)imidazo[1,5-a]pyrazin-1-yl)-3-methylphenyl)-2-(3-fluorophenyl)-2-hydroxyacetamide;

(S)—N-(4-(8-amino-3-methyl-5-(trifluoromethyl)imidazo[1,5-a]pyrazin-1-yl)-3-methylphenyl)-2-(3-fluorophenyl)-2-hydroxyacetamide;

N-(4-(8-amino-5-chloro-3-methylimidazo[1,5-a]pyrazin-1-yl)-3-methylphenyl)-2-(3-fluorophenyl)-2-hydroxyacetamide;

(R)—N-(4-(8-amino-5-chloro-3-methylimidazo[1,5-a]pyrazin-1-yl)-3-methylphenyl)-2-(3-fluorophenyl)-2-hydroxyacetamide;

(S)—N-(4-(8-amino-5-chloro-3-methylimidazo[1,5-a]pyrazin-1-yl)-3-methylphenyl)-2-(3-fluorophenyl)-2-hydroxyacetamide;

N-[4-[8-amino-3-(trideuteriomethyl)-5-(trifluoromethyl)imidazo[1,5-a]pyrazin-1-yl]-3-methyl-phenyl]-2-(3-fluorophenyl)-2-hydroxy-acetamide;

(R)—N-[4-[8-amino-3-(trideuteriomethyl)-5-(trifluoromethyl)imidazo[1,5-a]pyrazin-1-yl]-3-methyl-phenyl]-2-(3-fluorophenyl)-2-hydroxy-acetamide;

(S)—N-[4-[8-amino-3-(trideuteriomethyl)-5-(trifluoromethyl)imidazo[1,5-a]pyrazin-1-yl]-3-methyl-phenyl]-2-(3-fluorophenyl)-2-hydroxy-acetamide, N-[4-[8-amino-5-chloro-3-(trideuteriomethyl)imidazo[1,5-a]pyrazin-1-yl]-3-methyl-phenyl]-2-(3-fluorophenyl)-2-hydroxy-acetamide;

(R)—N-[4-[8-amino-5-chloro-3-(trideuteriomethyl)imidazo[1,5-a]pyrazin-1-yl]-3-methyl-phenyl]-2-(3-fluorophenyl)-2-hydroxy-acetamide;

(S)—N-[4-[8-amino-5-chloro-3-(trideuteriomethyl)imidazo[1,5-a]pyrazin-1-yl]-3-methyl-phenyl]-2-(3-fluorophenyl)-2-hydroxy-acetamide;
N-[4-[8-amino-6-methyl-3-(trideuteriomethyl)imidazo[1,5-a]pyrazin-1-yl]-3-methyl-phenyl]-2-(3-chlorophenyl)-2-hydroxy-acetamide;
(R)—N-[4-[8-amino-6-methyl-3-(trideuteriomethyl)imidazo[1,5-a]pyrazin-1-yl]-3-methyl-phenyl]-2-(3-chlorophenyl)-2-hydroxy-acetamide;
(S)—N-[4-[8-amino-6-methyl-3-(trideuteriomethyl)imidazo[1,5-a]pyrazin-1-yl]-3-methyl-phenyl]-2-(3-chlorophenyl)-2-hydroxy-acetamide;
N-[4-[8-amino-5-methyl-3-(trideuteriomethyl)imidazo[1,5-a]pyrazin-1-yl]-3-methyl-phenyl]-2-(3-chlorophenyl)-2-hydroxy-acetamide;
(R)—N-[4-[8-amino-5-methyl-3-(trideuteriomethyl)imidazo[1,5-a]pyrazin-1-yl]-3-methyl-phenyl]-2-(3-chlorophenyl)-2-hydroxy-acetamide;
(S)—N-[4-[8-amino-5-methyl-3-(trideuteriomethyl)imidazo[1,5-a]pyrazin-1-yl]-3-methyl-phenyl]-2-(3-chlorophenyl)-2-hydroxy-acetamide;
N-(4-(8-amino-3,5-dimethylimidazo[1,5-a]pyrazin-1-yl)-3-methylphenyl)-2-(3-chlorophenyl)-2-hydroxy acetamide,
(R)—N-(4-(8-amino-3,5-dimethylimidazo[1,5-a]pyrazin-1-yl)-3-methylphenyl)-2-(3-chlorophenyl)-2-hydroxyacetamide;
(S)—N-(4-(8-amino-3,5-dimethylimidazo[1,5-a]pyrazin-1-yl)-3-methylphenyl)-2-(3-chlorophenyl)-2-hydroxyacetamide;
N-[4-[8-amino-3-(trideuteriomethyl)-5-(trifluoromethyl)imidazo[1,5-a]pyrazin-1-yl]-3-methyl-phenyl]-2-(3-chlorophenyl)-2-hydroxy-acetamide;
(R)—N-[4-[8-amino-3-(trideuteriomethyl)-5-(trifluoromethyl)imidazo[1,5-a]pyrazin-1-yl]-3-methyl-phenyl]-2-(3-chlorophenyl)-2-hydroxy-acetamide,
(S)—N-[4-[8-amino-3-(trideuteriomethyl)-5-(trifluoromethyl)imidazo[1,5-a]pyrazin-1-yl]-3-methyl-phenyl]-2-(3-chlorophenyl)-2-hydroxy-acetamide;
N-[4-[8-amino-5-chloro-3-(trideuteriomethyl)imidazo[1,5-a]pyrazin-1-yl]-3-methyl-phenyl]-2-(3-chlorophenyl)-2-hydroxy-acetamide;
(R)—N-[4-[8-amino-5-chloro-3-(trideuteriomethyl)imidazo[1,5-a]pyrazin-1-yl]-3-methyl-phenyl]-2-(3-chlorophenyl)-2-hydroxy-acetamide,
(S)—N-[4-[8-amino-5-chloro-3-(trideuteriomethyl)imidazo[1,5-a]pyrazin-1-yl]-3-methyl-phenyl]-2-(3-chlorophenyl)-2-hydroxy-acetamide;
N-[4-[8-amino-6-methyl-3-(trideuteriomethyl)imidazo[1,5-a]pyrazin-1-yl]-3-methyl-phenyl]-2-(3,5-difluorophenyl)-2-hydroxy-acetamide;
(R)—N-[4-[8-amino-6-methyl-3-(trideuteriomethyl)imidazo[1,5-a]pyrazin-1-yl]-3-methyl-phenyl]-2-(3,5-difluorophenyl)-2-hydroxy-acetamide;
(S)—N-[4-[8-amino-6-methyl-3-(trideuteriomethyl)imidazo[1,5-a]pyrazin-1-yl]-3-methyl-phenyl]-2-(3,5-difluorophenyl)-2-hydroxy-acetamide;
N-[4-[8-amino-3-(trideuteriomethyl)-5-(trifluoromethyl)imidazo[1,5-a]pyrazin-1-yl]-3-methyl-phenyl]-2-(3,5-difluorophenyl)-2-hydroxy-acetamide;
(R)—N-[4-[8-amino-3-(trideuteriomethyl)-5-(trifluoromethyl)imidazo[1,5-a]pyrazin-1-yl]-3-methyl-phenyl]-2-(3,5-difluorophenyl)-2-hydroxy-acetamide;
(S)—N-[4-[8-amino-3-(trideuteriomethyl)-5-(trifluoromethyl)imidazo[1,5-a]pyrazin-1-yl]-3-methyl-phenyl]-2-(3,5-difluorophenyl)-2-hydroxy-acetamide,
N-[4-[8-amino-5-chloro-3-(trideuteriomethyl)imidazo[1,5-a]pyrazin-1-yl]-3-methyl-phenyl]-2-(3,5-difluorophenyl)-2-hydroxy-acetamide;
(R)—N-[4-[8-amino-5-chloro-3-(trideuteriomethyl)imidazo[1,5-a]pyrazin-1-yl]-3-methyl-phenyl]-2-(3,5-difluorophenyl)-2-hydroxy-acetamide;
(S)—N-[4-[8-amino-5-chloro-3-(trideuteriomethyl)imidazo[1,5-a]pyrazin-1-yl]-3-methyl-phenyl]-2-(3,5-difluorophenyl)-2-hydroxy-acetamide;
N-[4-[8-amino-5-methyl-3-(trideuteriomethyl)imidazo[1,5-a]pyrazin-1-yl]-3-methyl-phenyl]-2-(3,5-difluorophenyl)-2-hydroxy-acetamide,
(R)—N-[4-[8-amino-5-methyl-3-(trideuteriomethyl)imidazo[1,5-a]pyrazin-1-yl]-3-methyl-phenyl]-2-(3,5-difluorophenyl)-2-hydroxy-acetamide;
(S)—N-[4-[8-amino-5-methyl-3-(trideuteriomethyl)imidazo[1,5-a]pyrazin-1-yl]-3-methyl-phenyl]-2-(3,5-difluorophenyl)-2-hydroxy-acetamide;
N-[4-[8-amino-6-methyl-3-(trideuteriomethyl)imidazo[1,5-a]pyrazin-1-yl]-3-methyl-phenyl]-2-[3-fluoro-5-(trifluoromethyl)phenyl]-2-hydroxy-acetamide;
(R)—N-[4-[8-amino-6-methyl-3-(trideuteriomethyl)imidazo[1,5-a]pyrazin-1-yl]-3-methyl-phenyl]-2-[3-fluoro-5-(trifluoromethyl)phenyl]-2-hydroxy-acetamide;
(S)—N-[4-[8-amino-6-methyl-3-(trideuteriomethyl)imidazo[1,5-a]pyrazin-1-yl]-3-methyl-phenyl]-2-[3-fluoro-5-(trifluoromethyl)phenyl]-2-hydroxy-acetamide;
N-[4-[8-amino-5-methyl-3-(trideuteriomethyl)imidazo[1,5-a]pyrazin-1-yl]-3-methyl-phenyl]-2-[3-fluoro-5-(trifluoromethyl)phenyl]-2-hydroxy-acetamide;
(R)—N-[4-[8-amino-5-methyl-3-(trideuteriomethyl)imidazo[1,5-a]pyrazin-1-yl]-3-methyl-phenyl]-2-[3-fluoro-5-(trifluoromethyl)phenyl]-2-hydroxy-acetamide;
(S)—N-[4-[8-amino-5-methyl-3-(trideuteriomethyl)imidazo[1,5-a]pyrazin-1-yl]-3-methyl-phenyl]-2-[3-fluoro-5-(trifluoromethyl)phenyl]-2-hydroxy-acetamide;
N-[4-[8-amino-5-chloro-3-(trideuteriomethyl)imidazo[1,5-a]pyrazin-1-yl]-3-methyl-phenyl]-2-[3-fluoro-5-(trifluoromethyl)phenyl]-2-hydroxy-acetamide;
(R)—N-[4-[8-amino-5-chloro-3-(trideuteriomethyl)imidazo[1,5-a]pyrazin-1-yl]-3-methyl-phenyl]-2-[3-fluoro-5-(trifluoromethyl)phenyl]-2-hydroxy-acetamide,
(S)—N-[4-[8-amino-5-chloro-3-(trideuteriomethyl)imidazo[1,5-a]pyrazin-1-yl]-3-methyl-phenyl]-2-[3-fluoro-5-(trifluoromethyl)phenyl]-2-hydroxy-acetamide;
N-(4-(8-amino-3,5-dimethylimidazo[1,5-a]pyrazin-1-yl)-3-methylphenyl)-2-(3-fluoro-5-(trifluoromethyl)phenyl)-2-hydroxyacetamide;
(R)—N-(4-(8-amino-3,5-dimethylimidazo[1,5-a]pyrazin-1-yl)-3-methylphenyl)-2-(3-fluoro-5-(trifluoromethyl)phenyl)-2-hydroxyacetamide;
(S)—N-(4-(8-amino-3,5-dimethylimidazo[1,5-a]pyrazin-1-yl)-3-methylphenyl)-2-(3-fluoro-5-(trifluoromethyl)phenyl)-2-hydroxyacetamide,
N-[4-[8-amino-3-(trideuteriomethyl)-5-(trifluoromethyl)imidazo[1,5-a]pyrazin-1-yl]-3-methyl-phenyl]-2-[3-fluoro-5-(trifluoromethyl)phenyl]-2-hydroxy-acetamide;
(R)—N-[4-[8-amino-3-(trideuteriomethyl)-5-(trifluoromethyl)imidazo[1,5-a]pyrazin-1-yl]-3-methyl-phenyl]-2-[3-fluoro-5-(trifluoromethyl)phenyl]-2-hydroxy-acetamide;
(S)—N-[4-[8-amino-3-(trideuteriomethyl)-5-(trifluoromethyl)imidazo[1,5-a]pyrazin-1-yl]-3-methyl-phenyl]-2-[3-fluoro-5-(trifluoromethyl)phenyl]-2-hydroxy-acetamide, N-(4-(8-amino-3,5-dimethylimidazo[1,5-a]pyrazin-1-yl)-3-methylphenyl)-2-(3-fluoro-5-methylphenyl)-2-hydroxyacetamide;

(R)—N-(4-(8-amino-3,5-dimethylimidazo[1,5-a]pyrazin-1-yl)-3-methylphenyl)-2-(3-fluoro-5-methylphenyl)-2-hydroxyacetamide;

(S)—N-(4-(8-amino-3,5-dimethylimidazo[1,5-a]pyrazin-1-yl)-3-methylphenyl)-2-(3-fluoro-5-methylphenyl)-2-hydroxyacetamide;

N-(4-(8-amino-3,5-dimethylimidazo[1,5-a]pyrazin-1-yl)-2-fluoro-5-methylphenyl)-2-(3-fluorophenyl)-2-hydroxyacetamide;

(R)—N-(4-(8-amino-3,5-dimethylimidazo[1,5-a]pyrazin-1-yl)-2-fluoro-5-methylphenyl)-2-(3-fluorophenyl)-2-hydroxyacetamide;

(S)—N-(4-(8-amino-3,5-dimethylimidazo[1,5-a]pyrazin-1-yl)-2-fluoro-5-methylphenyl)-2-(3-fluorophenyl)-2-hydroxyacetamide;

N-(4-(8-amino-3,5-dimethylimidazo[1,5-a]pyrazin-1-yl)-3-ethylphenyl)-2-(3-fluorophenyl)-2-hydroxyacetamide, (R)—N-(4-(8-amino-3,5-dimethylimidazo[1,5-a]pyrazin-1-yl)-3-ethylphenyl)-2-(3-fluorophenyl)-2-hydroxyacetamide;

(S)—N-(4-(8-amino-3,5-dimethylimidazo[1,5-a]pyrazin-1-yl)-3-ethylphenyl)-2-(3-fluorophenyl)-2-hydroxyacetamide;

N-(4-(8-amino-3,5-dimethylimidazo[1,5-a]pyrazin-1-yl)phenyl)-2-(3-fluorophenyl)-2-hydroxyacetamide;

(R)—N-(4-(8-amino-3,5-dimethylimidazo[1,5-a]pyrazin-1-yl)phenyl)-2-(3-fluorophenyl)-2-hydroxyacetamide, (S)—N-(4-(8-amino-3,5-dimethylimidazo[1,5-a]pyrazin-1-yl)phenyl)-2-(3-fluorophenyl)-2-hydroxyacetamide;

N-(4-(8-amino-3,5-dimethylimidazo[1,5-a]pyrazin-1-yl)-3-fluorophenyl)-2-(3-fluorophenyl)-2-hydroxyacetamide;

(R)—N-(4-(8-amino-3,5-dimethylimidazo[1,5-a]pyrazin-1-yl)-3-fluorophenyl)-2-(3-fluorophenyl)-2-hydroxyacetamide, (S)—N-(4-(8-amino-3,5-dimethylimidazo[1,5-a]pyrazin-1-yl)-3-fluorophenyl)-2-(3-fluorophenyl)-2-hydroxyacetamide;

N-[4-[8-amino-5-methyl-3-(trideuteriomethyl)imidazo[1,5-a]pyrazin-1-yl]-3-fluoro-phenyl]-2-(3-fluorophenyl)-2-hydroxy-acetamide;

(R)—N-[4-[8-amino-5-methyl-3-(trideuteriomethyl)imidazo[1,5-a]pyrazin-1-yl]-3-fluoro-phenyl]-2-(3-fluorophenyl)-2-hydroxy-acetamide;

(S)—N-[4-[8-amino-5-methyl-3-(trideuteriomethyl)imidazo[1,5-a]pyrazin-1-yl]-3-fluoro-phenyl]-2-(3-fluorophenyl)-2-hydroxy-acetamide;

N-[4-[8-amino-5-chloro-3-(trideuteriomethyl)imidazo[1,5-a]pyrazin-1-yl]-3-fluoro-phenyl]-2-(3-fluorophenyl)-2-hydroxy-acetamide;

(R)—N-[4-[8-amino-5-chloro-3-(trideuteriomethyl)imidazo[1,5-a]pyrazin-1-yl]-3-fluoro-phenyl]-2-(3-fluorophenyl)-2-hydroxy-acetamide;

(S)—N-[4-[8-amino-5-chloro-3-(trideuteriomethyl)imidazo[1,5-a]pyrazin-1-yl]-3-fluoro-phenyl]-2-(3-fluorophenyl)-2-hydroxy-acetamide;

N-(4-(8-amino-3,5-dimethylimidazo[1,5-a]pyrazin-1-yl)-3-fluorophenyl)-2-(3-chlorophenyl)-2-hydroxyacetamide;

(R)—N-(4-(8-amino-3,5-dimethylimidazo[1,5-a]pyrazin-1-yl)-3-fluorophenyl)-2-(3-chlorophenyl)-2-hydroxyacetamide;

(S)—N-(4-(8-amino-3,5-dimethylimidazo[1,5-a]pyrazin-1-yl)-3-fluorophenyl)-2-(3-chlorophenyl)-2-hydroxyacetamide;

N-[4-[8-amino-6-methyl-3-(trideuteriomethyl)imidazo[1,5-a]pyrazin-1-yl]-3-fluoro-phenyl]-2-(3-chlorophenyl)-2-hydroxy-acetamide, (R)—N-[4-[8-amino-6-methyl-3-(trideuteriomethyl)imidazo[1,5-a]pyrazin-1-yl]-3-fluoro-phenyl]-2-(3-chlorophenyl)-2-hydroxy-acetamide;

(S)—N-[4-[8-amino-6-methyl-3-(trideuteriomethyl)imidazo[1,5-a]pyrazin-1-yl]-3-fluoro-phenyl]-2-(3-chlorophenyl)-2-hydroxy-acetamide;

N-[4-[8-amino-3-(trideuteriomethyl)-5-(trifluoromethyl)imidazo[1,5-a]pyrazin-1-yl]-3-fluoro-phenyl]-2-(3-chlorophenyl)-2-hydroxy-acetamide, (R)—N-[4-[8-amino-3-(trideuteriomethyl)-5-(trifluoromethyl)imidazo[1,5-a]pyrazin-1-yl]-3-fluoro-phenyl]-2-(3-chlorophenyl)-2-hydroxy-acetamide;

(S)—N-[4-[8-amino-3-(trideuteriomethyl)-5-(trifluoromethyl)imidazo[1,5-a]pyrazin-1-yl]-3-fluoro-phenyl]-2-(3-chlorophenyl)-2-hydroxy-acetamide;

N-[4-[8-amino-5-methyl-3-(trideuteriomethyl)imidazo[1,5-a]pyrazin-1-yl]-3-fluoro-phenyl]-2-(3-chlorophenyl)-2-hydroxy-acetamide;

(R)—N-[4-[8-amino-5-methyl-3-(trideuteriomethyl)imidazo[1,5-a]pyrazin-1-yl]-3-fluoro-phenyl]-2-(3-chlorophenyl)-2-hydroxy-acetamide;

(S)—N-[4-[8-amino-5-methyl-3-(trideuteriomethyl)imidazo[1,5-a]pyrazin-1-yl]-3-fluoro-phenyl]-2-(3-chlorophenyl)-2-hydroxy-acetamide;

N-[4-[8-amino-5-chloro-3-(trideuteriomethyl)imidazo[1,5-a]pyrazin-1-yl]-3-fluoro-phenyl]-2-(3-chlorophenyl)-2-hydroxy-acetamide;

(R)—N-[4-[8-amino-5-chloro-3-(trideuteriomethyl)imidazo[1,5-a]pyrazin-1-yl]-3-fluoro-phenyl]-2-(3-chlorophenyl)-2-hydroxy-acetamide;

(S)—N-[4-[8-amino-5-chloro-3-(trideuteriomethyl)imidazo[1,5-a]pyrazin-1-yl]-3-fluoro-phenyl]-2-(3-chlorophenyl)-2-hydroxy-acetamide;

N-(4-(8-amino-3,5-dimethylimidazo[1,5-a]pyrazin-1-yl)-3-fluorophenyl)-2-hydroxy-2-(m-tolyl)acetamide;

(R)—N-(4-(8-amino-3,5-dimethylimidazo[1,5-a]pyrazin-1-yl)-3-fluorophenyl)-2-hydroxy-2-(m-tolyl)acetamide;

(S)—N-(4-(8-amino-3,5-dimethylimidazo[1,5-a]pyrazin-1-yl)-3-fluorophenyl)-2-hydroxy-2-(m-tolyl)acetamide;

N-[4-[8-amino-5-methyl-3-(trideuteriomethyl)imidazo[1,5-a]pyrazin-1-yl]-3-fluoro-phenyl]-2-hydroxy-2-(m-tolyl)acetamide;

(R)—N-[4-[8-amino-5-methyl-3-(trideuteriomethyl)imidazo[1,5-a]pyrazin-1-yl]-3-fluoro-phenyl]-2-hydroxy-2-(m-tolyl)acetamide;

(S)—N-[4-[8-amino-5-methyl-3-(trideuteriomethyl)imidazo[1,5-a]pyrazin-1-yl]-3-fluoro-phenyl]-2-hydroxy-2-(m-tolyl)acetamide, N-(4-(8-amino-3,5-dimethylimidazo[1,5-a]pyrazin-1-yl)-3-fluorophenyl)-2-hydroxy-2-(3-(trifluoromethyl)phenyl)acetamide;

(R)—N-(4-(8-amino-3,5-dimethylimidazo[1,5-a]pyrazin-1-yl)-3-fluorophenyl)-2-hydroxy-2-(3-(trifluoromethyl)phenyl)acetamide;

(S)—N-(4-(8-amino-3,5-dimethylimidazo[1,5-a]pyrazin-1-yl)-3-fluorophenyl)-2-hydroxy-2-(3-(trifluoromethyl)phenyl)acetamide;

N-[4-[8-amino-5-methyl-3-(trideuteriomethyl)imidazo[1,5-a]pyrazin-1-yl]-3-fluoro-phenyl]-2-hydroxy-2-[3-(trifluoromethyl)phenyl]acetamide;

(R)—N-[4-[8-amino-5-methyl-3-(trideuteriomethyl)imidazo[1,5-a]pyrazin-1-yl]-3-fluoro-phenyl]-2-hydroxy-2-[3-(trifluoromethyl)phenyl]acetamide;

(S)—N-[4-[8-amino-5-methyl-3-(trideuteriomethyl)imidazo[1,5-a]pyrazin-1-yl]-3-fluoro-phenyl]-2-hydroxy-2-[3-(trifluoromethyl)phenyl]acetamide;
N-[4-[8-amino-6-methyl-3-(trideuteriomethyl)imidazo[1,5-a]pyrazin-1-yl]-3-fluoro-phenyl]-2-hydroxy-2-[3-(trifluoromethyl)phenyl]acetamide,
(R)—N-[4-[8-amino-6-methyl-3-(trideuteriomethyl)imidazo[1,5-a]pyrazin-1-yl]-3-fluoro-phenyl]-2-hydroxy-2-[3-(trifluoromethyl)phenyl]acetamide;
(S)—N-[4-[8-amino-6-methyl-3-(trideuteriomethyl)imidazo[1,5-a]pyrazin-1-yl]-3-fluoro-phenyl]-2-hydroxy-2-[3-(trifluoromethyl)phenyl]acetamide;
N-[4-[8-amino-3-(trideuteriomethyl)-5-(trifluoromethyl)imidazo[1,5-a]pyrazin-1-yl]-3-fluoro-phenyl]-2-hydroxy-2-[3-(trifluoromethyl)phenyl]acetamide;
(R)—N-[4-[8-amino-3-(trideuteriomethyl)-5-(trifluoromethyl)imidazo[1,5-a]pyrazin-1-yl]-3-fluoro-phenyl]-2-hydroxy-2-[3-(trifluoromethyl)phenyl]acetamide;
(S)—N-[4-[8-amino-3-(trideuteriomethyl)-5-(trifluoromethyl)imidazo[1,5-a]pyrazin-1-yl]-3-fluoro-phenyl]-2-hydroxy-2-[3-(trifluoromethyl)phenyl]acetamide;
N-[4-[8-amino-5-chloro-3-(trideuteriomethyl)imidazo[1,5-a]pyrazin-1-yl]-3-fluoro-phenyl]-2-hydroxy-2-[3-(trifluoromethyl)phenyl]acetamide;
(R)—N-[4-[8-amino-5-chloro-3-(trideuteriomethyl)imidazo[1,5-a]pyrazin-1-yl]-3-fluoro-phenyl]-2-hydroxy-2-[3-(trifluoromethyl)phenyl]acetamide;
(S)—N-[4-[8-amino-5-chloro-3-(trideuteriomethyl)imidazo[1,5-a]pyrazin-1-yl]-3-fluoro-phenyl]-2-hydroxy-2-[3-(trifluoromethyl)phenyl]acetamide;
N-[4-[8-amino-6-methyl-3-(trideuteriomethyl)imidazo[1,5-a]pyrazin-1-yl]-3-fluoro-phenyl]-2-(3,5-difluorophenyl)-2-hydroxy-acetamide;
(R)—N-[4-[8-amino-6-methyl-3-(trideuteriomethyl)imidazo[1,5-a]pyrazin-1-yl]-3-fluoro-phenyl]-2-(3,5-difluorophenyl)-2-hydroxy-acetamide;
(S)—N-[4-[8-amino-6-methyl-3-(trideuteriomethyl)imidazo[1,5-a]pyrazin-1-yl]-3-fluoro-phenyl]-2-(3,5-difluorophenyl)-2-hydroxy-acetamide;
N-[4-[8-amino-5-methyl-3-(trideuteriomethyl)imidazo[1,5-a]pyrazin-1-yl]-3-fluoro-phenyl]-2-(3,5-difluorophenyl)-2-hydroxy-acetamide;
(R)—N-[4-[8-amino-5-methyl-3-(trideuteriomethyl)imidazo[1,5-a]pyrazin-1-yl]-3-fluoro-phenyl]-2-(3,5-difluorophenyl)-2-hydroxy-acetamide;
(S)—N-[4-[8-amino-5-methyl-3-(trideuteriomethyl)imidazo[1,5-a]pyrazin-1-yl]-3-fluoro-phenyl]-2-(3,5-difluorophenyl)-2-hydroxy-acetamide,
N-[4-[8-amino-3-(trideuteriomethyl)-5-(trifluoromethyl)imidazo[1,5-a]pyrazin-1-yl]-3-fluoro-phenyl]-difluorophenyl)-2-hydroxy-acetamide;
(R)—N-[4-[8-amino-3-(trideuteriomethyl)-5-(trifluoromethyl)imidazo[1,5-a]pyrazin-1-yl]-3-fluoro-phenyl]-2-(3,5-difluorophenyl)-2-hydroxy-acetamide;
(S)—N-[4-[8-amino-3-(trideuteriomethyl)-5-(trifluoromethyl)imidazo[1,5-a]pyrazin-1-yl]-3-fluoro-phenyl]-2-(3,5-difluorophenyl)-2-hydroxy-acetamide;
N-[4-[8-amino-5-chloro-3-(trideuteriomethyl)imidazo[1,5-a]pyrazin-1-yl]-3-fluoro-phenyl]-2-(3,5-difluorophenyl)-2-hydroxy-acetamide,
(R)—N-[4-[8-amino-5-chloro-3-(trideuteriomethyl)imidazo[1,5-a]pyrazin-1-yl]-3-fluoro-phenyl]-2-(3,5-difluorophenyl)-2-hydroxy-acetamide;
(S)—N-[4-[8-amino-5-chloro-3-(trideuteriomethyl)imidazo[1,5-a]pyrazin-1-yl]-3-fluoro-phenyl]-2-(3,5-difluorophenyl)-2-hydroxy-acetamide;
N-[4-[8-amino-5-methyl-3-(trideuteriomethyl)imidazo[1,5-a]pyrazin-1-yl]-3-fluoro-phenyl]-2-[3-fluoro-5-(trifluoromethyl)phenyl]-2-hydroxy-acetamide,
(R)—N-[4-[8-amino-5-methyl-3-(trideuteriomethyl)imidazo[1,5-a]pyrazin-1-yl]-3-fluoro-phenyl]-2-[3-fluoro-5-(trifluoromethyl)phenyl]-2-hydroxy-acetamide;
(S)—N-[4-[8-amino-5-methyl-3-(trideuteriomethyl)imidazo[1,5-a]pyrazin-1-yl]-3-fluoro-phenyl]-2-[3-fluoro-5-(trifluoromethyl)phenyl]-2-hydroxy-acetamide;
N-[4-[8-amino-3-(trideuteriomethyl)-5-(trifluoromethyl)imidazo[1,5-a]pyrazin-1-yl]-3-fluoro-phenyl]-2-[3-fluoro-5-(trifluoromethyl)phenyl]-2-hydroxy-acetamide;
(R)—N-[4-[8-amino-3-(trideuteriomethyl)-5-(trifluoromethyl)imidazo[1,5-a]pyrazin-1-yl]-3-fluoro-phenyl]-2-[3-fluoro-5-(trifluoromethyl)phenyl]-2-hydroxy-acetamide;
(S)—N-[4-[8-amino-3-(trideuteriomethyl)-5-(trifluoromethyl)imidazo[1,5-a]pyrazin-1-yl]-3-fluoro-phenyl]-2-[3-fluoro-5-(trifluoromethyl)phenyl]-2-hydroxy-acetamide;
N-[4-[8-amino-5-chloro-3-(trideuteriomethyl)imidazo[1,5-a]pyrazin-1-yl]-3-fluoro-phenyl]-2-[3-fluoro-5-(trifluoromethyl)phenyl]-2-hydroxy-acetamide;
(R)—N-[4-[8-amino-5-chloro-3-(trideuteriomethyl)imidazo[1,5-a]pyrazin-1-yl]-3-fluoro-phenyl]-2-[3-fluoro-5-(trifluoromethyl)phenyl]-2-hydroxy-acetamide,
(S)—N-[4-[8-amino-5-chloro-3-(trideuteriomethyl)imidazo[1,5-a]pyrazin-1-yl]-3-fluoro-phenyl]-2-[3-fluoro-5-(trifluoromethyl)phenyl]-2-hydroxy-acetamide;
N-[4-[8-amino-6-methyl-3-(trideuteriomethyl)imidazo[1,5-a]pyrazin-1-yl]-3-fluoro-phenyl]-2-[3-fluoro-5-(trifluoromethyl)phenyl]-2-hydroxy-acetamide;
(R)—N-[4-[8-amino-6-methyl-3-(trideuteriomethyl)imidazo[1,5-a]pyrazin-1-yl]-3-fluoro-phenyl]-2-[3-fluoro-5-(trifluoromethyl)phenyl]-2-hydroxy-acetamide;
(S)—N-[4-[8-amino-6-methyl-3-(trideuteriomethyl)imidazo[1,5-a]pyrazin-1-yl]-3-fluoro-phenyl]-2-[3-fluoro-5-(trifluoromethyl)phenyl]-2-hydroxy-acetamide;
N-(4-(8-amino-3,6-dimethylimidazo[1,5-a]pyrazin-1-yl)-2-fluorophenyl)-2-(3-fluorophenyl)-2-hydroxyacetamide;
(R)—N-(4-(8-amino-3,6-dimethylimidazo[1,5-a]pyrazin-1-yl)-2-fluorophenyl)-2-(3-fluorophenyl)-2-hydroxyacetamide;
(S)—N-(4-(8-amino-3,6-dimethylimidazo[1,5-a]pyrazin-1-yl)-2-fluorophenyl)-2-(3-fluorophenyl)-2-hydroxyacetamide;
N-[4-[8-amino-6-methyl-3-(trideuteriomethyl)imidazo[1,5-a]pyrazin-1-yl]-2-fluorophenyl]-2-(3-fluorophenyl)-2-hydroxy-acetamide;
(R)—N-[4-[8-amino-6-methyl-3-(trideuteriomethyl)imidazo[1,5-a]pyrazin-1-yl]-2-fluorophenyl]-2-(3-fluorophenyl)-2-hydroxy-acetamide;
(S)—N-[4-[8-amino-6-methyl-3-(trideuteriomethyl)imidazo[1,5-a]pyrazin-1-yl]-2-fluorophenyl]-2-(3-fluorophenyl)-2-hydroxy-acetamide;
N-[4-[8-amino-5-methyl-3-(trideuteriomethyl)imidazo[1,5-a]pyrazin-1-yl]-2-fluorophenyl]-2-(3-fluorophenyl)-2-hydroxy-acetamide;
(R)—N-[4-[8-amino-5-methyl-3-(trideuteriomethyl)imidazo[1,5-a]pyrazin-1-yl]-2-fluoro-phenyl]-2-(3-fluorophenyl)-2-hydroxy-acetamide;
(S)—N-[4-[8-amino-5-methyl-3-(trideuteriomethyl)imidazo[1,5-a]pyrazin-1-yl]-2-fluoro-phenyl]-2-(3-fluorophenyl)-2-hydroxy-acetamide;
N-(4-(8-amino-3,5-dimethylimidazo[1,5-a]pyrazin-1-yl)-2-fluorophenyl)-2-(3-fluorophenyl)-2-hydroxyacetamide,
(R)—N-(4-(8-amino-3,5-dimethylimidazo[1,5-a]pyrazin-1-yl)-2-fluorophenyl)-2-(3-fluorophenyl)-2-hydroxyacetamide;

(S)—N-(4-(8-amino-3,5-dimethylimidazo[1,5-a]pyrazin-1-yl)-2-fluorophenyl)-2-(3-fluorophenyl)-2-hydroxyacetamide;

N-(4-(8-amino-3,5-dimethylimidazo[1,5-a]pyrazin-1-yl)-3-(trifluoromethoxy)phenyl)-2-(3-fluorophenyl)-2-hydroxyacetamide;

(R)—N-(4-(8-amino-3,5-dimethylimidazo[1,5-a]pyrazin-1-yl)-3-(trifluoromethoxy)phenyl)-2-(3-fluorophenyl)-2-hydroxyacetamide, (S)—N-(4-(8-amino-3,5-dimethylimidazo[1,5-a]pyrazin-1-yl)-3-(trifluoromethoxy)phenyl)-2-(3-fluorophenyl)-2-hydroxyacetamide;

N-(4-(8-amino-3,6-dimethylimidazo[1,5-a]pyrazin-1-yl)-2,3-difluorophenyl)-2-(3-fluorophenyl)-2-hydroxyacetamide;

(R)—N-(4-(8-amino-3,6-dimethylimidazo[1,5-a]pyrazin-1-yl)-2,3-difluorophenyl)-2-(3-fluorophenyl)-2-hydroxyacetamide, (S)—N-(4-(8-amino-3,6-dimethylimidazo[1,5-a]pyrazin-1-yl)-2,3-difluorophenyl)-2-(3-fluorophenyl)-2-hydroxyacetamide;

N-[4-[8-amino-6-methyl-3-(trideuteriomethyl)imidazo[1,5-a]pyrazin-1-yl]-2,3-difluoro-phenyl]-2-(3-fluorophenyl)-2-hydroxy-acetamide;

(R)—N-[4-[8-amino-6-methyl-3-(trideuteriomethyl)imidazo[1,5-a]pyrazin-1-yl]-2,3-difluoro-phenyl]-2-(3-fluorophenyl)-2-hydroxy-acetamide;

(S)—N-[4-[8-amino-6-methyl-3-(trideuteriomethyl)imidazo[1,5-a]pyrazin-1-yl]-2,3-difluoro-phenyl]-2-(3-fluorophenyl)-2-hydroxy-acetamide;

N-[4-[8-amino-5-methyl-3-(trideuteriomethyl)imidazo[1,5-a]pyrazin-1-yl]-2,3-difluoro-phenyl]-2-(3-fluorophenyl)-2-hydroxy-acetamide;

(R)—N-[4-[8-amino-5-methyl-3-(trideuteriomethyl)imidazo[1,5-a]pyrazin-1-yl]-2,3-difluoro-phenyl]-2-(3-fluorophenyl)-2-hydroxy-acetamide;

(S)—N-[4-[8-amino-5-methyl-3-(trideuteriomethyl)imidazo[1,5-a]pyrazin-1-yl]-2,3-difluoro-phenyl]-2-(3-fluorophenyl)-2-hydroxy-acetamide;

N-[4-[8-amino-3-(trideuteriomethyl)-5-(trifluoromethyl)imidazo[1,5-a]pyrazin-1-yl]-2,3-difluoro-phenyl]-2-(3-fluorophenyl)-2-hydroxy-acetamide;

(R)—N-[4-[8-amino-3-(trideuteriomethyl)-5-(trifluoromethyl)imidazo[1,5-a]pyrazin-1-yl]-2,3-difluoro-phenyl]-2-(3-fluorophenyl)-2-hydroxy-acetamide;

(S)—N-[4-[8-amino-3-(trideuteriomethyl)-5-(trifluoromethyl)imidazo[1,5-a]pyrazin-1-yl]-2,3-difluoro-phenyl]-2-(3-fluorophenyl)-2-hydroxy-acetamide;

N-[4-[8-amino-5-chloro-3-(trideuteriomethyl)imidazo[1,5-a]pyrazin-1-yl]-2,3-difluoro-phenyl]-2-(3-fluorophenyl)-2-hydroxy-acetamide;

(R)—N-[4-[8-amino-5-chloro-3-(trideuteriomethyl)imidazo[1,5-a]pyrazin-1-yl]-2,3-difluoro-phenyl]-2-(3-fluorophenyl)-2-hydroxy-acetamide;

(S)—N-[4-[8-amino-5-chloro-3-(trideuteriomethyl)imidazo[1,5-a]pyrazin-1-yl]-2,3-difluoro-phenyl]-2-(3-fluorophenyl)-2-hydroxy-acetamide;

N-[4-[8-amino-5-methyl-3-(trideuteriomethyl)imidazo[1,5-a]pyrazin-1-yl]-2,3-difluoro-phenyl]-2-(3-chlorophenyl)-2-hydroxy-acetamide, (R)—N-[4-[8-amino-5-methyl-3-(trideuteriomethyl)imidazo[1,5-a]pyrazin-1-yl]-2,3-difluoro-phenyl]-2-(3-chlorophenyl)-2-hydroxy-acetamide;

(S)—N-[4-[8-amino-5-methyl-3-(trideuteriomethyl)imidazo[1,5-a]pyrazin-1-yl]-2,3-difluoro-phenyl]-2-(3-chlorophenyl)-2-hydroxy-acetamide;

N-[4-[8-amino-6-methyl-3-(trideuteriomethyl)imidazo[1,5-a]pyrazin-1-yl]-2,3-difluoro-phenyl]-2-(3-chlorophenyl)-2-hydroxy-acetamide;

(R)—N-[4-[8-amino-6-methyl-3-(trideuteriomethyl)imidazo[1,5-a]pyrazin-1-yl]-2,3-difluoro-phenyl]-2-(3-chlorophenyl)-2-hydroxy-acetamide;

(S)—N-[4-[8-amino-6-methyl-3-(trideuteriomethyl)imidazo[1,5-a]pyrazin-1-yl]-2,3-difluoro-phenyl]-2-(3-chlorophenyl)-2-hydroxy-acetamide;

N-[4-[8-amino-3-(trideuteriomethyl)-5-(trifluoromethyl)imidazo[1,5-a]pyrazin-1-yl]-2,3-difluoro-phenyl]-2-(3-chlorophenyl)-2-hydroxy-acetamide;

(R)—N-[4-[8-amino-3-(trideuteriomethyl)-5-(trifluoromethyl)imidazo[1,5-a]pyrazin-1-yl]-2,3-difluoro-phenyl]-2-(3-chlorophenyl)-2-hydroxy-acetamide, (S)—N-[4-[8-amino-3-(trideuteriomethyl)-5-(trifluoromethyl)imidazo[1,5-a]pyrazin-1-yl]-2,3-difluoro-phenyl]-2-(3-chlorophenyl)-2-hydroxy-acetamide;

N-[4-[8-amino-5-chloro-3-(trideuteriomethyl)imidazo[1,5-a]pyrazin-1-yl]-2-difluoro-phenyl]-2-(3-chlorophenyl)-2-hydroxy-acetamide;

(R)—N-[4-[8-amino-5-chloro-3-(trideuteriomethyl)imidazo[1,5-a]pyrazin-1-yl]-2,3-difluoro-phenyl]-2-(3-chlorophenyl)-2-hydroxy-acetamide;

(S)—N-[4-[8-amino-5-chloro-3-(trideuteriomethyl)imidazo[1,5-a]pyrazin-1-yl]-2,3-difluoro-phenyl]-2-(3-chlorophenyl)-2-hydroxy-acetamide;

N-[4-[8-amino-5-methyl-3-(trideuteriomethyl)imidazo[1,5-a]pyrazin-1-yl]-2,3-difluoro-phenyl]-2-hydroxy-2-[3-(trifluoromethyl)phenyl]acetamide;

(R)—N-[4-[8-amino-5-methyl-3-(trideuteriomethyl)imidazo[1,5-a]pyrazin-1-yl]-2,3-difluoro-phenyl]-2-hydroxy-2-[3-(trifluoromethyl)phenyl]acetamide;

(S)—N-[4-[8-amino-5-methyl-3-(trideuteriomethyl)imidazo[1,5-a]pyrazin-1-yl]-2,3-difluoro-phenyl]-2-hydroxy-2-[3-(trifluoromethyl)phenyl]acetamide, N-[4-[8-amino-3-(trideuteriomethyl)-5-(trifluoromethyl)imidazo[1,5-a]pyrazin-1-yl]-2,3-difluoro-phenyl]-2-hydroxy-2-[3-(trifluoromethyl)phenyl]acetamide;

(R)—N-[4-[8-amino-3-(trideuteriomethyl)-5-(trifluoromethyl)imidazo[1,5-a]pyrazin-1-yl]-2,3-difluoro-phenyl]-2-hydroxy-2-[3-(trifluoromethyl)phenyl]acetamide;

(S)—N-[4-[8-amino-3-(trideuteriomethyl)-5-(trifluoromethyl)imidazo[1,5-a]pyrazin-1-yl]-2,3-difluoro-phenyl]-2-hydroxy-2-[3-(trifluoromethyl)phenyl]acetamide;

N-[4-[8-amino-6-methyl-3-(trideuteriomethyl)imidazo[1,5-a]pyrazin-1-yl]-2,3-difluoro-phenyl]-2-hydroxy-2-[3-(trifluoromethyl)phenyl]acetamide;

(R)—N-[4-[8-amino-6-methyl-3-(trideuteriomethyl)imidazo[1,5-a]pyrazin-1-yl]-2,3-difluoro-phenyl]-2-hydroxy-2-[3-(trifluoromethyl)phenyl]acetamide;

(S)—N-[4-[8-amino-6-methyl-3-(trideuteriomethyl)imidazo[1,5-a]pyrazin-1-yl]-2,3-difluoro-phenyl]-2-hydroxy-2-[3-(trifluoromethyl)phenyl]acetamide;

N-[4-[8-amino-5-chloro-3-(trideuteriomethyl)imidazo[1,5-a]pyrazin-1-yl]-2,3-difluoro-phenyl]-2-hydroxy-2-[3-(trifluoromethyl)phenyl]acetamide, (R)—N-[4-[8-amino-5-chloro-3-(trideuteriomethyl)imidazo[1,5-a]pyrazin-1-yl]-2,3-difluoro-phenyl]-2-hydroxy-2-[3-(trifluoromethyl)phenyl]acetamide;

(S)—N-[4-[8-amino-5-chloro-3-(trideuteriomethyl)imidazo[1,5-a]pyrazin-1-yl]-2,3-difluoro-phenyl]-2-hydroxy-2-[3-(trifluoromethyl)phenyl]acetamide;

N-[4-[8-amino-5-methyl-3-(trideuteriomethyl)imidazo[1,5-a]pyrazin-1-yl]-2,3-difluoro-phenyl]-2-(3,5-difluorophenyl)-2-hydroxy-acetamide;

(R)—N-[4-[8-amino-5-methyl-3-(trideuteriomethyl)imidazo[1,5-a]pyrazin-1-yl]-2,3-difluoro-phenyl]-2-(3,5-difluorophenyl)-2-hydroxy-acetamide,
(S)—N-[4-[8-amino-5-methyl-3-(trideuteriomethyl)imidazo[1,5-a]pyrazin-1-yl]-2,3-difluoro-phenyl]-2-(3,5-difluorophenyl)-2-hydroxy-acetamide;
N-[4-[8-amino-5-chloro-3-(trideuteriomethyl)imidazo[1,5-a]pyrazin-1-yl]-2-difluoro-phenyl]-2-(3,5-difluorophenyl)-2-hydroxy-acetamide;
(R)—N-[4-[8-amino-5-chloro-3-(trideuteriomethyl)imidazo[1,5-a]pyrazin-1-yl]-2,3-difluoro-phenyl]-2-(3,5-difluorophenyl)-2-hydroxy-acetamide,
(S)—N-[4-[8-amino-5-chloro-3-(trideuteriomethyl)imidazo[1,5-a]pyrazin-1-yl]-2,3-difluoro-phenyl]-2-(3,5-difluorophenyl)-2-hydroxy-acetamide;
N-[4-[8-amino-5-methyl-3-(trideuteriomethyl)imidazo[1,5-a]pyrazin-1-yl]-2,3-difluoro-phenyl]-2-[3-fluoro-5-(trifluoromethyl)phenyl]-2-hydroxy-acetamide;
(R)—N-[4-[8-amino-5-methyl-3-(trideuteriomethyl)imidazo[1,5-a]pyrazin-1-yl]-2,3-difluoro-phenyl]-2-[3-fluoro-5-(trifluoromethyl)phenyl]-2-hydroxy-acetamide;
(S)—N-[4-[8-amino-5-methyl-3-(trideuteriomethyl)imidazo[1,5-a]pyrazin-1-yl]-2,3-difluoro-phenyl]-2-[3-fluoro-5-(trifluoromethyl)phenyl]-2-hydroxy-acetamide;
N-[4-[8-amino-3-(trideuteriomethyl)-5-(trifluoromethyl)imidazo[1,5-a]pyrazin-1-yl]-2,3-difluoro-phenyl]-2-[3-fluoro-5-(trifluoromethyl)phenyl]-2-hydroxy-acetamide;
(R)—N-[4-[8-amino-3-(trideuteriomethyl)-5-(trifluoromethyl)imidazo[1,5-a]pyrazin-1-yl]-2,3-difluoro-phenyl]-2-[3-fluoro-5-(trifluoromethyl)phenyl]-2-hydroxy-acetamide;
(S)—N-[4-[8-amino-3-(trideuteriomethyl)-5-(trifluoromethyl)imidazo[1,5-a]pyrazin-1-yl]-2,3-difluoro-phenyl]-2-[3-fluoro-5-(trifluoromethyl)phenyl]-2-hydroxy-acetamide,
N-[4-[8-amino-5-chloro-3-(trideuteriomethyl)imidazo[1,5-a]pyrazin-1-yl]-2,3-difluoro-phenyl]-2-[3-fluoro-5-(trifluoromethyl)phenyl]-2-hydroxy-acetamide;
(R)—N-[4-[8-amino-5-chloro-3-(trideuteriomethyl)imidazo[1,5-a]pyrazin-1-yl]-2,3-difluoro-phenyl]-2-[3-fluoro-5-(trifluoromethyl)phenyl]-2-hydroxy-acetamide;
(S)—N-[4-[8-amino-5-chloro-3-(trideuteriomethyl)imidazo[1,5-a]pyrazin-1-yl]-2,3-difluoro-phenyl]-2-[3-fluoro-5-(trifluoromethyl)phenyl]-2-hydroxy-acetamide;
N-[4-[8-amino-6-methyl-3-(trideuteriomethyl)imidazo[1,5-a]pyrazin-1-yl]-2,3-difluoro-phenyl]-2-[3-fluoro-5-(trifluoromethyl)phenyl]-2-hydroxy-acetamide,
(R)—N-[4-[8-amino-6-methyl-3-(trideuteriomethyl)imidazo[1,5-a]pyrazin-1-yl]-2,3-difluoro-phenyl]-2-[3-fluoro-5-(trifluoromethyl)phenyl]-2-hydroxy-acetamide;
(S)—N-[4-[8-amino-6-methyl-3-(trideuteriomethyl)imidazo[1,5-a]pyrazin-1-yl]-2,3-difluoro-phenyl]-2-[3-fluoro-5-(trifluoromethyl)phenyl]-2-hydroxy-acetamide;
N-(4-(8-amino-3,5-dimethylimidazo[1,5-a]pyrazin-1-yl)-2-fluoro-3-methylphenyl)-2-(3-fluorophenyl)-2-hydroxyacetamide,
(R)—N-(4-(8-amino-3,5-dimethylimidazo[1,5-a]pyrazin-1-yl)-2-fluoro-3-methylphenyl)-2-(3-fluorophenyl)-2-hydroxyacetamide;
(S)—N-(4-(8-amino-3,5-dimethylimidazo[1,5-a]pyrazin-1-yl)-2-fluoro-3-methylphenyl)-2-(3-fluorophenyl)-2-hydroxyacetamide;
N-[5-[8-amino-6-methyl-3-(trideuteriomethyl)imidazo[1,5-a]pyrazin-1-yl]-6-methyl-2-pyridyl]-2-(3-fluorophenyl)-2-hydroxy-acetamide;
(R)—N-[4-[8-amino-6-methyl-3-(trideuteriomethyl)imidazo[1,5-a]pyrazin-1-yl]-6-methyl-2-pyridyl]-2-(3-fluorophenyl)-2-hydroxy-acetamide;
(S)—N-[5-[8-amino-6-methyl-3-(trideuteriomethyl)imidazo[1,5-a]pyrazin-1-yl]-6-methyl-2-pyridyl]-2-(3-fluorophenyl)-2-hydroxy-acetamide;
N-[5-[8-amino-5-methyl-3-(trideuteriomethyl)imidazo[1,5-a]pyrazin-1-yl]-6-methyl-2-pyridyl]-2-(3-fluorophenyl)-2-hydroxy-acetamide;
(R)—N-[5-[8-amino-5-methyl-3-(trideuteriomethyl)imidazo[1,5-a]pyrazin-1-yl]-6-methyl-2-pyridyl]-2-(3-fluorophenyl)-2-hydroxy-acetamide;
(S)—N-[5-[8-amino-5-methyl-3-(trideuteriomethyl)imidazo[1,5-a]pyrazin-1-yl]-6-methyl-2-pyridyl]-2-(3-fluorophenyl)-2-hydroxy-acetamide;
N-[5-[8-amino-5-methyl-3-(trideuteriomethyl)imidazo[1,5-a]pyrazin-1-yl]-6-methyl-2-pyridyl]-2-hydroxy-2-[3-(trifluoromethyl)phenyl]acetamide;
(R)—N-[5-[8-amino-5-methyl-3-(trideuteriomethyl)imidazo[1,5-a]pyrazin-1-yl]-6-methyl-2-pyridyl]-2-hydroxy-2-[3-(trifluoromethyl)phenyl]acetamide;
(S)—N-[5-[8-amino-5-methyl-3-(trideuteriomethyl)imidazo[1,5-a]pyrazin-1-yl]-6-methyl-2-pyridyl]-2-hydroxy-2-[3-(trifluoromethyl)phenyl]acetamide,
N-[5-[8-amino-6-methyl-3-(trideuteriomethyl)imidazo[1,5-a]pyrazin-1-yl]-4-methyl-2-pyridyl]-2-(3-fluorophenyl)-2-hydroxy-acetamide;
(R)—N-[4-[8-amino-6-methyl-3-(trideuteriomethyl)imidazo[1,5-a]pyrazin-1-yl]-4-methyl-2-pyridyl]-2-(3-fluorophenyl)-2-hydroxy-acetamide;
(S)—N-[4-[8-amino-6-methyl-3-(trideuteriomethyl)imidazo[1,5-a]pyrazin-1-yl]-4-methyl-2-pyridyl]-2-(3-fluorophenyl)-2-hydroxy-acetamide,
N-[5-[8-amino-5-methyl-3-(trideuteriomethyl)imidazo[1,5-a]pyrazin-1-yl]-4-methyl-2-pyridyl]-2-(3-fluorophenyl)-2-hydroxy-acetamide;
(R)—N-[4-[8-amino-5-methyl-3-(trideuteriomethyl)imidazo[1,5-a]pyrazin-1-yl]-4-methyl-2-pyridyl]-2-(3-fluorophenyl)-2-hydroxy-acetamide;
(S)—N-[4-[8-amino-5-methyl-3-(trideuteriomethyl)imidazo[1,5-a]pyrazin-1-yl]-4-methyl-2-pyridyl]-2-(3-fluorophenyl)-2-hydroxy-acetamide;
or a pharmaceutically acceptable salt thereof.

Embodiments of the present invention further provide a pharmaceutical composition, comprising a compound or a pharmaceutically acceptable salt thereof including one or more pharmaceutically acceptable carriers, diluents, or excipients.

Embodiments of the present invention further provide a method of treating cancer in a patient comprising administering to a patient in need thereof an effective amount of any of the above compounds, or a pharmaceutically acceptable salt thereof.

Embodiments of the present invention further provide a method of treating cancer in a patient comprising administering to a patient in need thereof an effective amount of any of the above compounds in combination with an anti-cancer agent, or pharmaceutically acceptable salts thereof.

Embodiments of the present invention further provide a compound or pharmaceutically acceptable salt thereof for use in therapy.

Embodiments of the present invention further provide a compound or pharmaceutically acceptable salt thereof according to any of the compounds for use in the treatment of cancer.

In some embodiments, the cancer is particularly pancreatic cancer, melanoma, or breast cancer, including BrCa positive breast cancer.

Embodiments of the present invention further provide a method of treating a disease in a patient in need of such treatment, said method comprising administering a PERK kinase modulating compound according to any of the above compounds, or a pharmaceutically acceptable salt thereof, wherein the disease is cancer.

The present invention provides a method of treating cancer in a patient in need of such treatment, comprising administering to the patient an effective amount of a compound of formula I, Ia, Ib, Ic Id, or Ie, or a pharmaceutically acceptable salt thereof. The present invention also provides a method of inhibiting PERK activity resulting in antitumor activity in a patient in need of such treatment, comprising administering to the patient an effective amount of a compound of formula I, Ia, Ib, Ic, Id, or Ie, or a pharmaceutically acceptable salt thereof.

In some embodiments of any of the above methods or uses, the subject is a human. In some embodiments of any of the above methods or uses, the compound and/or anti-cancer agent is orally administered to the subject. In some embodiments of any of the above methods or uses, the compound and/or anti-cancer agent is administered to the subject.

As used herein, the term "cancer" refers to all types of cancer, neoplasm or malignant tumors found in mammals, including leukemia, lymphoma, carcinomas and sarcomas. Exemplary cancers that may be treated with a compound, pharmaceutical composition, or method provided herein include multiple myeloma, blood cancers, lymphoma, sarcoma, bladder cancer, bone cancer, brain tumor, cervical cancer, colon cancer, esophageal cancer, gastric cancer, head and neck cancer, kidney cancer, myeloma, thyroid cancer, leukemia, prostate cancer, breast cancer (e.g. ER positive, ER negative, chemotherapy resistant, herceptin resistant, HER2 positive, doxorubicin resistant, tamoxifen resistant, ductal carcinoma, lobular carcinoma, primary, metastatic), ovarian cancer, pancreatic cancer, liver cancer (e.g. hepatocellular carcinoma), lung cancer (e.g. non-small cell lung carcinoma, squamous cell lung carcinoma, adenocarcinoma, large cell lung carcinoma, small cell lung carcinoma, carcinoid, sarcoma), glioblastoma multiforme, glioma, or melanoma. Additional examples include, cancer of the thyroid, endocrine system, brain, breast, cervix, colon, head & neck, liver, kidney, lung, non-small cell lung, melanoma, mesothelioma, ovary, sarcoma, stomach, uterus or Medulloblastoma, Hodgkin's Disease, Non-Hodgkin's Lymphoma, multiple myeloma, neuroblastoma, glioma, glioblastoma multiforme, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, Paget's Disease of the Nipple, Phyllodes Tumors, Lobular Carcinoma, Ductal Carcinoma, cancer of the pancreatic stellate cells, cancer of the hepatic stellate cells, or prostate cancer.

As used herein, a "symptom" associated with cancer includes any clinical or laboratory manifestation associated with the cancer and is not limited to what the subject can feel or observe.

As used herein, "treating", e.g. of a cancer, encompasses inducing prevention, inhibition, regression, or stasis of the disease or a symptom or condition associated with the cancer.

The contents of International Application Publication No. WO/2018/194885, published Oct. 25, 2018, are hereby incorporated by reference.

If a chiral center or another form of an isomeric center is present in a compound of the present invention, all forms of such isomer or isomers, including racemates, enantiomers and diastereomers, are intended to be covered herein. Compounds containing a chiral center may be used as a racemic mixture, an enantiomerically enriched mixture, or the racemic mixture may be separated using well-known techniques and an individual enantiomer may be used alone. The compoundsdescribed in the present invention are in racemic form or as individual enantiomers. The enantiomers can be separated using known techniques, such as those described in Pure and Applied Chemistry 69, 1469-1474, (1997) IUPAC. In cases in which compounds have unsaturated carbon-carbon double bonds, both the cis (Z) and trans (E) isomers are within the scope of this invention.

The compounds of the present invention may have spontaneous tautomeric forms. In cases wherein compounds may exist in tautomeric forms, such as keto-enol tautomers, each tautomeric form is contemplated as being included within this invention whether existing in equilibrium or predominantly in one form.

In the compound structures depicted herein, hydrogen atoms are not shown for carbon atoms having less than four bonds to non-hydrogen atoms. However, it is understood that enough hydrogen atoms exist on said carbon atoms to satisfy the octet rule.

This invention also provides isotopic variants of the compounds disclosed herein, including wherein the isotopic atom is 2H, 3H, 13C, 14C, 15N, and/or 18O. Accordingly, in the compounds provided herein hydrogen can be enriched in the deuterium isotope. It is to be understood that the invention encompasses all such isotopic forms.

In an alternative embodiment, compoundsdescribed herein may also comprise one or more isotopic substitutions. For example, hydrogen may be 2H (D or deuterium) or 3H (T or tritium); carbon may be, for example, 13C or 14C; oxygen may be, for example, 18O; nitrogen may be, for example, 15N, and the like. In other embodiments, a particular isotope (e.g., 3H, 13C, 14C, 18O, or 15N) can represent at least 1%, at least 5%, at least 10%, at least 15%, at least 20%, at least 25%, at least 30%, at least 35%, at least 40%, at least 45%, at least 50%, at least 60%, at least 65%, at least 70%, at least 75%, at least 80%, at least 85%, at least 90%, at least 95%, at least 99%, or at least 99.9% of the total isotopic abundance of an element that occupies a specific site of the compound.

It is understood that the structures described in the embodiments of the methods hereinabove can be the same as the structures of the compounds described hereinabove.

It is understood that where a numerical range is recited herein, the present invention contemplates each integer between, and including, the upper and lower limits, unless otherwise stated.

Except where otherwise specified, if the structure of a compound of this invention includes an asymmetric carbon atom, it is understood that the compound occurs as a racemate, racemic mixture, and isolated single enantiomer. All such isomeric forms of these compounds are expressly included in this invention. Except where otherwise specified, each stereogenic carbon may be of the R or S configuration. It is to be understood accordingly that the isomers arising from such asymmetry (e.g., all enantiomers and diastereomers) are included within the scope of this invention, unless indicated otherwise. Such isomers can be obtained in substantially pure form by classical separation techniques and by stereochemically controlled synthesis, such as those described in "Enantiomers, Racemates and Resolutions" by J. Jacques, A. Collet and S. Wilen, Pub. John Wiley & Sons, NY, 1981. For example, the resolution may be carried out by preparative chromatography on a chiral column.

The subject invention is also intended to include all isotopes of atoms occurring on the compounds disclosed herein. Isotopes include those atoms having the same atomic number but different mass numbers. By way of general example and without limitation, isotopes of hydrogen include tritium and deuterium. Isotopes of carbon include C-13 and C-14.

It will be noted that any notation of a carbon in structures throughout this application, when used without further notation, are intended to represent all isotopes of carbon, such as 12C, 13C, or 14C. Furthermore, any compounds containing 13C or 14C may specifically have the structure of any of the compounds disclosed herein.

It will also be noted that any notation of a hydrogen in structures throughout this application, when used without further notation, are intended to represent all isotopes of hydrogen, such as 1H, 2H, or 3H. Furthermore, any compounds containing 2H or 3H may specifically have the structure of any of the compounds disclosed herein.

Isotopically-labeled compounds can generally be prepared by conventional techniques known to those skilled in the art using appropriate isotopically-labeled reagents in place of the non-labeled reagents employed.

In the compounds used in the method of the present invention, the substituents may be substituted or unsubstituted, unless specifically defined otherwise.

In the compounds used in the method of the present invention, alkyl, heteroalkyl, monocycle, bicycle, aryl, heteroaryl and heterocycle groups can be further substituted by replacing one or more hydrogen atoms with alternative non-hydrogen groups. These include, but are not limited to, halo, hydroxy, mercapto, amino, carboxy, cyano, carbamoyl and aminocarbonyl and aminothiocarbonyl.

It is understood that substituents and substitution patterns on the compounds used in the method of the present invention can be selected by one of ordinary skill in the art to provide compounds that are chemically stable and that can be readily synthesized by techniques known in the art from readily available starting materials. If a substituent is itself substituted with more than one group, it is understood that these multiple groups may be on the same carbon or on different carbons, so long as a stable structure result.

In choosing the compounds used in the method of the present invention, one of ordinary skill in the art will recognize that the various substituents, i.e. R1, R2, etc. are to be chosen in conformity with well-known principles of chemical structure connectivity.

As used herein, "C0-4alkyl" for example is used to mean an alkyl having 0-4 carbons—that is, 0, 1, 2, 3, or 4 carbons in a straight or branched configuration. An alkyl having no carbon is hydrogen when the alkyl is a terminal group. An alkyl having no carbon is a direct bond when the alkyl is a bridging (connecting) group.

As used herein, "alkyl" is intended to include both branched and straight-chain saturated aliphatic hydrocarbon groups having the specified number of carbon atoms. Thus, C1-Cn as in "C1-Cn alkyl" is defined to include groups having 1, 2, . . . , n–1 or n carbons in a linear or branched arrangement, and specifically includes methyl, ethyl, propyl, butyl, pentyl, hexyl, heptyl, isopropyl, isobutyl, sec-butyl and so on. An embodiment can be C1-C12 alkyl, C2-C12 alkyl, C3-C12 alkyl, C4-C12 alkyl and so on.

"Alkoxy" or "Alkoxyl" represents an alkyl group as described above attached through an oxygen bridge. Thus, an alkoxy group is represented by C0-nalkyl-O—C0-malkyl in which oxygen is a bridge between 0, 1, 2, n–1, m–1, n or m carbons in a linear or branched arrangement. When n is zero, "—O—C0-malkyl" is attached directly to the preceding moiety. When m is zero, the alkoxy group is "C0-nalkyl-OH." Examples of alkoxy groups include methoxy, ethoxy, isopropoxy, tert-butoxy and so on.

The term "alkenyl" refers to a non-aromatic hydrocarbon radical, straight or branched, containing at least 1 carbon to carbon double bond, and up to the maximum possible number of non-aromatic carbon-carbon double bonds may be present. Thus, C2-Cn alkenyl is defined to include groups having 1, 2 . . . , n–1 or n carbons. For example, "C2-C6 alkenyl" means an alkenyl radical having 2, 3, 4, 5, or 6 carbon atoms, and at least 1 carbon-carbon double bond, and up to, for example, 3 carbon-carbon double bonds in the case of a C6 alkenyl, respectively. Alkenyl groups include ethenyl, propenyl, butenyl and cyclohexenyl. As described above with respect to alkyl, the straight, branched or cyclic portion of the alkenyl group may contain double bonds and may be substituted if a substituted alkenyl group is indicated. An embodiment can be C2-C12 alkenyl, C3-C12 alkenyl, C4-C12 alkenyl and so on.

The term "alkynyl" refers to a hydrocarbon radical straight or branched, containing at least 1 carbon to carbon triple bond, and up to the maximum possible number of non-aromatic carbon-carbon triple bonds may be present. Thus, C2-Cn alkynyl is defined to include groups having 1, 2 . . . , n–1 or n carbons. For example, "C2-C6 alkynyl" means an alkynyl radical having 2 or 3 carbon atoms, and 1 carbon-carbon triple bond, or having 4 or 5 carbon atoms, and up to 2 carbon-carbon triple bonds, or having 6 carbon atoms, and up to 3 carbon-carbon triple bonds. Alkynyl groups include ethynyl, propynyl and butynyl. As described above with respect to alkyl, the straight or branched portion of the alkynyl group may contain triple bonds and may be substituted if a substituted alkynyl group is indicated. An embodiment can be a C2-Cn alkynyl. An embodiment can be C2-C12 alkynyl, C3-C12 alkynyl, C4-C12 alkynyl and so on.

"Alkylene", "alkenylene" and "alkynylene" shall mean, respectively, a divalent alkane, alkene and alkyne radical, respectively. It is understood that an alkylene, alkenylene, and alkynylene may be straight or branched. An alkylene, alkenylene, and alkynylene may be unsubstituted or substituted.

As used herein, "heteroalkyl" includes both branched and straight-chain saturated aliphatic hydrocarbon groups having the specified number of carbon atoms and at least 1 heteroatom within the chain or branch.

As used herein, "heterocycle" or "heterocyclyl" as used herein is intended to mean a 5- to 10-membered nonaromatic ring containing from 1 to 4 heteroatoms selected from the group consisting of O, N and S, and includes bicyclic groups. "Heterocyclyl" therefore includes, but is not limited to the following: imidazolyl, piperazinyl, piperidinyl, pyrrolidinyl, morpholinyl, thiomorpholinyl, tetrahydropyranyl, dihydropiperidinyl, tetrahydrothiophenyl and the like. If the heterocycle contains a nitrogen, it is understood that the corresponding N-oxides thereof are also encompassed by this definition.

As herein, "cycloalkyl" shall mean cyclic rings of alkanes of three to eight total carbon atoms, or any number within this range (i.e., cyclopropyl, cyclobutyl, cyclopentyl, cyclohexyl, cycloheptyl or cyclooctyl).

As used herein, "monocycle" includes any stable polyatomic carbon ring of up to 12 atoms and may be unsubstituted or substituted. Examples of such non-aromatic monocycle elements include but are not limited to: cyclobutyl, cyclopentyl, cyclohexyl, and cycloheptyl. Examples of such aromatic monocycle elements include but are not limited to: phenyl.

As used herein, "bicycle" includes any stable polyatomic carbon ring of up to 12 atoms that is fused to a polyatomic carbon ring of up to 12 atoms with each ring being independently unsubstituted or substituted. Examples of such non-aromatic bicycle elements include but are not limited to: decahydronaphthalene. Examples of such aromatic bicycle elements include but are not limited to: naphthalene.

As used herein, "aryl" is intended to mean any stable monocyclic, bicyclic or polycyclic carbon ring of up to 12 atoms in each ring, wherein at least one ring is aromatic, and may be unsubstituted or substituted. Examples of such aryl elements include phenyl, p-toluenyl (4-methylphenyl), naphthyl, tetrahydro-naphthyl, indanyl, biphenyl, phenanthryl, anthryl or acenaphthyl. In cases where the aryl substituent is bicyclic and one ring is non-aromatic, it is understood that attachment is via the aromatic ring.

As used herein, the term "polycyclic" refers to unsaturated or partially unsaturated multiple fused ring structures, which may be unsubstituted or substituted.

The term "arylalkyl" refers to alkyl groups as described above wherein one or more bonds to hydrogen contained therein are replaced by a bond to an aryl group as described above. It is understood that an "arylalkyl" group is connected to a core molecule through a bond from the alkyl group and that the aryl group acts as a substituent on the alkyl group.

Examples of arylalkyl moieties include, but are not limited to, benzyl (phenylmethyl), p-trifluoromethylbenzyl (4-trifluoromethylphenylmethyl), 1-phenylethyl, 2-phenylethyl, 3-phenylpropyl, 2-phenylpropyl and the like.

The term "heteroaryl", as used herein, represents a stable monocyclic, bicyclic or polycyclic ring of up to 12 atoms in each ring, wherein at least one ring is aromatic and contains from 1 to 4 heteroatoms selected from the group consisting of O, N and S. Bicyclic aromatic heteroaryl groups include phenyl, pyridine, pyrimidine or pyridazine rings that are (a) fused to a 6-membered aromatic (unsaturated) heterocyclic ring having one nitrogen atom; (b) fused to a 5- or 6-membered aromatic (unsaturated) heterocyclic ring having two nitrogen atoms; (c) fused to a 5-membered aromatic (unsaturated) heterocyclic ring having one nitrogen atom together with either one oxygen or one sulfur atom; or (d) fused to a 5-membered aromatic (unsaturated) heterocyclic ring having one heteroatom selected from O, N or S. Heteroaryl groups within the scope of this definition include but are not limited to: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrazolyl, tetrazolopyridyl, thiadiazolyl, thiazolyl, thienyl, triazolyl, azetidinyl, aziridinyl, 1,4-dioxanyl, hexahydroazepinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, tetrahydrothienyl, acridinyl, carbazolyl, cinnolinyl, quinoxalinyl, pyrrazolyl, indolyl, benzotriazolyl, benzothiazolyl, benzoxazolyl, isoxazolyl, isothiazolyl, furanyl, thienyl, benzothienyl, benzofuranyl, quinolinyl, isoquinolinyl, oxazolyl, isoxazolyl, indolyl, pyrazinyl, pyridazinyl, pyridinyl, pyrimidinyl, pyrrolyl, tetra-hydroquinoline. In cases where the heteroaryl substituent is bicyclic and one ring is non-aromatic or contains no heteroatoms, it is understood that attachment is via the aromatic ring or via the heteroatom containing ring, respectively. If the heteroaryl contains nitrogen atoms, it is understood that the corresponding N-oxides thereof are also encompassed by this definition.

The term "alkylheteroaryl" refers to alkyl groups as described above wherein one or more bonds to hydrogen contained therein are replaced by a bond to an heteroaryl group as described above. It is understood that an "alkylheteroaryl" group is connected to a core molecule through a bond from the alkyl group and that the heteroaryl group acts as a substituent on the alkyl group. Examples of alkylheteroaryl moieties include, but are not limited to, —CH2-(C5H4N), —CH2-CH2-(C5H4N) and the like.

The term "heterocycle" or "heterocyclyl" refers to a mono- or poly-cyclic ring system which can be saturated or contains one or more degrees of unsaturation and contains one or more heteroatoms. Preferred heteroatoms include N, O, and/or S, including N-oxides, sulfur oxides, and dioxides. Preferably the ring is three to ten-membered and is either saturated or has one or more degrees of unsaturation. The heterocycle may be unsubstituted or substituted, with multiple degrees of substitution being allowed. Such rings may be optionally fused to one or more of another "heterocyclic" ring(s), heteroaryl ring(s), aryl ring(s), or cycloalkyl ring(s). Examples of heterocycles include, but are not limited to, tetrahydrofuran, pyran, 1,4-dioxane, 1,3-dioxane, piperidine, piperazine, pyrrolidine, morpholine, thiomorpholine, tetrahydrothiopyran, tetrahydrothiophene, 1,3-oxathiolane, and the like.

The alkyl, alkenyl, alkynyl, aryl, heteroaryl and heterocyclyl substituents may be substituted or unsubstituted, unless specifically defined otherwise. In the compounds of the present invention, alkyl, alkenyl, alkynyl, aryl, heterocyclyl and heteroaryl groups can be further substituted by replacing one or more hydrogen atoms with alternative non-hydrogen groups. These include, but are not limited to, halo, hydroxy, mercapto, amino, carboxy, cyano and carbamoyl.

As used herein, the term "halogen" or "halo" refers to F, Cl, Br, and I.

As used herein, the term "carbonyl" refers to a carbon atom double bonded to oxygen. A carbonyl group is denoted as RxC(O)Ry where Rx and Ry are bonded to the carbonyl carbon atom.

The terms "substitution", "substituted" and "substituent" refer to a functional group as described above in which one or more bonds to a hydrogen atom contained therein are replaced by a bond to non-hydrogen or non-carbon atoms, provided that normal valencies are maintained and that the substitution results in a stable compound. Substituted groups also include groups in which one or more bonds to a carbon(s) or hydrogen(s) atom are replaced by one or more bonds, including double or triple bonds, to a heteroatom. Examples of substituent groups include the functional groups described above, and halogens (i.e., F, Cl, Br, and I); alkyl groups, such as methyl, ethyl, n-propyl, isopropryl, n-butyl, tert-butyl, and trifluoromethyl; hydroxyl; alkoxy groups, such as methoxy, ethoxy, n-propoxy, and isopropoxy; aryloxy groups, such as phenoxy; arylalkyloxy, such as benzyloxy (phenylmethoxy) and p-trifluoromethyl-benzyloxy (4-trifluoromethylphenylmethoxy); heteroaryloxy groups; sulfonyl groups, such as trifluoromethanesulfonyl, methanesulfonyl, and p-toluenesulfonyl; nitro, nitrosyl; mercapto; sulfanyl groups, such as methyl sulfanyl, ethylsulfanyl and propylsulfanyl; cyano; amino groups, such as amino, methylamino, dimethylamino, ethyl amino, and diethylamino; and carboxyl. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure result.

In choosing the compounds of the present invention, one of ordinary skill in the art will recognize that the various substituents, i.e. R1, R2, etc. are to be chosen in conformity with well-known principles of chemical structure connectivity.

The various R groups attached to the aromatic rings of the compounds disclosed herein may be added to the rings by standard procedures, for example those set forth in Advanced Organic Chemistry: Part B: Reaction and Synthesis, Francis Carey and Richard Sundberg, (Springer) 5th ed. Edition. (2007), the content of which is hereby incorporated by reference.

The compounds used in the method of the present invention may be prepared by techniques well known in organic synthesis and familiar to a practitioner ordinarily skilled in the art. However, these may not be the only methods by which to synthesize or obtain the desired compounds.

The compounds used in the method of the present invention may be prepared by techniques described in Vogel's Textbook of Practical Organic Chemistry, A. I. Vogel, A. R. Tatchell, B. S. Furnis, A. J. Hannaford, P. W. G. Smith, (Prentice Hall) 5th Edition (1996), March's Advanced Organic Chemistry: Reactions, Mechanisms, and Structure, Michael B. Smith, Jerry March, (Wiley-Interscience) 5th Edition (2007), and references therein, which are incorporated by reference herein. However, these may not be the only methods by which to synthesize or obtain the desired compounds.

Another aspect of the invention comprises a compound used in the method of the present invention as a pharmaceutical composition.

In some embodiments, a pharmaceutical composition comprises the compound of the present invention and a pharmaceutically acceptable carrier.

As used herein, the term "pharmaceutically active agent" means any substance or compound suitable for administration to a subject and furnishes biological activity or other direct effect in the treatment, cure, mitigation, diagnosis, or prevention of disease, or affects the structure or any function of the subject. Pharmaceutically active agents include, but are not limited to, substances and compoundsdescribed in the Physicians' desk Reference (PDR Network, LLC; 64th edition; Nov. 15, 2009) and "Approved Drug Products with Therapeutic Equivalence Evaluations" (U.S. Department Of Health And Human Services, 30th edition, 2010), which are hereby incorporated by reference. Pharmaceutically active agents which have pendant carboxylic acid groups may be modified in accordance with the present invention using standard esterification reactions and methods readily available and known to those having ordinary skill in the art of chemical synthesis. Where a pharmaceutically active agent does not possess a carboxylic acid group, the ordinarily skilled artisan will be able to design and incorporate a carboxylic acid group into the pharmaceutically active agent where esterification may subsequently be carried out so long as the modification does not interfere with the pharmaceutically active agent's biological activity or effect.

The compounds used in the method of the present invention may be in a salt form. As used herein, a "salt" is a salt of the instant compounds which has been modified by making acid or base salts of the compounds. Examples of pharmaceutically acceptable salts include, but are not limited to, mineral or organic acid salts of basic residues such as amines; alkali or organic salts of acidic residues such as phenols. The salts can be made using an organic or inorganic acid. Such acid salts are chlorides, bromides, sulfates, nitrates, phosphates, sulfonates, formates, tartrates, maleates, malates, citrates, benzoates, salicylates, ascorbates, and the like. Phenolate salts are the alkaline earth metal salts, sodium, potassium or lithium. The term "pharmaceutically acceptable salt" in this respect, refers to the relatively non-toxic, inorganic and organic acid or base addition salts of compounds of the present invention. These salts can be prepared in situ during the final isolation and purification of the compounds of the invention, or by separately reacting a purified compound of the invention in its free base or free acid form with a suitable organic or inorganic acid or base, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, e.g., Berge et al. (1977) "Pharmaceutical Salts", J. Pharm. Sci. 66:1-19).

The compounds of the present invention may also form salts with basic amino acids such a lysine, arginine, etc. and with basic sugars such as N-methylglucamine, 2-amino-2-deoxyglucose, etc. and any other physiologically non-toxic basic substance.

As used herein, "administering" an agent may be performed using any of the various methods or delivery systems well known to those skilled in the art. The administering can be performed, for example, orally, parenterally, intraperitoneally, intravenously, intraarterially, transdermally, sublingually, intramuscularly, rectally, transbuccally, intranasally, liposomally, via inhalation, vaginally, intraoccularly, via local delivery, subcutaneously, intraadiposally, intraarticularly, intrathecally, into a cerebral ventricle, intraventicularly, intratumorally, into cerebral parenchyma or intraparenchchymally.

The compounds used in the method of the present invention may be administered in various forms, including those detailed herein. The treatment with the compound may be a component of a combination therapy or an adjunct therapy, i.e. the subject or patient in need of the drug is treated or given another drug for the disease in conjunction with one or more of the instant compounds. This combination therapy can be sequential therapy where the patient is treated first with one drug and then the other or the two drugs are given simultaneously. These can be administered independently by the same route or by two or more different routes of administration depending on the dosage forms employed.

As used herein, a "pharmaceutically acceptable carrier" is a pharmaceutically acceptable solvent, suspending agent or vehicle, for delivering the instant compounds to the animal or human. The carrier may be liquid or solid and is selected with the planned manner of administration in mind. Liposomes are also a pharmaceutically acceptable carrier as are slow-release vehicles.

The dosage of the compounds administered in treatment will vary depending upon factors such as the pharmacodynamic characteristics of a specific chemotherapeutic agent and its mode and route of administration; the age, sex, metabolic rate, absorptive efficiency, health and weight of the recipient; the nature and extent of the symptoms; the kind of concurrent treatment being administered; the frequency of treatment with; and the desired therapeutic effect.

A dosage unit of the compounds used in the method of the present invention may comprise a single compound or mixtures thereof with additional antitumor agents. The compounds can be administered in oral dosage forms as tablets, capsules, pills, powders, granules, elixirs, tinctures, suspensions, syrups, and emulsions. The compounds may also be administered in intravenous (bolus or infusion), intraperitoneal, subcutaneous, or intramuscular form, or introduced directly, e.g. by injection, topical application, or other methods, into or topically onto a site of disease or lesion, all using dosage forms well known to those of ordinary skill in the pharmaceutical arts.

The compounds used in the method of the present invention can be administered in admixture with suitable pharmaceutical diluents, extenders, excipients, or in carriers such as the novel programmable sustained-release multi-compartmental nanospheres (collectively referred to herein as a pharmaceutically acceptable carrier) suitably selected with respect to the intended form of administration and as consistent with conventional pharmaceutical practices. The unit will be in a form suitable for oral, nasal, rectal, topical, intravenous or direct injection or parenteral administration. The compounds can be administered alone or mixed with a pharmaceutically acceptable carrier. This carrier can be a solid or liquid, and the type of carrier is generally chosen based on the type of administration being used. The active agent can be co-administered in the form of a tablet or capsule, liposome, as an agglomerated powder or in a liquid form. Capsule or tablets can be easily formulated and can be made easy to swallow or chew; other solid forms include granules, and bulk powders. Tablets may contain suitable binders, lubricants, diluents, disintegrating agents, coloring agents, flavoring agents, flow-inducing agents, and melting agents. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents. Oral dosage forms optionally contain flavorants and coloring agents. Parenteral and intravenous forms may also include minerals and other materials to make them compatible with the type of injection or delivery system chosen.

Techniques and compositions for making dosage forms useful in the present invention are described in the following references: 7 Modern Pharmaceutics, Chapters 9 and 10 (Banker & Rhodes, Editors, 1979); Pharmaceutical Dosage Forms: Tablets (Lieberman et al., 1981); Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol. 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications: Drugs and the Pharmaceutical Sciences, Vol 61 (Alain Rolland, Ed., 1993); Drug delivery to the Gastrointestinal Tract (Ellis Horwood Books in the Biological Sciences. Series in Pharmaceutical Technology; J. G. Hardy, S. S. Davis, Clive G. Wilson, Eds.); Modem Pharmaceutics Drugs and the Pharmaceutical Sciences, Vol 40 (Gilbert S. Banker, Christopher T. Rhodes, Eds.). All of the aforementioned publications are incorporated by reference herein.

For instance, for oral administration in the dosage unit form of a tablet or capsule, the active drug component can be combined with an oral, non-toxic, pharmaceutically acceptable, inert carrier.

The compounds used in the method of the present invention may also be administered in the form of liposome delivery systems, such as small unilamellar vesicles, large unilamellar vesicles, and multilamellar vesicles.

The compounds used in the method of the present invention may also be coupled to soluble polymers as targetable drug carriers or as a prodrug. Furthermore, the compounds may be coupled to a class of biodegradable polymers useful in achieving controlled release of a drug.

Gelatin capsules may contain the active ingredient compounds and powdered carriers/diluents. Similar diluents can be used to make compressed tablets. Both tablets and capsules can be manufactured as immediate release products or as sustained release products to provide for continuous release of medication over a period of hours. Compressed tablets can be sugar-coated or film-coated to mask any unpleasant taste and protect the tablet from the atmosphere, or enteric coated for selective disintegration in the gastrointestinal tract.

For oral administration in liquid dosage form, the oral drug components can be combined with any oral, non-toxic, pharmaceutically acceptable inert carrier. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents.

Liquid dosage forms for oral administration can contain coloring and flavoring to increase patient acceptance. Solutions for parenteral administration preferably contain a water-soluble salt of the active ingredient, suitable stabilizing agents, and if necessary, buffer substances. In addition, parenteral solutions can contain preservatives. Suitable pharmaceutical carriers are described in Remington's Pharmaceutical Sciences, Mack Publishing Company, a standard reference text in this field.

The compounds used in the method of the present invention may also be administered in intranasal form via use of suitable intranasal vehicles, or via transdermal routes, using those forms of transdermal skin patches well known to those of ordinary skill in that art. To be administered in the form of a transdermal delivery system, the dosage administration will generally be continuous rather than intermittent throughout the dosage regimen.

Parenteral and intravenous forms may also include minerals and other materials such as solutol and/or ethanol to make them compatible with the type of injection or delivery system chosen.

The compounds and compositions of the present invention can be administered in oral dosage forms as tablets, capsules, pills, powders, granules, elixirs, tinctures, suspensions, syrups, and emulsions. The compounds may also be administered in intravenous (bolus or infusion), intraperitoneal, subcutaneous, or intramuscular form, or introduced directly, e.g. by topical administration, injection or other methods, to the afflicted area, such as a wound, including ulcers of the skin, all using dosage forms well known to those of ordinary skill in the pharmaceutical arts.

Specific examples of pharmaceutically acceptable carriers and excipients that may be used to formulate oral dosage forms of the present invention are described in U.S. Pat. No. 3,903,297 to Robert, issued Sep. 2, 1975. Techniques and compositions for making dosage forms useful in the present invention are described-in the following references: 7 Modern Pharmaceutics, Chapters 9 and 10 (Banker & Rhodes, Editors, 1979); Pharmaceutical Dosage Forms: Tablets (Lieberman et al., 1981); Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications: Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modern Pharmaceutics Drugs and the Pharmaceutical Sciences, Vol 40 (Gilbert S. Banker, Christopher T. Rhodes, Eds.). All of the aforementioned publications are incorporated by reference herein.

The active ingredient can be administered orally in solid dosage forms, such as capsules, tablets, powders, and chewing gum; or in liquid dosage forms, such as elixirs, syrups, and suspensions, including, but not limited to, mouthwash and toothpaste. It can also be administered parentally, in sterile liquid dosage forms.

Solid dosage forms, such as capsules and tablets, may be enteric-coated to prevent release of the active ingredient compounds before they reach the small intestine.

The compounds and compositions of the invention can be coated onto stents for temporary or permanent implantation into the cardiovascular system of a subject.

Variations on those general synthetic methods will be readily apparent to those of ordinary skill in the art and are deemed to be within the scope of the present invention.

Each embodiment disclosed herein is contemplated as being applicable to each of the other disclosed embodiments. Thus, all combinations of the various elements described herein are within the scope of the invention.

This invention will be better understood by reference to the Experimental details which follow, but those skilled in the art will readily appreciate that the specific experiments detailed are only illustrative of the invention as described more fully in the claims which follow thereafter.

Experimental Details

The following materials and methods are used to test the compounds of the present invention.

PERK In Vitro Activity Assay (isolated):

In vitro Inhibition of PERK Enzyme Activity (isolated) Recombinant human EIF2AK2 (PKR) catalytic domain (amino acids 252-551), EIF2AK3 (PERK) catalytic domain (amino acids 536-1116), GFP-eIF2a substrate, and Terbium-labelled phospho-eIF2a antibody is obtained (Invitrogen, Carlsbad, CA).

Express and purify HIS-SUMO-GCN2 catalytic domain (amino acids 584-1019) from *E. coli*. Perform TR-FRET kinase assays in the absence or presence of inhibitors in a reaction buffer consisting of 50 mM HEPES, pH 7.5, 10 mM MgCb, 1.0 mM EGTA, and 0.01% Brij-35, and 100-200 nM GFP-eIF2a substrate. PKR assays contain 14 ng/mL enzyme and 2.5 µM ATP (Km, ~2.5 µM), PERK assays contain 62.5 ng/mL enzyme and 1.5 µM ATP (Km. app ~1.5 uM), and GCN2 assays contain 3 nM enzyme and 90 µM ATP (Km, ~200 uM). Add test compound, initiate the reaction by addition of enzyme, and incubate at room temperature for 45 minutes. Stop the reaction by addition of EDTA to a final concentration of 10 mM, add Terbium-labelled phospho-eIF2a antibody at a final concentration of 2 nM, and incubate for 90 minutes. Monitor the resulting fluorescence in an EnVison® Multilabel reader (PerkinElmer, Waltham, MA). Determine TR-FRET ratios and the resulting IC50 values using a 4-parameter nonlinear logistic equation as shown: $Y=(A+((B-A)/(1+(C/x)AD))))$ where, $Y=\%$ specific inhibition, A=Bottom of the curve, B=Top of the curve, C=absolute IC50 (concentration causing 50% inhibition), and D=hill slope.

The compounds of Examples 1 to 187 were tested essentially as described above and exhibited IC50 values shown in Table 1. These data demonstrate that the compounds of Examples 1 to 187 inhibit isolated PERK enzyme activity in vitro.

PERK Cellular Assay

Stable cell lines were created in HEK293 cells using lentiviral particles harboring an expression vector for GFP-eIF2α. Cells were selected using puromycin and enriched using fluorescence activated cell sorting against GFP. HEK293-EGFP-eIF2α cells were plated at 5000 cells/well in 384-well assay plates and incubated overnight at 37° C., 5% CO2. Inhibitor compounds were added to the wells by Echo acoustic dispensing and incubated for 30 minutes at 37° C., 5% CO2 prior to induction of ER stress by addition of tunicamycin to 1 mM for 2 hours. Cells were lysed and TR-FRET was measured in an EnVision plate reader (PerkinElmer). FRET ratio data was normalized to signal from lysates treated with DMSO vehicle control and plotted as percent inhibition against 10-point; 3-fold dilution series of inhibitors. IC50 values were calculated using 4-parameter logistical fitting in XLFit.

The compounds of Examples 1 to 187 were tested essentially as described above and exhibited cellular IC50 values shown in Table 1. These data demonstrate that the compounds of Examples 1 to 187 inhibit EIF2a in vitro.

The results of exemplary compounds of formula (I) are shown in Table 1. Key: A is 0.001 to 0.025 µM; B is 0.026 to 0.050 µM; C is 0.051 to 0.100 µM; D is 0.101 to 0.250 µM; E is 0.251 to 0.500 µM; F is 0.501 to 1.00 µM; G is 1.001 µM to 2.00 µM; H is 2.001 µM to 3.00 µM; I is 3.001 to 4.00 µM; J is 4.001 to 5.00 µM, K is >5.00 µM; and N/A is "not available".

TABLE 1

Biochemical and cellular IC$_{50}$ data of Compounds of Formula 1:

| Example | Biochemical IC$_{50}$ (µM) | Cellular eIF2α IC$_{50}$ (µM) |
| --- | --- | --- |
| 1 | A | B |
| 2 | B | E |
| 3 | A | B |
| 4 | C | E |
| 5 | A | A |
| 6 | N/A | N/A |
| 7 | N/A | N/A |
| 8 | A | B |
| 9 | C | E |
| 10 | A | A |
| 11 | A | A |
| 12 | N/A | N/A |
| 13 | N/A | N/A |
| 14 | A | B |
| 15 | D | E |
| 16 | G | K |
| 17 | A | D |
| 18 | A | A |
| 19 | A | B |
| 20 | A | B |
| 21 | C | F |
| 22 | N/A | N/A |
| 23 | N/A | N/A |
| 24 | N/A | D |
| 25 | N/A | G |
| 26 | A | B |
| 27 | A | E |
| 28 | A | A |
| 29 | A | B |
| 30 | A | A |
| 31 | A | E |
| 32 | A | A |
| 33 | A | C |
| 34 | A | B |
| 35 | D | G |
| 36 | A | A |
| 37 | A | C |
| 38 | A | A |
| 39 | A | D |
| 40 | A | N/A |
| 41 | A | N/A |
| 42 | A | A |
| 43 | A | B |
| 44 | A | D |
| 45 | C | G |
| 46 | A | B |
| 47 | B | D |
| 48 | A | A |
| 49 | A | A |
| 50 | A | A |
| 51 | A | C |
| 52 | A | B |
| 53 | D | F |
| 54 | A | A |
| 55 | A | D |
| 56 | A | A |
| 57 | A | B |
| 58 | A | B |
| 59 | A | D |
| 60 | A | B |
| 61 | C | E |
| 62 | A | A |
| 63 | A | C |
| 64 | C | F |
| 65 | A | A |
| 66 | A | B |
| 67 | A | D |
| 68 | A | D |
| 69 | A | A |
| 70 | A | A |
| 71 | A | C |
| 72 | A | A |
| 73 | A | N/A |
| 74 | A | A |
| 75 | A | B |
| 76 | A | A |
| 77 | A | C |
| 78 | A | A |
| 79 | A | N/A |
| 80 | A | A |
| 81 | A | D |
| 82 | A | A |
| 83 | A | C |
| 84 | A | A |
| 85 | A | C |
| 86 | A | N/A |
| 87 | A | N/A |
| 88 | A | A |
| 89 | A | C |
| 90 | A | B |
| 91 | A | C |
| 92 | A | A |
| 93 | A | C |
| 94 | A | A |
| 95 | A | C |
| 96 | A | A |
| 97 | c | E |
| 98 | A | B |
| 99 | B | D |
| 100 | A | A |
| 101 | A | A |
| 102 | A | A |
| 103 | A | E |
| 104 | A | A |
| 105 | A | B |
| 106 | A | A |
| 107 | A | B |
| 108 | A | A |
| 109 | A | A |
| 110 | A | A |
| 111 | A | B |
| 112 | A | A |
| 113 | C | D |
| 114 | A | A |
| 115 | A | B |
| 116 | A | A |
| 117 | C | E |
| 118 | N/A | J |
| 119 | N/A | B |
| 120 | N/A | G |
| 121 | N/A | C |
| 122 | B | E |
| 123 | A | A |
| 124 | B | F |
| 125 | A | A |
| 126 | D | F |
| 127 | A | D |
| 128 | A | A |
| 129 | F | K |

TABLE 1-continued

Biochemical and cellular IC$_{50}$ data of Compounds of Formula 1:

| Example | Biochemical IC$_{50}$ (μM) | Cellular eIF2α IC$_{50}$ (μM) |
|---|---|---|
| 130 | A | A |
| 131 | F | I |
| 132 | A | A |
| 133 | A | D |
| 134 | A | A |
| 135 | D | F |
| 136 | A | A |
| 137 | A | E |
| 138 | A | A |
| 139 | A | D |
| 140 | A | A |
| 141 | C | F |
| 142 | A | A |
| 143 | E | E |
| 144 | A | C |
| 145 | A | A |
| 146 | A | A |
| 147 | B | D |
| 148 | A | A |
| 149 | F | E |
| 150 | A | B |
| 151 | C | E |
| 152 | A | A |
| 153 | B | D |
| 154 | A | A |
| 155 | A | C |
| 156 | A | A |
| 157 | A | C |
| 158 | A | A |
| 159 | C | E |
| 160 | A | A |
| 161 | A | D |
| 162 | A | A |
| 163 | E | E |
| 164 | A | A |
| 165 | B | D |
| 166 | A | A |
| 167 | B | D |
| 168 | A | E |
| 169 | A | A |
| 170 | A | D |
| 171 | G | K |
| 172 | c | F |
| 173 | A | B |
| 174 | A | B |
| 175 | A | D |
| 176 | A | C |
| 177 | D | F |
| 178 | E | J |
| 179 | A | E |
| 180 | B | F |
| 181 | A | B |
| 182 | A | D |
| 183 | E | H |
| 184 | N/A | N/A |
| 185 | N/A | N/A |
| 186 | N/A | N/A |
| 187 | N/A | N/A |

HPLC Conditions:

Method A

Column: Polaris C18-A 2.6 μm C18 (100×3.0 mm)

Mobile Phase A: Water containing 0.05% v/v Trifluoroacetic Acid

Mobile Phase B: Acetonitrile containing 0.05% v/v Trifluoroacetic Acid

Detection: 230 nm

Method A Gradient

| Time (min) | Flow (mL/min) | % A | % B |
|---|---|---|---|
| 0.0 | 0.8 | 95.0 | 5.0 |
| 3.0 | 0.8 | 95.0 | 5.0 |
| 6.0 | 0.8 | 10.0 | 90.0 |
| 12.0 | 0.8 | 10.0 | 90.0 |

Method B

Column: Eclipse plus C18 3.5 μm C18 (100×4.6 mm)

Mobile Phase A: Water containing 0.05% v/v Trifluoroacetic Acid

Mobile Phase B: Acetonitrile containing 0.05% v/v Trifluoroacetic Acid

Detection: 254 nm

Method B Gradient

| Time (min) | Flow (mL/min) | % A | % B |
|---|---|---|---|
| 0.0 | 0.8 | 95.0 | 5.0 |
| 3.0 | 0.8 | 95.0 | 5.0 |
| 6.0 | 0.8 | 10.0 | 90.0 |
| 12.0 | 0.8 | 10.0 | 90.0 |

Method C

Column: Eclipse plus C18 3.5 μm C18 (100×4.6 mm)

Mobile Phase A: Water containing 0.05% v/v Trifluoroacetic Acid

Mobile Phase B: Acetonitrile containing 0.05% v/v Trifluoroacetic Acid

Detection: 270 nm

Method C Gradient

| Time (min) | Flow (mL/min) | % A | % B |
|---|---|---|---|
| 0.0 | 0.8 | 95.0 | 5.0 |
| 3.0 | 0.8 | 95.0 | 5.0 |
| 6.0 | 0.8 | 10.0 | 90.0 |
| 12.0 | 0.8 | 10.0 | 90.0 |

Method D

Column: Luna C18(2) 5 μm C18 (150×4.6 mm)

Mobile Phase A: Water containing 0.1% v/v Trifluoroacetic Acid

Mobile Phase B: Acetonitrile containing 0.1% v/v Trifluoroacetic Acid

Detection: 254 nm

Method D Gradient

| Time (min) | Flow (mL/min) | % A | % B |
|---|---|---|---|
| 0.0 | 2.0 | 95.0 | 5.0 |
| 10.0 | 2.0 | 0.0 | 100.0 |
| 13.0 | 2.0 | 0.0 | 100.0 |
| 14.0 | 2.0 | 95.0 | 5.0 |

Analytical SFC Conditions:

Method A

Column: Chiralcel OX—H

Mobile Phase: 30% Methanol in CO$_2$

Temperature: 40° C.

Run Time: 10.0 min

Detection: 210 nm

Method B
  Column: Chiralpak IC
  Mobile Phase: 30% Methanol in $CO_2$
  Temperature: 40° C.
  Run Time: 8.0 min
  Detection: 215 nm
Method C
  Column: Chiralcel OD-H
  Mobile Phase: 25% Methanol in $CO_2$
  Temperature: 40° C.
  Run Time: 10.0 min
  Detection: 215 nm
Method D
  Column: Chiralpak IA
  Mobile Phase: 40% Methanol in $CO_2$
  Temperature: 40° C.
  Run Time: 8.0 min
  Detection: 210 nm
Method E
  Column: Chiralcel OJ-H
  Mobile Phase: 30% Methanol in $CO_2$
  Temperature: 40° C.
  Run Time: 8.0 min
  Detection: 254 nm

ABBREVIATIONS

RBF: Round bottom flask;
NMR: nuclear magnetic resonance;
mHz: megahertz;
DMSO-$d_6$: dimethyl sulfoxide-$d_6$;
$CDCl_3$: deuterated chloroform;
δ: chemical shift;
MS: mass spectrometry;
HPLC: high performance liquid chromatography;
SFC: Supercritical fluid chromatography
m/z: mass-to-charge ratio;
[M+H]: molecular ion peak in mass spectrum;
ESI: electrospray ionization;
$ESI^+$: electrospray ionization positive mode;
EST: electrospray ionization negative mode;
rt or RT: room temperature:
min: minute(s);
h: hour(s)
mg: milligram;
g: gram;
kg: kilogram;
mL: milliliter;
L: liter;
mmol: millimole;
μM: micromole;
MTBE: methyl tert-butyl ether;
THF: tetrahydrofuran;
HATU: (1-[bis(dimethylamino)methylene]-1H-1,2,3-triazolo[4,5-b]pyridinium 3-oxid hexafluorophosphate;
DIPEA or DIEA: N,N-diisopropylethylamine;
HOBt: hydroxybenzotriazole;
Pd(dppf)$Cl_2$: [1,1'-bis(diphenylphosphino)ferrocene]dichloropalladium(II);
EDC: 1-ethyl-3-(3-dimethylaminopropyl)carbodiimide;
Togni's reagent: 1-Trifluoromethyl-1,2-benziodoxol-3-(1H)-one;
T3P: Propanephosphonic acid anhydride.

Scheme A

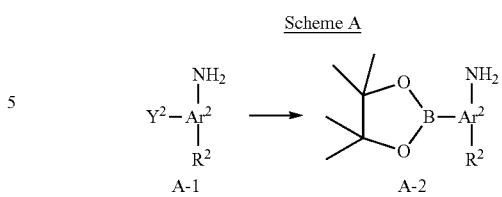

Compounds of Formula A-2 where $Ar^2$=phenyl and $R^2$=3-methyl can be synthesized as described below for compound A-2.1:

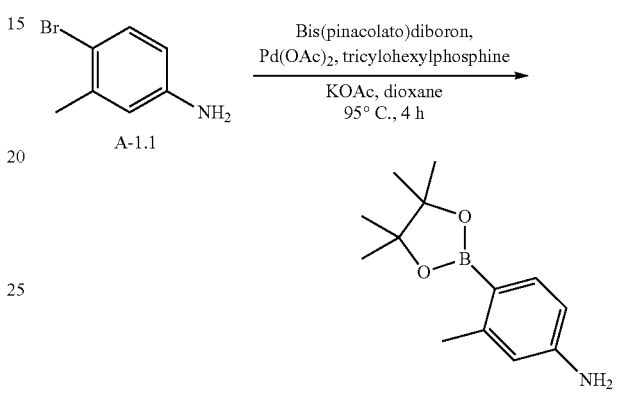

Synthesis of 3-Methyl-4-(4,4,5,5-tetramethyl-1,3,2-dioxaborolan-2-yl)aniline (A-2.1)

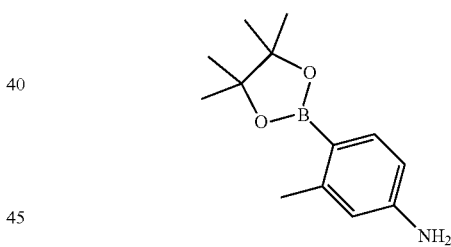

To a stirred solution of tricyclohexylphosphine (7.18 g, 25.7 mmol) in 1,4-dioxane (1.2 L) under argon atmosphere were added bis(pinacolato)diboron (89.62 g, 352.9 mmol) and potassium acetate (62.98 g, 641.7 mmol), followed by 4-bromo-3-methylaniline (A-1.1, 60.00 g, 320.8 mmol). The reaction mixture was purged with argon for 10 min. Palladium(II) acetate (5.77 g, 25.7 mmol) was added, and the mixture was purged with argon for 10 min. The reaction mixture was heated at 95° C. with stirring for 16 h. After this time, the reaction mixture was allowed to cool to room temperature, passed through a bed of diatomaceous earth, and washed with methyl text-butyl ether (4×250 mL). The filtrate was washed with water (2×500 mL) and brine (2×250 mL). The organic layer was separated, dried over anhydrous sodium sulfate and concentrated under reduced pressure. The crude product was purified by column chromatography (silica gel, 10% ethyl acetate/hexanes) to afford 3-methyl-4-(4,4,5,5-tetramethyl-1,3,2-dioxaborolan-2-yl)aniline (A-2.1, 44.80 g, yield: 60%) as a pale brown solid: ESI (m/z) 234 $[C_{13}H_{20}BNO_2+H]^+$.

The compounds of formula A-2 (Table A) can be synthesized according to the procedures described for compound A-2.1:

TABLE A

Compounds A-2:

| Compound | Name | Structure | MS |
|---|---|---|---|
| A-2.1 | 3-methyl-4-(4,4,5,5-tetramethyl-1,3,2-dioxaborolan-2-yl)aniline | 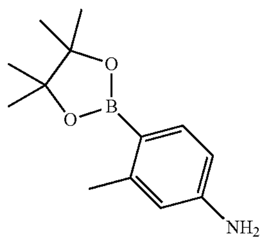 [SMILES: Cc1cc(N)ccc1B1OC(C)(C)C(C)(C)O1] | ESI (m/z) 234 [$C_{13}H_{20}BNO_2$ + H]$^+$ |
| A-2.2 | 4-(4,4,5,5-tetramethyl-1,3,2-dioxaborolan-2-yl)aniline | 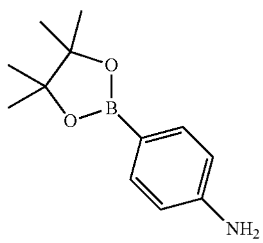 [SMILES: CC1(C)OB(c2ccc(N)cc2)OC1(C)C] | ESI (m/z) 220 [$C_{12}H_{18}BNO_2$ + H]$^+$ |
| A-2.3 | 3-fluoro-4-(4,4,5,5-tetramethyl-1,3,2-dioxaborolan-2-yl)aniline | 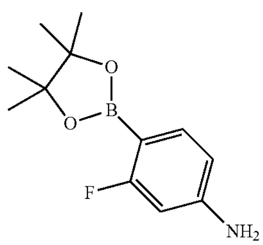 [SMILES: CC1(C)OB(c2ccc(N)cc2F)OC1(C)C] | ESI (m/z) 238 [$C_{12}H_{17}BFNO_2$ + H]$^+$ |
| A-2.4 | 3-chloro-4-(4,4,5,5-tetramethyl-1,3,2-dioxaborolan-2-yl)aniline | 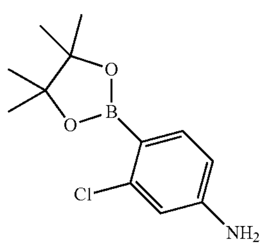 [SMILES: CC1(C)OB(c2ccc(N)cc2Cl)OC1(C)C] | ESI (m/z) 253, 255 [$C_{12}H_{17}BClNO_2$ + H]$^+$ |
| A-2.5 | 4-(4,4,5,5-tetramethyl-1,3,2-dioxaborolan-2-yl)-3-(trifluoromethoxy)aniline | 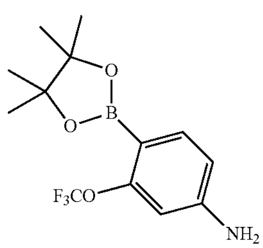 [SMILES: CC1(C)OB(c2ccc(N)cc2OC(F)(F)F)OC1(C)C] | ESI (m/z) 304 [$C_{13}H_{17}BF_3NO_3$ + H]$^+$ |
| A-2.6 | 4-(4,4,5,5-tetramethyl-1,3,2-dioxaborolan-2-yl)-3-(trifluoromethyl)aniline | 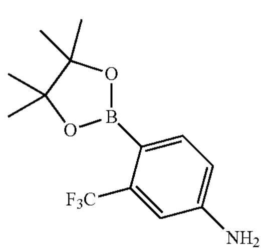 [SMILES: CC1(C)OB(c2ccc(N)cc2C(F)(F)F)OC1(C)C] | ESI (m/z) 288 [$C_{13}H_{17}BF_3NO_2$ + H]$^+$ |

TABLE A-continued

Compounds A-2:

| Compound | Name | Structure | MS |
|---|---|---|---|
| A-2.7 | 3-ethyl-4-(4,4,5,5-tetramethyl-1,3,2-dioxaborolan-2-yl)aniline | 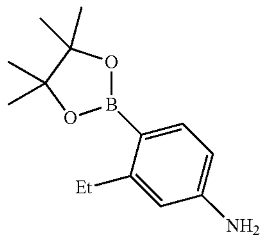 [SMILES: CCc1cc(N)ccc1B1OC(C)(C)C(C)(C)O1] | ESI (m/z) 248 [$C_{14}H_{22}BNO_2$ + H]$^+$ |
| A-2.8 | 3-methoxy-4-(4,4,5,5-tetramethyl-1,3,2-dioxaborolan-2-yl)aniline | 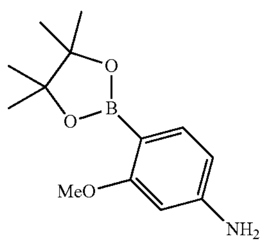 [SMILES: COc1cc(N)ccc1B1OC(C)(C)C(C)(C)O1] | ESI (m/z) 250 [$C_{13}H_{20}BNO_3$ + H]$^+$ |
| A-2.9 | 2-fluoro-3-methyl-4-(4,4,5,5-tetramethyl-1,3,2-dioxaborolan-2-yl)aniline | 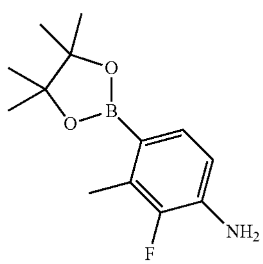 [SMILES: Cc1c(B2OC(C)(C)C(C)(C)O2)ccc(N)c1F] | ESI (m/z) 252 [$C_{13}H_{19}BFNO_2$ + H]$^+$ |

Scheme B

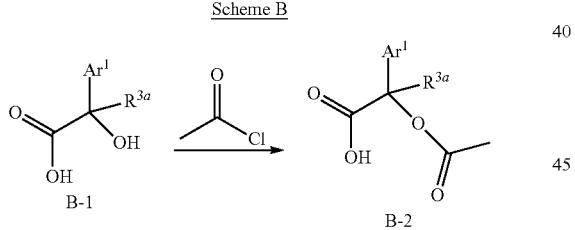

Compounds of Formula B-2 where Ar$^1$=3-chlorophenyl and R$^{3a}$=H can be synthesized as described below for compound B-1.2:

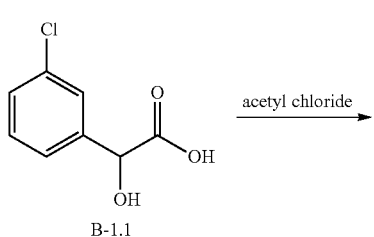

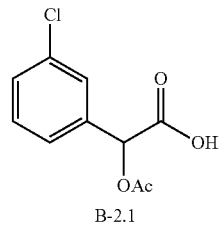

Synthesis of 2-acetoxy-2-(3-chlorophenyl)acetic acid (B-2.1)

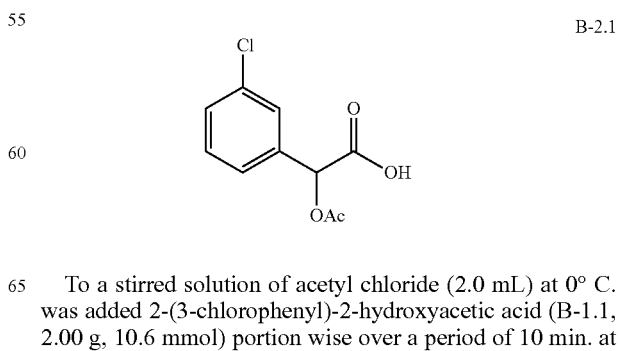

To a stirred solution of acetyl chloride (2.0 mL) at 0° C. was added 2-(3-chlorophenyl)-2-hydroxyacetic acid (B-1.1, 2.00 g, 10.6 mmol) portion wise over a period of 10 min. at same temperature. The reaction mixture was allowed to warm to room temperature and stirred for 1 h. After this time, the reaction mixture was concentrated under reduced pressure to get crude material followed by co-distilled with hexanes to afford 2-acetoxy-2-(3-chlorophenyl)acetic acid (B-2.1, 2.10 g, yield: 86%) as a white solid; $^1$H NMR (400 MHz, DMSO-$d_6$): δ 7.54-7.44 (m, 4H), 5.87 (s, 1H), 2.14 (s, 3H); ESI (m/z) 228.6 $[C_{10}H_9ClO_4+H]^+$.

The compounds of formula B-2 (Table B) can be synthesized according to the procedures described for compound B-2.1:

TABLE B

Compounds B-2:

| Compound | Name | Structure | MS |
|---|---|---|---|
| B-2.1 | 2-acetoxy-2-(3-chlorophenyl)acetic acid | 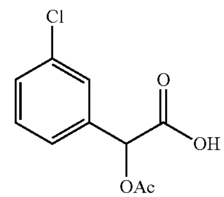 [SMILES: CC(=O)OC(C(=O)O)c1cccc(Cl)c1] | ESI (m/z) 228.6 $[C_{10}H_9ClO_4 + H]^+$ |
| B-2.2 | 2-acetoxy-2-(2-fluorophenyl)acetic acid | 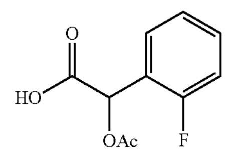 [SMILES: CC(=O)OC(C(=O)O)c1ccccc1F] | ESI (m/z) 213 $[C_{10}H_9FO_4 + H]^+$ |
| B-2.3 | 2-acetoxy-2-(3-fluorophenyl)acetic acid | 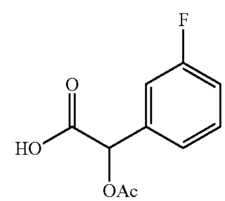 [SMILES: CC(=O)OC(C(=O)O)c1cccc(F)c1] | ESI (m/z) 213 $[C_{10}H_9FO_4 + H]^+$ |
| B-2.4 | 2-acetoxy-2-(2-chlorophenyl)acetic acid | 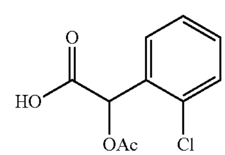 [SMILES: CC(=O)OC(C(=O)O)c1ccccc1Cl] | ESI (m/z) 229 $[C_{10}H_9ClO_4 + H]^+$ |
| B-2.5 | 2-acetoxy-2-(o-tolyl)acetic acid | 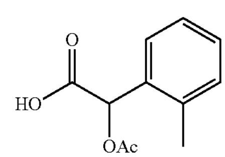 | ESI (m/z) 209 $[C_{11}H_{12}O_4 + H]^+$ |
| B-2.6 | 2-acetoxy-2-(m-tolyl)acetic acid | 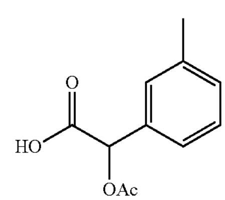 | ESI (m/z) 208.2 $[C_{11}H_{12}O_4 + H]^+$ |
| B-2.7 | 2-acetoxy-2-(2-(trifluoromethyl)phenyl)acetic acid | 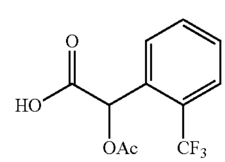 [SMILES: CC(=O)OC(C(=O)O)c1ccccc1C(F)(F)F] | ESI (m/z) 262.2 $[C_{11}H_9F_3O_4 + H]^+$ |

TABLE B-continued

Compounds B-2:

| Compound | Name | Structure | MS |
|---|---|---|---|
| B-2.8 | 2-acetoxy-2-(3-fluoro-5-methylphenyl)acetic acid | 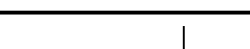 | ESI (m/z) 226.2 [$C_{11}H_{11}FO_4$ + H]$^+$ |

Scheme B1

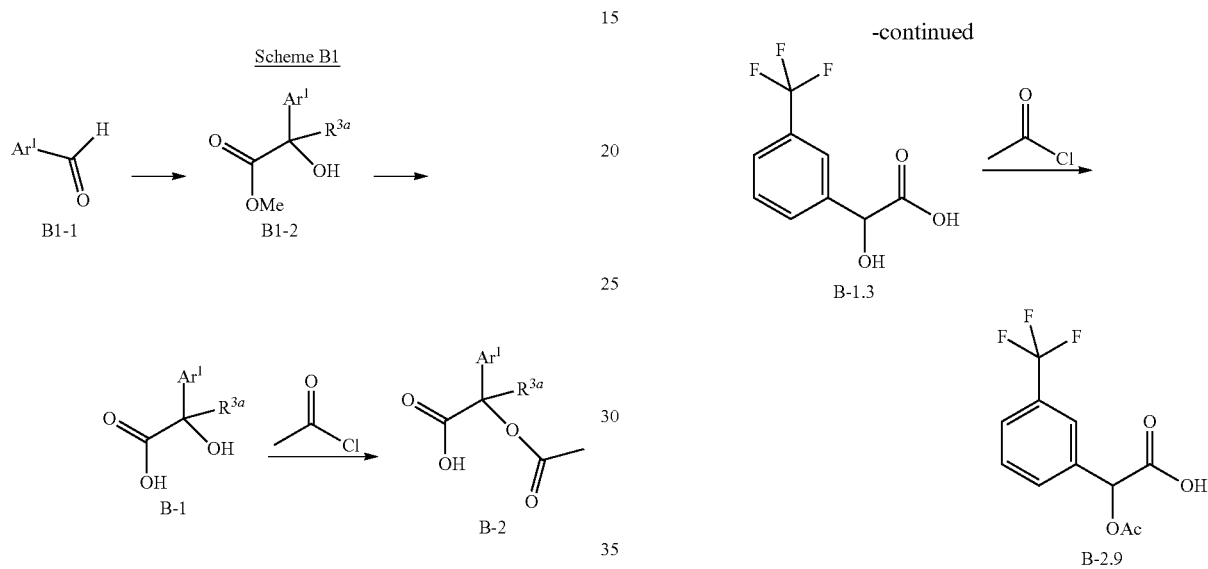

Compounds of Formula B-2 where $Ar^1$=3-trifluoromethylphenyl and $R^{3a}$=H can be synthesized as described below for compound B-2.8:

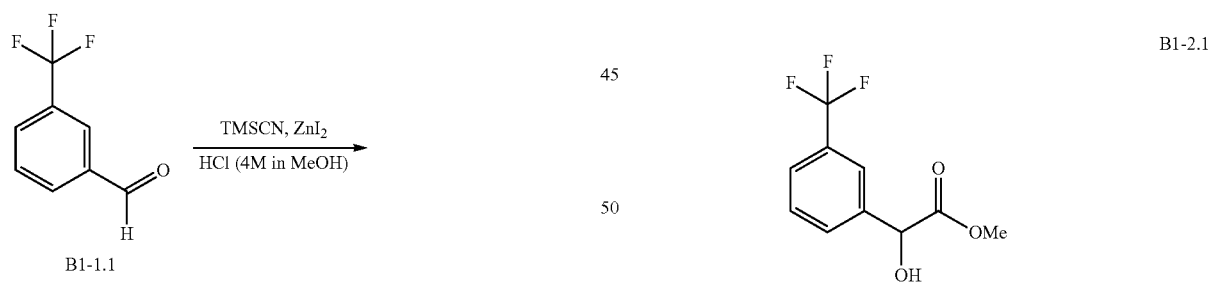

Step-1: Synthesis of methyl 2-hydroxy-2-(3-(trifluoromethyl)phenyl)acetate (B1-2.1)

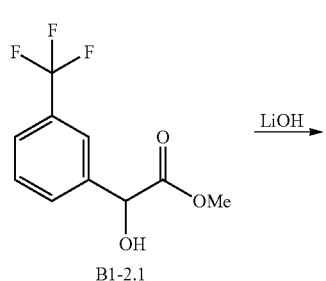

To a stirred solution of 3-(trifluoromethyl)benzaldehyde (B1-1.1, 25.00 g, 143 mmol) at 0° C. was added ZnI (4.50 g, 14.3 mmol), followed drop wise addition of trimethylsilyl cyanide (17.0 mL, 172.0 mmol) and resulting reaction mixture was stirred at 0° C. for 2 h. After this time, to the above reaction mixture HCl (4N in MeOH) (100 mL) was added at 0° C. The reaction mixture was allowed to warm to room temperature and stirred for 12 h. After this, the reaction mixture was concentrated under reduced pressure to get crude, which was quenched with saturated NaHCO$_3$ solution up to pH ~8, then added EtOAc (200 mL). The organic layer was washed with water (4×200 mL), followed by brine (200 mL). The organic layer was separated, dried over anhydrous sodium sulphate and concentrated under reduced pressure to afford methyl 2-hydroxy-2-(3-(trifluoromethyl)phenyl)acetate (B1-2.1, 28 g, yield: 83%) as a yellow liquid; ESI (m/z) 235 [$C_{10}H_9F_3O_3$+H]$^-$.

Step 2: Synthesis of 2-hydroxy-2-(3-(trifluoromethyl)phenyl)acetic acid (B-1.3)

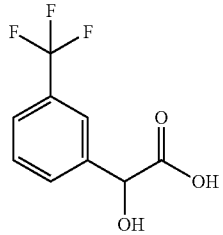

B-1.3

To a stirred solution of methyl 2-hydroxy-2-(3-(trifluoromethyl)phenyl)acetate (B1-2.1, 28 g, 119 mmol) in THF (70 mL), Water (20 mL), MeOH (50 mL), at room temperature LiOH (6.00 g, 143 mmol) was added and resulting reaction mixture was stirred for 12 h at same temperature. After this, the reaction mixture was concentrated under reduced pressure to get crude, which was quenched with water (100 mL). An aqueous layer was washed with EtOAc (200 mL) to remove impurities. Then water layer was acidified with 2N HCl (pH~2), an aqueous layer extracted with EtOAc (2×150 mL). Combined organic layers were dried over anhydrous sodium sulphate and concentrated under reduced pressure to afford 2-hydroxy-2-(3-(trifluoromethyl)phenyl)acetic acid (B-1.3, 25.00 g, yield: 95%) as a color less liquid: ESI (m/z) 219.1 [$C_9H_7F_3O_3$—H]$^-$.

Step-3: Synthesis of 2-acetoxy-2-(3-(trifluoromethyl)phenyl)acetic acid (B-2.8)

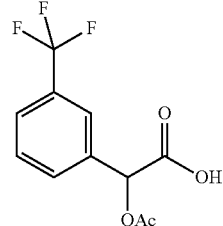 [SMILES: CC(=O)OC(C(=O)O)c1cccc(C(F)(F)F)c1]

B-2.9

To a stirred solution of acetyl chloride (50 mL) at 0° C. was added 2-hydroxy-2-(3-trifluoro methyl)phenyl)acetic acid (B-1.3, 25.00 g, 113 mmol) portion wise over a period of 30 min. at same temperature. The reaction mixture was allowed to warm to room temperature and stirred for 1 h. After this time, the reaction mixture was concentrated under reduced pressure to get crude material followed by co-distilled with hexanes to afford 2-acetoxy-2-(3-(trifluoromethyl)phenyl)acetic acid (B-2.9, 21.00 g, yield: 70%) as a white solid; $^1$H NMR (400 MHz, DMSO-$d_6$): δ 7.80 (t, J=8.0 Hz, 3H), 7.68 (t, J=8.0 Hz, 1H), 6.00 (s, 1H), 2.15 (s, 3H); ESI (m/z) 262.2 [$C_{11}H_9F_3O_4$+H]$^+$.

The compounds of formula B-2 (Table B1) can be synthesized according to the procedures described for compound B-2.9:

TABLE B1

| Compounds B-2: | | | |
|---|---|---|---|
| Compound | Name | Structure | MS |
| B-2.9 | 2-acetoxy-2-(3-(trifluoromethyl)phenyl)acetic acid | | ESI (m/z) 262.2 [$C_{11}H_9F_3O_4$ + H]$^+$ |
| B-2.10 | 2-acetoxy-2-(3-ethylphenyl)acetic acid | | ESI (m/z) 223 [$C_{12}H_{14}O_4$ + H]$^+$ |
| B-2.11 | 2-acetoxy-2-(3-fluoro-5-(trifluoromethyl)phenyl)acetic acid | | ESI (m/z) 281 [$C_{11}H_8F_4O_4$ + H]$^+$ |

TABLE B1-continued
Compounds B-2:
| Compound | Name | Structure | MS |
|---|---|---|---|
| B-2.12 | 2-acetoxy-2-(3-ethyl-5-fluorophenyl)acetic acid | 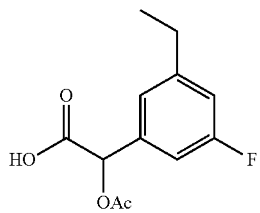 [SMILES: CCc1cc(F)cc(C(OC(C)=O)C(=O)O)c1] | ESI (m/z) 241 $[C_{12}H_{13}FO_4 + H]^+$ |
| B-2.13 | 2-acetoxy-2-(m-tolyl)acetic acid | 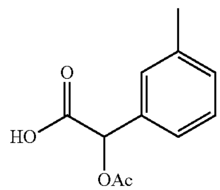 | ESI (m/z) 208.2 $[C_{11}H_{12}O_4 + H]^+$ |
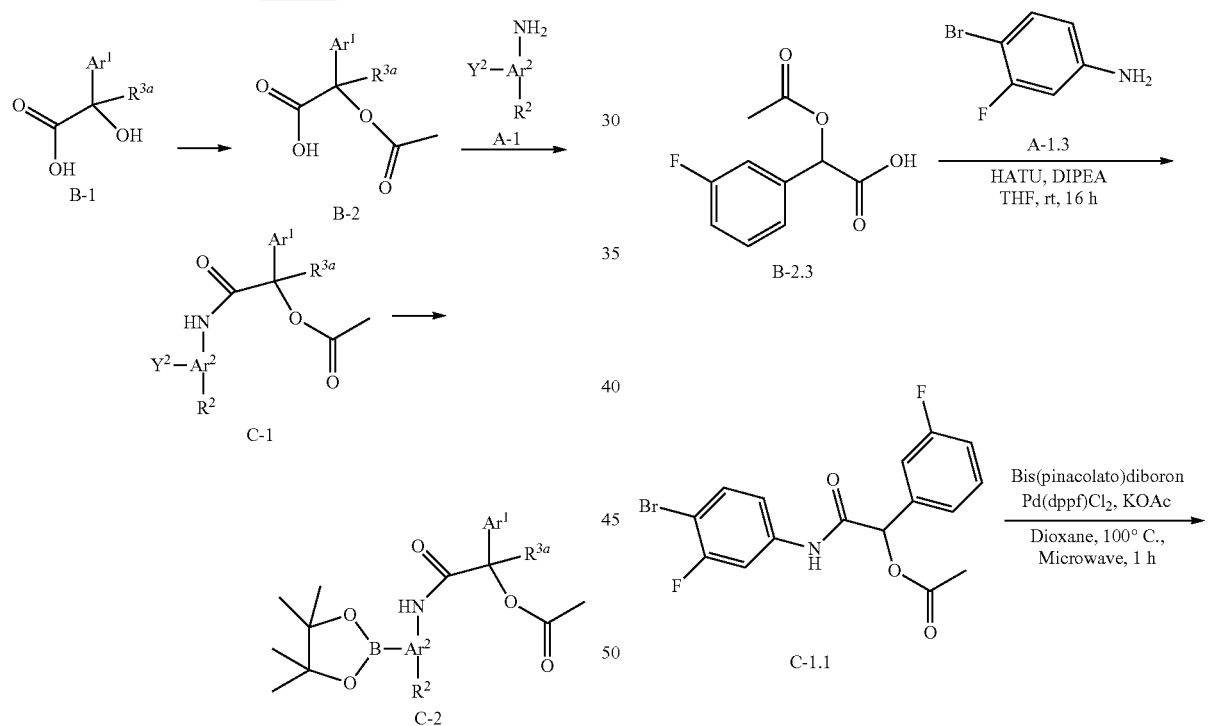
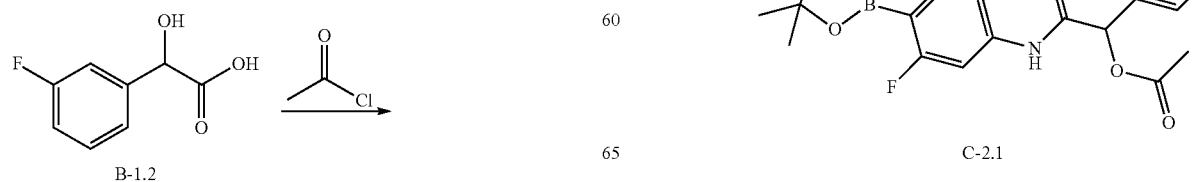
Compounds of Formula C-2 where $Ar^2$=phenyl, $R^2$=3—F, $Y^2$=Br, $R^{3a}$=H, $Ar^1$=phenyl-$R^1$ and $R^1$=3—F can be synthesized as described below for compound C-2.1:

Step-1: Synthesis of 2-acetoxy-2-(3-fluorophenyl)acetic acid (C—B-2.3)

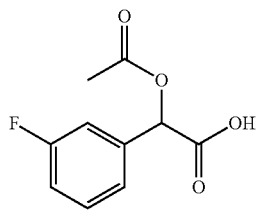

To a stirred solution of acetyl chloride (1.0 mL) at 0° C. was added 2-(3-fluorophenyl)-2-hydroxyacetic acid (B-1.2, 0.601 g, 3.53 mmol) portionwise. The reaction mixture was allowed to warm to room temperature and stirred for 1 h. After this time, the reaction mixture was concentrated to crude under vacuum and co-distilled with hexanes to afford 2-acetoxy-2-(3-fluorophenyl)acetic acid (B-2.3, 0.70 g, yield: 94%) as a white solid: ESI (m/z) 211 $[C_{10}H_9FO_4–H]^-$.

Step-2: Synthesis of 2-((4-bromo-3-fluorophenyl)amino)-1-(3-fluorophenyl)-2-oxoethyl acetate (C-1.1)

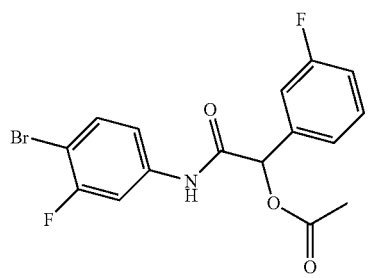 [SMILES: CC(=O)OC(C(=O)Nc1ccc(Br)c(F)c1)c1cccc(F)c1]

To a solution of 2-acetoxy-2-(3-fluorophenyl)acetic acid (B-2.3, 0.558 g, 2.63 mmol) and 4-bromo-3-fluoroaniline (A-1.3, 0.600 g, 3.16 mmol) in tetrahydrofuran (20 mL) were added N,N-diisopropylethylamine (0.90 mL, 5.3 mmol) followed by 1-[bis(dimethylamino)methylene]-1H-1,2,3-triazolo[4,5-b]pyridinium 3-oxide hexafluorophosphate (HATU) (1.50 g, 3.94 mmol) at room temperature and stirred for 16 h. After this time, the reaction mixture was diluted with dichloromethane (6.0 mL) and washed with water (4×4 mL) and brine (4 mL). The organic layer was separated, dried over anhydrous sodium sulfate and concentrated under reduced pressure. The crude product was purified by column chromatography (silica gel, 4% methanol/dichloromethane) to afford 2-((4-bromo-3-fluorophenyl)amino)-1-(3-fluorophenyl)-2-oxoethyl acetate (C-1.1, 500 mg, yield: 60%) as a pale brown solid: ESI (m/z) 385 $[C_{16}H_{12}BrF_2NO_3]^+$.

Step-3: Synthesis of 2-((3-fluoro-4-(4,4,5,5-tetramethyl-1,3,2-dioxaborolan-2-yl)phenyl)amino)-1-(3-fluorophenyl)-2-oxoethyl acetate (C-2.1)

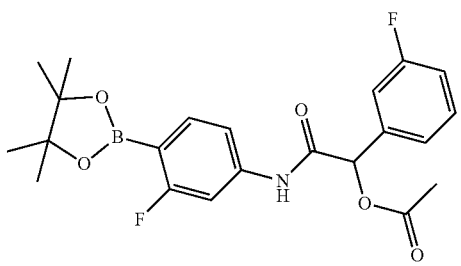 [SMILES: CC(=O)OC(C(=O)Nc1ccc(B2OC(C)(C)C(C)(C)O2)c(F)c1)c1cccc(F)c1]

To a stirred solution of 2-((4-bromo-3-fluorophenyl)amino)-1-(3-fluorophenyl)-2-oxoethyl acetate (C-1.1, 0.10 g, 0.26 mmol) in 1,4-dioxane (3.0 mL) under argon atmosphere were added bis(pinacolato)diboron (0.13 g, 0.52 mmol) and potassium acetate (51 mg, 0.52 mmol. The reaction mixture was purged with argon for 10 min. 1,1-Bis(diphenylphosphino)ferrocene-palladium(II)dichloride dichloromethane complex (9.5 mg, 0.01 mmol) was added and the mixture was purged with argon for 10 min. The reaction mixture was exposed to microwave irradiation (SEM Company) at 100° C. for 1 h. After this time, the reaction mixture was allowed to cool to room temperature, passed through a bed of diatomaceous earth, and washed with ethyl acetate (2×15 mL). The filtrate was washed with water (2×10 mL) and brine (2×10 mL). The organic layer was dried over anhydrous sodium sulfate and concentrated under reduced pressure. The crude product was purified by column chromatography (silica gel, 10% ethyl acetate/hexanes) to afford 2-((3-fluoro-4-(4,4,5,5-tetramethyl-1,3,2-dioxaborolan-2-yl)phenyl)amino)-1-(3-fluorophenyl)-2-oxoethyl acetate (C-2.1, 50 mg, yield: 60%) as a pale brown solid: ESI (m/z) 432 $[C_{22}H_{24}BF_2NO_5+H]^+$.

The compounds of formula C-2 (Table C) can be synthesized according to the procedures described for compound C-2.1:

TABLE C

Compounds C-2:

| Compound | Name | Structure | MS |
|---|---|---|---|
| C-2.1 | 2-((3-fluoro-4-(4,4,5,5-tetramethyl-1,3,2-dioxaborolan-2-yl)phenyl)amino)-1-(3-fluorophenyl)-2-oxoethyl acetate | 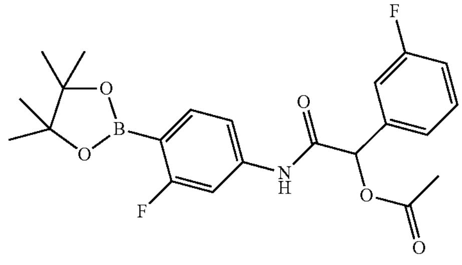 [SMILES: CC(=O)OC(C(=O)Nc1ccc(B2OC(C)(C)C(C)(C)O2)c(F)c1)c1cccc(F)c1] | ESI (m/z) 432 $[C_{22}H_{24}BF_2NO_5 + H]^+$ |

TABLE C-continued

| | Compounds C-2: | | |
|---|---|---|---|
| Compound | Name | Structure | MS |
| C-2.2 | 1-(3-fluorophenyl)-2-((3-methyl-4-(4,4,5,5-tetramethyl-1,3,2-dioxaborolan-2-yl)phenyl)amino)-2-oxoethyl acetate | | ESI (m/z) 428 $[C_{23}H_{27}BFNO_5 + H]^+$ |
| C-2.3 | 2-((3-chloro-4-(4,4,5,5-tetramethyl-1,3,2-dioxaborolan-2-yl)phenyl)amino)-1-(3-fluorophenyl)-2-oxoethyl acetate | | ESI (m/z) 448, 450 $[C_{22}H_{24}BClFNO_5 + H]^+$ |
| C-2.4 | 1-(3-fluorophenyl)-2-oxo-2-((4-(4,4,5,5-tetramethyl-1,3,2-dioxaborolan-2-yl)-3-(trifluoromethyl)phenyl)amino) ethyl acetate | | ESI (m/z) 482 $[C_{23}H_{24}BF_4NO_5 + H]^+$ |
| C-2.5 | 1-(3-fluorophenyl)-2-oxo-2-((4-(4,4,5,5-tetramethyl-1,3,2-dioxaborolan-2-yl)-3-(trifluoromethoxy)phenyl)amino)ethyl acetate | | ESI (m/z) 498 $[C_{23}H_{24}BF_4NO_6 + H]^+$ |
| C-2.6 | 2-((3-chloro-4-(4,4,5,5-tetramethyl-1,3,2-dioxaborolan-2-yl)phenyl)amino)-1-(3,5-difluorophenyl)-2-oxoethyl acetate | | ESI (m/z) 466 $[C_{22}H_{23}BClF_2NO_5 + H]^+$ |

TABLE C-continued

| Compounds C-2: | | | |
|---|---|---|---|
| Compound | Name | Structure | MS |
| C-2.7 | (R)-2-((3-chloro-4-(4,4,5,5-tetramethyl-1,3,2-dioxaborolan-2-yl)phenyl)amino)-1-(3-fluorophenyl)-2-oxoethyl acetate | | ESI (m/z) 448, 450 [$C_{22}H_{24}BClFNO_5$ + H]$^+$ |
| C-2.8 | 1-(3-fluorophenyl)-2-((3-methoxy-4-(4,4,5,5-tetramethyl-1,3,2-dioxaborolan-2-yl)phenyl)amino)-2-oxoethyl acetate | | ESI (m/z) 444 [$C_{23}H_{27}BFNO_6$ + H]$^+$ |
| C-2.9 | N-(3-ethyl-4-(4,4,5,5-tetramethyl-1,3,2-dioxaborolan-2-yl)phenyl)-2-(3-fluorophenyl)-2-hydroxyacetamide | | ESI (m/z) 400 [$C_{27}H_{27}BFNO_4$ + H]$^+$ |
| C-2.10 | 2-((2-fluoro-3-methyl-4-(4,4,5,5-tetramethyl-1,3,2-dioxaborolan-2-yl)phenyl)amino)-1-(3-fluorophenyl)-2-oxoethyl acetate | | ESI (m/z) 446 [$C_{23}H_{26}BF_2NO_5$ + H]$^+$ |
| C-2.11 | 2-((3,5-dimethyl-4-(4,4,5,5-tetramethyl-1,3,2-dioxaborolan-2-yl)phenyl)amino)-1-(3-fluorophenyl)-2-oxoethyl acetate | | ESI (m/z) 442 [$C_{24}H_{29}BFNO_5$ + H]$^+$ |
| C-2.12 | 2-((2-fluoro-5-methyl-4-(4,4,5,5-tetramethyl-1,3,2-dioxaborolan-2-yl)phenyl)amino)-1-(3-fluorophenyl)-2-oxoethyl acetate | | ESI (m/z) 446 [$C_{23}H_{26}BF_2NO_5$ + H]$^+$ |

TABLE C-continued

| | | Compounds C-2: | |
|---|---|---|---|
| Compound | Name | Structure | MS |
| C-2.13 | 2-((2,5-difluoro-4-(4,4,5,5-tetramethyl-1,3,2-dioxaborolan-2-yl)phenyl)amino)-1-(3-fluorophenyl)-2-oxoethyl acetate | | ESI (m/z) 450 $[C_{22}H_{23}BF_3NO_5 + H]^+$ |
| C-2.14 | 2-((3-fluoro-5-methyl-4-(4,4,5,5-tetramethyl-1,3,2-dioxaborolan-2-yl)phenyl)amino)-1-(3-fluorophenyl)-2-oxoethyl acetate | | ESI (m/z) 446 $[C_{23}H_{26}BF_2NO_5 + H]^+$ |
| C-2.15 | 1-(3-fluorophenyl)-2-((6-methyl-5-(4,4,5,5-tetramethyl-1,3,2-dioxaborolan-2-yl)pyridin-2-yl)amino)-2-oxoethyl acetate | | ESI (m/z) 429 $[C_{22}H_{26}BFN_2O_5 + H]^+$ |
| C-2.16 | 1-(3-fluorophenyl)-2-((4-methyl-5-(4,4,5,5-tetramethyl-1,3,2-dioxaborolan-2-yl)pyridin-2-yl)amino)-2-oxoethyl acetate | | ESI (m/z) 429 $[C_{22}H_{26}BFN_2O_5 + H]^+$ |
| C-2.17 | 2-((4-methyl-5-(4,4,5,5-tetramethyl-1,3,2-dioxaborolan-2-yl)pyridin-2-yl)amino)-2-oxo-1-(3-(trifluoromethyl)phenyl)ethyl acetate | | ESI (m/z) 479 $[C_{23}H_{26}BF_3N_2O_5 + H]^+$ |
| C-2.18 | 2-((6-methyl-5-(4,4,5,5-tetramethyl-1,3,2-dioxaborolan-2-yl)pyridin-2-yl)amino)-2-oxo-1-(3-(trifluoromethyl)phenyl)ethyl acetate | | ESI (m/z) 479 $[C_{23}H_{26}BF_3N_2O_5 + H]^+$ |

Scheme D

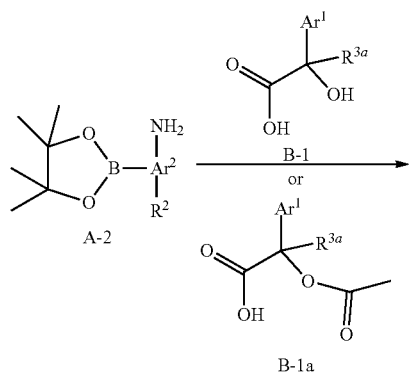

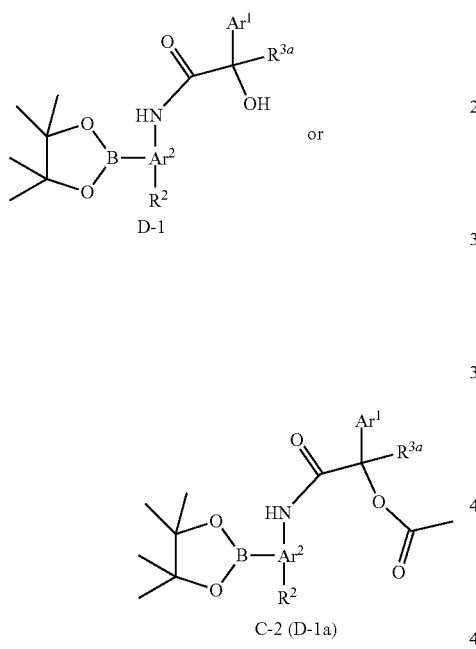

Compounds of Formula D-1 where Ar² =phenyl, R²=3-methyl, R³ᵃ=H, Ar¹=phenyl-R¹ and R¹=3—F can be synthesized as described below for compound D-1.1:

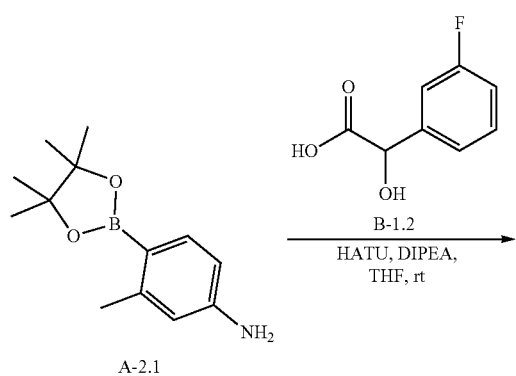

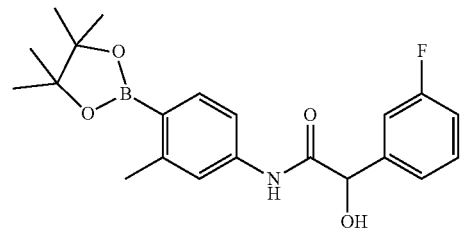

Synthesis of 2-(3-Fluorophenyl)-2-hydroxy-N-(3-methyl-4-(4,4,5,5-tetramethyl-1,3,2-dioxaborolan-2-yl)phenyl)acetamide (Compound D-1.1)

To a solution of 3-methyl-4-(4,4,5,5-tetramethyl-1,3,2-dioxaborolan-2-yl)aniline (A-2.1, 0.298 g, 1.28 mmol) and 2-(3-fluorophenyl)-2-hydroxyacetic acid (B-1.2, 0.196 g, 1.15 mmol) in tetrahydrofuran (10 mL) were added N,N-diisopropylethylamine (0.26 mL, 1.5 mmol) followed by 1-[bis(dimethylamino)methylene]-1H-1,2,3-triazolo[4,5-b]pyridinium 3-oxide hexafluorophosphate (HATU) (0.586, 1.54 mmol) at 0° C. The reaction mixture was allowed to warm to room temperature and stirred for 12 h. After this time, the reaction mixture was diluted with methylene chloride (6.0 mL) and washed with water (4×4 mL) and brine (4 mL). The organic layer was separated, dried over anhydrous sodium sulfate, and concentrated under reduced pressure. The crude product was purified by column chromatography (silica gel, 4% methanol/dichloromethane) to afford 2-(3-fluorophenyl)-2-hydroxy-N-(3-methyl-4-(4,4,5,5-tetramethyl-1,3,2-dioxaborolan-2-yl)phenyl)acetamide (D-1.1, 0.25 g, yield: 52%) as a pale brown solid: ESI (m/z) 386 $[C_{21}H_{25}BFNO_4+H]^+$.

The compounds of formula D-1 (Table D) can be synthesized according to the procedures described for compound D-1.1:

TABLE D

| | Compounds D-1: | | |
|---|---|---|---|
| Compound | Name | Structure | MS |
| D-1.1 | 2-(3-fluorophenyl)-2-hydroxy-N-(3-methyl-4-(4,4,5,5-tetramethyl-1,3,2-dioxaborolan-2-yl)phenyl)acetamide | | ESI (m/z) 386 $[C_{21}H_{25}BFNO_4 + H]^+$ |
| D-1.2 | N-(2,3-difluoro-4-(4,4,5,5-tetramethyl-1,3,2-dioxaborolan-2-yl)phenyl)-2-(3-fluorophenyl)-2-hydroxyacetamide | | ESI (m/z) 408 $[C_{20}H_{21}BF_3NO_4 + H]^+$ |
| D-1.3 | 1-(3-fluorophenyl)-2-((3-methyl-4-(4,4,5,5-tetramethyl-1,3,2-dioxaborolan-2-yl)phenyl)amino)-2-oxoethyl acetate | | ESI (m/z) 428 $[C_{23}H_{27}BFNO_5 + H]^+$ |
| D-1.4 | 1-(3,5-difluorophenyl)-2-((3-methyl-4-(4,4,5,5-tetramethyl-1,3,2-dioxaborolan-2-yl)phenyl)amino)-2-oxoethyl acetate | | ESI (m/z) 446 $[C_{23}H_{26}BF_2NO_5 + H]^+$ |
| D-1.5 | 1-(3-fluoro-5-(trifluoromethyl)phenyl)-2-((3-methyl-4-(4,4,5,5-tetramethyl-1,3,2-dioxaborolan-2-yl)phenyl)amino)-2-oxoethyl acetate | | ESI (m/z) 496 $[C_{24}H_{26}BF_4NO_5 + H]^+$ |
| D-1.6 | 1-(3-fluoro-5-methylphenyl)-2-((3-methyl-4-(4,4,5,5-tetramethyl-1,3,2-dioxaborolan-2-yl)phenyl)amino)-2-oxoethyl acetate | | ESI (m/z) 442 $[C_{24}H_{29}BFNO_5 + H]^+$ |

TABLE D-continued

Compounds D-1:

| Compound | Name | Structure | MS |
|---|---|---|---|
| D-1.7 | 2-((3-ethyl-4-(4,4,5,5-tetramethyl-1,3,2-dioxaborolan-2-yl)phenyl)amino)-1-(3-fluorophenyl)-2-oxoethyl acetate | 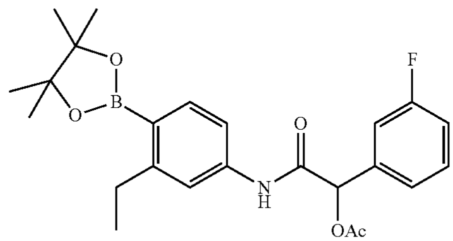 [SMILES: CCc1cc(NC(=O)C(OC(C)=O)c2cccc(F)c2)ccc1B1OC(C)(C)C(C)(C)O1] | ESI (m/z) 442 [$C_{24}H_{29}BFNO_5$ + H]$^+$ |
| D-1.8 | 1-(3-fluorophenyl)-2-oxo-2-((4-(4,4,5,5-tetramethyl-1,3,2-dioxaborolan-2-yl)phenyl)amino)ethyl acetate | 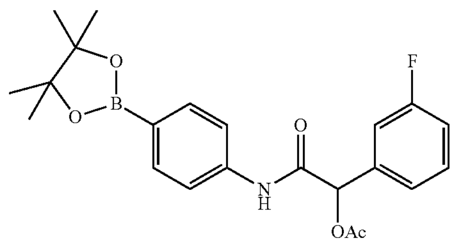 [SMILES: CC(=O)OC(C(=O)Nc1ccc(B2OC(C)(C)C(C)(C)O2)cc1)c1cccc(F)c1] | ESI (m/z) 414 [$C_{22}H_{25}BFNO_5$ + H]$^+$ |
| D-1.9 | 2-((3-fluoro-4-(4,4,5,5-tetramethyl-1,3,2-dioxaborolan-2-yl)phenyl)amino)-1-(3-fluorophenyl)-2-oxoethyl acetate | 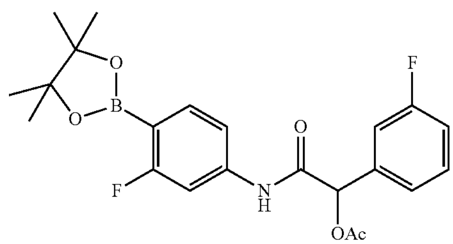 | ESI (m/z) 432 [$C_{22}H_{24}BF_2NO_5$ + H]$^+$ |
| D-1.10 | 1-(3-chlorophenyl)-2-((3-fluoro-4-(4,4,5,5-tetramethyl-1,3,2-dioxaborolan-2-yl)phenyl)amino)-2-oxoethyl acetate | 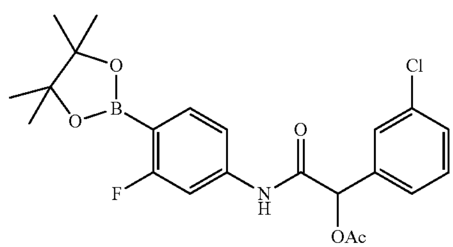 [SMILES: CC(=O)OC(C(=O)Nc1ccc(B2OC(C)(C)C(C)(C)O2)c(F)c1)c1cccc(Cl)c1] | ESI (m/z) 447 [$C_{22}H_{24}BClFNO_5$ + H]$^+$ |
| D-1.11 | 2-((3-fluoro-4-(4,4,5,5-tetramethyl-1,3,2-dioxaborolan-2-yl)phenyl)amino)-2-oxo-1-(m-tolyl)ethyl acetate | 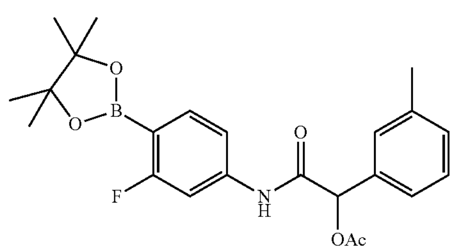 [SMILES: CC(=O)OC(C(=O)Nc1ccc(B2OC(C)(C)C(C)(C)O2)c(F)c1)c1cccc(C)c1] | ESI (m/z) 428 [$C_{23}H_{27}BFNO_5$ + H]$^+$ |
| D-1.12 | 2-((3-fluoro-4-(4,4,5,5-tetramethyl-1,3,2-dioxaborolan-2-yl)phenyl)amino)-2-oxo-1-(3-(trifluoromethyl)phenyl)ethyl acetate | 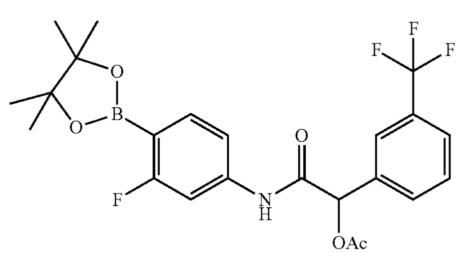 [SMILES: CC(=O)OC(C(=O)Nc1ccc(B2OC(C)(C)C(C)(C)O2)c(F)c1)c1cccc(C(F)(F)F)c1] | ESI (m/z) 482 [$C_{23}H_{24}BF_4NO_5$ + H]$^+$ |

TABLE D-continued

Compounds D-1:

| Compound | Name | Structure | MS |
|---|---|---|---|
| D-1.13 | 1-(3,5-difluorophenyl)-2-((3-fluoro-4-(4,4,5,5-tetramethyl-1,3,2-dioxaborolan-2-yl)phenyl)amino)-2-oxoethyl acetate | 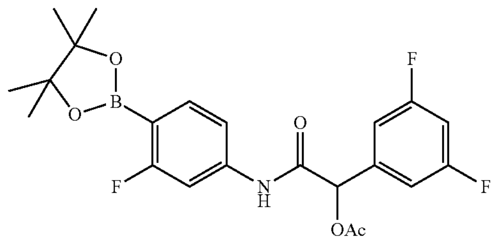 [SMILES: CC(=O)OC(C(=O)Nc1ccc(B2OC(C)(C)C(C)(C)O2)c(F)c1)c1cc(F)cc(F)c1] | ESI (m/z) 450 [$C_{22}H_{23}BF_3NO_5$ + H]$^+$ |
| D-1.14 | 2-((3-fluoro-4-(4,4,5,5-tetramethyl-1,3,2-dioxaborolan-2-yl)phenyl)amino)-1-(3-fluoro-5-(trifluoromethyl)phenyl)-2-oxoethyl acetate | 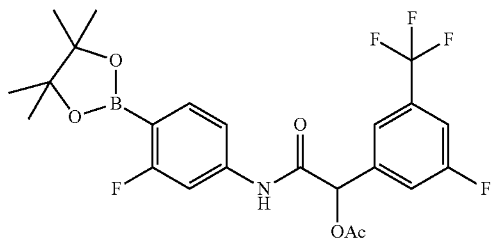 [SMILES: CC(=O)OC(C(=O)Nc1ccc(B2OC(C)(C)C(C)(C)O2)c(F)c1)c1cc(F)cc(C(F)(F)F)c1] | ESI (m/z) 500 [$C_{23}H_{23}BF_5NO_5$ + H]$^+$ |
| D-1.15 | 2-((2-fluoro-4-(4,4,5,5-tetramethyl-1,3,2-dioxaborolan-2-yl)phenyl)amino)-1-(3-fluorophenyl)-2-oxoethyl acetate | 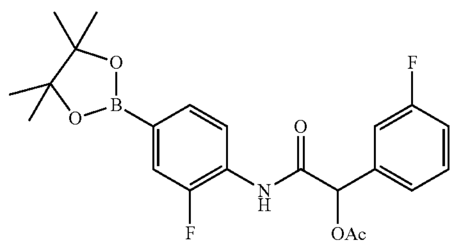 [SMILES: CC(=O)OC(C(=O)Nc1ccc(B2OC(C)(C)C(C)(C)O2)cc1F)c1cccc(F)c1] | ESI (m/z) 432 [$C_{22}H_{24}BF_2NO_5$ + H]$^+$ |
| D-1.16 | 1-(3-fluorophenyl)-2-oxo-2-((4-(4,4,5,5-tetramethyl-1,3,2-dioxaborolan-2-yl)-3-(trifluoromethoxy)phenyl)amino)ethyl acetate | 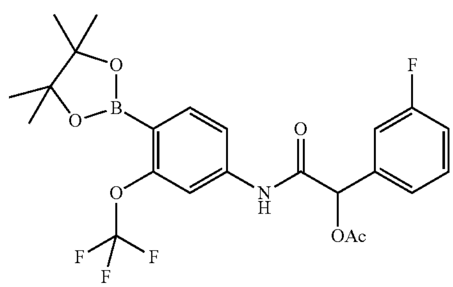 [SMILES: CC(=O)OC(C(=O)Nc1ccc(B2OC(C)(C)C(C)(C)O2)c(OC(F)(F)F)c1)c1cccc(F)c1] | ESI (m/z) 498 [$C_{23}H_{24}BF_4NO_6$ + H]$^+$ |
| D-1.17 | 1-(3-chlorophenyl)-2-((2,3-difluoro-4-(4,4,5,5-tetramethyl-1,3,2-dioxaborolan-2-yl)phenyl)amino)-2-oxoethyl acetate | 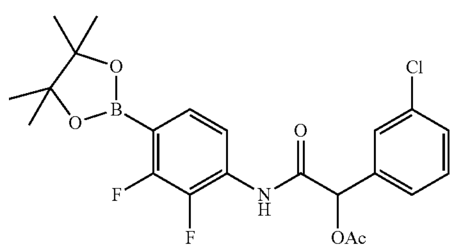 [SMILES: CC(=O)OC(C(=O)Nc1ccc(B2OC(C)(C)C(C)(C)O2)c(F)c1F)c1cccc(Cl)c1] | ESI (m/z) 465 [$C_{22}H_{23}BClF_2NO_5$ + H]$^+$ |
| D-1.18 | 2-((2,3-difluoro-4-(4,4,5,5-tetramethyl-1,3,2-dioxaborolan-2-yl)phenyl)amino)-2-oxo-1-(3-(trifluoromethyl)phenyl)ethyl acetate | 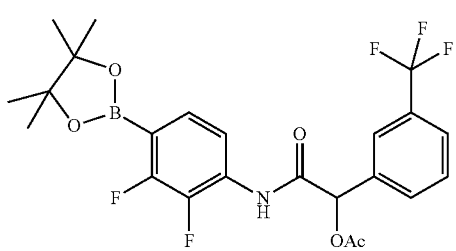 [SMILES: CC(=O)OC(C(=O)Nc1ccc(B2OC(C)(C)C(C)(C)O2)c(F)c1F)c1cccc(C(F)(F)F)c1] | ESI (m/z) 500 [$C_{23}H_{23}BF_5NO_5$ + H]$^+$ |

TABLE D-continued

Compounds D-1:

| Compound | Name | Structure | MS |
|---|---|---|---|
| D-1.19 | 2-((2,3-difluoro-4-(4,4,5,5-tetramethyl-1,3,2-dioxaborolan-2-yl)phenyl)amino)-1-(3,5-difluorophenyl)-2-oxoethyl acetate | 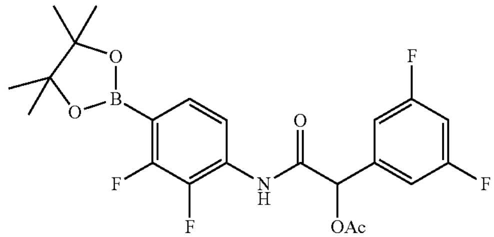 [SMILES: CC(=O)OC(C(=O)Nc1ccc(B2OC(C)(C)C(C)(C)O2)c(F)c1F)c1cc(F)cc(F)c1] | ESI (m/z) 468 $[C_{22}H_{22}BF_4NO_5 + H]^+$ |
| D-1.20 | 2-((2,3-difluoro-4-(4,4,5,5-tetramethyl-1,3,2-dioxaborolan-2-yl)phenyl)amino)-1-(3-fluoro-5-(trifluoromethyl)phenyl)-2-oxoethyl acetate | 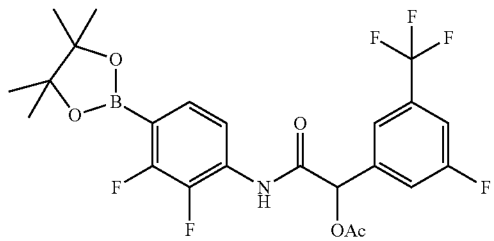 [SMILES: CC(=O)OC(C(=O)Nc1ccc(B2OC(C)(C)C(C)(C)O2)c(F)c1F)c1cc(F)cc(C(F)(F)F)c1] | ESI (m/z) 418 $[C_{23}H_{22}BF_6NO_5 + H]^+$ |

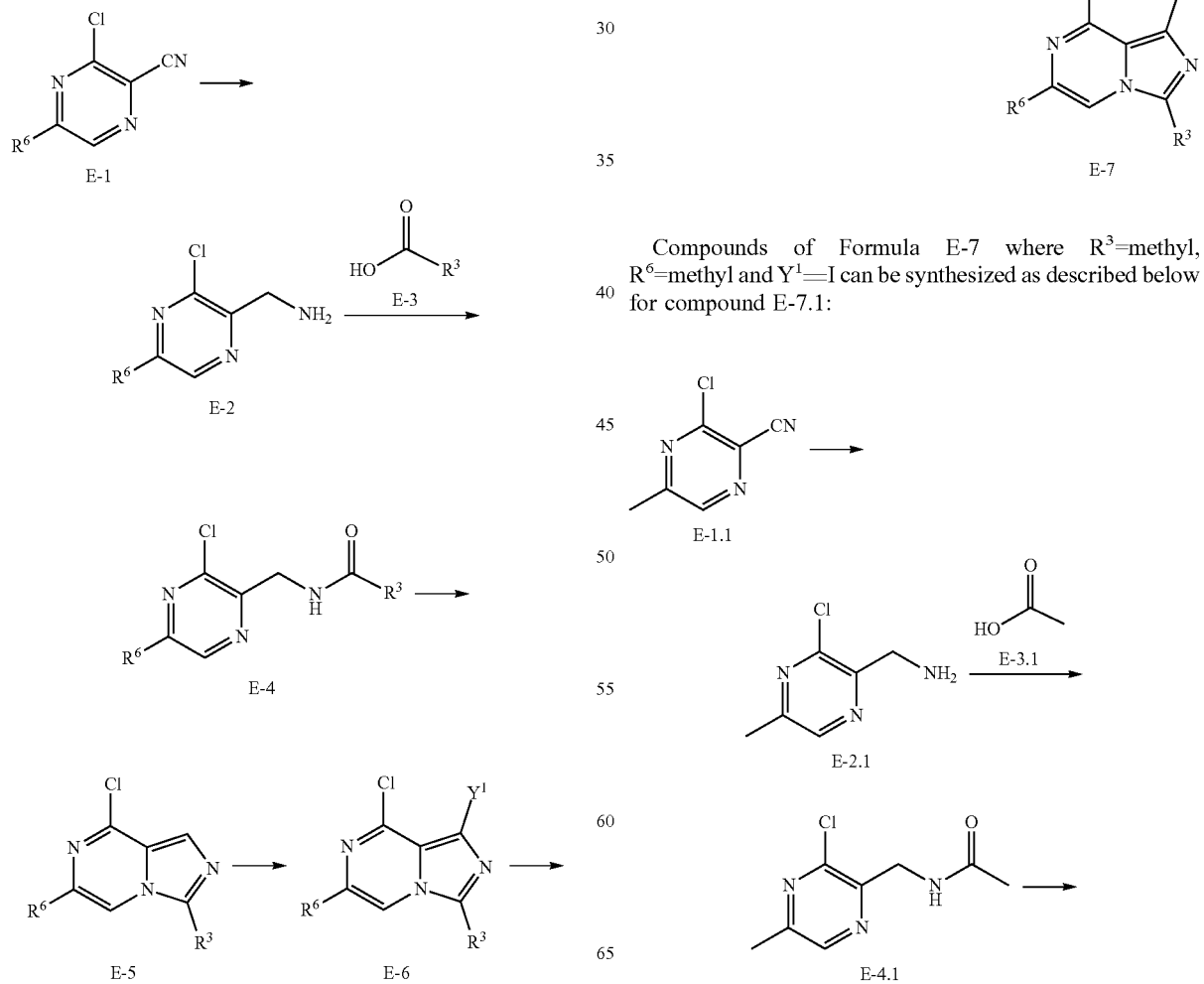

Compounds of Formula E-7 where $R^3$=methyl, $R^6$=methyl and $Y^1$=I can be synthesized as described below for compound E-7.1:

-continued

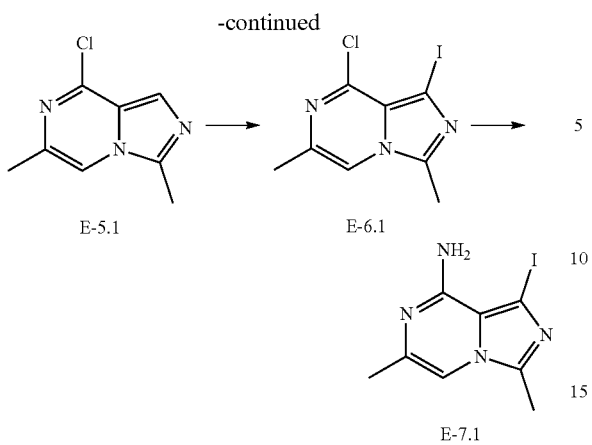

E-5.1 → E-6.1 →

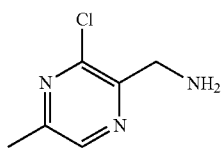

E-7.1

Step-1: Synthesis of (3-Chloro-5-methylpyrazin-2-yl)methanamine (E-2.1)

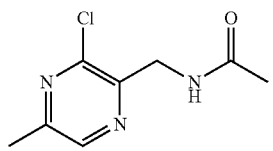

To a stirred solution of 3-chloro-5-methylpyrazine-2-carbonitrile (E-1.1, 1.00 g, 6.51 mmol) in acetic acid (20.0 mL) was added Raney Nickel (0.055 g, 0.65 mmol) under inert atmosphere. This reaction mixture was stirred for 20 h under hydrogen bladder pressure at room temperature. After this time, the reaction mixture was passed through a bed of diatomaceous earth and washed with ethyl acetate (2×20 mL). The organic layer was concentrated under vacuum and diluted with 2N hydrochloric acid (15 mL) and extracted with ethyl acetate (2×15 mL). The aqueous layer was concentrated to give the crude product, which was triturated with acetonitrile (5 mL) to afford (3-chloro-5-methylpyrazin-2-yl)methanamine (E-2.1, 1.0 g, yield: 78%) as a light brown solid: ESI (m/z) 158 $[C_6H_8ClN_3+H]^+$.

Step-2: Synthesis of N-((3-Chloro-5-methylpyrazin-2-yl)methyl)acetamide (E-4.1)

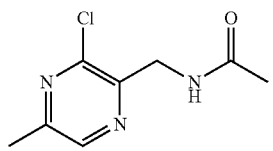

To a stirred solution of (3-chloro-5-methylpyrazin-2-yl)methanamine (E-2.1, 0.652 g, 4.14 mmol) in methylene chloride (15.0 mL) were added N,N-diisopropylethylamine (362 mg, 2.80 mmol) followed by acetic anhydride (E-3.1, 320 mg, 0.84 mmol) at 0° C. and stirred for 14 h. After this time, the reaction mixture was diluted with dichloromethane (15 mL) and washed with water (4×4 mL) and brine (4 mL). The organic layer was separated, dried over anhydrous sodium sulfate, and concentrated under reduced pressure. The crude material was purified by column chromatography (silica gel, 1% methanol/dichloromethane) to afford N-((3-chloro-5-methylpyrazin-2-yl)methyl)acetamide (E-4.1, 0.65 g, yield: 65%) as a pale brown solid: ESI (m/z) 200 $[C_8H_{10}ClN_3O+H]^+$.

Step-3: Synthesis of 8-chloro-3,6-dimethylimidazo[1,5-a]pyrazine (E-5.1)

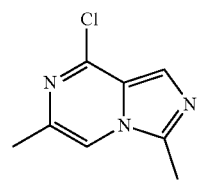

To a stirred solution of N-((3-chloro-5-methylpyrazin-2-yl)methyl)acetamide (E-4.1, 0.65 g, 3.2 mmol) in acetonitrile (10.0 mL) were added N,N-dimethylformamide (0.3 mL) followed by phosphorous (V) oxychloride (1.5 g, 9.7 mmol) at 0° C. This reaction mixture was heated to 80° C. and stirred for 2 h. After this time, the reaction mixture was cooled to room temperature and poured into a mixture of saturated aqueous sodium bicarbonate solution (50 mL) and ethyl acetate (100 mL). The organic layer was separated, dried over anhydrous sodium sulfate, and concentrated under reduced pressure. The crude material was purified by column chromatography (silica gel, 80% ethyl acetate/hexanes) to afford 8-chloro-3,6-dimethylimidazo[1,5-α]pyrazine (E-5.1, 0.51 g, yield: 86%) as a pale brown solid: ESI (m/z) 182 $[C_8H_8ClN_3+H]^+$.

Step-4: Synthesis of 1-iodo-8-chloro-3,6-dimethyl-imidazo[1,5-a]pyrazine (E-6.1)

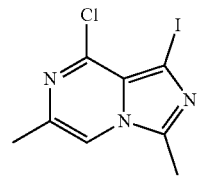

To a stirred solution of 8-chloro-3,6-dimethylimidazo[1,5-a]pyrazine (E-5.1, 0.561 g, 3.09 mmol) in N,N-dimethylformamide (8.0 mL) was added N-iodosuccinimide (0.835 g, 3.71 mmol) at room temperature. This reaction mixture was heated to 60° C. and stirred for 3 h. After this time, the reaction mixture was cooled to room temperature, diluted with methylene chloride (15 mL), and adsorbed onto silica gel (100-200 mesh). The crude product was purified by column chromatography (silica gel, 30% ethyl acetate/hexanes) to afford 1-iodo-8-chloro-3,6-dimethylimidazo[1,5-α]pyrazine (E-6.1, 0.70 g, yield: 80%) as yellow solid: ESI (m/z) 308 $[C_8H_7ClIN_3+H]^+$.

Step-5: Synthesis of 1-iodo-3,6-dimethylimidazo[1,5-a]pyrazin-8-amine (E-7.1)

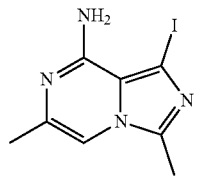

A stirred solution of 1-iodo-8-chloro-3,6-dimethylimidazo[1,5-α]pyrazine (E-6.1, 0.701 g, 2.28 mmol) in 2.0 M ammonia in isopropanol (200.0 mL) was stirred in an autoclave for 48 h at 120° C. After this time, the reaction mixture was cooled to room temperature, and solids were filtered to afford 1-iodo-3,6-dimethylimidazo[1,5-α]pyrazin-8-amine (E-7.1, 0.50 g, yield: 76%) as a pale brown solid: ESI (m/z) 289 [C$_8$H$_9$IN$_4$+H]$^+$.

The compounds of formula E-7 (Table E) can be synthesized according to the procedures described for compound E-7.1:

TABLE E

Compound E-7:

| Compound | Name | Structure | MS |
|---|---|---|---|
| E-7.1 | 1-iodo-3,6-dimethylimidazo[1,5-a]pyrazin-8-amine | 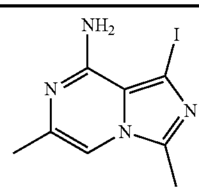 | ESI (m/z) 289 [C$_8$H$_9$IN$_4$ + H]$^+$ |
| E-7.2 | 1-iodo-3-methylimidazo[1,5-a]pyrazin-8-amine | 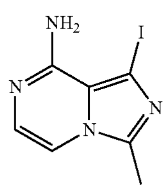 | ESI (m/z) 275 [C$_7$H$_7$IN$_4$ + H]$^+$ |
| E-7.3 | 1-iodo-6-methyl-3-(trideutriomethyl)imidazo[1,5-a]pyrazin-8-amine | 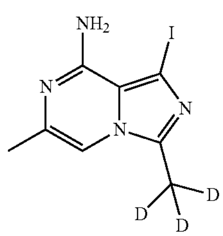 [SMILES: [2H]C([2H])([2H])c1nc(I)c2c(N)nc(C)cn12] | ESI (m/z) 292 [C$_8$H$_6$D$_3$IN$_4$ + H]$^+$ |

Scheme F

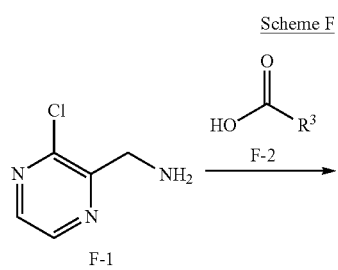

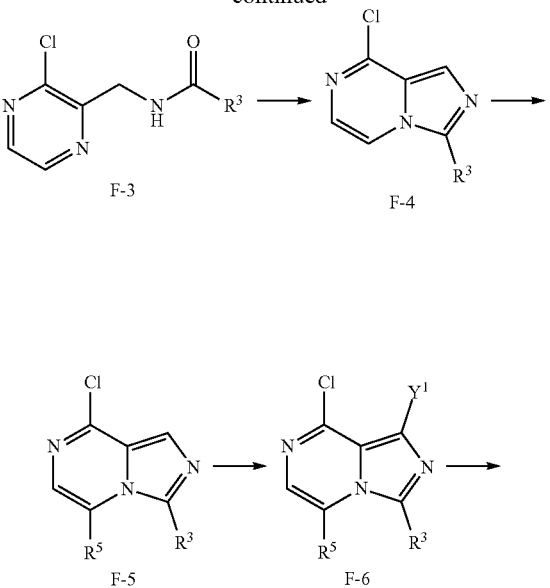

-continued

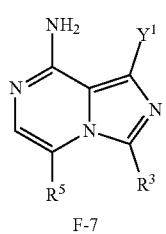

Compounds of Formula F-7 where $R^5$=methyl, $R^3$=$CD_3$, and $Y^1$=Br can be synthesized as described below for compound F-7.1:

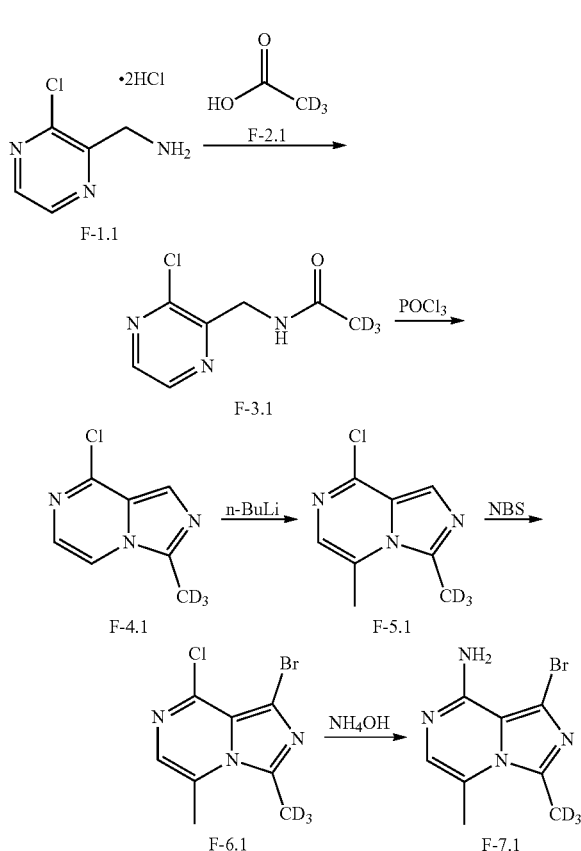

Step-1 Synthesis of N-[(3-chloropyrazin-2-yl)methyl]-2,2,2-trideuterio-acetamide (F-3.1)

To a stirred solution of (3-chloropyrazin-2-yl)methanamine dihydrochloride (F-1.1, 50.00 g, 231.4 mmol) in THF (700 mL) were added N,N-diisopropylethylamine (121 mL, 694.4 mmol) followed by acetic acid-$d_3$ (F-2.1, 21.80 g, 347.1 mmol) and EDC·HCl (66.00 g, 347.1 mmol) at 0° C. and stirred for 4 h. After this time, the reaction mixture was quenched with water (150 mL), an aqueous layer extracted with EtOAc (3×500 mL). The combined organic layer was dried over $Na_2SO_4$, filtered and concentrated to obtain crude material, which was purified by column chromatography (silica gel, 100% ethyl acetate/hexanes) to afford N-[(3-chloropyrazin-2-yl)methyl]-2,2,2-trideuterio-acetamide (F-3.1, 40.00 g, yield: 91%) as an off white solid; ESI (m/z) 188 $[C_7H_5D_3ClN_3O+H]^+$.

Step-2: Synthesis of 8-chloro-3-(trideuteriomethyl)imidazo[1,5-a]pyrazine (F-4.1)

To a stirred solution of N-[(3-chloropyrazin-2-yl)methyl]-2,2,2-trideuterio-acetamide (F-3.1, 40.00 g, 212.7 mmol) in EtOAc (500 mL) were added dimethylformamide (20 mL) followed by phosphoryl chloride (81.3 g, 531.9 mmol) at 0° C. and the resulting reaction mixture was stirred for 16 h at room temperature. After this time, the reaction mixture was poured into mixture of sat. sodium bicarbonate solution (500 mL), EtOAc (500 mL) at 10° C. and then adjusted pH of reaction mixture up to ~8. The organic layer was separated, washed with sodium bicarbonate solution (500 mL), brine (100 mL), combined organic layer was dried over anhydrous sodium sulfate and concentrated under reduced pressure. The crude material was purified by column chromatography (silica gel, 80-100% ethyl acetate/hexanes) to afford 8-chloro-3-(trideuteriomethyl)imidazo[1,5-a]pyrazine (F-4.1, 30.00 g, yield: 83%) as a light yellow solid; ESI (m/z) 171 $[C_7H_3D_3ClN_3+H]^+$.

Step-3: Synthesis of 8-chloro-5-methyl-3-(trideuteriomethyl)imidazo[1,5-a]pyrazine (F-5.1)

To a stirred solution of 8-chloro-3-(trideuteriomethyl)imidazo[1,5-a]pyrazine (F-4.1, 10.00 g, 58.8 mmol) in THF (350 mL) at −78° C., n-butyllithium (2.5 M, 35.2 mL, 88.23 mmol) was added drop-wise and resulting reaction mixture was stirred for 10 min. at the same temperature. Then, methyl iodide (7.5 mL, 117.6 mmol) was added to it and stirred for 15 min. at −78° C. After this time, the reaction mixture was quenched with sat. ammonium chloride solution (50 mL) at −78° C. The reaction was warm to room temperature, stirred for 20 min. and extracted with EtOAc (2×200 mL). The organic layer was separated, washed with brine (50 mL), dried over anhydrous sodium sulfate and concentrated under reduced pressure. The crude material was purified by column chromatography (silica gel, 70-100% ethyl acetate/hexanes) to afford 8-chloro-5-methyl-3-(trideuteriomethyl)imidazo[1,5-a]pyrazine (F-5.1, 7.50 g, yield: 69%) as a pale yellow solid; ESI (m/z) 185 $[C_8H_5D_3ClN_3+H]^+$.

Step-4: Synthesis of 1-bromo-8-chloro-5-methyl-3-(trideuteriomethyl)imidazo[1,5-a]pyrazine (F-6.1)

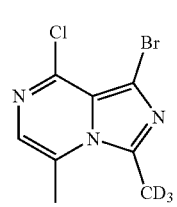

F-6.1

To a stirred solution of 8-chloro-5-methyl-3-(trideuteriomethyl)imidazo[1,5-a]pyrazine (F-5.1, 25.00 g, 135 mmol) in dichloromethane (400 mL) was added N-bromosuccinimide (29.10 g, 163 mmol) portion-wise at room temperature and stirred for 1 h at same temperature. After this time, the reaction mixture was diluted with dichloromethane (400 mL), washed with water (400 mL) and brine (100 mL). The combined organic layer was dried over anhydrous sodium sulfate, concentrated under reduced pressure to get crude material which was washed with 20% ethyl acetate in hexanes to obtain 1-bromo-8-chloro-5-methyl-3-(trideuteriomethyl)imidazo[1,5-a]pyrazine (F-6.1, 31.70 g, yield: 89%) as a yellow solid; ESI (m/z) 263 [$C_8H_4D_3BrClN_3$+H]$^+$.

Step-5: Synthesis of 1-bromo-5-methyl-3-(trideuteriomethyl)imidazo[1,5-a]pyrazin-8-amine (F-7.1)

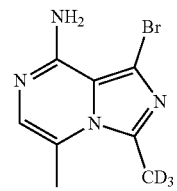

F-7.1

In a 5 L autoclave, 1-bromo-8-chloro-5-methyl-3-(trideuteriomethyl)imidazo[1,5-a]pyrazine (F-6.1, 30.00 g, 114 mmol) and ammonia (2 M in isopropanol) (2 L) was stirred for 40 h at 120° C. After this time, the reaction mixture was cooled to room temperature, excess of solvent was distilled off to obtain crude material, which was washed with 20% acetonitrile in water (150 mL) and dried under vacuum to afford 1-bromo-5-methyl-3-(trideuteriomethyl)imidazo[1,5-a]pyrazin-8-amine (F-7.1, 23.00 g, 83%) as a pale brown solid; ESI (m/z) 244 [$C_8H_6D_3BrN_4$+H]$^+$. 101731 The compounds of formula F-7 (Table F) can be synthesized according to the procedures described for compound F-7.1:

TABLE F

| Compound F-7: | | | |
|---|---|---|---|
| Compound | Name | Structure | MS |
| F-7.1 | 1-bromo-5-methyl-3-(trideuteriomethyl)imidazo[1,5-a]pyrazin-8-amine | | ESI (m/z) 244 [$C_8H_6D_3BrN_4$ + H]$^+$ |
| F-7.2 | 1-bromo-3,5-dimethylimidazo[1,5-a]pyrazin-8-amine | | ESI (m/z) 241 [$C_8H_9BrN_4$ + H]$^+$ |
| F-7.3 | 1-bromo-3,6-dimethylimidazo[1,5-a]pyrazin-8-amine | | ESI (m/z) 241 [$C_8H_9BrN_4$ + H]$^+$ |
| F-7.4 | 1-bromo-6-methyl-3-(trideuteriomethyl)imidazo[1,5-a]pyrazin-8-amine | | ESI (m/z) 244 [$C_8H_6D_3BrN_4$ + H]$^+$ |

Scheme G

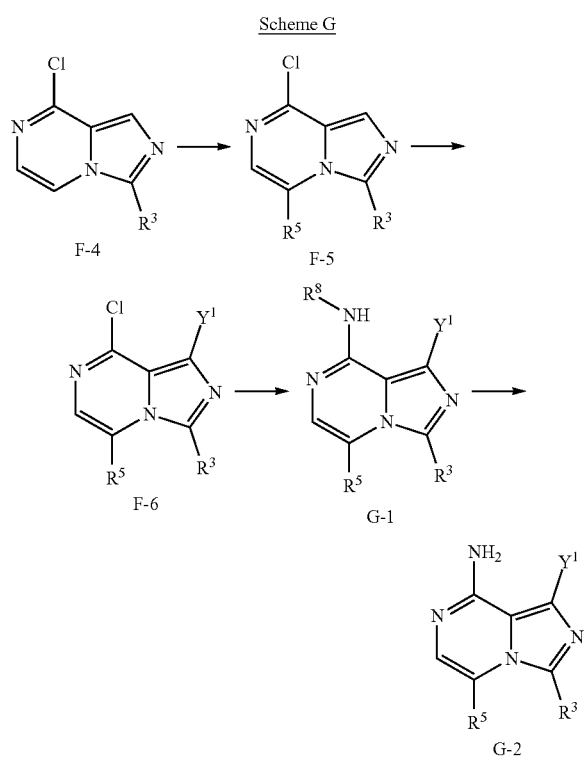

Compounds of Formula G-2 where $R^5$=Cl, $R^3$=CD$_3$, $Y^1$=Br, and $R^8$=(2,4-dimethoxyphenyl)methanamino can be synthesized as described below for compound G-2.1:

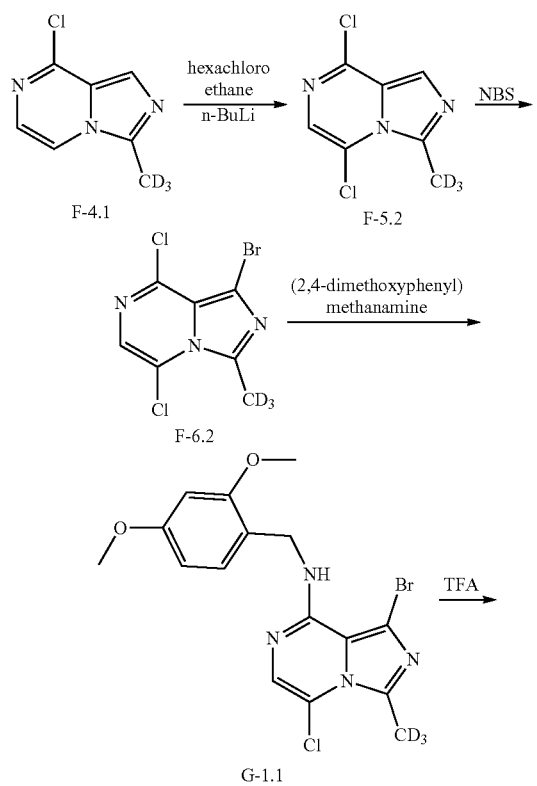

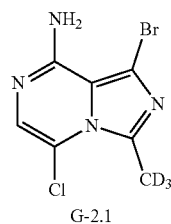

G-2.1

Step-1 Synthesis of 5,8-dichloro-3-(trideuteriomethyl)imidazo[1,5-a]pyrazine (F-5.2)

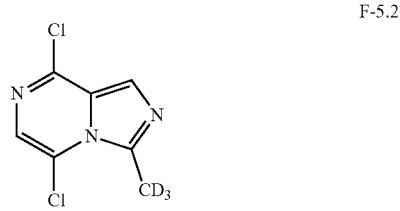 [SMILES: [2H]C([2H])([2H])c1ncc2c(Cl)ncc(Cl)n12]

To a stirred solution of 8-chloro-3-(trideuteriomethyl)imidazo[1,5-a]pyrazine (F-4.1, 5.00 g, 29.4 mmol) in THF (150 mL) n-butyllithium (2.5 M, 17.6 mL, 44.1 mmol) was added drop-wise at −78° C. and stirred for 10 min. at the same temperature. Then, the solution of hexachloroethane (10.40 g, 44.1 mmol) in THF (20 mL) was added drop-wise to the above reaction mixture at −78° C. and stirred for 15 min. at same temperature. After this time, the reaction mixture was quenched with sat. aqueous ammonium chloride solution (50 mL) at −78° C. The reaction was warm to room temperature and stirred for 20 min, an aqueous layer was extracted with EtOAC (2×200 mL). The combined organic layer was washed with brine (50 mL), dried over anhydrous sodium sulfate and concentrated under reduced pressure. The crude material was purified by column chromatography (silica gel, 70-100% ethyl acetate/hexanes) to afford 5,8-dichloro-3-(trideuteriomethyl)imidazo[1,5-a]pyrazine (F-5.2, 4.20 g, yield: 69%) as a pale yellow solid; ESI (m/z) 204 [C$_7$H$_2$D$_3$Cl$_2$N$_3$+H]$^+$.

Step-2: Synthesis of 1-bromo-5,8-dichloro-3-(trideuteriomethyl)imidazo[1,5-a]pyrazine (F-6.2)

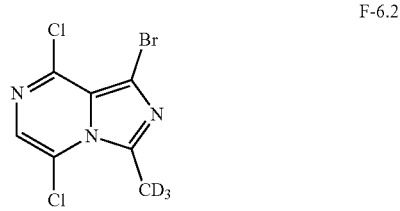 [SMILES: [2H]C([2H])([2H])c1nc(Br)c2c(Cl)ncc(Cl)n12]

To a stirred solution of 5,8-dichloro-3-(trideuteriomethyl)imidazo[1,5-a]pyrazine (F-5.2, 8.50 g, 41.4 mmol) in DMF (90 mL), N-bromosuccinimide (8.80 g, 49.7 mmol) was added portion-wise at room temperature and stirred for 4 h. After this time, the reaction mixture was quenched with ice cold water (200 mL). Solid was precipitated out, was filtered, washed with water (100 mL), dried under vacuum to obtained 1-bromo-5,8-dichloro-3-(trideuteriomethyl)imidazo[1,5-a]pyrazine (F-6.2, 11.20 g, yield: 95%) as an off white solid; ESI (m/z) 282 [$C_7HD_3BrCl_2N_3$+H]$^+$.

Step-3: Synthesis of 1-bromo-5-chloro-N-[(2,4-dimethoxyphenyl)methyl]-3-(trideuteriomethyl)imidazo[1,5-a]pyrazin-8-amine (G-1.1)

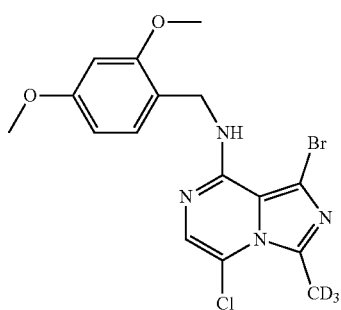

G-1.1

Step-4: Synthesis of 1-bromo-5-chloro-3-(trideuteriomethyl)imidazo[1,5-a]pyrazin-8-amine (G-2.1)

G-2.1

In a 1 L multi neck RBF, 1-bromo-5-chloro-N-[(2,4-dimethoxyphenyl)methyl]-3-(trideuteriomethyl)imidazo[1,5-a]pyrazin-8-amine (G-1.1, 15.00 g, 36.3 mmol.) and TFA (150 mL) was stirred for 3 h at 80° C. After this time, the reaction mixture was cooled to room temperature and excess of TFA was distilled off to obtain crude viscous mass. The crude viscous mass was quenched with 10% NaOH solution and adjusted pH up to ~8. Solid was precipitated out, was filtered, and dried under vacuum, which was purified by column chromatography (silica gel, 5-10% MeOH/dichloromethane) to afford 1-bromo-5-chloro-3-(trideuteriomethyl)imidazo[1,5-a]pyrazin-8-amine (G-2.1, 7.00 g, yield: 73%) as an off white solid: ESI (m/z) 264 [$C_7H_3D_3BrClN_4$+H]$^+$.

The compounds of formula G-2 (Table G) can be synthesized according to the procedures described for compound G-2.1:

TABLE G

Compound G-2:

| Compound | Name | Structure | MS |
| --- | --- | --- | --- |
| G-2.1 | 1-bromo-5-chloro-3-(trideuteriomethyl)imidazo[1,5-a]pyrazin-8-amine | 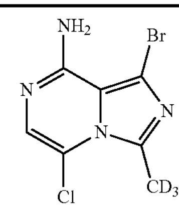 | ESI (m/z) 264 [$C_7H_3D_3BrClN_4$ + H]$^+$ |
| G-2.2 | 1-bromo-5-chloro-3-methylimidazo[1,5-a]pyrazin-8-amine | 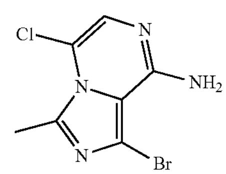 | ESI (m/z) 261 [$C_7H_6BrClN_4$]$^+$ |

To a stirred solution of 1-bromo-5,8-dichloro-3-(trideuteriomethyl)imidazo[1,5-a]pyrazine (F-6.2, 11.20 g, 39.4 mmol) in 1,4-dioxane (150 mL) were added DIPEA (13.1 g, 78.9 mmol) followed by (2,4-dimethoxyphenyl)methanamine (13.90 g, 78.9 mmol) at room temperature. This reaction mixture was stirred for 48 h at room temperature. After this time, the reaction mixture was quenched with ice cold water (200 mL). Solid was precipitated out, was filtered, washed with water (100 mL), dried under vacuum to obtain 1-bromo-5-chloro-N-[(2,4-dimethoxyphenyl)methyl]-3-(trideuteriomethyl)imidazo[1,5-a]pyrazin-8-amine (G-1.1, 15.20 g, yield: 92%) an off white solid; ESI (m/z) 414 [$C_{16}H_{13}D_3BrClN_4O_2$+H]$^+$.

Scheme H

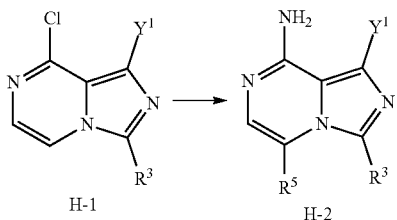

Compounds of Formula H-2 where $R^5$=$CF_3$, $R^3$=$CH_3$, and $Y^1$=Br can be synthesized as described below for compound H-2.1:

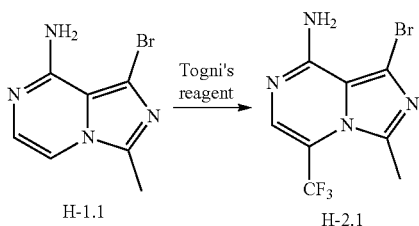

cooled to room temperature and excess of solvent was distilled off under reduced pressure to obtain crude material. The crude material was basified with aqueous ammonia solution, an aqueous layer was extracted with EtOAc (2×200 mL). The combined organic layer was washed with brine (50 mL), dried over anhydrous sodium sulfate and concentrated under reduced pressure. The crude was triturated with acetonitrile (20 mL) to obtain solid compound, was filtered and dried under vacuum to obtained 1-bromo-3-methyl-5-(trifluoromethyl)imidazo[1,5-a]pyrazin-8-amine (H-2.1, 3.20 g, yield: 50%) an off white solid; ESI (m/z) 295 $[C_8H_6BrF_3N_4+H]^+$.

The compounds of formula H-2 (Table H) can be synthesized according to the procedures described for compound H-2.1:

TABLE H

| Compound | Name | Structure | MS |
|---|---|---|---|
| H-2.1 | 1-bromo-3-methyl-5-(trifluoromethyl)imidazo[1,5-a]pyrazin-8-amine | 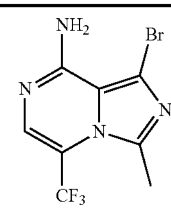 | ESI (m/z) 295 $[C_8H_6BrF_3N_4 + H]^+$ |
| H-2.2 | 1-bromo-3-(trideuteriomethyl)-5-(trifluoromethyl)imidazo[1,5-a]pyrazin-8-amine | 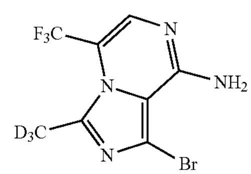 [SMILES: [2H]C([2H])([2H])c1nc(Br)c2c(N)ncc(C(F)(F)F)n12] | ESI (m/z) 298 $[C_8H_3D_3BrF_3N_4]^+$ |

Synthesis of 1-bromo-3-methyl-5(trifluoromethyl)imidazo[1,5-a]pyrazin-8-amine (H-2.1)

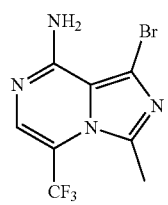

H-2.1

To a stirred solution of 1-bromo-3-methylimidazo[1,5-a]pyrazin-8-amine (H-1.1, 5.00 g, 22 mmol) in acetonitrile (200 mL) were added Togni's reagent (7.2 g, 22 mmol) followed by tris(trimethylsilyl)silane (6.2 g, 22 mmol) at room temperature and resulting reaction mixture was heated at 80° C. for 4 h. After this time, the reaction mixture was Scheme I: Synthesis of 1-bromo-8-chloro-3,5,6-trimethylimidazo[1,5-a]pyrazine (I-9)

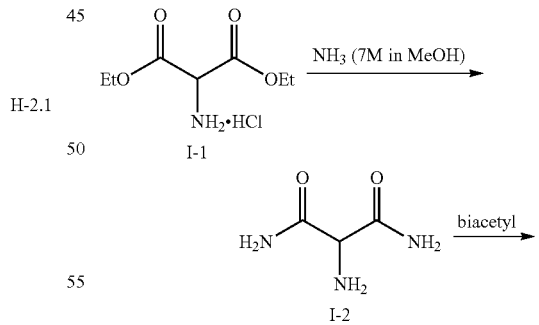

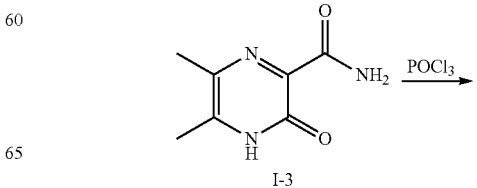

-continued

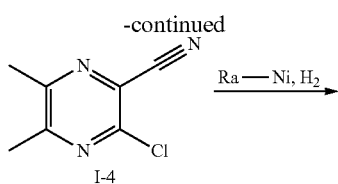

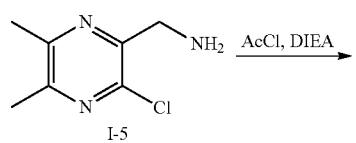

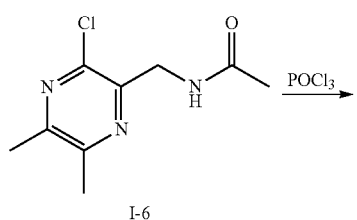

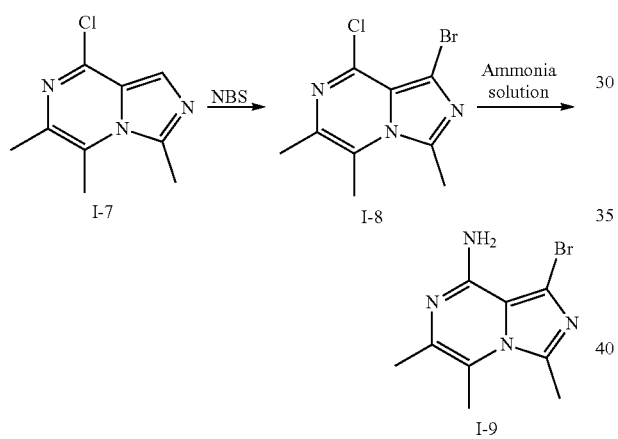

Step-1: Synthesis of 2-aminomalonamide (I-2)

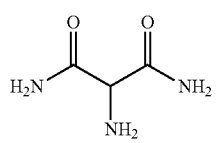

In a 450 mL autoclave, diethyl 2-aminomalonate hydrochloride (I-1, 36.00 g, 165.89 mmol) and ammonia solution (7 M in MeOH, 150 mL) was stirred for 20 h at room temperature. After this time, excess of MeOH was distilled off and dried under vacuum to afford 2-aminomalonamide (I-2, 19.00 g, yield: 95%) as a yellow solid (which was taken to next step without any purification): $^1$H NMR (400 MHz, DMSO-d$_6$) δ 7.51 (s, 2H), 7.24 (s, 1H), 3.71 (s, 1H), 2.30 (s, 2H); ESI (m/z) 118 [C$_3$H$_7$N$_3$O$_2$+H]$^+$.

Step-2: Synthesis of 5,6-dimethyl-3-oxo-3,4-dihydropyrazine-2-carboxamide (I-3)

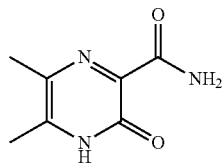

To a stirred suspension of 2-aminomalonamide (I-2, 17.68 g, 151.16 mmol) and biacetyl (13 g, 151.16 mmol) in water (25 mL) was added aqueous NaOH (50% solution) (15 mL, 188.95 mmol) over a period of 20 min at 10° C. After completion of addition, resulting reaction mixture was stirred for additional 2 h at the same temperature, pH of reaction mixture was adjusted to 6.0 (by acetic acid). The solid was precipitated out, was filtered and dried under vacuum to afford 5,6-dimethyl-3-oxo-3,4-dihydropyrazine-2-carboxamide (I-3, 13.00 g, yield: 51%) as a light yellow solid: $^1$H NMR (400 MHz, DMSO-d$_6$) δ 13.22 (s, 1H), 8.71 (s, 1H), 8.15 (s, 1H), 2.38 (s, 3H), 2.32 (s, 3H); ESI (m/z) 168 [C$_7$H$_9$N$_3$O$_2$+H]$^+$.

Step-3: Synthesis of 3-chloro-5,6-dimethylpyrazine-2-carbonitrile (I-4)

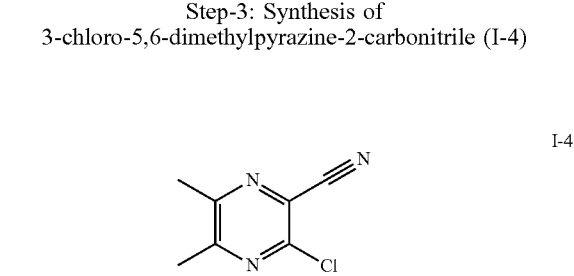

To a stirred solution of 5,6-dimethyl-3-oxo-3,4-dihydropyrazine-2-carboxamide (I-3, 12.00 g, 71.85 mmol) in chlorobenzene (60 mL) was added phosphoryl chloride (26.8 mL, 287.4 mmol) at room temperature. The resulting reaction mixture was heated to 60° C. and then added DIEA (37.57 mL, 215.55 mmol) dropwise over 30 min. Then the reaction mixture was stirred at 90° C. for another 3 h. After this time, the reaction mixture was cooled to room temperature, poured into mixture of sat. sodium bicarbonate solution (150 mL) and ethyl acetate (200 mL). The organic layer was separated, dried over anhydrous sodium sulfate and concentrated under reduced pressure. The crude material was purified by column chromatography (silica gel, 60% ethyl acetate/hexanes) to afford 3-chloro-5,6-dimethylpyrazine-2-carbonitrile (1-4, 8.31 g, yield: 69%) as a pale brown solid: $^1$H NMR (400 MHz, DMSO-d$_6$) δ 2.62 (s, 3H), 2.55 (s, 3H); ESI (m/z) 168 [C$_7$H$_9$N$_3$O$_2$+H]$^+$.

Step-4: Synthesis of (3-chloro-5,6-dimethylpyrazin-2-yl)methanamine (1-5)

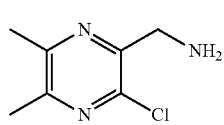

In 450 mL autoclave, to a stirred solution of 3-chloro-5,6-dimethylpyrazine-2-carbonitrile (I-4, 8.00 g, 47.9 mmol) in acetic acid (150 mL) was added Raney Nickel (1.6 g) under inert atmosphere and resulting reaction mixture was stirred for 20 h under hydrogen atmosphere (100 psi) at room temperature. After this time, the reaction mixture was passed through the celite bed and washed with acetic acid (2×20 mL). Excess of acetic acid was distilled off under reduced pressure, left behind viscous mass, poured into mixture of sat. sodium bicarbonate solution (150 mL) and ethyl acetate (200 mL). The organic layer was separated, dried over anhydrous sodium sulfate and concentrated under reduced pressure to afford 3-chloro-5,6-dimethylpyrazin-2-yl)methanamine (I-5, 5.00 g, yield: 60%) as a green solid: $^1$H NMR (400 MHz, DMSO-$d_6$) δ 3.83 (s, 2H), 2.62 (s, 3H), 2.55 (s, 3H); ESI (m/z) 172 $[C_7H_{10}ClN_3+H]^+$.

Step-5: Synthesis of N-((3-chloro-5,6-dimethylpyrazin-2-yl)methyl)acetamide (I-6)

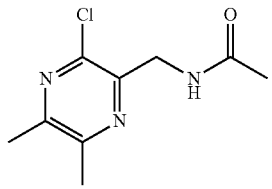

I-6

To a stirred solution of (3-chloro-5,6-dimethylpyrazin-2-yl)methanamine (I-5, 5.00 g, 29.13 mmol) in dichloromethane (50 mL) was added DIEA (10.15 mL, 58.27 mmol) followed by acetic anhydride (5.5 mL, 58.27 mmol) at 0° C. After, that reaction mixture was stirred for 2 h. After this time, the reaction mixture was diluted with dichloromethane (100 mL), washed with saturated NaCl solution (100 mL). The organic layer was separated, dried over anhydrous sodium sulfate and concentrated under reduced pressure. The crude product was purified by column chromatography (silica gel, 30% ethyl acetate/hexanes) to afford N-((3-chloro-5,6-dimethylpyrazin-2-yl)methyl) acetamide (I-6, 5.00 g, yield: 80%) as a yellow solid: $^1$H NMR (400 MHz, DMSO-$d_6$) δ 4.44 (d, J=5.6 Hz, 2H), 3.40 (brs, 1H), 2.52 (s, 3H), 2.50 (s, 3H), 1.85 (s, 3H).

Step-6: Synthesis of 8-chloro-3,5,6-trimethylimidazo[1,5-a]pyrazine (I-7)

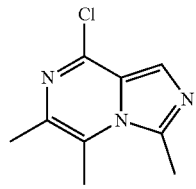

I-7

To a stirred solution of N-((3-chloro-5,6-dimethylpyrazin-2-yl)methyl) acetamide (I-6, 5.00 g, 29.94 mmol.) in acetonitrile (100 mL) were added dimethylformamide (0.50 mL) followed by phosphoryl chloride (8.3 mL, 153.3 mmol) at 0° C. This reaction mixture was heated to 80° C. and stirred for 2 h. After this time, the reaction mixture was cooled to room temperature and poured into mixture of saturated aqueous sodium bicarbonate solution (50 mL) and ethyl acetate (100 mL). The organic layer was separated, dried over anhydrous sodium sulfate and concentrated under reduced pressure. The crude material was purified by column chromatography (silica gel, 30% ethyl acetate/hexanes) to afford 8-chloro-3,5,6-trimethylimidazo[1,5-a]pyrazine (I-7, 3.50 g, yield: 77%) as a pale brown solid: $^1$H NMR (400 MHz, DMSO-$d_6$) δ 7.67 (s, 1H), 2.90 (s, 3H), 2.70 (s, 3H), 2.30 (s, 3H); ESI (m/z) 196 $[C_9H_{10}ClN_3+H]^+$.

Step-7: Synthesis of 1-bromo-8-chloro-3,5,6-trimethylimidazo[1,5-a]pyrazine (I-8)

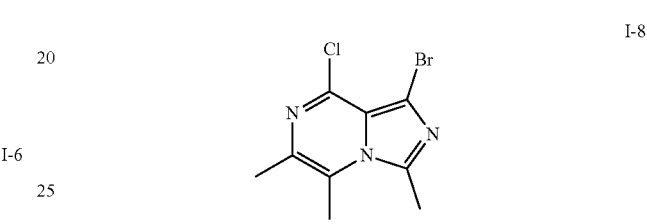

I-8

To a stirred solution of 8-chloro-3,5,6-trimethylimidazo[1,5-a]pyrazine (I-7, 5.00 g, 25.64 mmol) in dimethylformamide (50 mL) was added N-bromosuccinimide (4.56 g, 25.64 mmol) at 0° C. and stirred for 1 h. After this time, the reaction mixture was diluted with water (150 mL) and EtOAc (150 mL). The organic layer was separated, dried over anhydrous sodium sulfate and concentrated under reduced pressure. The crude material was purified by column chromatography (silica gel, 30% ethyl acetate/hexanes) to afford 1-bromo-8-chloro-3,5,6-trimethylimidazo[1,5-a]pyrazine (I-8, 6.00 g, yield: 85%) as a pale yellow solid: $^1$H NMR (400 MHz, DMSO-$d_6$) δ 2.90 (s, 3H), 2.70 (s, 3H), 2.30 (s, 3H); ESI (m/z) 274 $[C_9H_9BrClN_3+H]^+$.

Step-8: Synthesis of 1-bromo-8-chloro-3,5,6-trimethylimidazo[1,5-a]pyrazine (I-9)

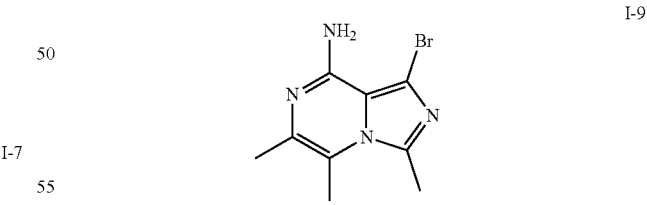

I-9

In a 1 L autoclave, a mixture of 1-bromo-8-chloro-3,5,6-trimethylimidazo[1,5-a]pyrazine (I-8, 6.00 g, 21.81 mmol) and ammonia (2M in isopropanol) (500 mL) was stirred for 12 h at 120° C. After this time, the reaction mixture was cooled to room temperature, excess of IPA was distilled off under reduced pressure to afford 1-bromo-3,6-dimethylimidazo[1,5-a]pyrazin-8-amine (I-9, 4.50 g, yield: 81%) as a pale yellow solid: $^1$H NMR (400 MHz, DMSO-$d_6$) δ 6.33 (s, 2H), 2.81 (s, 3H), 2.60 (s, 3H), 2.12 (s, 3H); ESI (m/z) 255 $[C_9H_{11}BrN_4+H]^+$.

Scheme J: Synthesis of 3-(8-amino-1-bromo-6-methylimidazo[1,5-a]pyrazin-3-yl)-1-methylcyclobutanol (J-2)

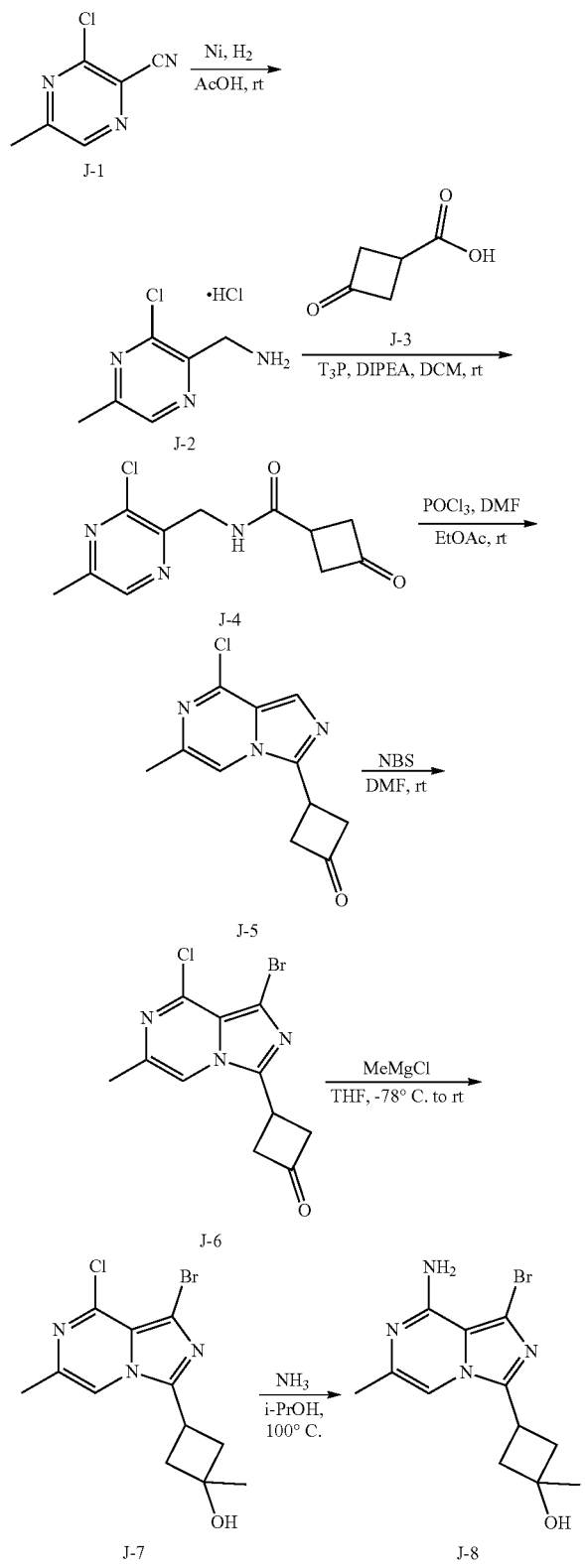

Step-1: Synthesis of (3-chloro-5-methylpyrazin-2-yl)methanamine (J-2)

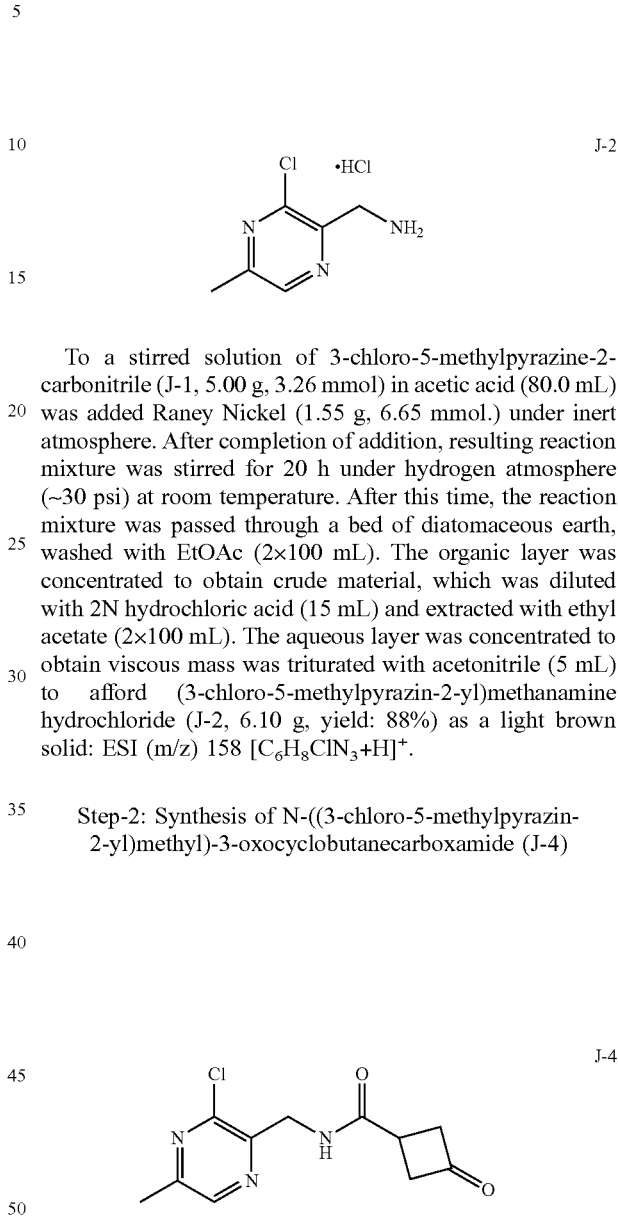

To a stirred solution of 3-chloro-5-methylpyrazine-2-carbonitrile (J-1, 5.00 g, 3.26 mmol) in acetic acid (80.0 mL) was added Raney Nickel (1.55 g, 6.65 mmol.) under inert atmosphere. After completion of addition, resulting reaction mixture was stirred for 20 h under hydrogen atmosphere (~30 psi) at room temperature. After this time, the reaction mixture was passed through a bed of diatomaceous earth, washed with EtOAc (2×100 mL). The organic layer was concentrated to obtain crude material, which was diluted with 2N hydrochloric acid (15 mL) and extracted with ethyl acetate (2×100 mL). The aqueous layer was concentrated to obtain viscous mass was triturated with acetonitrile (5 mL) to afford (3-chloro-5-methylpyrazin-2-yl)methanamine hydrochloride (J-2, 6.10 g, yield: 88%) as a light brown solid: ESI (m/z) 158 $[C_6H_8ClN_3+H]^+$.

Step-2: Synthesis of N-((3-chloro-5-methylpyrazin-2-yl)methyl)-3-oxocyclobutanecarboxamide (J-4)

To a stirred solution of (3-chloro-5-methylpyrazin-2-yl)methanamine hydrochloride (J-2, 3.00 g, 26.3 mmol) in dichloromethane (80 mL) were added N,N-diisopropylethylamine (22.9 mL, 131.5 mmol), T₃P (50% in EtOAc) (12 mL, 39.47 mmol) followed by 3-oxocyclobutanecarboxylic acid (J-3, 5.10 g, 26.31 mmol) at 0° C. and stirred for 1 h. After this time, the reaction mixture was diluted with dichloromethane (100 mL), washed with water (2×50 mL) and brine (50 mL). The combined organic layer was dried over anhydrous sodium sulfate and concentrated under reduced pressure. The crude material was washed with hexanes to afford N-((3-chloro-5-methylpyrazin-2-yl)methyl)-3-oxo cyclobutanecarboxamide (J-4, 4.65 g, yield: 71%) as an off white solid; ESI (m/z) 254 $[C_{11}H_{12}ClN_3O_2]+H]^+$.

Step-3: Synthesis of 3-(1-bromo-8-chloro-6-methyl-imidazo[1,5-a]pyrazin-3-yl)cyclobutanone (J-5)

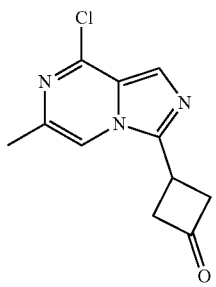

J-5

To a stirred solution of N-((3-chloro-5-methylpyrazin-2-yl)methyl)-3-oxocyclobutanecarboxamide (J-4, 4.70 g, 18.5 mmol) in EtOAc (80 mL) were added dimethylformamide (3 mL) followed by phosphoryl chloride (5.3 mL, 55.7 mmol) at 0° C. This reaction mixture was stirred at room temperature for 1 h. After this time, the reaction mixture was cooled to room temperature and poured into mixture of sat. sodium carbonate solution (100 mL) and ethyl acetate (200 mL). The organic layer was separated, dried over anhydrous sodium sulfate and concentrated under reduced pressure. The crude material was washed with hexanes to afford 3-(1-bromo-8-chloro-6-methylimidazo[1,5-a]pyrazin-3-yl)cyclobutanone (J-5, 3.10 g, yield: 70%) as an off white solid; ESI (m/z) 236 $[C_{11}H_{10}ClN_3O+H]^+$.

Step-4: Synthesis of 3-(1-bromo-8-chloro-6-methyl-imidazo[1,5-a]pyrazin-3-yl)cyclobutanone (J-6)

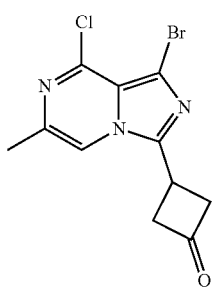

J-6

To a stirred solution of 3-(1-bromo-8-chloro-6-methyl-imidazo[1,5-a]pyrazin-3-yl)cyclobutanone (J-5, 3.00 g, 12.7 mmol) in dimethylformamide (15 mL) was added N-Bromosuccinimide (2.21 g, 12.7 mmol.) at room temperature. This reaction mixture was stirred at room temperature for 40 min. After this time, ice cool water (50 ml) was added, solid was precipitated out, was filtered and dried to afford 3-(1-bromo-8-chloro-6-methylimidazo[1,5-a]pyrazin-3-yl)cyclobutanone (J-6, 3.30 g, yield: 82%) as an off white solid; ESI (m/z) 313 $[C_{11}H_9BrClN_3O+H]^+$.

Step-5: Synthesis of 3-(1-bromo-8-chloro-6-methyl-imidazo[1,5-a]pyrazin-3-yl)-1-methylcyclobutanol J-7)

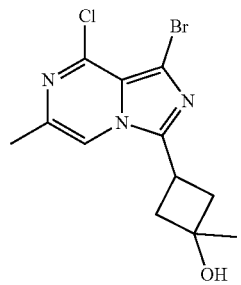

J-7

To a stirred solution of 3-(1-bromo-8-chloro-6-methyl-imidazo[1,5-a]pyrazin-3-yl)cyclobutanone (J-6, 3.30 g, 10.57 mmol) in anhydrous THF (35 mL) was charged methylmagnesium chloride (3M in THF) (7.1 mL, 21.15 mmol) dropwise at −78° C. over a period of 15 min under N2 and resulting mixture was stirred at −78° C. for an additional 2 h. After 2 h, then reaction mixture was warmed to −20° C. for 30 min. The mixture was cooled back to −78° C., quenched with sat. NH4Cl (60 mL) at same temperature and then warmed to room temperature. An aqueous layer extracted with EtOAc (100 mL×2), combined filtrate was washed with brine (50 mL). The combined organic layer was separated, dried over anhydrous Na2SO4 and concentrated under reduced pressure. The crude material was purified by column chromatography (silica gel, 50% EtOAc in hexanes) to afford 3-(1-bromo-8-chloro-6-methylimidazo[1,5-a]pyrazin-3-yl)-1-methylcyclobutanol (J-7, 2.31 g, yield: 62%) as a white solid; ESI (m/z) 331 $[C_{12}H_{13}BrClN_3O+H]^+$.

Step-6: Synthesis of 3-(8-amino-1-bromo-6-methyl-imidazo[1,5-a]pyrazin-3-yl)-1-methylcyclobutanol (J-8)

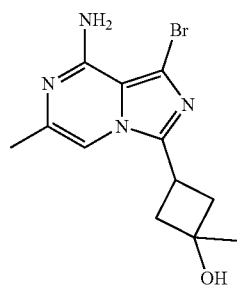

J-8

In a 450 mL autoclave, a mixture of 3-(1-bromo-8-chloro-6-methylimidazo[1,5-a]pyrazin-3-yl)-1-methylcyclobutanol (J-7, 1.50 g, 4.54 mmol) and ammonia (2M in isopropanol) (150 mL) was stirred for 18 h at 120° C. After this time, the reaction mixture was cooled to room temperature, excess of solvent was distilled off to afford 3-(8-amino-1-bromo-6-methylimidazo[1,5-a]pyrazin-3-yl)-1-methylcyclobutanol (J-8, 1.20 g, yield: 86%) as a pale brown solid; ESI (m/z) 312 $[C_{12}H_{15}BrN_4O+H]^+$.

Scheme K

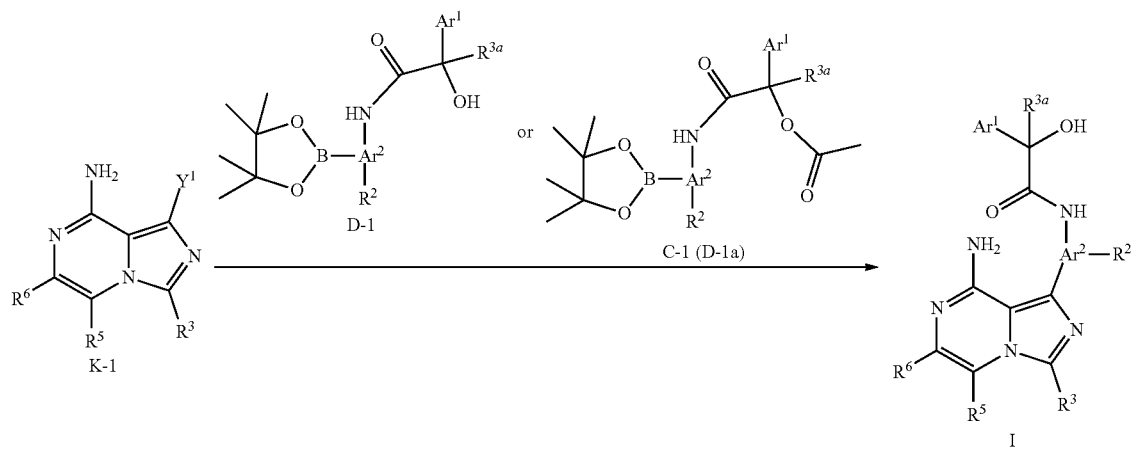

Compounds of Formula I can be synthesized according to the procedures for the synthesis of compound 1.1 wherein $R^6$=methyl, $R^5$=H, $R^3$=methyl, $Y^1$=I, $Ar^2$=phenyl, $R^2$=3-methyl, $R^{3a}$=H, $Ar^1$=phenyl-$R^1$ and $R^1$=3—F:

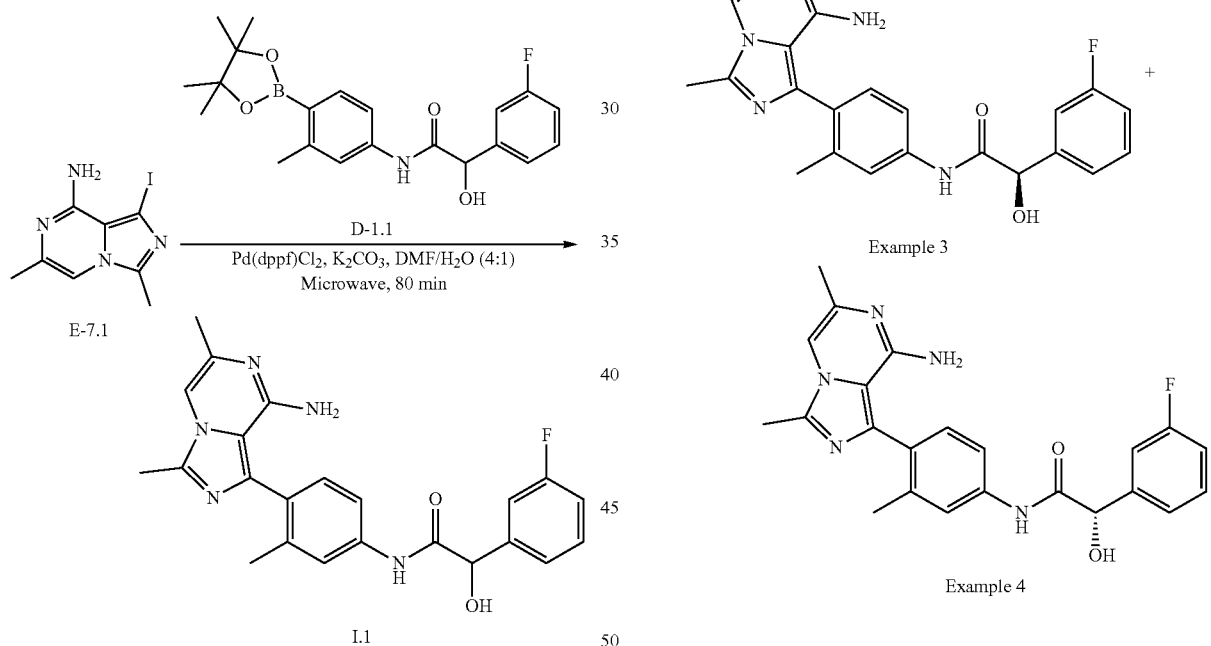

Synthesis of N-(4-(8-amino-3,6-dimethylimidazo[1,5-a]pyrazin-1-yl)-3-methylphenyl)-2-(3-fluorophenyl)-2-hydroxyacetamide (I.1: Racemate, Example 3 and Example 4)

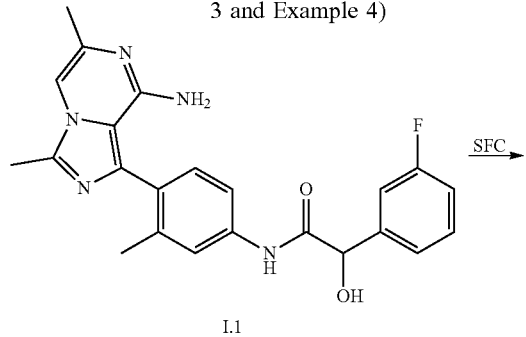

To a stirred solution of 1-iodo-3,6-dimethylimidazo[1,5-a]pyrazin-8-amine (E-7.1, 0.120 g, 0.417 mmol) and 2-(3-fluorophenyl)-2-hydroxy-N-(3-methyl-4-(4,4,5,5-tetramethyl-1,3,2-dioxaborolan-2-yl)phenyl)acetamide (D-1.1, 0.192 g, 0.5 mmol) in a mixture of N,N-dimethylformamide and H₂O (8.0 mL, 8:2) was added potassium carbonate (0.115 g, 0.832 mmol) and degassed with argon for 5 min. [1,1'-bis(diphenylphosphino)ferrocene]dichloropalladium (II) (0.015 g, 0.020 mmol) was added and the reaction mixture was degassed with argon gas for 5 min. This reaction mixture was exposed to microwave irradiation (SEM Company) at 120° C. for 80 min. After this time, the reaction mixture was diluted with ethyl acetate (15 mL) and washed with water (2×5 mL). The organic layer was separated, dried over anhydrous sodium sulphate and concentrated under reduced pressure. The crude material was purified by column chromatography (silica gel, 1% methanol/methylene chloride) to afford N-(4-(8-amino-3,6-dimethylimidazo[1,5-a]pyrazin-1-yl)-3-methylphenyl)-2-(3-fluorophenyl)-2-hydroxyacetamide (I.1, 40 mg, yield: 22%) as a pale brown solid: ESI (m/z) 420 [$C_{23}H_{22}FN_5O_2$+H]$^+$.

The mixture of enantiomers was purified by chiral supercritical fluid chromatography (SFC) (Chiralcel® OX—H column, 30% methanol in $CO_2$, 40° C. temperature) to afford:

Isomer 1 (Example 3) as a pale brown solid: $^1$H NMR (400 MHz, DMSO-$d_6$) δ 10.05 (s, 1H), 7.69 (s, 1H), 7.63 (d, J=7.6 Hz, 1H), 7.42-7.34 (m, 3H), 7.18-7.11 (m, 2H), 6.63 (s, 2H), 6.35 (br s, 2H), 5.16 (s, 1H), 2.84 (s, 3H), 2.59 (s, 3H) 2.10 (s, 3H); ESI (m/z) 420 [$C_{23}H_{22}FN_5O_2$+H]$^+$; HPLC (Method D) 99.0% (AUC), $t_R$=4.82 min; Chiral SFC (Chiralcel OJ-H, Method E)>99% (AUC), $t_R$=2.18 min.

Isomer (Example 4) as a pale brown solid: $^1$H NMR (400 MHz, DMSO-$d_6$) δ 10.05 (s, 1H), 7.69 (s, 1H), 7.63 (d, J=7.6 Hz, 1H), 7.42-7.34 (m, 3H), 7.18-7.11 (m, 2H), 6.63 (s, 2H), 6.35 (br s, 2H), 5.16 (s, 1H), 2.84 (s, 3H), 2.59 (s, 3H) 2.10 (s, 3H); ESI (m/z) 420 [$C_{23}H_{22}FN_5O_2$+H]$^+$, HPLC (Method D) 97.9% (AUC), $t_R$=4.58 min; Chiral SFC (Chiralcel OJ-H, Method E)>99% (AUC), $t_R$=2.77 min.

The compounds of formula I (Table 1) can be synthesized according to the procedures described in Scheme K:

TABLE 1

Compounds of Formula I:

| Example | Name | Compounds I-B-3 | MS | Method |
|---|---|---|---|---|
| 1 | N-(4-(8-amino-3-methylimidazo[1,5-a]pyrazin-1-yl)-3-methylphenyl)-2-(3-fluorophenyl)-2-hydroxyacetamide | Isomer 1 | ESI (m/z) 406 [$C_{22}H_{20}FN_5O_2$ + H]$^+$ | Scheme K |
| 2 | N-(4-(8-amino-3-methylimidazo[1,5-a]pyrazin-1-yl)-3-methylphenyl)-2-(3-fluorophenyl)-2-hydroxyacetamide | Isomer 2 | ESI (m/z) 406 [$C_{22}H_{20}FN_5O_2$ + H]$^+$ | Scheme K |
| 3 | N-(4-(8-amino-3,6-dimethylimidazo[1,5-a]pyrazin-1-yl)-3-methylphenyl)-2-(3-fluorophenyl)-2-hydroxyacetamide | Isomer 1 | ESI (m/z) 420 [$C_{23}H_{22}FN_5O_2$ + H]$^+$ | Scheme K |

TABLE 1-continued

Compounds of Formula I:

| Example | Name | Compounds I-B-3 | MS | Method |
|---|---|---|---|---|
| 4 | N-(4-(8-amino-3,6-dimethylimidazo[1,5-a]pyrazin-1-yl)-3-methylphenyl)-2-(3-fluorophenyl)-2-hydroxyacetamide | 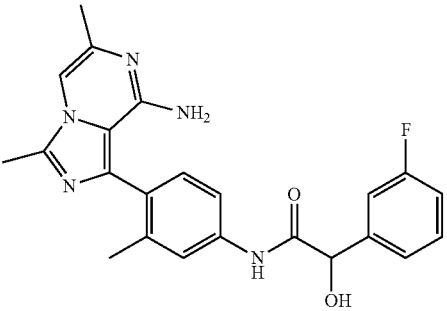 Isomer 2 | ESI (m/z) 420 $[C_{23}H_{22}FN_5O_2 + H]^+$ | Scheme K |
| 5 | N-(4-(8-amino-6-methyl-3-(trideuteriomethyl)imidazo[1,5-a]pyrazin-1-yl)-3-methylphenyl)-2-(3-fluorophenyl)-2-hydroxyacetamide | 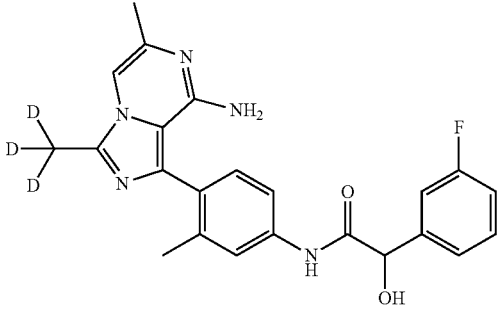 Racemate | ESI (m/z) 423 $[C_{23}H_{19}D_3FN_5O_2 + H]^+$ | Scheme K |
| 6 | N-(4-(8-amino-3-methylimidazo[1,5-a]pyrazin-1-yl)-3-methylphenyl)-2-(3-fluorophenyl)-2-hydroxyacetamide | 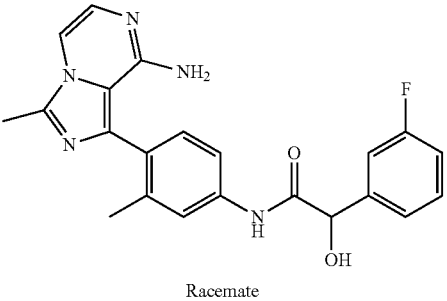 [SMILES: Cc1cc(NC(=O)C(O)c2cccc(F)c2)ccc1-c1nc(C)n2ccnc(N)c12] Racemate | ESI (m/z) 406 $[C_{22}H_{20}FN_5O_2 + H]^+$ | Scheme K |
| 7 | N-(4-(8-amino-3,6-dimethylimidazo[1,5-a]pyrazin-1-yl)-3-methylphenyl)-2-(3-fluorophenyl)-2-hydroxyacetamide | 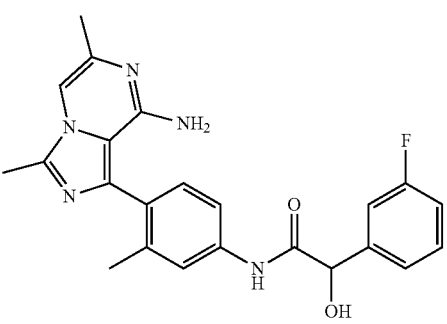 Racemate | ESI (m/z) 420 $[C_{23}H_{22}FN_5O_2 + H]^+$ | Scheme K |

TABLE 1-continued

Compounds of Formula I:

| Example | Name | Compounds I-B-3 | MS | Method |
|---|---|---|---|---|
| 8 | N-(4-(8-amino-3,5-dimethylimidazo[1,5-a]pyrazin-1-yl)-3-methylphenyl)-2-(3-fluorophenyl)-2-hydroxyacetamide | 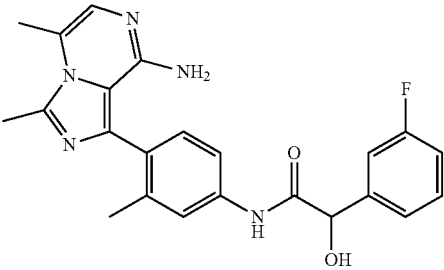<br>Isomer 1 | ESI (m/z) 420 $[C_{23}H_{22}FN_5O_2 + H]^+$ | Scheme K |
| 9 | N-(4-(8-amino-3,5-dimethylimidazo[1,5-a]pyrazin-1-yl)-3-methylphenyl)-2-(3-fluorophenyl)-2-hydroxyacetamide | 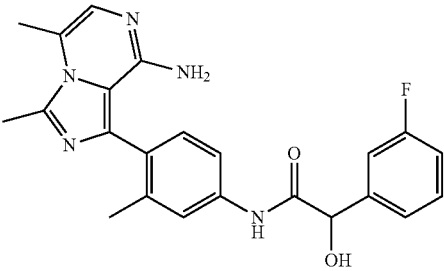<br>Isomer 2 | ESI (m/z) 420 $[C_{23}H_{22}FN_5O_2 + H]^+$ | Scheme K |
| 10 | N-(4-(8-amino-5-methyl-3-(trideuteriomethyl)imidazo[1,5-a]pyrazin-1-yl)-3-methylphenyl)-2-(3-fluorophenyl)-2-hydroxyacetamide | 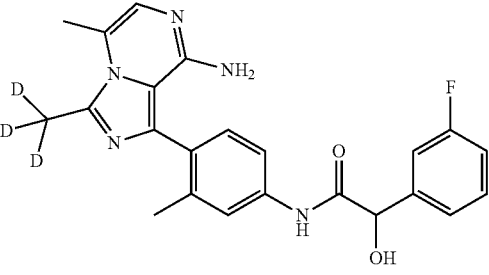<br>Racemate | ESI (m/z) 423 $[C_{23}H_{19}D_3FN_5O_2 + H]^+$ | Scheme K |
| 11 | N-(4-(8-amino-5-methyl-3-(trideuteriomethyl)imidazo[1,5-a]pyrazin-1-yl)-3-methylphenyl)-2-(3-fluorophenyl)-2-hydroxyacetamide | 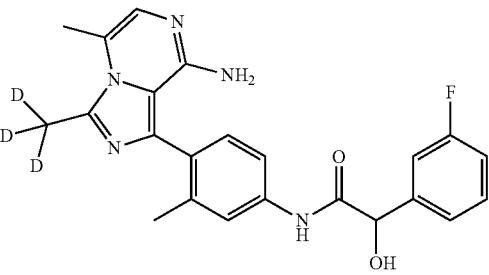<br>Isomer 1 | ESI (m/z) 423 $[C_{23}H_{19}D_3FN_5O_2 + H]^+$ | Scheme K |

TABLE 1-continued

Compounds of Formula I:

| Example | Name | Compounds I-B-3 | MS | Method |
|---|---|---|---|---|
| 12 | N-(4-(8-amino-5-methyl-3-(trideuteriomethyl)imidazo[1,5-a]pyrazin-1-yl)-3-methylphenyl)-2-(3-fluorophenyl)-2-hydroxyacetamide | 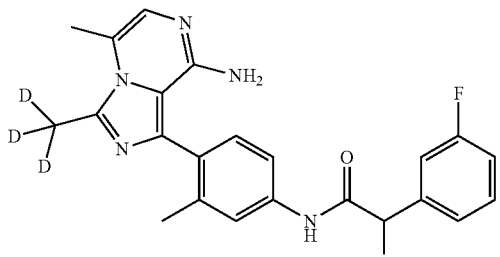<br>Isomer 2 | ESI (m/z) 423 $[C_{23}H_{19}D_3FN_5O_2 + H]^+$ | Scheme K |
| 13 | N-(4-(8-amino-3,6-dimethylimidazo[1,5-a]pyrazin-1-yl)-3-methylphenyl)-2-(3-fluorophenyl)-2-hydroxyacetamide | 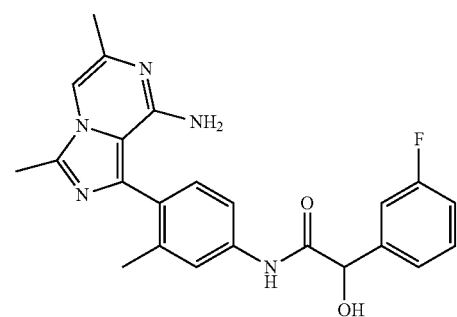<br>Racemate | ESI (m/z) 420 $[C_{23}H_{22}FN_5O_2 + H]^+$ | Scheme K |
| 14 | N-[4-[8-amino-6-methyl-3-(trideuteriomethyl)imidazo[1,5-a]pyrazin-1-yl]-3-methyl-phenyl]-2-hydroxy-2-[3-(trifluoromethyl)phenyl]acetamide | 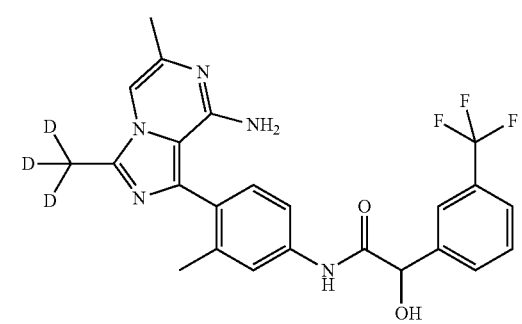<br>Isomer 1 | ESI (m/z) 473 $[C_{24}H_{19}D_3F_3N_5O_2 + H]^+$ | Scheme K |
| 15 | N-[4-[8-amino-6-methyl-3-(trideuteriomethyl)imidazo[1,5-a]pyrazin-1-yl]-3-methyl-phenyl]-2-hydroxy-2-[3-(trifluoromethyl)phenyl]acetamide | 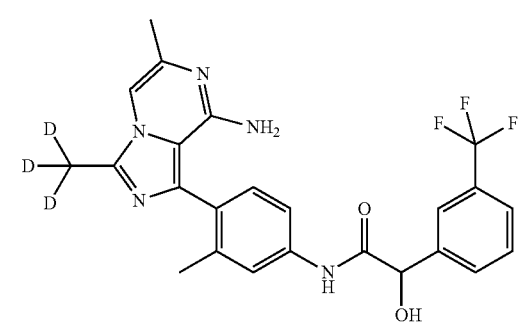<br>Isomer 2 | ESI (m/z) 473 $[C_{24}H_{19}D_3F_3N_5O_2 + H]^+$ | Scheme K |

TABLE 1-continued

Compounds of Formula I:

| Example | Name | Compounds I-B-3 | MS | Method |
|---|---|---|---|---|
| 16 | N-[4-[8-amino-5-methyl-3-(trideuteriomethyl)imidazo[1,5-a]pyrazin-1-yl]-3-methyl-phenyl]-2-hydroxy-2-[3-(trifluoromethyl)phenyl]acetamide | 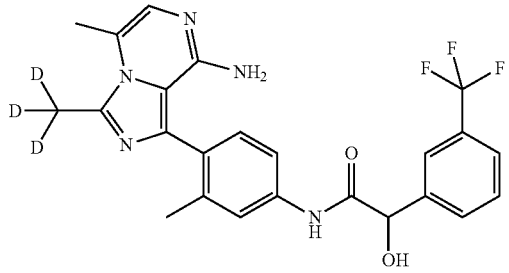 Isomer 1 | ESI (m/z) 473 $[C_{24}H_{19}D_3F_3N_5O_2 + H]^+$ | Scheme K |
| 17 | N-[4-[8-amino-5-methyl-3-(trideuteriomethyl)imidazo[1,5-a]pyrazin-1-yl]-3-methyl-phenyl]-2-hydroxy-2-[3-(trifluoromethyl)phenyl]acetamide | 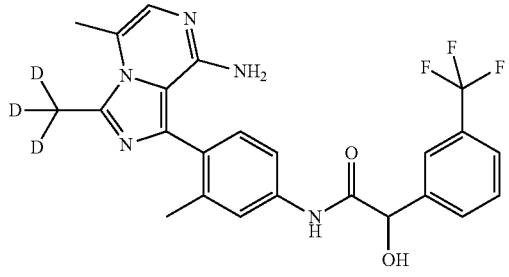 Isomer 2 | ESI (m/z) 473 $[C_{24}H_{19}D_3F_3N_5O_2 + H]^+$ | Scheme K |
| 18 | N-[4-[8-amino-5-chloro-3-(trideuteriomethyl)imidazo[1,5-a]pyrazin-1-yl]-3-methyl-phenyl]-2-hydroxy-2-[3-(trifluoromethyl)phenyl]acetamide | 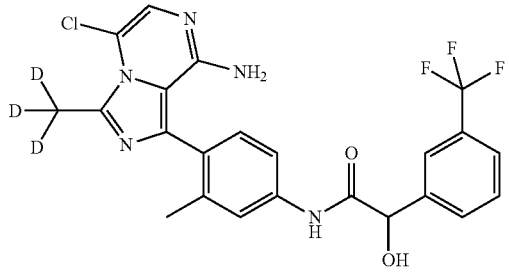 Isomer 1 | ESI (m/z) 493 $[C_{23}H_{16}D_3ClF_3N_5O_2 + H]^+$ | Scheme K |
| 19 | N-[4-[8-amino-5-chloro-3-(trideuteriomethyl)imidazo[1,5-a]pyrazin-1-yl]-3-methyl-phenyl]-2-hydroxy-2-[3-(trifluoromethyl)phenyl]acetamide | 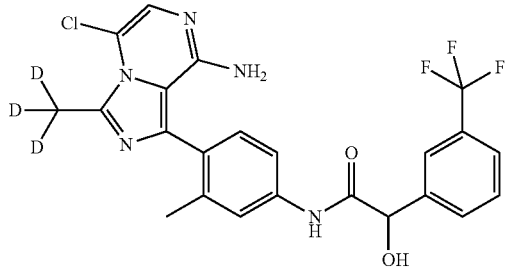 Isomer 2 | ESI (m/z) 493 $[C_{23}H_{16}D_3ClF_3N_5O_2 + H]^+$ | Scheme K |

TABLE 1-continued

Compounds of Formula I:

| Example | Name | Compounds I-B-3 | MS | Method |
|---|---|---|---|---|
| 20 | N-[4-[8-amino-3-(trideuteriomethyl)-5-(trifluoromethyl)imidazo[1,5-a]pyrazin-1-yl]-3-methyl-phenyl]-2-hydroxy-2-[3-(trifluoromethyl)phenyl]acetamide | 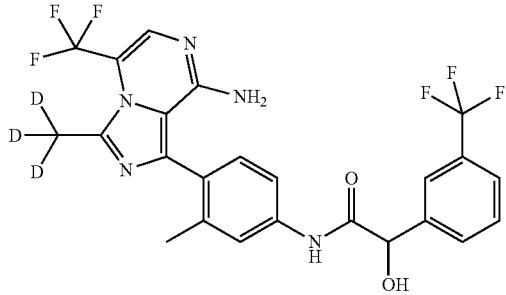 Isomer 1 | ESI (m/z) 527 $[C_{24}H_{16}D_3F_6N_5O_2 + H]^+$ | Scheme K |
| 21 | N-[4-[8-amino-3-(trideuteriomethyl)-5-(trifluoromethyl)imidazo[1,5-a]pyrazin-1-yl]-3-methyl-phenyl]-2-hydroxy-2-[3-(trifluoromethyl)phenyl]acetamide | 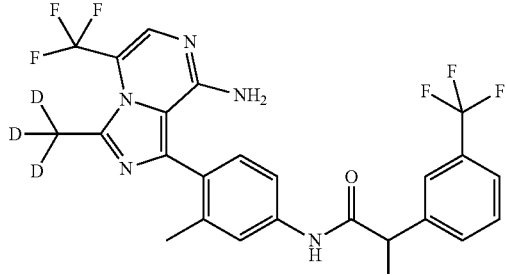 Isomer 2 | ESI (m/z) 527 $[C_{24}H_{16}D_3F_6N_5O_2 + H]^+$ | Scheme K |
| 22 | N-(4-(8-amino-3,5,6-trimethylimidazo[1,5-a]pyrazin-1-yl)-3-methyl-phenyl)-2-(3-fluorophenyl)-2-hydroxyacetamide | 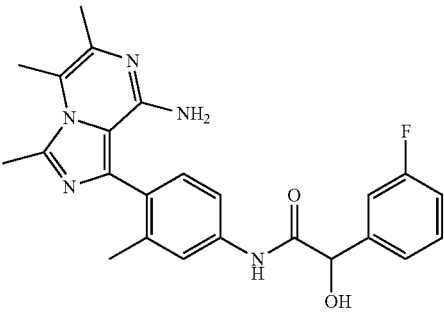 Isomer 1 | ESI (m/z) 434 $[C_{24}H_{24}FN_5O_2 + H]^+$ | Scheme K |
| 23 | N-(4-(8-amino-3,5,6-trimethylimidazo[1,5-a]pyrazin-1-yl)-3-methyl-phenyl)-2-(3-fluorophenyl)-2-hydroxyacetamide | 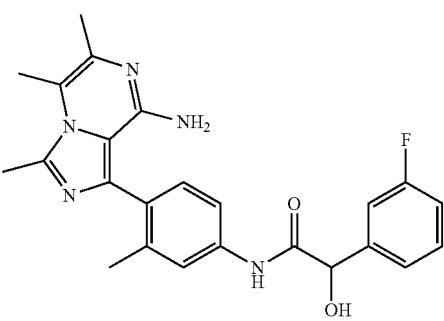 Isomer 2 | ESI (m/z) 434 $[C_{24}H_{24}FN_5O_2 + H]^+$ | Scheme K |

TABLE 1-continued

Compounds of Formula I:

| Example | Name | Compounds I-B-3 | MS | Method |
|---|---|---|---|---|
| 24 | N-(4-(8-amino-3-(3-hydroxy-3-methylcyclobutyl)-6-methylimidazo[1,5-a]pyrazin-1-yl)-3-methylphenyl)-2-(3-fluorophenyl)-2-hydroxyacetamide | 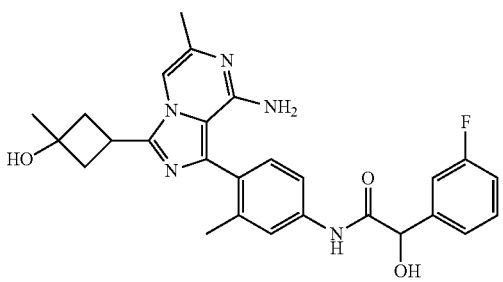<br>Isomer 1 | ESI (m/z) 490 $[C_{27}H_{28}FN_5O_3 + H]^+$ | Scheme K |
| 25 | N-(4-(8-amino-3-(3-hydroxy-3-methylcyclobutyl)-6-methylimidazo[1,5-a]pyrazin-1-yl)-3-methylphenyl)-2-(3-fluorophenyl)-2-hydroxyacetamide | 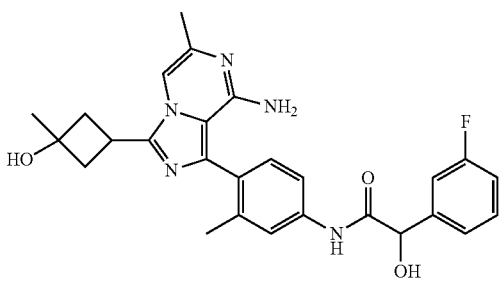<br>Isomer 2 | ESI (m/z) 490 $[C_{27}H_{28}FN_5O_3 + H]^+$ | Scheme K |
| 26 | N-(4-(8-amino-3-methyl-5-(trifluoromethyl)imidazo[1,5-a]pyrazin-1-yl)-3-methylphenyl)-2-(3-fluorophenyl)-2-hydroxyacetamide | 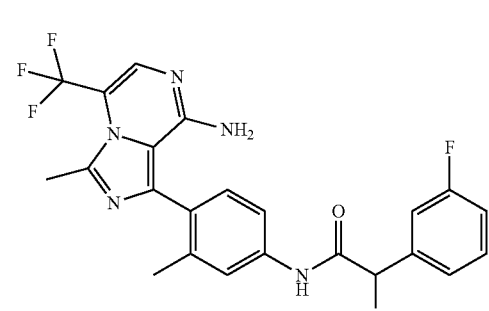<br>Isomer 1 | ESI (m/z) 474 $[C_{23}H_{19}F_4N_5O_2 + H]^+$ | Scheme K |
| 27 | N-(4-(8-amino-3-methyl-5-(trifluoromethyl)imidazo[1,5-a]pyrazin-1-yl)-3-methylphenyl)-2-(3-fluorophenyl)-2-hydroxyacetamide | 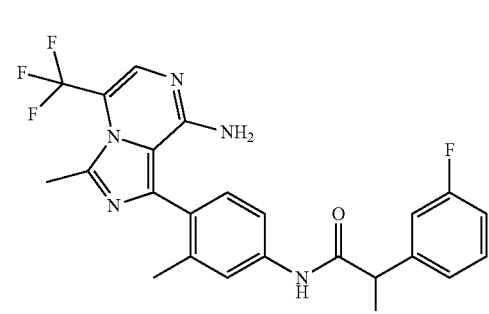<br>Isomer 2 | ESI (m/z) 474 $[C_{23}H_{19}F_4N_5O_2 + H]^+$ | Scheme K |

TABLE 1-continued

Compounds of Formula I:

| Example | Name | Compounds I-B-3 | MS | Method |
|---|---|---|---|---|
| 28 | N-(4-(8-amino-5-chloro-3-methylimidazo[1,5-a]pyrazin-1-yl)-3-methylphenyl)-2-(3-fluorophenyl)-2-hydroxyacetamide | 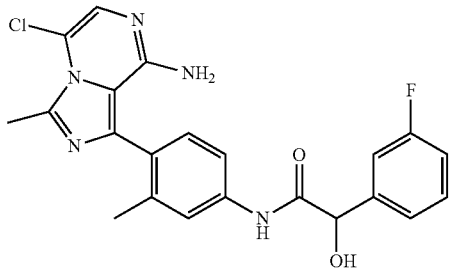 Isomer 1 | ESI (m/z) 440 $[C_{22}H_{19}ClFN_5O_2 + H]^+$ | Scheme K |
| 29 | N-(4-(8-amino-5-chloro-3-methylimidazo[1,5-a]pyrazin-1-yl)-3-methylphenyl)-2-(3-fluorophenyl)-2-hydroxyacetamide | 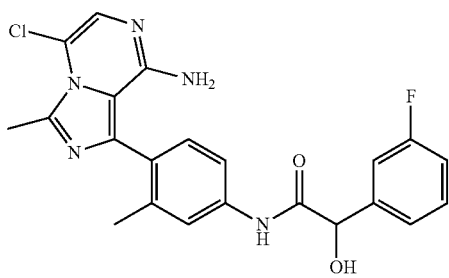 Isomer 2 | ESI (m/z) 440 $[C_{22}H_{19}ClFN_5O_2 + H]^+$ | Scheme K |
| 30 | N-[4-[8-amino-3-(trideuteriomethyl)-5-(trifluoromethyl)imidazo[1,5-a]pyrazin-1-yl]-3-methyl-phenyl]-2-(3-fluorophenyl)-2-hydroxy-acetamide | 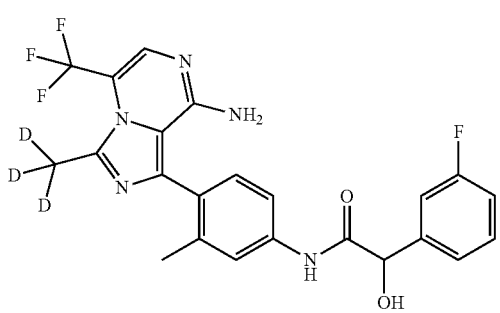 Isomer 1 | ESI (m/z) 477 $[C_{23}H_{16}D_3F_4N_5O_2 + H]^+$ | Scheme K |
| 31 | N-[4-[8-amino-3-(trideuteriomethyl)-5-(trifluoromethyl)imidazo[1,5-a]pyrazin-1-yl]-3-methyl-phenyl]-2-(3-fluorophenyl)-2-hydroxy-acetamide | 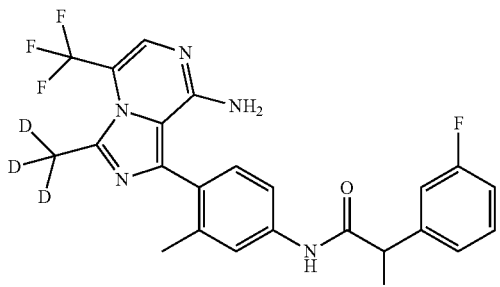 Isomer 2 | ESI (m/z) 477 $[C_{23}H_{16}D_3F_4N_5O_2 + H]^+$ | Scheme K |

TABLE 1-continued

| | | Compounds of Formula I: | | |
|---|---|---|---|---|
| Example | Name | Compounds I-B-3 | MS | Method |
| 32 | N-[4-[8-amino-5-chloro-3-(trideuteriomethyl)imidazo[1,5-a]pyrazin-1-yl]-3-methyl-phenyl]-2-(3-fluorophenyl)-2-hydroxy-acetamide | 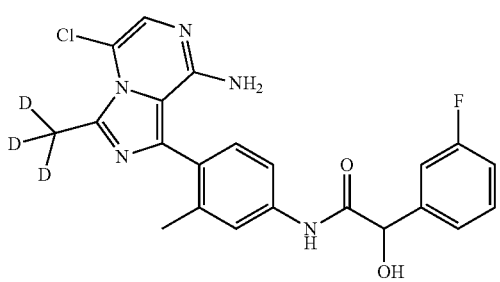<br>Isomer 1 | ESI (m/z) 443 $[C_{22}H_{16}D_3ClFN_5O_2 + H]^+$ | Scheme K |
| 33 | N-[4-[8-amino-5-chloro-3-(trideuteriomethyl)imidazo[1,5-a]pyrazin-1-yl]-3-methyl-phenyl]-2-(3-fluorophenyl)-2-hydroxy-acetamide | 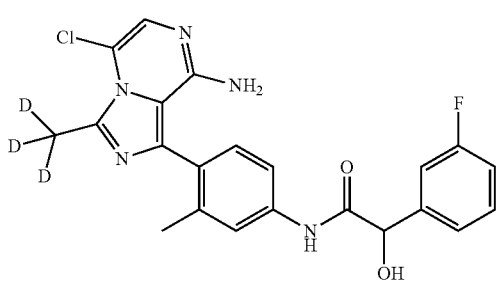<br>Isomer 2 | ESI (m/z) 443 $[C_{22}H_{16}D_3ClFN_5O_2 + H]^+$ | Scheme K |
| 34 | N-[4-[8-amino-6-methyl-3-(trideuteriomethyl)imidazo[1,5-a]pyrazin-1-yl]-3-methyl-phenyl]-2-(3-chlorophenyl)-2-hydroxy-acetamide | 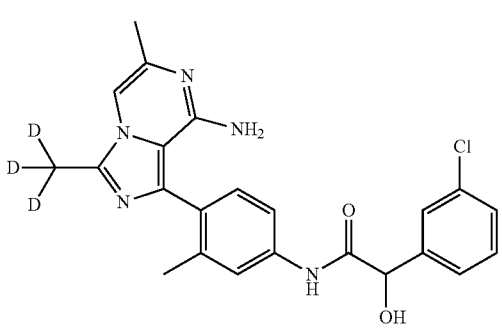<br>Isomer 1 | ESI (m/z) 439 $[C_{23}H_{19}D_3ClN_5O_2 + H]^+$ | Scheme K |
| 35 | N-[4-[8-amino-6-methyl-3-(trideuteriomethyl)imidazo[1,5-a]pyrazin-1-yl]-3-methyl-phenyl]-2-(3-chlorophenyl)-2-hydroxy-acetamide | 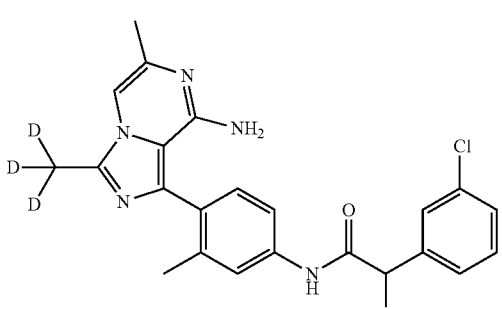<br>Isomer 2 | ESI (m/z) 439 $[C_{23}H_{19}D_3ClN_5O_2 + H]^+$ | Scheme K |

TABLE 1-continued

Compounds of Formula I:

| Example | Name | Compounds I-B-3 | MS | Method |
|---|---|---|---|---|
| 36 | N-[4-[8-amino-5-methyl-3-(trideuteriomethyl)imidazo[1,5-a]pyrazin-1-yl]-3-methyl-phenyl]-2-(3-chlorophenyl)-2-hydroxy-acetamide | 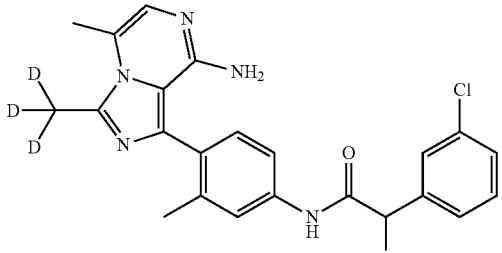 Isomer 1 | ESI (m/z) 439 [$C_{23}H_{19}D_3ClN_5O_2$ + H]$^+$ | Scheme K |
| 37 | N-[4-[8-amino-5-methyl-3-(trideuteriomethyl)imidazo[1,5-a]pyrazin-1-yl]-3-methyl-phenyl]-2-(3-chlorophenyl)-2-hydroxy-acetamide | 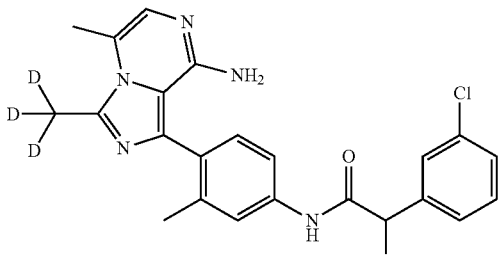 Isomer 2 | ESI (m/z) 439 [$C_{23}H_{19}D_3ClN_5O_2$ + H]$^+$ | Scheme K |
| 38 | N-(4-(8-amino-3,5-dimethylimidazo[1,5-a]pyrazin-1-yl)-3-methyl-phenyl)-2-(3-chlorophenyl)-2-hydroxyacetamide | 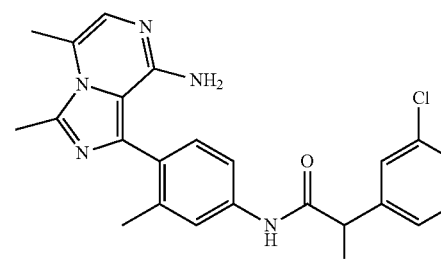 Isomer 1 | ESI (m/z) 436 [$C_{23}H_{22}ClN_5O_2$ + H]$^+$ | Scheme K |
| 39 | N-(4-(8-amino-3,5-dimethylimidazo[1,5-a]pyrazin-1-yl)-3-methyl-phenyl)-2-(3-chlorophenyl)-2-hydroxyacetamide | 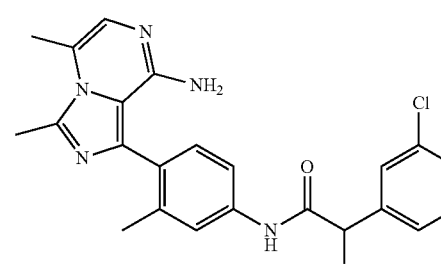 Isomer 2 | ESI (m/z) 436 [$C_{23}H_{22}ClN_5O_2$ + H]$^+$ | Scheme K |

TABLE 1-continued

Compounds of Formula I:

| Example | Name | Compounds I-B-3 | MS | Method |
|---|---|---|---|---|
| 40 | N-[4-[8-amino-3-(trideuteriomethyl)-5-(trifluoromethyl)imidazo[1,5-a]pyrazin-1-yl]-3-methyl-phenyl]-2-(3-chlorophenyl)-2-hydroxy-acetamide | 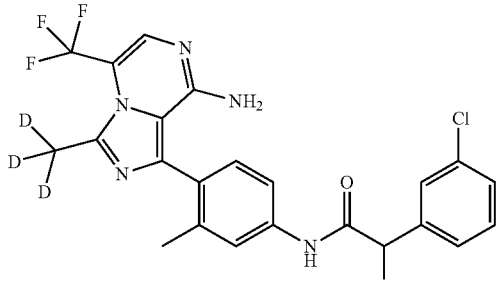<br>Isomer 1 | ESI (m/z) 493 $[C_{23}H_{16}D_3ClF_3N_5O_2 + H]^+$ | Scheme K |
| 41 | N-[4-[8-amino-3-(trideuteriomethyl)-5-(trifluoromethyl)imidazo[1,5-a]pyrazin-1-yl]-3-methyl-phenyl]-2-(3-chlorophenyl)-2-hydroxy-acetamide | 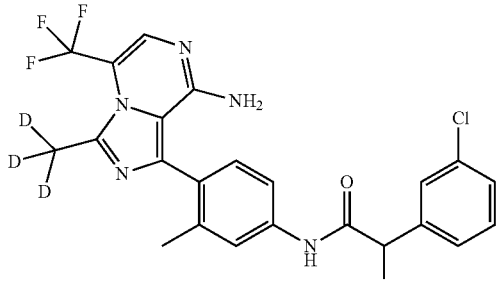<br>Isomer 2 | ESI (m/z) 493 $[C_{23}H_{16}D_3ClF_3N_5O_2 + H]^+$ | Scheme K |
| 42 | N-[4-[8-amino-5-chloro-3-(trideuteriomethyl)imidazo[1,5-a]pyrazin-1-yl]-3-methyl-phenyl]-2-(3-chlorophenyl)-2-hydroxy-acetamide | 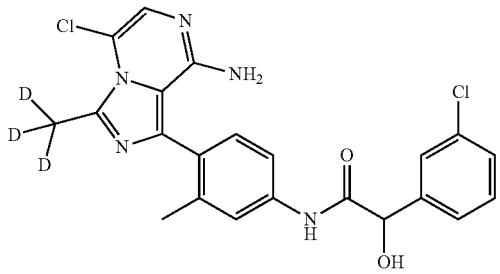<br>Isomer 1 | ESI (m/z) 459 $[C_{22}H_{16}D_3Cl_2N_5O_2 + H]^+$ | Scheme K |
| 43 | N-[4-[8-amino-5-chloro-3-(trideuteriomethyl)imidazo[1,5-a]pyrazin-1-yl]-3-methyl-phenyl]-2-(3-chlorophenyl)-2-hydroxy-acetamide | 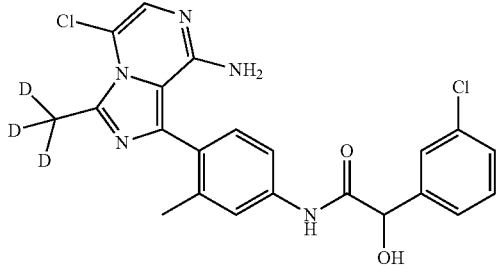<br>Isomer 2 | ESI (m/z) 459 $[C_{22}H_{16}D_3Cl_2N_5O_2 + H]^+$ | Scheme K |

TABLE 1-continued

Compounds of Formula I:

| Example | Name | Compounds I-B-3 | MS | Method |
|---|---|---|---|---|
| 44 | N-[4-[8-amino-6-methyl-3-(trideuteriomethyl)imidazo[1,5-a]pyrazin-1-yl]-3-methyl-phenyl]-2-(3,5-difluoro-phenyl)-2-hydroxy-acetamide | Isomer 1 | ESI (m/z) 441 $[C_{23}H_{18}D_3F_2N_5O_2 + H]^+$ | Scheme K |
| 45 | N-[4-[8-amino-6-methyl-3-(trideuteriomethyl)imidazo[1,5-a]pyrazin-1-yl]-3-methyl-phenyl]-2-(3,5-difluoro-phenyl)-2-hydroxy-acetamide | Isomer 2 | ESI (m/z) 441 $[C_{23}H_{18}D_3F_2N_5O_2 + H]^+$ | Scheme K |
| 46 | N-[4-[8-amino-3-(trideuteriomethyl)-5-(trifluoromethyl)imidazo[1,5-a]pyrazin-1-yl]-3-methyl-phenyl]-2-(3,5-difluoro-phenyl)-2-hydroxy-acetamide | Isomer 1 | ESI (m/z) 495 $[C_{23}H_{15}D_3F_5N_5O_2 + H]^+$ | Scheme K |
| 47 | N-[4-[8-amino-3-(trideuteriomethyl)-5-(trifluoromethyl)imidazo[1,5-a]pyrazin-1-yl]-3-methyl-phenyl]-2-(3,5-difluoro-phenyl)-2-hydroxy-acetamide | Isomer 2 | ESI (m/z) 495 $[C_{23}H_{15}D_3F_5N_5O_2 + H]^+$ | Scheme K |

TABLE 1-continued

Compounds of Formula I:

| Example | Name | Compounds I-B-3 | MS | Method |
|---|---|---|---|---|
| 48 | N-[4-[8-amino-5-chloro-3-(trideuteriomethyl)imidazo[1,5-a]pyrazin-1-yl]-3-methyl-phenyl]-2-(3,5-difluorophenyl)-2-hydroxy-acetamide | 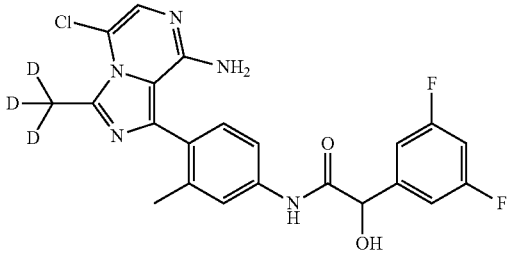<br>Isomer 1 | ESI (m/z) 461 [$C_{22}H_{15}D_3ClF_2N_5O_2$ + H]$^+$ | Scheme K |
| 49 | N-[4-[8-amino-5-chloro-3-(trideuteriomethyl)imidazo[1,5-a]pyrazin-1-yl]-3-methyl-phenyl]-2-(3,5-difluorophenyl)-2-hydroxy-acetamide | 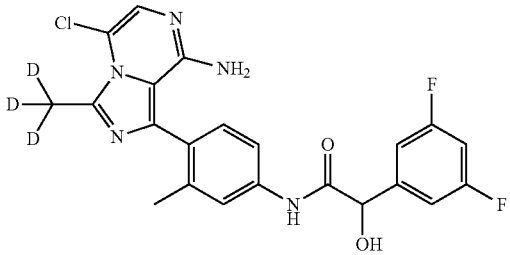<br>Isomer 2 | ESI (m/z) 461 [$C_{22}H_{15}D_3ClF_2N_5O_2$ + H]$^+$ | Scheme K |
| 50 | N-[4-[8-amino-5-methyl-3-(trideuteriomethyl)imidazo[1,5-a]pyrazin-1-yl]-3-methyl-phenyl]-2-(3,5-difluorophenyl)-2-hydroxy-acetamide | 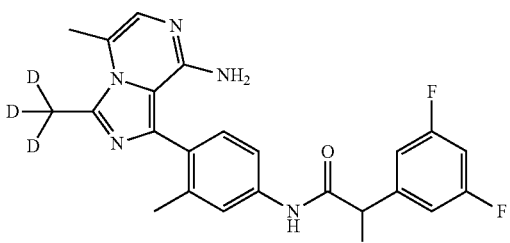<br>Isomer 1 | ESI (m/z) 441 [$C_{23}H_{18}D_3F_2N_5O_2$ + H]$^+$ | Scheme K |
| 51 | N-[4-[8-amino-5-methyl-3-(trideuteriomethyl)imidazo[1,5-a]pyrazin-1-yl]-3-methyl-phenyl]-2-(3,5-difluorophenyl)-2-hydroxy-acetamide | 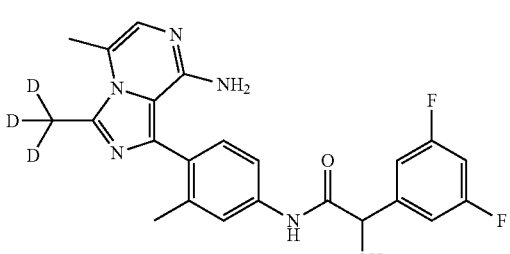<br>Isomer 2 | ESI (m/z) 441 [$C_{23}H_{18}D_3F_2N_5O_2$ + H]$^+$ | Scheme K |
| 52 | N-[4-[8-amino-6-methyl-3-(trideuteriomethyl)imidazo[1,5-a]pyrazin-1-yl]-3-methyl-phenyl]-2-[3-fluoro-5-(trifluoromethyl)phenyl]-2-hydroxy-acetamide | 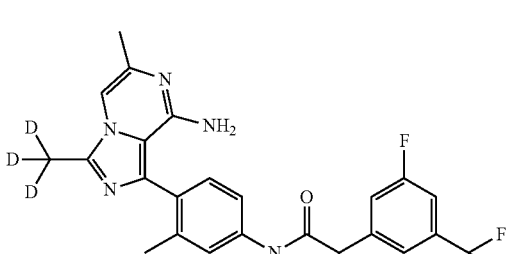<br>Isomer 1 | ESI (m/z) 491 [$C_{24}H_{18}D_3F_4N_5O_2$ + H]$^+$ | Scheme K |

TABLE 1-continued

Compounds of Formula I:

| Example | Name | Compounds I-B-3 | MS | Method |
|---|---|---|---|---|
| 53 | N-[4-[8-amino-6-methyl-3-(trideuteriomethyl)imidazo[1,5-a]pyrazin-1-yl]-3-methyl-phenyl]-2-[3-fluoro-5-(trifluoromethyl)phenyl]-2-hydroxy-acetamide | 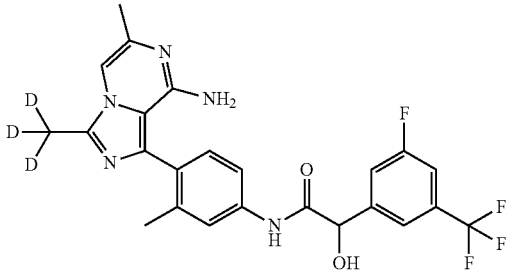<br>Isomer 2 | ESI (m/z) 491 [$C_{24}H_{18}D_3F_4N_5O_2$ + H]$^+$ | Scheme K |
| 54 | N-[4-[8-amino-5-methyl-3-(trideuteriomethyl)imidazo[1,5-a]pyrazin-1-yl]-3-methyl-phenyl]-2-[3-fluoro-5-(trifluoromethyl)phenyl]-2-hydroxy-acetamide | 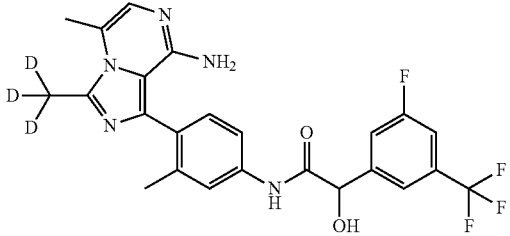<br>Isomer 1 | ESI (m/z) 490 [$C_{24}H_{18}D_3F_4N_5O_2$ + H]$^+$ | Scheme K |
| 55 | N-[4-[8-amino-5-methyl-3-(trideuteriomethyl)imidazo[1,5-a]pyrazin-1-yl]-3-methyl-phenyl]-2-[3-fluoro-5-(trifluoromethyl)phenyl]-2-hydroxy-acetamide | 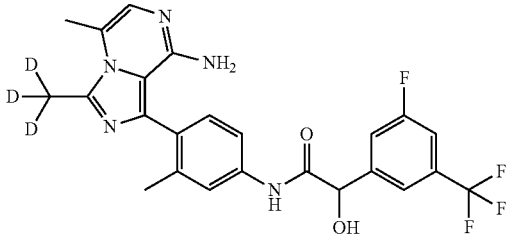<br>Isomer 2 | ESI (m/z) 490 [$C_{24}H_{18}D_3F_4N_5O_2$ + H]$^+$ | Scheme K |
| 56 | N-[4-[8-amino-5-chloro-3-(trideuteriomethyl)imidazo[1,5-a]pyrazin-1-yl]-3-methyl-phenyl]-2-[3-fluoro-5-(trifluoromethyl)phenyl]-2-hydroxy-acetamide | 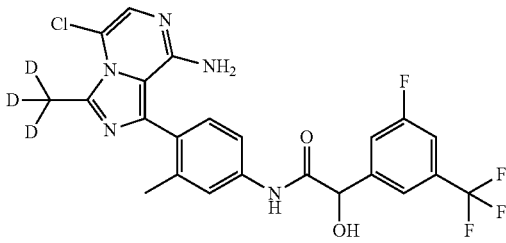<br>Isomer 1 | ESI (m/z) 511 [$C_{23}H_{15}D_3ClF_4N_5O_2$ + H]$^+$ | Scheme K |
| 57 | N-[4-[8-amino-5-chloro-3-(trideuteriomethyl)imidazo[1,5-a]pyrazin-1-yl]-3-methyl-phenyl]-2-[3-fluoro-5-(trifluoromethyl)phenyl]-2-hydroxy-acetamide | 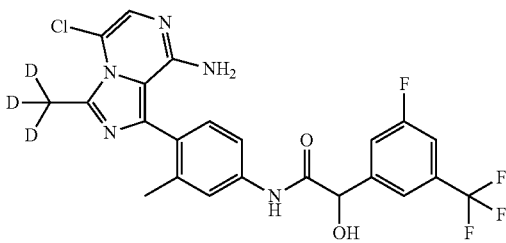<br>Isomer 2 | ESI (m/z) 511 [$C_{23}H_{15}D_3ClF_4N_5O_2$ + H]$^+$ | Scheme K |

TABLE 1-continued

Compounds of Formula I:

| Example | Name | Compounds I-B-3 | MS | Method |
|---|---|---|---|---|
| 58 | N-(4-(8-amino-3,5-dimethylimidazo[1,5-a]pyrazin-1-yl)-3-methylphenyl)-2-(3-fluoro-5-(trifluoromethyl)phenyl)-2-hydroxyacetamide | Isomer 1 | ESI (m/z) 488 [$C_{24}H_{21}F_4N_5O_2$ + H]$^+$ | Scheme K |
| 59 | N-(4-(8-amino-3,5-dimethylimidazo[1,5-a]pyrazin-1-yl)-3-methylphenyl)-2-(3-fluoro-5-(trifluoromethyl)phenyl)-2-hydroxyacetamide | Isomer 2 | ESI (m/z) 488 [$C_{24}H_{21}F_4N_5O_2$ + H]$^+$ | Scheme K |
| 60 | N-[4-[8-amino-3-(trideuteriomethyl)-5-(trifluoromethyl)imidazo[1,5-a]pyrazin-1-yl]-3-methyl-phenyl]-2-[3-fluoro-5-(trifluoromethyl)phenyl]-2-hydroxy-acetamide | Isomer 1 | ESI (m/z) 545 [$C_{24}H_{15}D_3F_7N_5O_2$ + H]$^+$ | Scheme K |
| 61 | N-[4-[8-amino-3-(trideuteriomethyl)-5-(trifluoromethyl)imidazo[1,5-a]pyrazin-1-yl]-3-methyl-phenyl]-2-[3-fluoro-5-(trifluoromethyl)phenyl]-2-hydroxy-acetamide | Isomer 2 | ESI (m/z) 545 [$C_{24}H_{15}D_3F_7N_5O_2$ + H]$^+$ | Scheme K |
| 62 | N-(4-(8-amino-3,5-dimethylimidazo[1,5-a]pyrazin-1-yl)-3-methylphenyl)-2-(3-fluoro-5-methylphenyl)-2-hydroxyacetamide | Isomer 1 | ESI (m/z) 434 [$C_{24}H_{24}FN_5O_2$ + H]$^+$ | Scheme K |

TABLE 1-continued

Compounds of Formula I:

| Example | Name | Compounds I-B-3 | MS | Method |
|---|---|---|---|---|
| 63 | N-(4-(8-amino-3,5-dimethylimidazo[1,5-a]pyrazin-1-yl)-3-methylphenyl)-2-(3-fluoro-5-methylphenyl)-2-hydroxyacetamide | 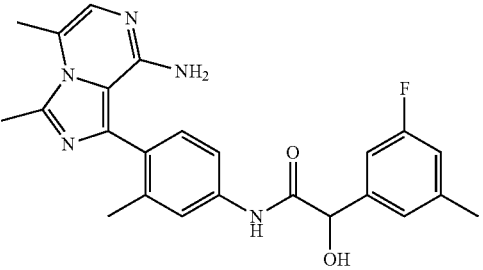 Isomer 2 | ESI (m/z) 434 $[C_{24}H_{24}FN_5O_2 + H]^+$ | Scheme K |
| 64 | N-(4-(8-amino-3,5-dimethylimidazo[1,5-a]pyrazin-1-yl)-2-fluoro-5-methylphenyl)-2-(3-fluorophenyl)-2-hydroxy-acetamide | 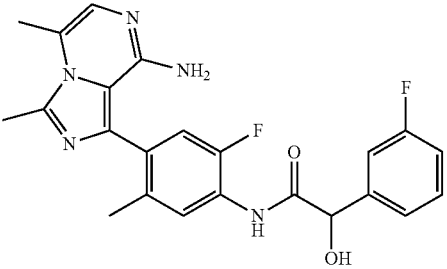 Isomer 1 | ESI (m/z) 438 $[C_{23}H_{21}F_2N_5O_2 + H]^+$ | Scheme K |
| 65 | N-(4-(8-amino-3,5-dimethylimidazo[1,5-a]pyrazin-1-yl)-2-fluoro-5-methylphenyl)-2-(3-fluorophenyl)-2-hydroxy-acetamide | 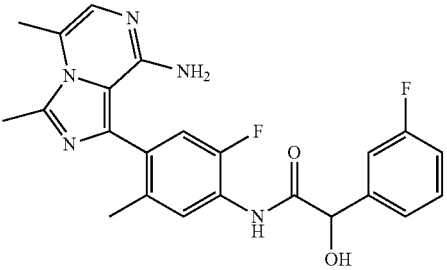 Isomer 2 | ESI (m/z) 438 $[C_{23}H_{21}F_2N_5O_2 + H]^+$ | Scheme K |
| 66 | N-(4-(8-amino-3,5-dimethylimidazo[1,5-a]pyrazin-1-yl)-3-ethylphenyl)-2-(3-fluorophenyl)-2-hydroxy-acetamide | 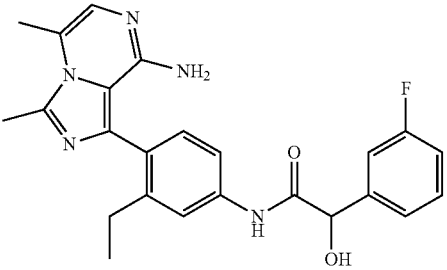 Isomer 1 | ESI (m/z) 434 $[C_{24}H_{24}FN_5O_2 + H]^+$ | Scheme K |

TABLE 1-continued

Compounds of Formula I:

| Example | Name | Compounds I-B-3 | MS | Method |
|---|---|---|---|---|
| 67 | N-(4-(8-amino-3,5-dimethylimidazo[1,5-a]pyrazin-1-yl)-3-ethylphenyl)-2-(3-fluorophenyl)-2-hydroxyacetamide | 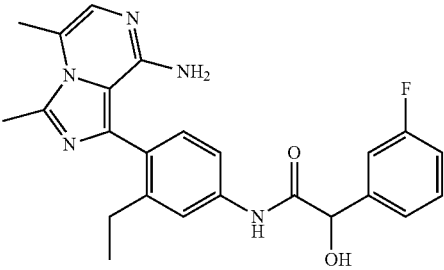 Isomer 2 | ESI (m/z) 434 $[C_{24}H_{24}FN_5O_2 + H]^+$ | Scheme K |
| 68 | N-(4-(8-amino-3,5-dimethylimidazo[1,5-a]pyrazin-1-yl)phenyl)-2-(3-fluorophenyl)-2-hydroxyacetamide | 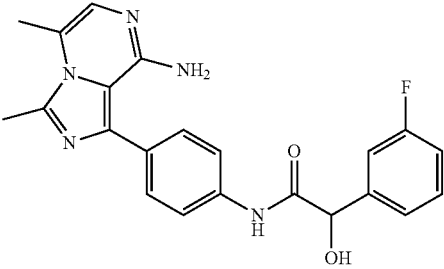 Isomer 1 | ESI (m/z) 406 $[C_{22}H_{20}FN_5O_2 + H]^+$ | Scheme K |
| 69 | N-(4-(8-amino-3,5-dimethylimidazo[1,5-a]pyrazin-1-yl)phenyl)-2-(3-fluorophenyl)-2-hydroxyacetamide | 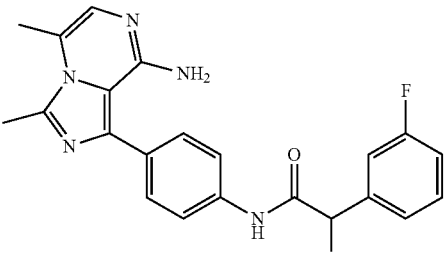 Isomer 2 | ESI (m/z) 406 $[C_{22}H_{20}FN_5O_2 + H]^+$ | Scheme K |
| 70 | N-(4-(8-amino-3,5-dimethylimidazo[1,5-a]pyrazin-1-yl)-3-fluorophenyl)-2-(3-fluorophenyl)-2-hydroxyacetamide | 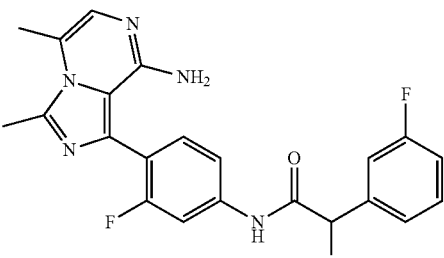 Isomer 1 | ESI (m/z) 424 $[C_{22}H_{19}F_2N_5O_2 + H]^+$ | Scheme K |

TABLE 1-continued

Compounds of Formula I:

| Example | Name | Compounds I-B-3 | MS | Method |
|---|---|---|---|---|
| 71 | N-(4-(8-amino-3,5-dimethylimidazo[1,5-a]pyrazin-1-yl)-3-fluorophenyl)-2-(3-fluorophenyl)-2-hydroxy-acetamide | 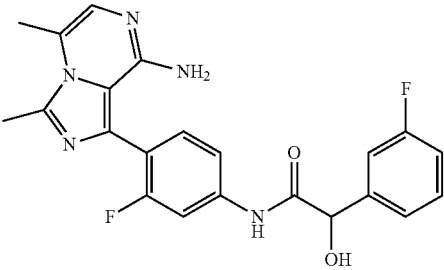<br>Isomer 2 | ESI (m/z) 424 $[C_{22}H_{19}F_2N_5O_2 + H]^+$ | Scheme K |
| 72 | N-[4-[8-amino-5-methyl-3-(trideuteriomethyl)imidazo[1,5-a]pyrazin-1-yl]-3-fluoro-phenyl]-2-(3-fluorophenyl)-2-hydroxy-acetamide | 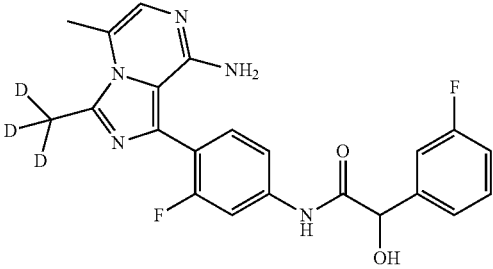<br>Isomer 1 | ESI (m/z) 427 $[C_{22}H_{16}D_3F_2N_5O_2 + H]^+$ | Scheme K |
| 73 | N-[4-[8-amino-5-methyl-3-(trideuteriomethyl)imidazo[1,5-a]pyrazin-1-yl]-3-fluoro-phenyl]-2-(3-fluorophenyl)-2-hydroxy-acetamide | 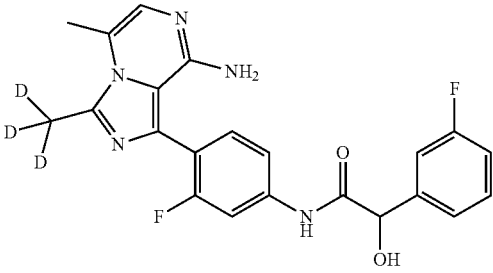<br>Isomer 2 | ESI (m/z) 427 $[C_{22}H_{16}D_3F_2N_5O_2 + H]^+$ | Scheme K |
| 74 | N-[4-[8-amino-5-chloro-3-(trideuteriomethyl)imidazo[1,5-a]pyrazin-1-yl]-3-fluoro-phenyl]-2-(3-fluorophenyl)-2-hydroxy-acetamide | 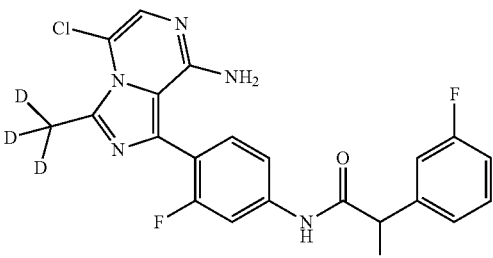<br>Isomer 1 | ESI (m/z) 447 $[C_{21}H_{13}D_3ClF_2N_5O_2 + H]^+$ | Scheme K |

TABLE 1-continued

Compounds of Formula I:

| Example | Name | Compounds I-B-3 | MS | Method |
|---|---|---|---|---|
| 75 | N-[4-[8-amino-5-chloro-3-(trideuteriomethyl)imidazo[1,5-a]pyrazin-1-yl]-3-fluoro-phenyl]-2-(3-fluorophenyl)-2-hydroxy-acetamide | 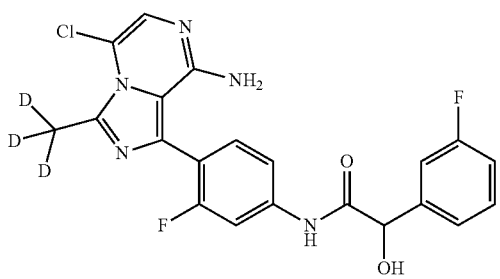 Isomer 2 | ESI (m/z) 447 $[C_{21}H_{13}D_3ClF_2N_5O_2 + H]^+$ | Scheme K |
| 76 | N-[4-[8-amino-3-(trideuteriomethyl)-5-(trifluoromethyl)imidazo[1,5-a]pyrazin-1-yl]-3-fluoro-phenyl]-2-(3-fluorophenyl)-2-hydroxy-acetamide | 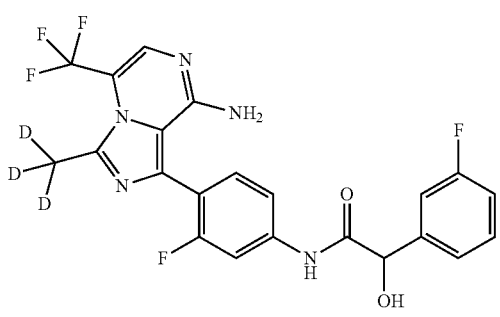 Isomer 1 | ESI (m/z) 481 $[C_{22}H_{13}D_3F_5N_5O_2 + H]^+$ | Scheme K |
| 77 | N-[4-[8-amino-3-(trideuteriomethyl)-5-(trifluoromethyl)imidazo[1,5-a]pyrazin-1-yl]-3-fluoro-phenyl]-2-(3-fluorophenyl)-2-hydroxy-acetamide | 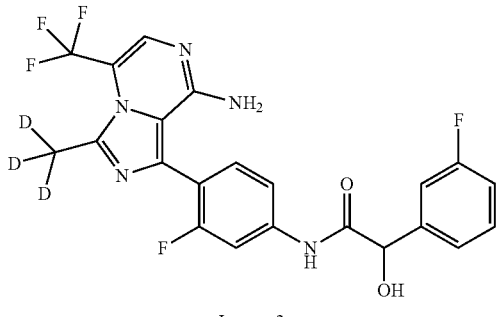 Isomer 2 | ESI (m/z) 481 $[C_{22}H_{13}D_3F_5N_5O_2 + H]^+$ | Scheme K |
| 78 | N-(4-(8-amino-3,5-dimethylimidazo[1,5-a]pyrazin-1-yl)-3-fluorophenyl)-2-(3-chlorophenyl)-2-hydroxy-acetamide | 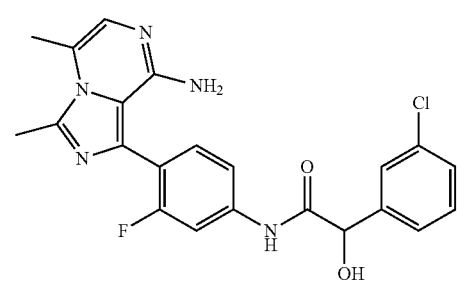 Isomer 1 | ESI (m/z) 440 $[C_{22}H_{19}D_3ClFN_5O_2 + H]^+$ | Scheme K |

TABLE 1-continued

Compounds of Formula I:

| Example | Name | Compounds I-B-3 | MS | Method |
|---|---|---|---|---|
| 79 | N-(4-(8-amino-3,5-dimethylimidazo[1,5-a]pyrazin-1-yl)-3-fluorophenyl)-2-(3-chlorophenyl)-2-hydroxy-acetamide | 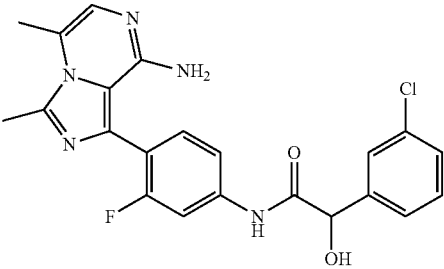 Isomer 2 | ESI (m/z) 440 $[C_{22}H_{19}D_3ClFN_5O_2 + H]^+$ | Scheme K |
| 80 | N-[4-[8-amino-6-methyl-3-(trideuteriomethyl)imidazo[1,5-a]pyrazin-1-yl]-3-fluoro-phenyl]-2-(3-chlorophenyl)-2-hydroxy-acetamide | 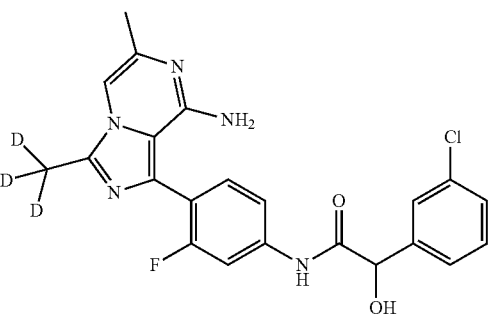 Isomer 1 | ESI (m/z) 443 $[C_{22}H_{16}D_3ClFN_5O_2 + H]^+$ | Scheme K |
| 81 | N-[4-[8-amino-6-methyl-3-(trideuteriomethyl)imidazo[1,5-a]pyrazin-1-yl]-3-fluoro-phenyl]-2-(3-chlorophenyl)-2-hydroxy-acetamide | 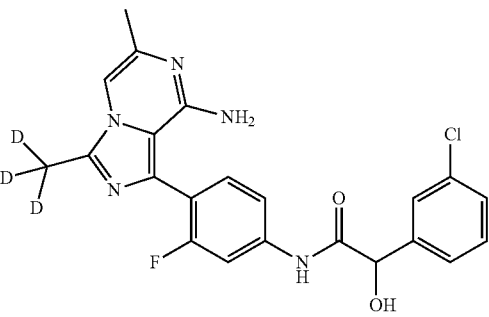 Isomer 2 | ESI (m/z) 443 $[C_{22}H_{16}D_3ClFN_5O_2 + H]^+$ | Scheme K |
| 82 | N-[4-[8-amino-3-(trideuteriomethyl)-5-(trifluoromethyl)imidazo[1,5-a]pyrazin-1-yl]-3-fluoro-phenyl]-2-(3-chlorophenyl)-2-hydroxy-acetamide | 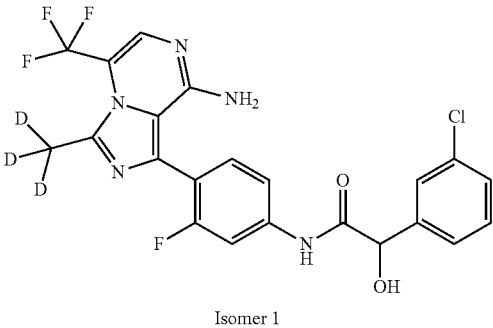 [SMILES: [2H]C([2H])([2H])c1nc(-c2ccc(NC(=O)C(O)c3cccc(Cl)c3)cc2F)c2c(N)ncc(C(F)(F)F)n12] Isomer 1 | ESI (m/z) 497 $[C_{22}H_{13}D_3ClF_4N_5O_2 + H]^+$ | Scheme K |

TABLE 1-continued

Compounds of Formula I:

| Example | Name | Compounds I-B-3 | MS | Method |
|---|---|---|---|---|
| 83 | N-[4-[8-amino-3-(trideuteriomethyl)-5-(trifluoromethyl)imidazo[1,5-a]pyrazin-1-yl]-3-fluoro-phenyl]-2-(3-chlorophenyl)-2-hydroxy-acetamide | 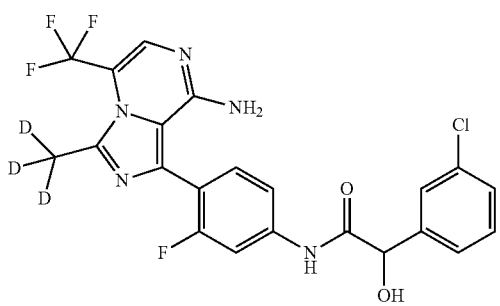<br>Isomer 2 | ESI (m/z) 497 $[C_{22}H_{13}D_3ClF_4N_5O_2 + H]^+$ | Scheme K |
| 84 | N-[4-[8-amino-5-methyl-3-(trideuteriomethyl)imidazo[1,5-a]pyrazin-1-yl]-3-fluoro-phenyl]-2-(3-chlorophenyl)-2-hydroxy-acetamide | 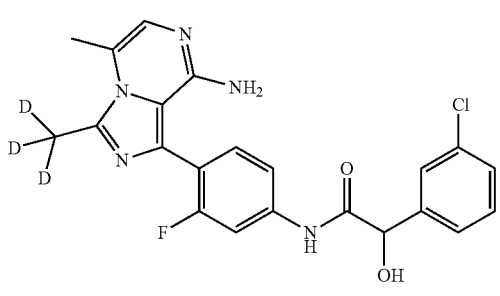<br>Isomer 1 | ESI (m/z) 443 $[C_{22}H_{16}D_3ClFN_5O_2 + H]^+$ | Scheme K |
| 85 | N-[4-[8-amino-5-methyl-3-(trideuteriomethyl)imidazo[1,5-a]pyrazin-1-yl]-3-fluoro-phenyl]-2-(3-chlorophenyl)-2-hydroxy-acetamide | 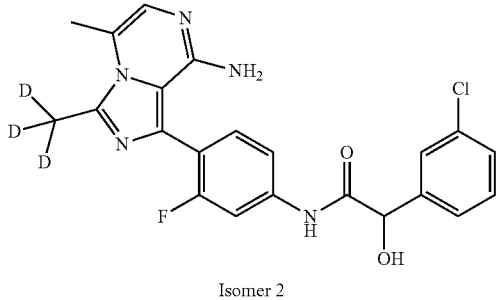 [SMILES: [2H]C([2H])([2H])c1nc(-c2ccc(NC(=O)C(O)c3cccc(Cl)c3)cc2F)c2c(N)ncc(C)n12]<br>Isomer 2 | ESI (m/z) 443 $[C_{22}H_{16}D_3ClFN_5O_2 + H]^+$ | Scheme K |
| 86 | N-[4-[8-amino-5-chloro-3-(trideuteriomethyl)imidazo[1,5-a]pyrazin-1-yl]-3-fluoro-phenyl]-2-(3-chlorophenyl)-2-hydroxy-acetamide | 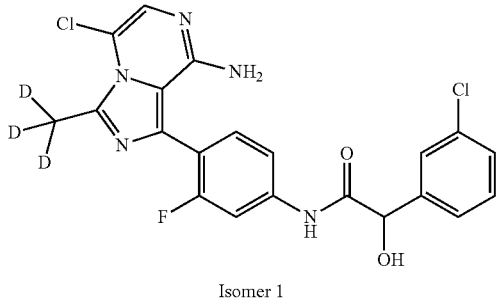 [SMILES: [2H]C([2H])([2H])c1nc(-c2ccc(NC(=O)C(O)c3cccc(Cl)c3)cc2F)c2c(N)ncc(Cl)n12]<br>Isomer 1 | ESI (m/z) 463 $[C_{21}H_{13}D_3Cl_2FN_5O_2 + H]^+$ | Scheme K |

TABLE 1-continued

Compounds of Formula I:

| Example | Name | Compounds I-B-3 | MS | Method |
|---|---|---|---|---|
| 87 | N-[4-[8-amino-5-chloro-3-(trideuteriomethyl)imidazo[1,5-a]pyrazin-1-yl]-3-fluoro-phenyl]-2-(3-chlorophenyl)-2-hydroxy-acetamide | 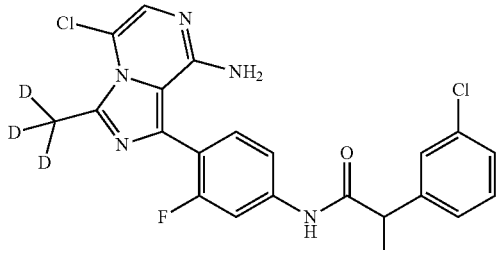 Isomer 2 | ESI (m/z) 463 [$C_{21}H_{13}D_3Cl_2FN_5O_2$ + H]$^+$ | Scheme K |
| 88 | N-(4-(8-amino-3,5-dimethylimidazo[1,5-a]pyrazin-1-yl)-3-fluoro-phenyl)-2-hydroxy-2-(m-tolyl)acetamide | 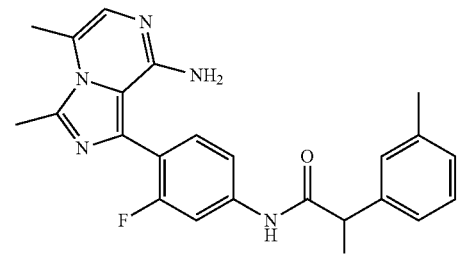 Isomer 1 | ESI (m/z) 420 [$C_{23}H_{22}FN_5O_2$ + H]$^+$ | Scheme K |
| 89 | N-(4-(8-amino-3,5-dimethylimidazo[1,5-a]pyrazin-1-yl)-3-fluoro-phenyl)-2-hydroxy-2-(m-tolyl)acetamide | 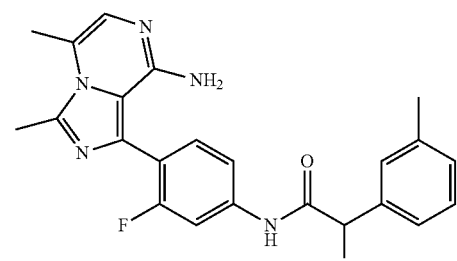 Isomer 2 | ESI (m/z) 420 [$C_{23}H_{22}FN_5O_2$ + H]$^+$ | Scheme K |
| 90 | N-[4-[8-amino-5-methyl-3-(trideuteriomethyl)imidazo[1,5-a]pyrazin-1-yl]-3-fluoro-phenyl]-2-hydroxy-2-(m-tolyl)acetamide | 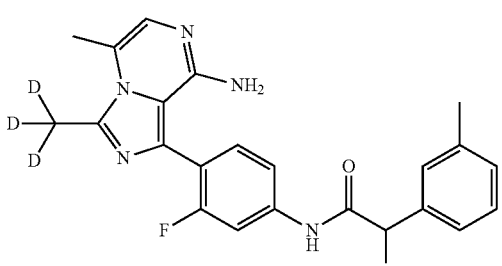 Isomer 1 | ESI (m/z) 423 [$C_{23}H_{19}D_3FN_5O_2$ + H]$^+$ | Scheme K |

TABLE 1-continued

Compounds of Formula I:

| Example | Name | Compounds I-B-3 | MS | Method |
|---|---|---|---|---|
| 91 | N-[4-[8-amino-5-methyl-3-(trideuteriomethyl)imidazo[1,5-a]pyrazin-1-yl]-3-fluoro-phenyl]-2-hydroxy-2-(m-tolyl)acetamide | 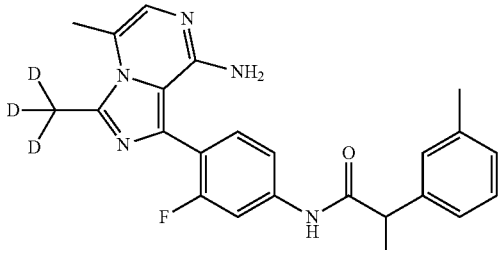 Isomer 2 | ESI (m/z) 423 $[C_{23}H_{19}D_3FN_5O_2 + H]^+$ | Scheme K |
| 92 | N-(4-(8-amino-3,5-dimethylimidazo[1,5-a]pyrazin-1-yl)-3-fluoro-phenyl)-2-hydroxy-2-(3-(trifluoromethyl)phenyl)acetamide | 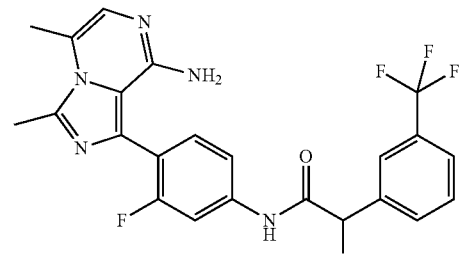 Isomer 1 | ESI (m/z) 474 $[C_{23}H_{19}F_4N_5O_2 + H]^+$ | Scheme K |
| 93 | N-(4-(8-amino-3,5-dimethylimidazo[1,5-a]pyrazin-1-yl)-3-fluoro-phenyl)-2-hydroxy-2-(3-(trifluoromethyl)phenyl)acetamide | 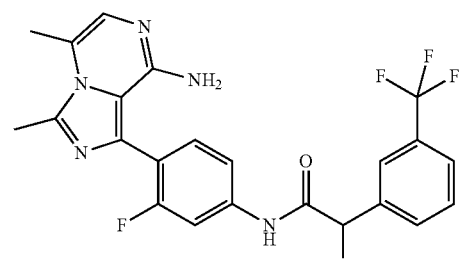 Isomer 2 | ESI (m/z) 474 $[C_{23}H_{19}F_4N_5O_2 + H]^+$ | Scheme K |
| 94 | N-[4-[8-amino-5-methyl-3-(trideuteriomethyl)imidazo[1,5-a]pyrazin-1-yl]-3-fluoro-phenyl]-2-hydroxy-2-[3-(trifluoromethyl)phenyl]acetamide | 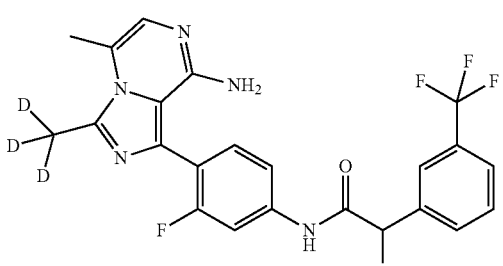 Isomer 1 | ESI (m/z) 477 $[C_{23}H_{16}D_3F_4N_5O_2 + H]^+$ | Scheme K |

TABLE 1-continued

Compounds of Formula I:

| Example | Name | Compounds I-B-3 | MS | Method |
|---|---|---|---|---|
| 95 | N-[4-[8-amino-5-methyl-3-(trideuteriomethyl)imidazo[1,5-a]pyrazin-1-yl]-3-fluoro-phenyl]-2-hydroxy-2-[3-(trifluoromethyl)phenyl]acetamide | Isomer 2 | ESI (m/z) 477 [$C_{23}H_{16}D_3F_4N_5O_2$ + H]$^+$ | Scheme K |
| 96 | N-[4-[8-amino-6-methyl-3-(trideuteriomethyl)imidazo[1,5-a]pyrazin-1-yl]-3-fluoro-phenyl]-2-hydroxy-2-[3-(trifluoromethyl)phenyl]acetamide | Isomer 1 | ESI (m/z) 477 [$C_{23}H_{16}D_3F_4N_5O_2$ + H]$^+$ | Scheme K |
| 97 | N-[4-[8-amino-6-methyl-3-(trideuteriomethyl)imidazo[1,5-a]pyrazin-1-yl]-3-fluoro-phenyl]-2-hydroxy-2-[3-(trifluoromethyl)phenyl]acetamide | Isomer 2 | ESI (m/z) 477 [$C_{23}H_{16}D_3F_4N_5O_2$ + H]$^+$ | Scheme K |
| 98 | N-[4-[8-amino-3-(trideuteriomethyl)-5-(trifluoromethyl)imidazo[1,5-a]pyrazin-1-yl]-3-fluoro-phenyl]-2-hydroxy-2-[3-(trifluoromethyl)phenyl]acetamide | Isomer 1 | ESI (m/z) 531 [$C_{23}H_{13}D_3F_7N_5O_2$ + H]$^+$ | Scheme K |

TABLE 1-continued

Compounds of Formula I:

| Example | Name | Compounds I-B-3 | MS | Method |
|---|---|---|---|---|
| 99 | N-[4-[8-amino-3-(trideuteriomethyl)-5-(trifluoromethyl)imidazo[1,5-a]pyrazin-1-yl]-3-fluoro-phenyl]-2-hydroxy-2-[3-(trifluoromethyl)phenyl]acetamide<br><br>Isomer 2 | | ESI (m/z) 531 $[C_{23}H_{13}D_3F_7N_5O_2 + H]^+$ | Scheme K |
| 100 | N-[4-[8-amino-5-chloro-3-(trideuteriomethyl)imidazo[1,5-a]pyrazin-1-yl]-3-fluoro-phenyl]-2-hydroxy-2-[3-(trifluoromethyl)phenyl]acetamide<br><br>Isomer 1 | | ESI (m/z) 497 $[C_{22}H_{13}D_3ClF_4N_5O_2 + H]^+$ | Scheme K |
| 101 | N-[4-[8-amino-5-chloro-3-(trideuteriomethyl)imidazo[1,5-a]pyrazin-1-yl]-3-fluoro-phenyl]-2-hydroxy-2-[3-(trifluoromethyl)phenyl]acetamide<br><br>Isomer 2 | | ESI (m/z) 497 $[C_{22}H_{13}D_3ClF_4N_5O_2 + H]^+$ | Scheme K |
| 102 | N-[4-[8-amino-6-methyl-3-(trideuteriomethyl)imidazo[1,5-a]pyrazin-1-yl]-3-fluoro-phenyl]-2-(3,5-difluoro-phenyl)-2-hydroxy-acetamide<br><br>Isomer 1 | | ESI (m/z) 445 $[C_{22}H_{15}D_3F_3N_5O_2 + H]^+$ | Scheme K |

TABLE 1-continued

Compounds of Formula I:

| Example | Name | Compounds I-B-3 | MS | Method |
|---|---|---|---|---|
| 103 | N-[4-[8-amino-6-methyl-3-(trideuteriomethyl)imidazo[1,5-a]pyrazin-1-yl]-3-fluoro-phenyl]-2-(3,5-difluoro-phenyl)-2-hydroxy-acetamide | 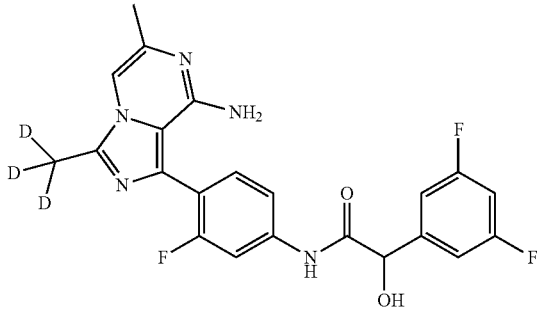<br>Isomer 2 | ESI (m/z) 445 $[C_{22}H_{15}D_3F_3N_5O_2 + H]^+$ | Scheme K |
| 104 | N-[4-[8-amino-5-methyl-3-(trideuteriomethyl)imidazo[1,5-a]pyrazin-1-yl]-3-fluoro-phenyl]-2-(3,5-difluoro-phenyl)-2-hydroxy-acetamide | 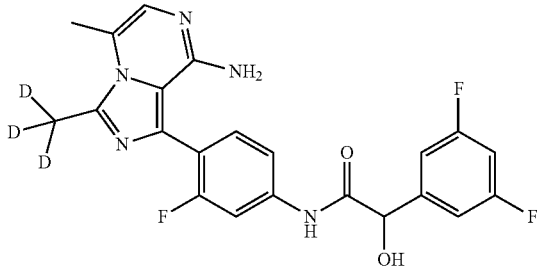<br>Isomer 1 | ESI (m/z) 445 $[C_{22}H_{15}D_3F_3N_5O_2 + H]^+$ | Scheme K |
| 105 | N-[4-[8-amino-5-methyl-3-(trideuteriomethyl)imidazo[1,5-a]pyrazin-1-yl]-3-fluoro-phenyl]-2-(3,5-difluoro-phenyl)-2-hydroxy-acetamide | 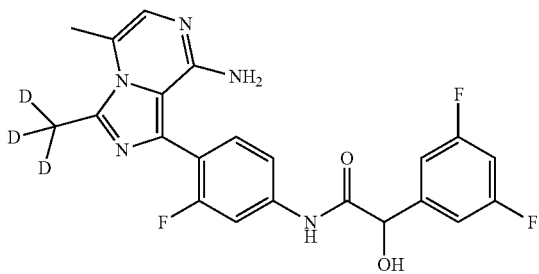<br>Isomer 2 | ESI (m/z) 445 $[C_{22}H_{15}D_3F_3N_5O_2 + H]^+$ | Scheme K |
| 106 | N-[4-[8-amino-3-(trideuteriomethyl)-5-(trifluoromethyl)imidazo[1,5-a]pyrazin-1-yl]-3-fluoro-phenyl]-2-(3,5-difluoro-phenyl)-2-hydroxy-acetamide | 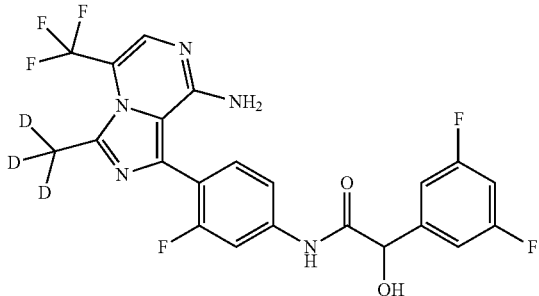<br>Isomer 1 | ESI (m/z) 499 $[C_{22}H_{12}D_3F_6N_5O_2 + H]^+$ | Scheme K |

TABLE 1-continued

Compounds of Formula I:

| Example | Name | Compounds I-B-3 | MS | Method |
|---|---|---|---|---|
| 107 | N-[4-[8-amino-3-(trideuteriomethyl)-5-(trifluoromethyl) imidazo[1,5-a]pyrazin-1-yl]-3-fluoro-phenyl]-2-(3,5-difluoro-phenyl)-2-hydroxy-acetamide | 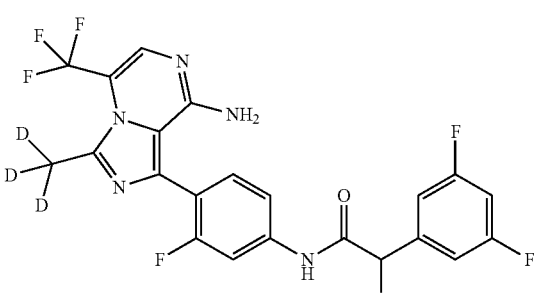<br>Isomer 2 | ESI (m/z) 499 $[C_{22}H_{12}D_3F_6N_5O_2 + H]^+$ | Scheme K |
| 108 | N-[4-[8-amino-5-chloro-3-(trideuteriomethyl) imidazo[1,5-a]pyrazin-1-yl]-3-fluoro-phenyl]-2-(3,5-difluoro-phenyl)-2-hydroxy-acetamide | 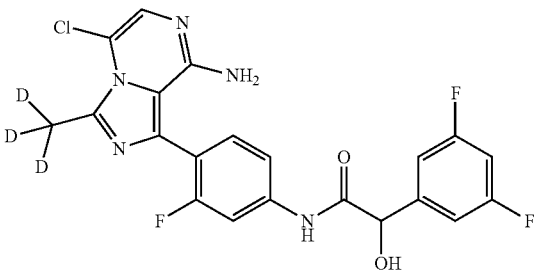<br>Isomer 1 | ESI (m/z) 465 $[C_{21}H_{12}D_3ClF_3N_5O_2 + H]^+$ | Scheme K |
| 109 | N-[4-[8-amino-5-chloro-3-(trideuteriomethyl) imidazo[1,5-a]pyrazin-1-yl]-3-fluoro-phenyl]-2-(3,5-difluoro-phenyl)-2-hydroxy-acetamide | 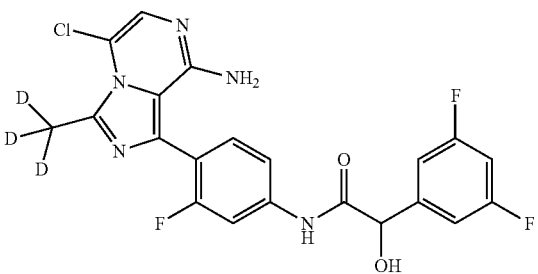<br>Isomer 2 | ESI (m/z) 465 $[C_{21}H_{12}D_3ClF_3N_5O_2 + H]^+$ | Scheme K |
| 110 | N-[4-[8-amino-5-methyl-3-(trideuteriomethyl) imidazo[1,5-a]pyrazin-1-yl]-3-fluoro-phenyl]-2-[3-fluoro-5-(trifluoromethyl) phenyl]-2-hydroxy-acetamide | 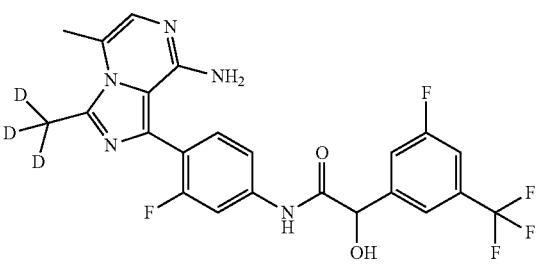<br>Isomer 1 | ESI (m/z) 495 $[C_{23}H_{15}D_3F_5N_5O_2 + H]^+$ | Scheme K |

TABLE 1-continued

Compounds of Formula I:

| Example | Name | Compounds I-B-3 | MS | Method |
|---|---|---|---|---|
| 111 | N-[4-[8-amino-5-methyl-3-(trideuteriomethyl)imidazo[1,5-a]pyrazin-1-yl]-3-fluoro-phenyl]-2-[3-fluoro-5-(trifluoromethyl)phenyl]-2-hydroxy-acetamide | Isomer 2 | ESI (m/z) 495 [$C_{23}H_{15}D_3F_5N_5O_2$ + H]$^+$ | Scheme K |
| 112 | N-[4-[8-amino-3-(trideuteriomethyl)-5-(trifluoromethyl)imidazo[1,5-a]pyrazin-1-yl]-3-fluoro-phenyl]-2-[3-fluoro-5-(trifluoromethyl)phenyl]-2-hydroxy-acetamide | Isomer 1 | ESI (m/z) 549 [$C_{23}H_{12}D_3F_8N_5O_2$ + H]$^+$ | Scheme K |
| 113 | N-[4-[8-amino-3-(trideuteriomethyl)-5-(trifluoromethyl)imidazo[1,5-a]pyrazin-1-yl]-3-fluoro-phenyl]-2-[3-fluoro-5-(trifluoromethyl)phenyl]-2-hydroxy-acetamide | Isomer 2 | ESI (m/z) 549 [$C_{23}H_{12}D_3F_8N_5O_2$ + H]$^+$ | Scheme K |
| 114 | N-[4-[8-amino-5-chloro-3-(trideuteriomethyl)imidazo[1,5-a]pyrazin-1-yl]-3-fluoro-phenyl]-2-[3-fluoro-5-(trifluoromethyl)phenyl]-2-hydroxy-acetamide | Isomer 1 | ESI (m/z) 515 [$C_{22}H_{12}D_3ClF_5N_5O_2$ + H]$^+$ | Scheme K |
| 115 | N-[4-[8-amino-5-chloro-3-(trideuteriomethyl)imidazo[1,5-a]pyrazin-1-yl]-3-fluoro-phenyl]-2-[3-fluoro-5-(trifluoromethyl)phenyl]-2-hydroxy-acetamide | Isomer 2 | ESI (m/z) 515 [$C_{22}H_{12}D_3ClF_5N_5O_2$ + H]$^+$ | Scheme K |

TABLE 1-continued

Compounds of Formula I:

| Example | Name | Compounds I-B-3 | MS | Method |
|---|---|---|---|---|
| 116 | N-[4-[8-amino-6-methyl-3-(trideuteriomethyl)imidazo[1,5-a]pyrazin-1-yl]-3-fluoro-phenyl]-2-[3-fluoro-5-(trifluoromethyl)phenyl]-2-hydroxy-acetamide | 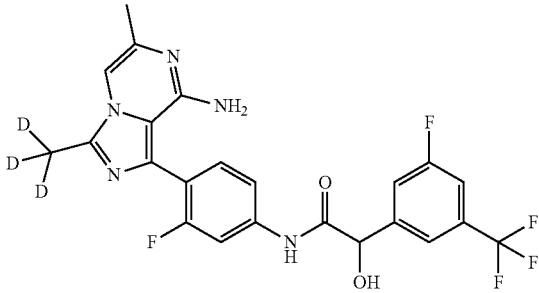 Isomer 1 | ESI (m/z) 495 $[C_{23}H_{15}D_3F_5N_5O_2 + H]^+$ | Scheme K |
| 117 | N-[4-[8-amino-6-methyl-3-(trideuteriomethyl)imidazo[1,5-a]pyrazin-1-yl]-3-fluoro-phenyl]-2-[3-fluoro-5-(trifluoromethyl)phenyl]-2-hydroxy-acetamide | 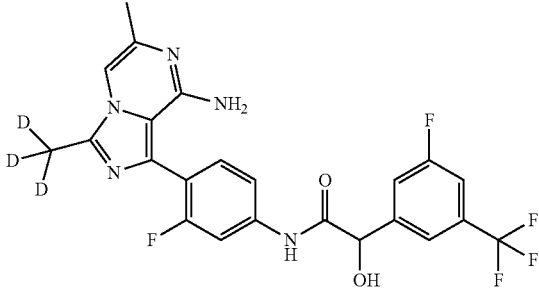 Isomer 2 | ESI (m/z) 495 $[C_{23}H_{15}D_3F_5N_5O_2 + H]^+$ | Scheme K |
| 118 | N-(4-(8-amino-3,6-dimethyl-imidazo[1,5-a]pyrazin-1-yl)-2-fluorophenyl)-2-(3-fluorophenyl)-2-hydroxy-acetamide | 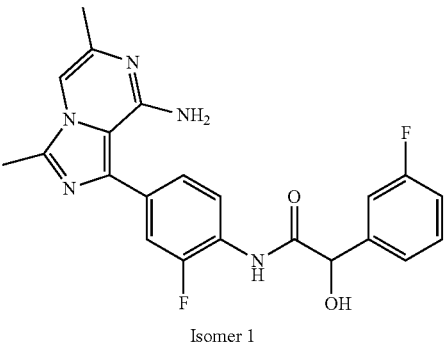 [SMILES: Cc1cn2c(C)nc(-c3ccc(NC(=O)C(O)c4cccc(F)c4)c(F)c3)c2c(N)n1] Isomer 1 | ESI (m/z) 424 $[C_{22}H_{19}F_2N_5O_2 + H]^+$ | Scheme K |
| 119 | N-(4-(8-amino-3,6-dimethyl-imidazo[1,5-a]pyrazin-1-yl)-2-fluorophenyl)-2-(3-fluorophenyl)-2-hydroxy-acetamide | 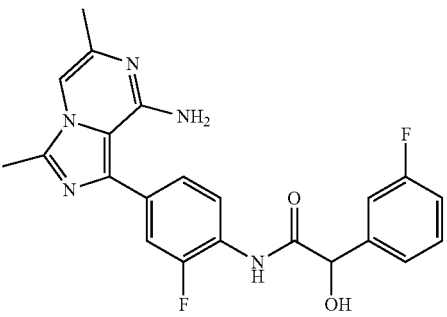 Isomer 2 | ESI (m/z) 424 $[C_{22}H_{19}F_2N_5O_2 + H]^+$ | Scheme K |

TABLE 1-continued

Compounds of Formula I:

| Example | Name | Compounds I-B-3 | MS | Method |
|---|---|---|---|---|
| 120 | N-[4-[8-amino-6-methyl-3-(trideuteriomethyl)imidazo[1,5-a]pyrazin-1-yl]-2-fluorophenyl]-2-(3-fluorophenyl)-2-hydroxy-acetamide | 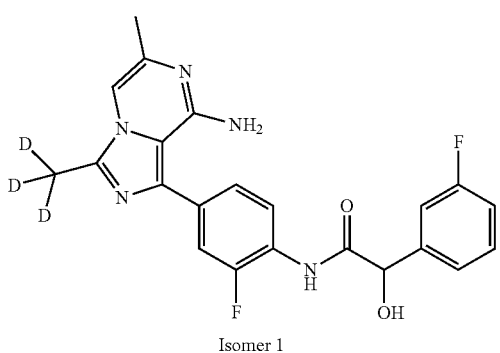 [SMILES: [2H]C([2H])([2H])c1nc(-c2ccc(NC(=O)C(O)c3cccc(F)c3)c(F)c2)c2c(N)nc(C)cn12]<br>Isomer 1 | ESI (m/z) 427 $[C_{22}H_{16}D_3F_2N_5O_2 + H]^+$ | Scheme K |
| 121 | N-[4-[8-amino-6-methyl-3-(trideuteriomethyl)imidazo[1,5-a]pyrazin-1-yl]-2-fluorophenyl]-2-(3-fluorophenyl)-2-hydroxy-acetamide | 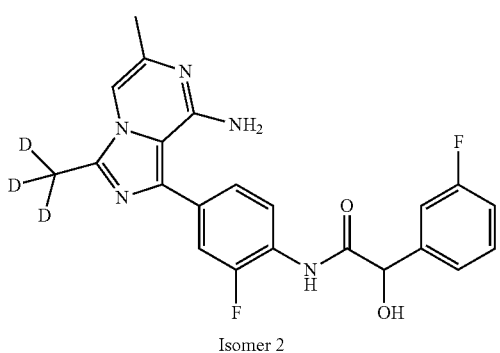 [SMILES: [2H]C([2H])([2H])c1nc(-c2ccc(NC(=O)C(O)c3cccc(F)c3)c(F)c2)c2c(N)nc(C)cn12]<br>Isomer 2 | ESI (m/z) 427 $[C_{22}H_{16}D_3F_2N_5O_2 + H]^+$ | Scheme K |
| 122 | N-[4-[8-amino-5-methyl-3-(trideuteriomethyl)imidazo[1,5-a]pyrazin-1-yl]-2-fluoro-phenyl]-2-(3-fluorophenyl)-2-hydroxy-acetamide | 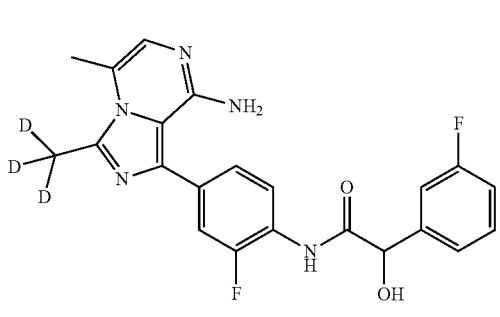<br>Isomer 1 | ESI (m/z) 427 $[C_{22}H_{16}D_3F_2N_5O_2 + H]^+$ | Scheme K |
| 123 | N-[4-[8-amino-5-methyl-3-(trideuteriomethyl)imidazo[1,5-a]pyrazin-1-yl]-2-fluoro-phenyl]-2-(3-fluorophenyl)-2-hydroxy-acetamide | 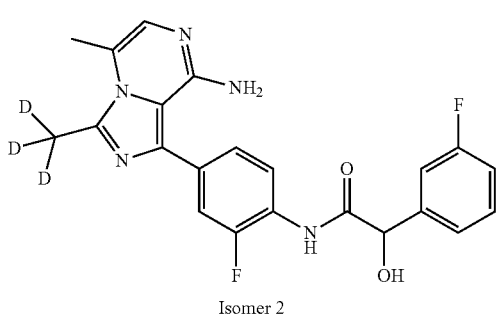 [SMILES: [2H]C([2H])([2H])c1nc(-c2ccc(NC(=O)C(O)c3cccc(F)c3)c(F)c2)c2c(N)ncc(C)n12]<br>Isomer 2 | ESI (m/z) 427 $[C_{22}H_{16}D_3F_2N_5O_2 + H]^+$ | Scheme K |

TABLE 1-continued

Compounds of Formula I:

| Example | Name | Compounds I-B-3 | MS | Method |
|---|---|---|---|---|
| 124 | N-(4-(8-amino-3,5-dimethyl-imidazo[1,5-a]pyrazin-1-yl)-2-fluorophenyl)-2-(3-fluorophenyl)-2-hydroxy-acetamide | 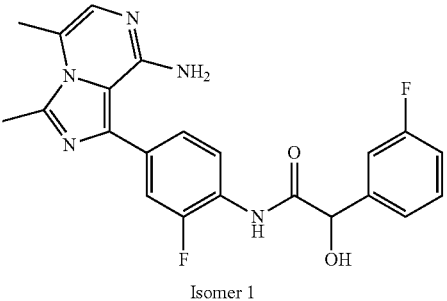 [SMILES: Cc1cnc(N)c2c(-c3ccc(NC(=O)C(O)c4cccc(F)c4)c(F)c3)nc(C)n12] Isomer 1 | ESI (m/z) 424 $[C_{22}H_{19}F_2N_5O_2 + H]^+$ | Scheme K |
| 125 | N-(4-(8-amino-3,5-dimethyl-imidazo[1,5-a]pyrazin-1-yl)-2-fluorophenyl)-2-(3-fluorophenyl)-2-hydroxy-acetamide | 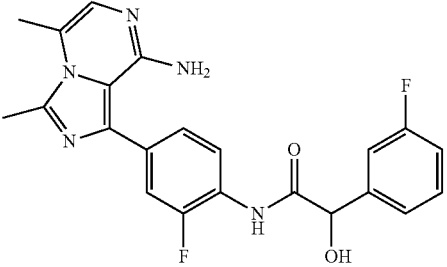 Isomer 2 | ESI (m/z) 424 $[C_{22}H_{19}F_2N_5O_2 + H]^+$ | Scheme K |
| 126 | N-(4-(8-amino-3,5-dimethyl-imidazo[1,5-a]pyrazin-1-yl)-3-(trifluoromethoxy)phenyl)-2-(3-fluorophenyl)-2-hydroxyacetamide | 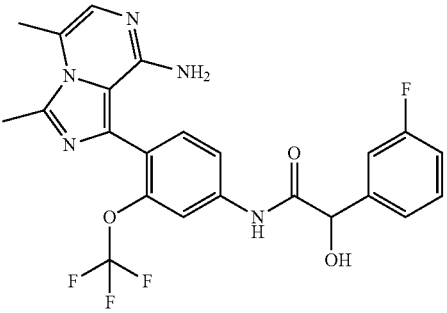 Isomer 1 | ESI (m/z) 490 $[C_{23}H_{19}F_4N_5O_3 + H]^+$ | Scheme K |
| 127 | N-(4-(8-amino-3,5-dimethyl-imidazo[1,5-a]pyrazin-1-yl)-3-(trifluoromethoxy)phenyl)-2-(3-fluorophenyl)-2-hydroxyacetamide | 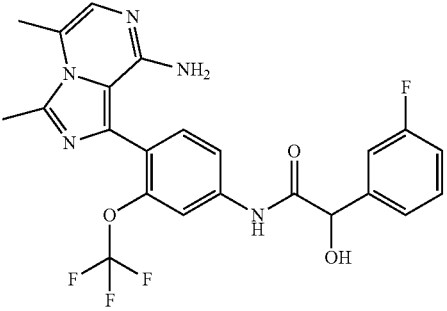 Isomer 2 | ESI (m/z) 490 $[C_{23}H_{19}F_4N_5O_3 + H]^+$ | Scheme K |

TABLE 1-continued

Compounds of Formula I:

| Example | Name | Compounds I-B-3 | MS | Method |
|---|---|---|---|---|
| 128 | N-(4-(8-amino-3,6-dimethyl-imidazo[1,5-a]pyrazin-1-yl)-2,3-difluoro-phenyl)-2-(3-fluorophenyl)-2-hydroxyacetamide | 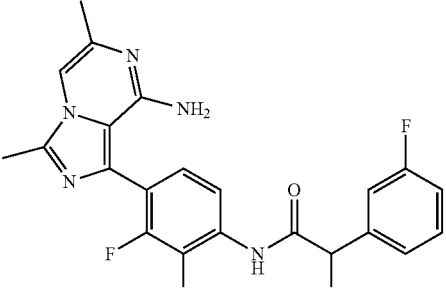 Isomer 1 | ESI (m/z) 442 [C$_{22}$H$_{18}$F$_3$N$_5$O$_2$ + H]$^+$ | Scheme K |
| 129 | N-(4-(8-amino-3,6-dimethyl-imidazo[1,5-a]pyrazin-1-yl)-2,3-difluoro-phenyl)-2-(3-fluorophenyl)-2-hydroxyacetamide | 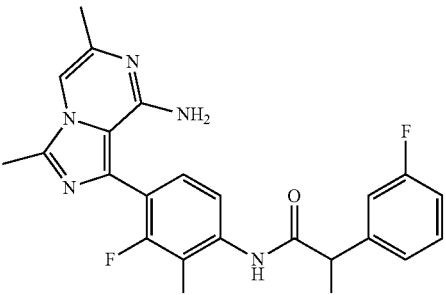 Isomer 2 | ESI (m/z) 442 [C$_{22}$H$_{18}$F$_3$N$_5$O$_2$ + H]$^+$ | Scheme K |
| 130 | N-[4-[8-amino-6-methyl-3-(trideuteriomethyl)imidazo[1,5-a]pyrazin-1-yl]-2,3-difluoro-phenyl]-2-(3-fluoro-phenyl)-2-hydroxy-acetamide | 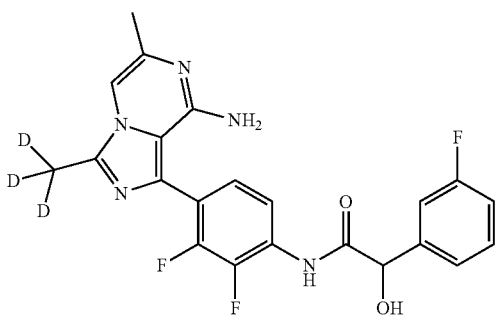 Isomer 1 | ESI (m/z) 445 [C$_{22}$H$_{15}$D$_3$F$_3$N$_5$O$_2$ + H]$^+$ | Scheme K |
| 131 | N-[4-[8-amino-6-methyl-3-(trideuteriomethyl)imidazo[1,5-a]pyrazin-1-yl]-2,3-difluoro-phenyl]-2-(3-fluoro-phenyl)-2-hydroxy-acetamide | 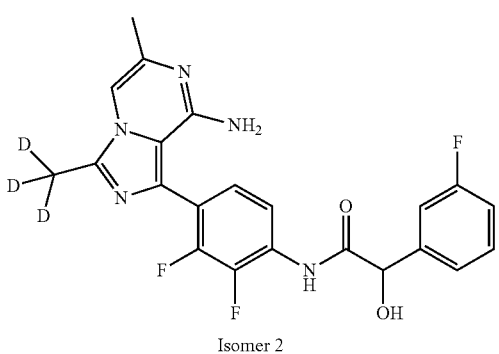 [SMILES: [2H]C([2H])([2H])c1nc(-c2ccc(NC(=O)C(O)c3cccc(F)c3)c(F)c2F)c2c(N)nc(C)cn12] Isomer 2 | ESI (m/z) 445 [C$_{22}$H$_{15}$D$_3$F$_3$N$_5$O$_2$ + H]$^+$ | Scheme K |

TABLE 1-continued

| | | Compounds of Formula I: | | |
|---|---|---|---|---|
| Example | Name | Compounds I-B-3 | MS | Method |
| 132 | N-[4-[8-amino-5-methyl-3-(trideuteriomethyl)imidazo[1,5-a]pyrazin-1-yl]-2,3-difluoro-phenyl]-2-(3-fluoro-phenyl)-2-hydroxy-acetamide | 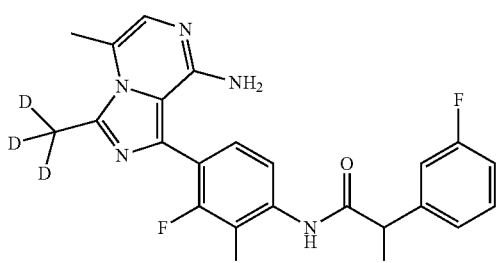<br>Isomer 1 | ESI (m/z) 445 $[C_{22}H_{15}D_3F_3N_5O_2 + H]^+$ | Scheme K |
| 133 | N-[4-[8-amino-5-methyl-3-(trideuteriomethyl)imidazo[1,5-a]pyrazin-1-yl]-2,3-difluoro-phenyl]-2-(3-fluoro-phenyl)-2-hydroxy-acetamide | 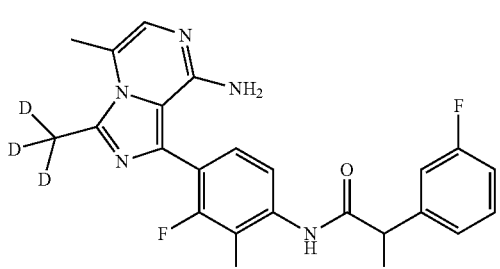<br>Isomer 2 | ESI (m/z) 445 $[C_{22}H_{15}D_3F_3N_5O_2 + H]^+$ | Scheme K |
| 134 | N-[4-[8-amino-3-(trideuteriomethyl)-5-(trifluoromethyl)imidazo[1,5-a]pyrazin-1-yl]-2,3-difluoro-phenyl]-2-(3-fluorophenyl)-2-hydroxy-acetamide | 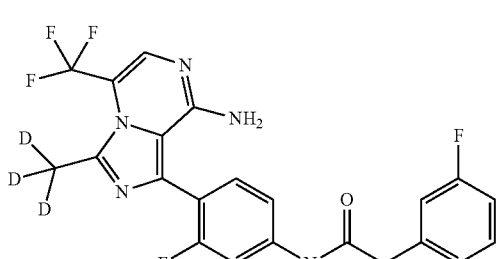<br>Isomer 1 | ESI (m/z) 499 $[C_{22}H_{12}D_3F_6N_5O_2 + H]^+$ | Scheme K |
| 135 | N-[4-[8-amino-3-(trideuteriomethyl)-5-(trifluoromethyl)imidazo[1,5-a]pyrazin-1-yl]-2,3-difluoro-phenyl]-2-(3-fluorophenyl)-2-hydroxy-acetamide | 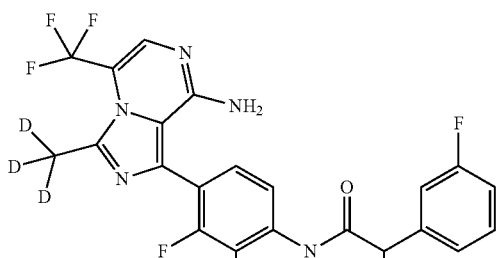<br>Isomer 2 | ESI (m/z) 499 $[C_{22}H_{12}D_3F_6N_5O_2 + H]^+$ | Scheme K |

TABLE 1-continued

Compounds of Formula I:

| Example | Name | Compounds I-B-3 | MS | Method |
|---|---|---|---|---|
| 136 | N-[4-[8-amino-5-chloro-3-(trideuteriomethyl)imidazo[1,5-a]pyrazin-1-yl]-2,3-difluoro-phenyl]-2-(3-fluoro-phenyl)-2-hydroxy-acetamide | Isomer 1 | ESI (m/z) 465 [$C_{21}H_{12}D_3ClF_3N_5O_2$ + H]$^+$ | Scheme K |
| 137 | N-[4-[8-amino-5-chloro-3-(trideuteriomethyl)imidazo[1,5-a]pyrazin-1-yl]-2,3-difluoro-phenyl]-2-(3-fluoro-phenyl)-2-hydroxy-acetamide | Isomer 2 | ESI (m/z) 465 [$C_{21}H_{12}D_3ClF_3N_5O_2$ + H]$^+$ | Scheme K |
| 138 | N-[4-[8-amino-5-methyl-3-(trideuteriomethyl)imidazo[1,5-a]pyrazin-1-yl]-2,3-difluoro-phenyl]-2-(3-chloro-phenyl)-2-hydroxy-acetamide | Isomer 1 | ESI (m/z) 461 [$C_{23}H_{15}D_3F_5N_5O_2$ + H]$^+$ | Scheme K |
| 139 | N-[4-[8-amino-5-methyl-3-(trideuteriomethyl)imidazo[1,5-a]pyrazin-1-yl]-2,3-difluoro-phenyl]-2-(3-chlorophenyl)-2-hydroxy-acetamide | Isomer 2 | ESI (m/z) 461 [$C_{23}H_{15}D_3F_5N_5O_2$ + H]$^+$ | Scheme K |

TABLE 1-continued

Compounds of Formula I:

| Example | Name | Compounds I-B-3 | MS | Method |
|---|---|---|---|---|
| 140 | N-[4-[8-amino-6-methyl-3-(trideuteriomethyl)imidazo[1,5-a]pyrazin-1-yl]-2,3-difluorophenyl]-2-(3-chlorophenyl)-2-hydroxyacetamide | 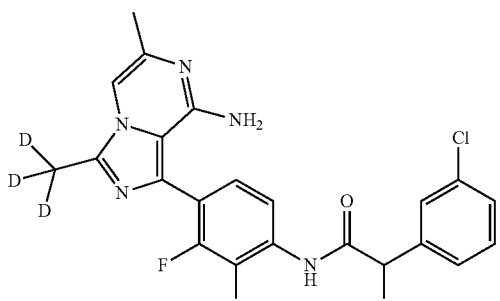 Isomer 1 | ESI (m/z) 461 $[C_{22}H_{15}D_3ClF_2N_5O_2 + H]^+$ | Scheme K |
| 141 | N-[4-[8-amino-6-methyl-3-(trideuteriomethyl)imidazo[1,5-a]pyrazin-1-yl]-2,3-difluorophenyl]-2-(3-chlorophenyl)-2-hydroxyacetamide | 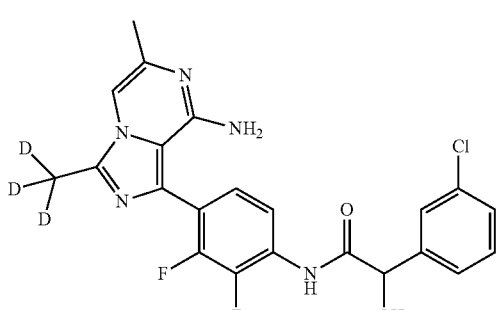 Isomer 2 | ESI (m/z) 461 $[C_{22}H_{15}D_3ClF_2N_5O_2 + H]^+$ | Scheme K |
| 142 | N-[4-[8-amino-3-(trideuteriomethyl)-5-(trifluoromethyl)imidazo[1,5-a]pyrazin-1-yl]-2,3-difluorophenyl]-2-(3-chlorophenyl)-2-hydroxyacetamide | 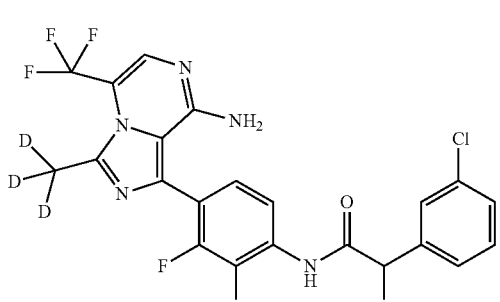 Isomer 1 | ESI (m/z) 515 $[C_{22}H_{12}D_3ClF_5N_5O_2 + H]^+$ | Scheme K |
| 143 | N-[4-[8-amino-3-(trideuteriomethyl)-5-(trifluoromethyl)imidazo[1,5-a]pyrazin-1-yl]-2,3-difluorophenyl]-2-(3-chlorophenyl)-2-hydroxyacetamide | 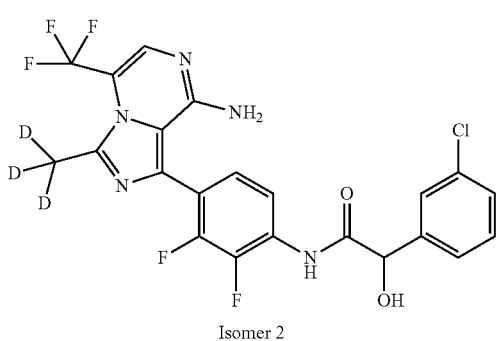 [SMILES: [2H]C([2H])([2H])c1nc(-c2ccc(NC(=O)C(O)c3cccc(Cl)c3)c(F)c2F)c2c(N)ncc(C(F)(F)F)n12] Isomer 2 | ESI (m/z) 515 $[C_{22}H_{12}D_3ClF_5N_5O_2 + H]^+$ | Scheme K |

TABLE 1-continued

Compounds of Formula I:

| Example | Name | Compounds I-B-3 | MS | Method |
|---|---|---|---|---|
| 144 | N-[4-[8-amino-5-chloro-3-(trideuteriomethyl)imidazo[1,5-a]pyrazin-1-yl]-2,3-difluoro-phenyl]-2-(3-chlorophenyl)-2-hydroxy-acetamide | 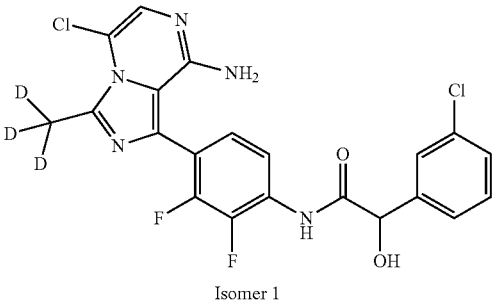<br>Isomer 1 | ESI (m/z) 481 $[C_{21}H_{12}D_3Cl_2F_2N_5O_2 + H]^+$ | Scheme K |
| 145 | N-[4-[8-amino-5-chloro-3-(trideuteriomethyl)imidazo[1,5-a]pyrazin-1-yl]-2,3-difluoro-phenyl]-2-(3-chlorophenyl)-2-hydroxy-acetamide | 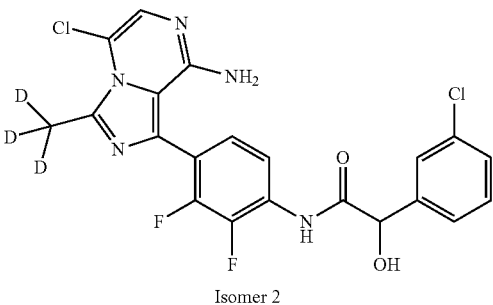 [SMILES: [2H]C([2H])([2H])c1nc(-c2ccc(NC(=O)C(O)c3cccc(Cl)c3)c(F)c2F)c2c(N)ncc(Cl)n12]<br>Isomer 2 | ESI (m/z) 481 $[C_{21}H_{12}D_3Cl_2F_2N_5O_2 + H]^+$ | Scheme K |
| 146 | N-[4-[8-amino-5-methyl-3-(trideuteriomethyl)imidazo[1,5-a]pyrazin-1-yl]-2,3-difluoro-phenyl]-2-hydroxy-2-[3-(trifluoromethyl)phenyl]acetamide | 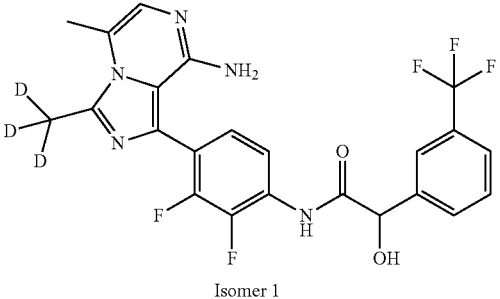 [SMILES: [2H]C([2H])([2H])c1nc(-c2ccc(NC(=O)C(O)c3cccc(C(F)(F)F)c3)c(F)c2F)c2c(N)ncc(C)n12]<br>Isomer 1 | ESI (m/z) 495 $[C_{23}H_{15}D_3F_5N_5O_2 + H]^+$ | Scheme K |
| 147 | N-[4-[8-amino-5-methyl-3-(trideuteriomethyl)imidazo[1,5-a]pyrazin-1-yl]-2,3-difluoro-phenyl]-2-hydroxy-2-[3-(trifluoromethyl)phenyl]acetamide | 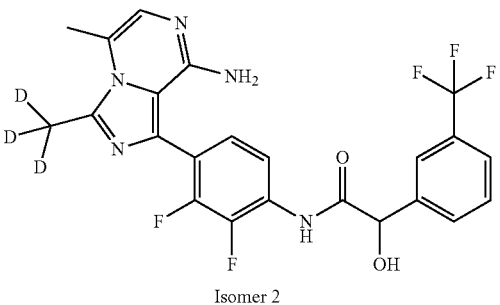 [SMILES: [2H]C([2H])([2H])c1nc(-c2ccc(NC(=O)C(O)c3cccc(C(F)(F)F)c3)c(F)c2F)c2c(N)ncc(C)n12]<br>Isomer 2 | ESI (m/z) 495 $[C_{23}H_{15}D_3F_5N_5O_2 + H]^+$ | Scheme K |

TABLE 1-continued

Compounds of Formula I:

| Example | Name | Compounds I-B-3 | MS | Method |
|---|---|---|---|---|
| 148 | N-[4-[8-amino-3-(trideuteriomethyl)-5-(trifluoromethyl)imidazo[1,5-a]pyrazin-1-yl]-2,3-difluoro-phenyl]-2-hydroxy-2-[3-(trifluoromethyl)phenyl]acetamide | 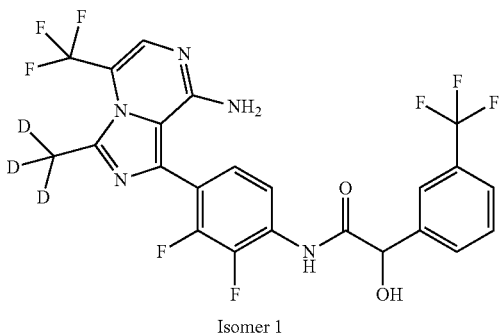 [SMILES: [2H]C([2H])([2H])c1nc(-c2ccc(NC(=O)C(O)c3cccc(C(F)(F)F)c3)c(F)c2F)c2c(N)ncc(C(F)(F)F)n12]<br>Isomer 1 | ESI (m/z) 549 [$C_{23}H_{12}D_3F_8N_5O_2$ + H]$^+$ | Scheme K |
| 149 | N-[4-[8-amino-3-(trideuteriomethyl)-5-(trifluoromethyl)imidazo[1,5-a]pyrazin-1-yl]-2,3-difluoro-phenyl]-2-hydroxy-2-[3-(trifluoromethyl)phenyl]acetamide | 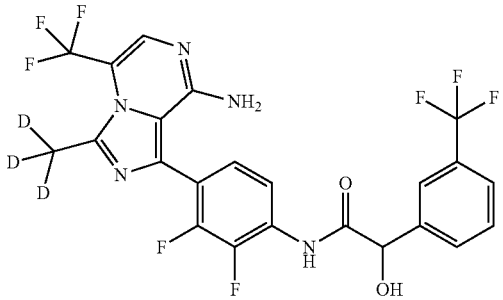<br>Isomer 2 | ESI (m/z) 549 [$C_{23}H_{12}D_3F_8N_5O_2$ + H]$^+$ | Scheme K |
| 150 | N-[4-[8-amino-6-methyl-3-(trideuteriomethyl)imidazo[1,5-a]pyrazin-1-yl]-2,3-difluoro-phenyl]-2-hydroxy-2-[3-(trifluoromethyl)phenyl]acetamide | 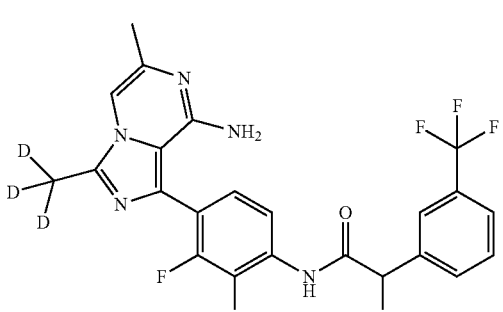<br>Isomer 1 | ESI (m/z) 495 [$C_{23}H_{15}D_3F_5N_5O_2$ + H]$^+$ | Scheme K |
| 151 | N-[4-[8-amino-6-methyl-3-(trideuteriomethyl)imidazo[1,5-a]pyrazin-1-yl]-2,3-difluoro-phenyl]-2-hydroxy-2-[3-(trifluoromethyl)phenyl]acetamide | 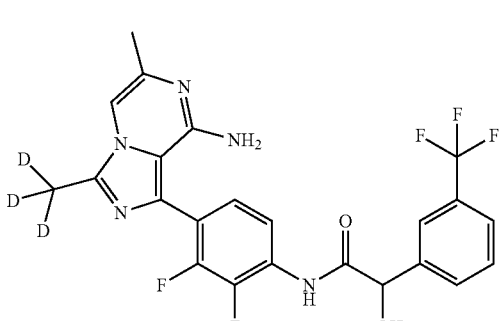<br>Isomer 2 | ESI (m/z) 495 [$C_{23}H_{15}D_3F_5N_5O_2$ + H]$^+$ | Scheme K |

TABLE 1-continued

Compounds of Formula I:

| Example | Name | Compounds I-B-3 | MS | Method |
|---|---|---|---|---|
| 152 | N-[4-[8-amino-5-chloro-3-(trideuteriomethyl)imidazo[1,5-a]pyrazin-1-yl]-2,3-difluorophenyl]-2-hydroxy-2-[3-(trifluoromethyl)phenyl]acetamide | 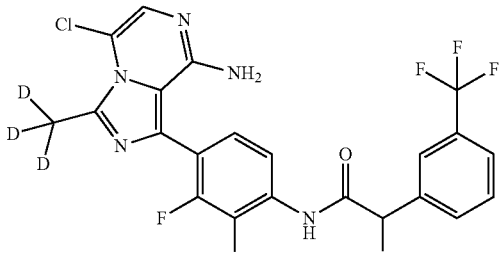 Isomer 1 | ESI (m/z) 515 $[C_{22}H_{12}D_3ClF_5N_5O_2 + H]^+$ | Scheme K |
| 153 | N-[4-[8-amino-5-chloro-3-(trideuteriomethyl)imidazo[1,5-a]pyrazin-1-yl]-2,3-difluorophenyl]-2-hydroxy-2-[3-(trifluoromethyl)phenyl]acetamide | 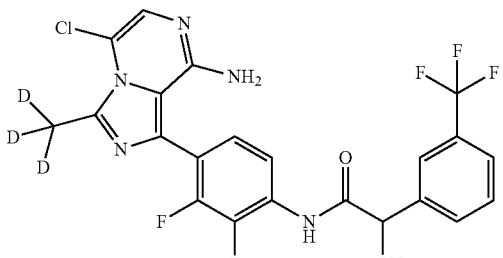 Isomer 2 | ESI (m/z) 515 $[C_{22}H_{12}D_3ClF_5N_5O_2 + H]^+$ | Scheme K |
| 154 | N-[4-[8-amino-5-methyl-3-(trideuteriomethyl)imidazo[1,5-a]pyrazin-1-yl]-2,3-difluorophenyl]-2-(3,5-difluorophenyl)-2-hydroxyacetamide | 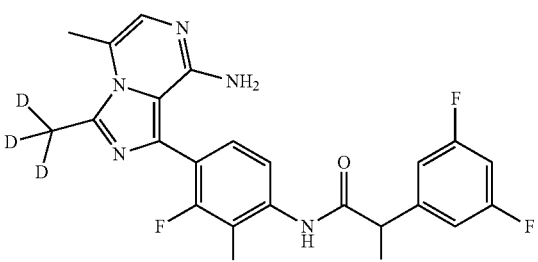 Isomer 1 | ESI (m/z) 463 $[C_{22}H_{14}D_3F_4N_5O_2 + H]^+$ | Scheme K |
| 155 | N-[4-[8-amino-5-methyl-3-(trideuteriomethyl)imidazo[1,5-a]pyrazin-1-yl]-2,3-difluorophenyl]-2-(3,5-difluorophenyl)-2-hydroxyacetamide | 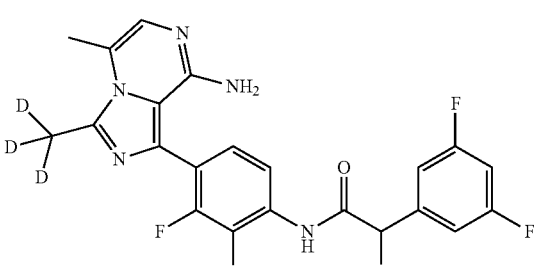 Isomer 2 | ESI (m/z) 463 $[C_{22}H_{14}D_3F_4N_5O_2 + H]^+$ | Scheme K |

TABLE 1-continued

Compounds of Formula I:

| Example | Name | Compounds I-B-3 | MS | Method |
|---|---|---|---|---|
| 156 | N-[4-[8-amino-5-chloro-3-(trideuteriomethyl)imidazo[1,5-a]pyrazin-1-yl]-2,3-difluorophenyl]-2-(3,5-difluorophenyl)-2-hydroxyacetamide | 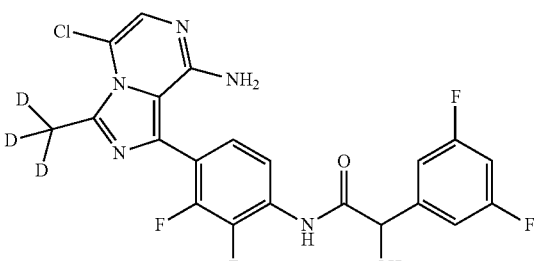<br>Isomer 1 | ESI (m/z) 483 $[C_{21}H_{11}D_3ClF_4N_5O_2 + H]^+$ | Scheme K |
| 157 | N-[4-[8-amino-5-chloro-3-(trideuteriomethyl)imidazo[1,5-a]pyrazin-1-yl]-2,3-difluorophenyl]-2-(3,5-difluorophenyl)-2-hydroxyacetamide | 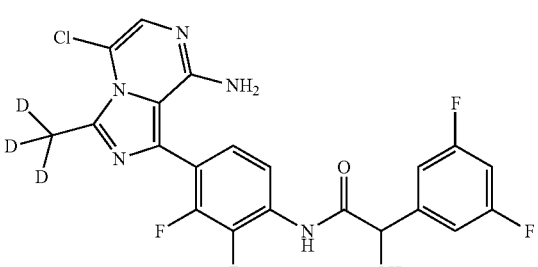<br>Isomer 2 | ESI (m/z) 483 $[C_{21}H_{11}D_3ClF_4N_5O_2 + H]^+$ | Scheme K |
| 158 | N-[4-[8-amino-3-(trideuteriomethyl)-5-(trifluoromethyl)imidazo[1,5-a]pyrazin-1-yl]-2,3-difluorophenyl]-2-(3,5-difluorophenyl)-2-hydroxyacetamide | 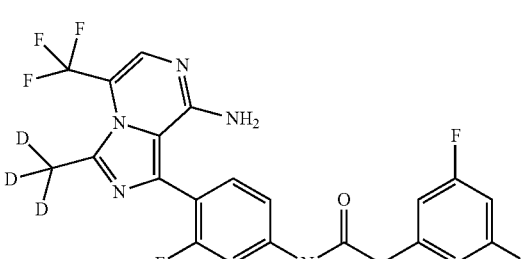<br>Isomer 1 | ESI (m/z) 517 $[C_{22}H_{11}D_3F_7N_5O_2 + H]^+$ | Scheme K |
| 159 | N-[4-[8-amino-3-(trideuteriomethyl)-5-(trifluoromethyl)imidazo[1,5-a]pyrazin-1-yl]-2,3-difluorophenyl]-2-(3,5-difluorophenyl)-2-hydroxyacetamide | 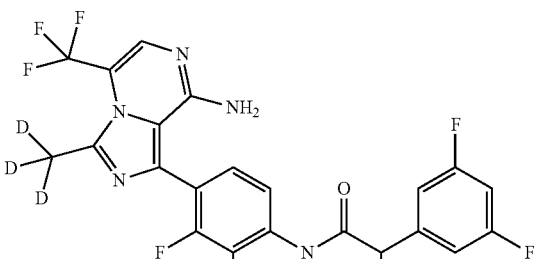<br>Isomer 2 | ESI (m/z) 517 $[C_{22}H_{11}D_3F_7N_5O_2 + H]^+$ | Scheme K |

TABLE 1-continued

Compounds of Formula I:

| Example | Name | Compounds I-B-3 | MS | Method |
|---|---|---|---|---|
| 160 | N-[4-[8-amino-5-methyl-3-(trideuteriomethyl)imidazo[1,5-a]pyrazin-1-yl]-2,3-difluoro-phenyl]-2-[3-fluoro-5-(trifluoromethyl)phenyl]-2-hydroxy-acetamide | 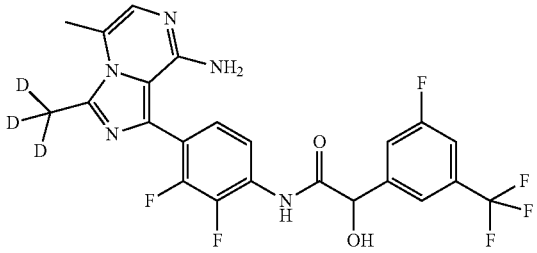<br>Isomer 1 | ESI (m/z) 513 $[C_{23}H_{14}D_3F_6N_5O_2 + H]^+$ | Scheme K |
| 161 | N-[4-[8-amino-5-methyl-3-(trideuteriomethyl)imidazo[1,5-a]pyrazin-1-yl]-2,3-difluoro-phenyl]-2-[3-fluoro-5-(trifluoromethyl)phenyl]-2-hydroxy-acetamide | 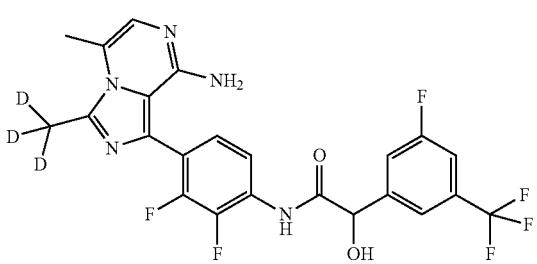<br>Isomer 2 | ESI (m/z) 513 $[C_{23}H_{14}D_3F_6N_5O_2 + H]^+$ | Scheme K |
| 162 | N-[4-[8-amino-3-(trideuteriomethyl)-5-(trifluoromethyl)imidazo[1,5-a]pyrazin-1-yl]-2,3-difluoro-phenyl]-2-[3-fluoro-5-(trifluoromethyl)phenyl]-2-hydroxy-acetamide | 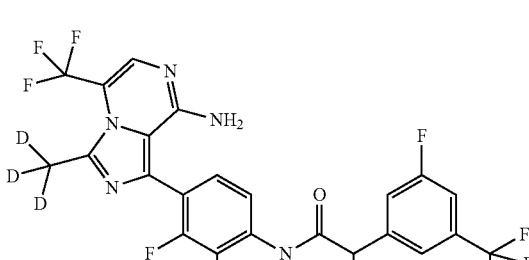<br>Isomer 1 | ESI (m/z) 567 $[C_{23}H_{11}D_3F_9N_5O_2 + H]^+$ | Scheme K |
| 163 | N-[4-[8-amino-3-(trideuteriomethyl)-5-(trifluoromethyl)imidazo[1,5-a]pyrazin-1-yl]-2,3-difluoro-phenyl]-2-[3-fluoro-5-(trifluoromethyl)phenyl]-2-hydroxy-acetamide | 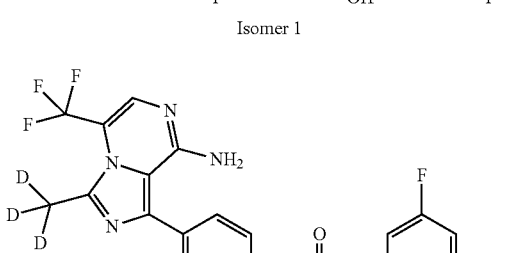<br>Isomer 2 | ESI (m/z) 567 $[C_{23}H_{11}D_3F_9N_5O_2 + H]^+$ | Scheme K |
| 164 | N-[4-[8-amino-5-chloro-3-(trideuteriomethyl)imidazo[1,5-a]pyrazin-1-yl]-2,3-difluoro-phenyl]-2-[3-fluoro-5-(trifluoromethyl)phenyl]-2-hydroxy-acetamide | 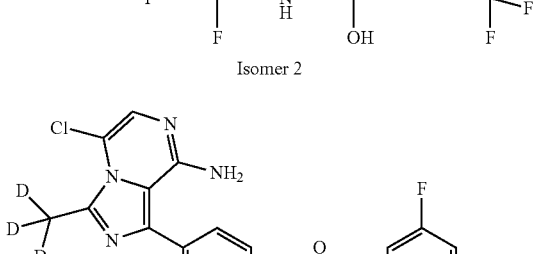<br>Isomer 1 | ESI (m/z) 533 $[C_{22}H_{11}D_3ClF_6N_5O_2 + H]^+$ | Scheme K |

TABLE 1-continued

Compounds of Formula I:

| Example | Name | Compounds I-B-3 | MS | Method |
|---|---|---|---|---|
| 165 | N-[4-[8-amino-5-chloro-3-(trideuteriomethyl)imidazo[1,5-a]pyrazin-1-yl]-2,3-difluoro-phenyl]-2-[3-fluoro-5-(trifluoromethyl)phenyl]-2-hydroxy-acetamide | 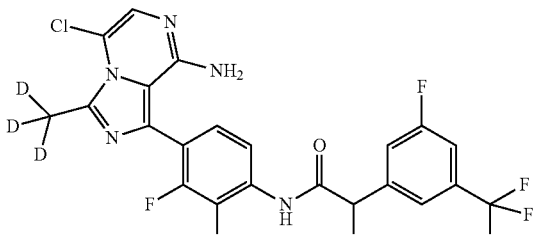 Isomer 2 | ESI (m/z) 533 [$C_{22}H_{11}D_3ClF_6N_5O_2$ + H]$^+$ | Scheme K |
| 166 | N-[4-[8-amino-6-methyl-3-(trideuteriomethyl)imidazo[1,5-a]pyrazin-1-yl]-2,3-difluoro-phenyl]-2-[3-fluoro-5-(trifluoromethyl)phenyl]-2-hydroxy-acetamide | 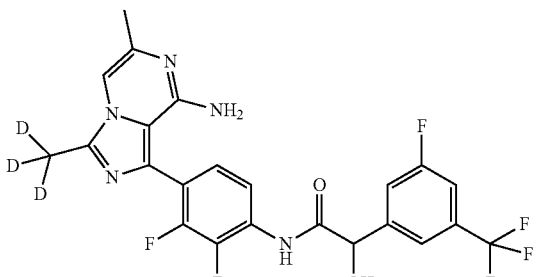 Isomer 1 | ESI (m/z) 495 [$C_{23}H_{14}D_3F_6N_5O_2$ + H]$^+$ | Scheme K |
| 167 | N-[4-[8-amino-6-methyl-3-(trideuteriomethyl)imidazo[1,5-a]pyrazin-1-yl]-2,3-difluoro-phenyl]-2-[3-fluoro-5-(trifluoromethyl)phenyl]-2-hydroxy-acetamide | 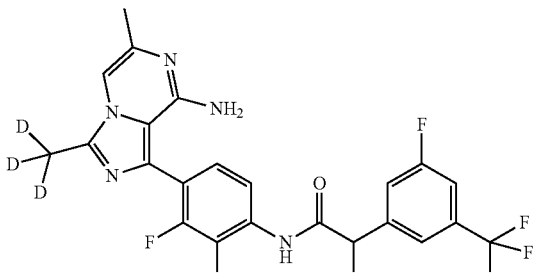 Isomer 2 | ESI (m/z) 495 [$C_{23}H_{14}D_3F_6N_5O_2$ + H]$^+$ | Scheme K |
| 168 | N-(4-(8-amino-3,5-dimethyl-imidazo[1,5-a]pyrazin-1-yl)-2-fluoro-3-methyl-phenyl)-2-(3-fluorophenyl)-2-hydroxy-acetamide | 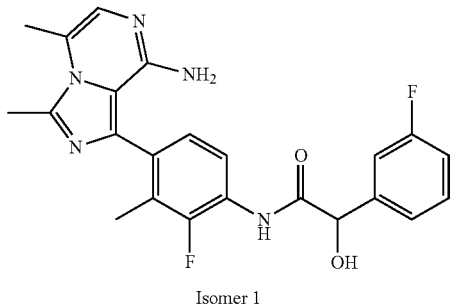 [SMILES: Cc1c(-c2nc(C)n3c(C)cnc(N)c23)ccc(NC(=O)C(O)c2cccc(F)c2)c1F] Isomer 1 | ESI (m/z) 438 [$C_{23}H_{21}F_2N_5O_2$ + H]$^+$ | Scheme K |

TABLE 1-continued

Compounds of Formula I:

| Example | Name | Compounds I-B-3 | MS | Method |
|---|---|---|---|---|
| 169 | N-(4-(8-amino-3,5-dimethyl-imidazo[1,5-a]pyrazin-1-yl)-2-fluoro-3-methyl-phenyl)-2-(3-fluorophenyl)-2-hydroxy-acetamide | 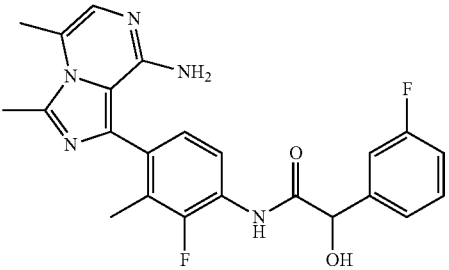 Isomer 2 | ESI (m/z) 438 $[C_{23}H_{21}F_2N_5O_2 + H]^+$ | Scheme K |
| 170 | N-[5-[8-amino-6-methyl-3-(trideuteriomethyl)imidazo[1,5-a]pyrazin-1-yl]-6-methyl-2-pyridyl]-2-(3-fluorophenyl)-2-hydroxy-acetamide | 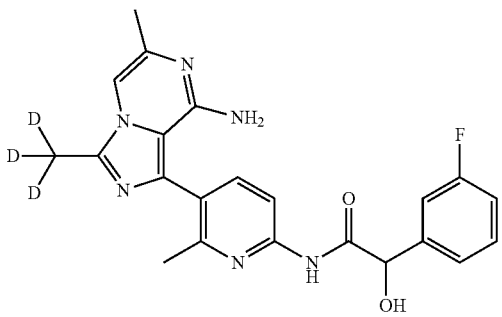 Isomer 1 | ESI (m/z) 424 $[C_{22}H_{18}D_3FN_6O_2 + H]^+$ | Scheme K |
| 171 | N-[5-[8-amino-6-methyl-3-(trideuteriomethyl)imidazo[1,5-a]pyrazin-1-yl]-6-methyl-2-pyridyl]-2-(3-fluorophenyl)-2-hydroxy-acetamide | 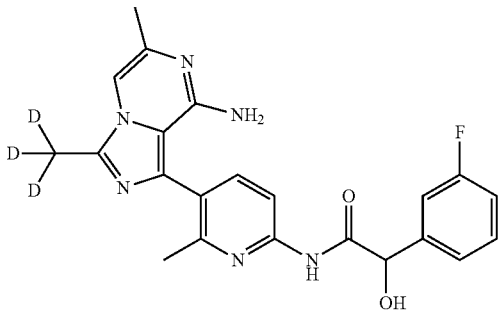 Isomer 2 | ESI (m/z) 424 $[C_{22}H_{18}D_3FN_6O_2 + H]^+$ | Scheme K |
| 172 | N-[5-[8-amino-5-methyl-3-(trideuteriomethyl)imidazo[1,5-a]pyrazin-1-yl]-6-methyl-2-pyridyl]-2-(3-fluorophenyl)-2-hydroxy-acetamide | 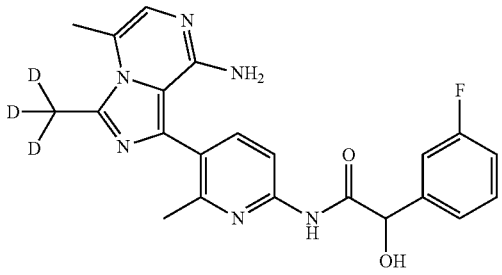 Isomer 1 | ESI (m/z) 424 $[C_{22}H_{18}D_3FN_6O_2 + H]^+$ | Scheme K |

TABLE 1-continued

Compounds of Formula I:

| Example | Name | Compounds I-B-3 | MS | Method |
|---|---|---|---|---|
| 173 | N-[5-[8-amino-5-methyl-3-(trideuteriomethyl)imidazo[1,5-a]pyrazin-1-yl]-6-methyl-2-pyridyl]-2-(3-fluorophenyl)-2-hydroxy-acetamide | Isomer 2 | ESI (m/z) 424 [$C_{22}H_{18}D_3FN_6O_2$ + H]$^+$ | Scheme K |
| 174 | N-[5-[8-amino-5-methyl-3-(trideuteriomethyl)imidazo[1,5-a]pyrazin-1-yl]-6-methyl-2-pyridyl]-2-hydroxy-2-[3-(trifluoromethyl)phenyl]acetamide | Isomer 1 | ESI (m/z) 474 [$C_{23}H_{18}D_3F_3N_6O_2$ + H]$^+$ | Scheme K |
| 175 | N-[5-[8-amino-5-methyl-3-(trideuteriomethyl)imidazo[1,5-a]pyrazin-1-yl]-6-methyl-2-pyridyl]-2-hydroxy-2-[3-(trifluoromethyl)phenyl]acetamide | Isomer 2 | ESI (m/z) 474 [$C_{23}H_{18}D_3F_3N_6O_2$ + H]$^+$ | Scheme K |
| 176 | N-[5-[8-amino-6-methyl-3-(trideuteriomethyl)imidazo[1,5-a]pyrazin-1-yl]-6-methyl-2-pyridyl]-2-hydroxy-2-[3-(trifluoromethyl)phenyl]acetamide | Isomer 1 | ESI (m/z) 474 [$C_{23}H_{18}D_3F_3N_6O_2$ + H]$^+$ | Scheme K |

TABLE 1-continued

Compounds of Formula I:

| Example | Name | Compounds I-B-3 | MS | Method |
|---|---|---|---|---|
| 177 | N-[5-[8-amino-6-methyl-3-(trideuteriomethyl)imidazo[1,5-a]pyrazin-1-yl]-6-methyl-2-pyridyl]-2-hydroxy-2-[3-(trifluoromethyl)phenyl]acetamide | 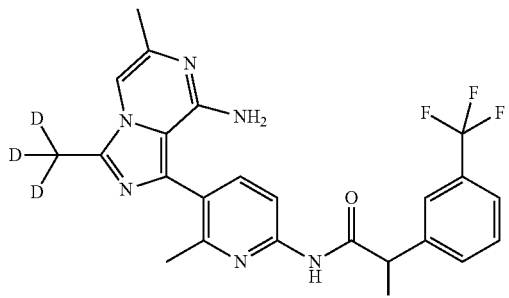<br>Isomer 2 | ESI (m/z) 474 $[C_{23}H_{18}D_3F_3N_6O_2 + H]^+$ | Scheme K |
| 178 | N-[5-[8-amino-6-methyl-3-(trideuteriomethyl)imidazo[1,5-a]pyrazin-1-yl]-4-methyl-2-pyridyl]-2-(3-fluorophenyl)-2-hydroxy-acetamide | 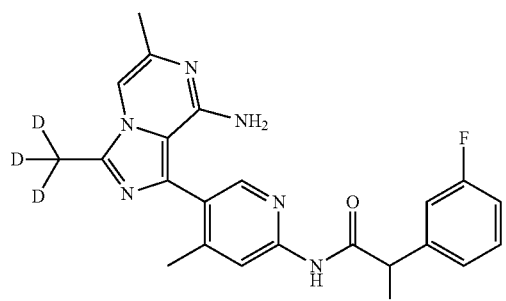<br>Isomer 1 | ESI (m/z) 424 $[C_{22}H_{18}D_3FN_6O_2 + H]^+$ | Scheme K |
| 179 | N-[5-[8-amino-6-methyl-3-(trideuteriomethyl)imidazo[1,5-a]pyrazin-1-yl]-4-methyl-2-pyridyl]-2-(3-fluorophenyl)-2-hydroxy-acetamide | 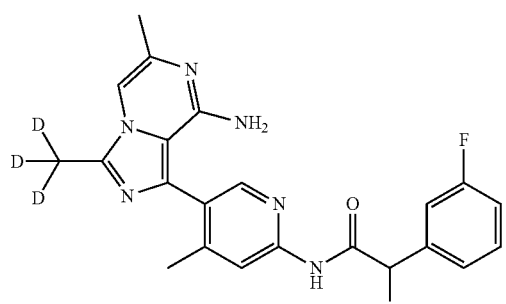<br>Isomer 2 | ESI (m/z) 424 $[C_{22}H_{18}D_3FN_6O_2 + H]^+$ | Scheme K |
| 180 | N-[5-[8-amino-5-methyl-3-(trideuteriomethyl)imidazo[1,5-a]pyrazin-1-yl]-4-methyl-2-pyridyl]-2-(3-fluorophenyl)-2-hydroxy-acetamide | 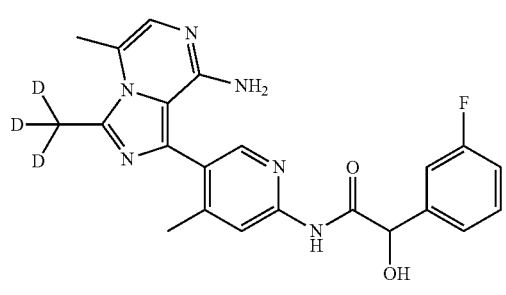<br>Isomer 1 | ESI (m/z) 424 $[C_{22}H_{18}D_3FN_6O_2 + H]^+$ | Scheme K |

TABLE 1-continued

Compounds of Formula I:

| Example | Name | Compounds I-B-3 | MS | Method |
|---|---|---|---|---|
| 181 | N-[5-[8-amino-5-methyl-3-(trideuteriomethyl)imidazo[1,5-a]pyrazin-1-yl]-4-methyl-2-pyridyl]-2-(3-fluorophenyl)-2-hydroxy-acetamide | Isomer 2 | ESI (m/z) 424 [$C_{22}H_{18}D_3FN_6O_2$ + H]$^+$ | Scheme K |
| 182 | N-[5-[8-amino-6-methyl-3-(trideuteriomethyl)imidazo[1,5-a]pyrazin-1-yl]-4-methyl-2-pyridyl]-2-hydroxy-2-[3-(trifluoromethyl)phenyl]acetamide | Isomer 1 | ESI (m/z) 474 [$C_{23}H_{18}D_3F_3N_6O_2$ + H]$^+$ | Scheme K |
| 183 | N-[5-[8-amino-6-methyl-3-(trideuteriomethyl)imidazo[1,5-a]pyrazin-1-yl]-4-methyl-2-pyridyl]-2-hydroxy-2-[3-(trifluoromethyl)phenyl]acetamide | Isomer 2 | ESI (m/z) 474 [$C_{23}H_{18}D_3F_3N_6O_2$ + H]$^+$ | Scheme K |
| 184 | N-[5-[8-amino-5-methyl-3-(trideuteriomethyl)imidazo[1,5-a]pyrazin-1-yl]-4-methyl-2-pyridyl]-2-hydroxy-2-[3-(trifluoromethyl)phenyl]acetamide | Isomer 1 | ESI (m/z) 474 [$C_{23}H_{18}D_3F_3N_6O_2$ + H]$^+$ | Scheme K |

TABLE 1-continued

Compounds of Formula I:

| Example | Name | Compounds I-B-3 | MS | Method |
|---|---|---|---|---|
| 185 | N-[5-[8-amino-5-methyl-3-(trideuteriomethyl)imidazo[1,5-a]pyrazin-1-yl]-4-methyl-2-pyridyl]-2-hydroxy-2-[3-(trifluoromethyl)phenyl]acetamide | Isomer 2 | ESI (m/z) 474 $[C_{23}H_{18}D_3F_3N_6O_2 + H]^+$ | Scheme K |
| 186 | N-[5-[8-amino-5-methyl-3-(trideuteriomethyl)imidazo[1,5-a]pyrazin-1-yl]-4-methyl-pyrimidin-2-yl]-2-(3-fluorophenyl)-2-hydroxyacetamide | Isomer 1 | ESI (m/z) 425 $[C_{21}H_{17}D_3FN_7O_2 + H]^+$ | Scheme K |
| 187 | N-[5-[8-amino-5-methyl-3-(trideuteriomethyl)imidazo[1,5-a]pyrazin-1-yl]-4-methyl-pyrimidin-2-yl]-2-(3-fluorophenyl)-2-hydroxyacetamide | Isomer 2 | ESI (m/z) 425 $[C_{21}H_{17}D_3FN_7O_2 + H]^+$ | Scheme K |

REFERENCES

Adrian L. Smith et al., Discovery of 1H-Pyrazol-3(2H)-ones as Potent and Selective Inhibitors of Protein Kinase R-like Endoplasmic Reticulum Kinase (PERK), *J. Med. Chem.*, 2015, 58 (3), pp 1426-1441

Ron, D.; Walter, P. Signal integration in the endoplasmic reticulum unfolded protein response *Nat. Rev. Mol. Cell Biol.* 2007, 8, 519-529

Shore, G. C.; Papa, F. R.; Oakes, S. A. Signaling cell death from the endoplasmic reticulum stress response *Curr. Opin. Cell Biol.* 2011, 23, 143-149

Carrara, M.; Prischi, F.; Ali, M. M. U. UPR signal activation by luminal sensor domains *Int. J. Mol. Sci.* 2013, 14, 6454-6466

Ma, Y.; Hendershot, L. M. The role of the unfolded protein response in tumor development: friend or foe? *Nat. Rev. Cancer* 2004, 4, 966-977

Walter, P.; Ron, D. The unfolded protein response: from stress pathway to homeostatic regulation *Science* 2011, 334, 1081-1086

Vandewynckel, Y. P.; Laukens, D.; Geerts, A.; Bogaerts, E.; Paridaens, A.; Verhelst, X.; Jans sens, S.; Heindryckx, F.; van Vlierberghe, H. The paradox of the unfolded protein response in cancer *Anticancer Res.* 2013, 33, 4683-4694

Gao, Y.; Sartori, D. J.; Li, C.; Yu, Q.-C.; Kushner, J. A.; Simon, M. C.; Diehl, J. A. PERK is required in the adult pancreas and is essential for maintenance of glucose homeostasis *Mol. Cell. Biol.* 2012, 32, 5129-5139

Bi, M.; Naczki, C.; Koritzinsky, M.; Fels, D.; Blais, J.; Hu, N.; Harding, H.; Novoa, I.; Varia, M.; Raleigh, J.; Scheuner, D.; Kaufman, R. J.; Bell, J.; Ron, D.; Wouters, B. G.; Koumenis, C. ER stress-regulated translation increases tolerance to extreme hypoxia and promotes tumor growth *EMBO J.* 2005, 24, 3470-3481

Kim, I.; Xu, W.; Reed, J. C. Cell death and endoplasmic reticulum stress: disease relevance and therapeutic opportunities *Nat. Rev. Drug Discovery* 2008, 7, 1013-1030

Fels, D. R.; Koumenis, C. The PERK/eIF2α/ATF4 module of the UPR in hypoxia resistance and tumor growth *Cancer Biol. Ther.* 2006, 5, 723-728

WO2018/194885

U.S. Publication No. 2017/0165259

U.S. Pat. No. 8,598,156

What is claimed is:

1. A compound of the formula (I):

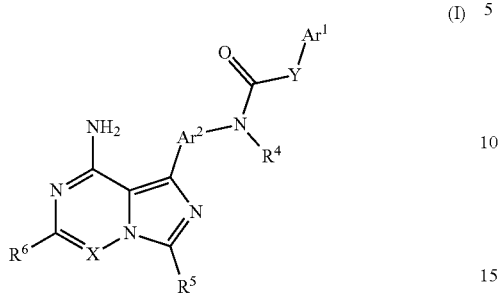

Ar$^1$ is aryl, heteroaryl, or cycloalkyl, optionally substituted by one or more independent R$^1$ substituents;

Ar$^2$ is aryl or heteroaryl, optionally substituted by one or more independent R$^2$ substituents;

Y is CR$^{3a}$R$^{3b}$, C(O), CF$_2$, or CNOR$^{3bb}$;

R$^{3a}$ is H, alkyl, or cycloalkyl;

R$^{3b}$ is H, alkyl, OR$^{3c}$, or NR$^{3d}$R$^{3e}$;

R$^{3bb}$ is H or alkyl;

R$^4$ is H, alkyl, or OH;

X is CR$^7$ or N;

R$^1$ is one or more independent H, deuterium, halo, CN, NO$_2$, alkyl, cycloalkyl, C$_{0-6}$alkyl-O—C$_{1-12}$alkyl, C$_{0-6}$alkyl-OH, C$_{0-6}$alkyl-O—C$_{3-12}$cycloalkyl, or C$_{0-6}$alkyl-O—C$_{3-12}$heterocycloalkyl, optionally substituted by one or more independent G$^1$ substituents;

R$^2$ is one or more independent H, deuterium, halo, CN, NO$_2$, alkyl, C$_{0-6}$alkylcycloalkyl, C$_{0-6}$alkyl-O—C$_{1-12}$alkyl, C$_{0-6}$alkyl-OH, or C$_{0-6}$alkyl-O—C$_{3-12}$cycloalkyl, optionally substituted by one or more independent G$^2$ substituents;

R$^{3c}$, R$^{3d}$ and R$^{3e}$ are each independently H, alkyl, or cycloalkyl, optionally substituted by one or more independent G$^3$ substituents;

R$^5$ is H, deuterium, halo, alkyl, cycloalkyl, or heterocycloalkyl, optionally substituted by one or more independent G$^4$ substituents;

R$^6$ is H, alkyl, CD$_3$, or CF$_3$;

R$^7$ is H, deuterium, halo, CN, alkyl, cycloalkyl, heterocycloalkyl, aryl, or heteroaryl, optionally substituted by one or more independent H, deuterium or halo;

G$^1$, G$^2$, G$^3$, or G$^4$ are each independently H, deuterium, halo, CN, NO$_2$, C$_{1-12}$alkyl, C$_{0-12}$alkylC$_{3-12}$cycloalkyl, C$_{0-12}$alkylC$_{3-12}$heterocycloalkyl, OR$^8$, NR$^8$R$^9$, C(O)R$^8$, C(O)OR$^8$, C(O)NR$^8$R$^9$, OC(O)R$^8$, OC(O)OR$^8$, OC(O)NR$^8$R$^9$, N(R$^{10}$)C(O)R$^8$, N(R$^{10}$)C(O)OR$^8$, N(R$^{10}$)C(O)NR$^8$R$^9$, S(O)$_n$R$^8$, S(O)$_n$OR$^8$, S(O)$_n$NR$^8$R$^9$, N(R$^{10}$)S(O)$_n$R$^8$, N(R$^{10}$)S(O)$_n$OR$^8$, or N(R$^{10}$)S(O)$_n$NR$^8$R$^9$, optionally substituted by one or more independent H, deuterium, halo, OH, CN, or NO$_2$;

R$^8$, R$^9$, or R$^{10}$ are each independently selected from H, deuterium, halo, CN, NO$_2$, alkyl, cycloalkyl or heterocycloalkyl, optionally substituted by one or more independent H, deuterium, halo, OH, CN, or NO$_2$;

n is 0, 1, or 2;

or a pharmaceutically acceptable salt thereof.

2. The compound of claim 1 of the formula (Ia):

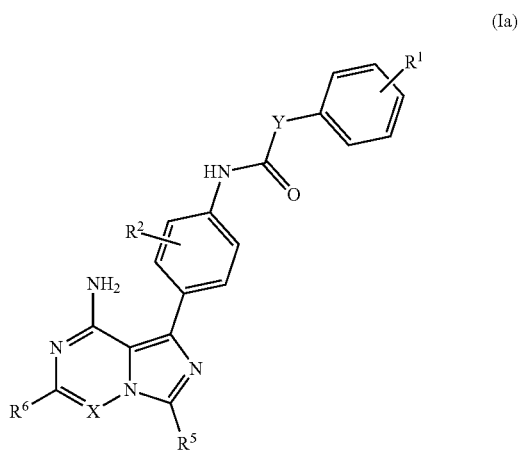

Y is CR$^{3a}$R$^{3b}$;

R$^{3a}$ is H or alkyl;

R$^{3b}$ is OR$^{3e}$ or NR$^{3d}$R$^{3e}$;

R$^1$ is one or more independent H, deuterium, halo, alkyl, cycloalkyl, C$_{0-6}$alkyl-O—C$_{1-12}$alkyl, C$_{0-6}$alkyl-OH, or C$_{0-6}$alkyl-O—C$_{3-12}$cycloalkyl, optionally substituted by one or more independent G$^1$ substituents;

R$^2$ is one or more independent H, deuterium, halo, alkyl, C$_{0-6}$alkylcycloalkyl, C$_{0-6}$alkyl-O—C$_{1-12}$alkyl, C$_{0-6}$alkyl-OH, or C$_{0-6}$alkyl-O—C$_{3-12}$cycloalkyl, optionally substituted by one or more independent G$^2$ substituents;

R$^{3c}$, R$^{3d}$ and R$^{3e}$ are each independently H or alkyl, optionally substituted by one or more independent G$^3$ substituents;

X is CR$^7$ or N;

R$^5$ is H, deuterium, halo, alkyl, cycloalkyl, or heterocycloalkyl, optionally substituted by one or more independent G$^4$ substituents;

R$^6$ is H, alkyl, CD$_3$, or CF$_3$;

R$^7$ is H, deuterium, halo, CN, alkyl, cycloalkyl, heterocycloalkyl, aryl, or heteroaryl, optionally substituted by one or more independent H, deuterium or halo;

G$^1$, G$^2$, G$^3$, or G are each independently H, deuterium, halo, CN, NO$_2$, C$_{1-12}$alkyl, C$_{0-12}$alkylC$_{3-12}$cycloalkyl, C$_{0-12}$alkylC$_{3-12}$heterocycloalkyl, OR$^8$, NR$^8$R$^9$, C(O)R$^8$, C(O)OR$^8$, C(O)NR$^8$R$^9$, OC(O)R$^8$, OC(O)OR$^8$, OC(O)NR$^8$R$^9$, N(R$^{10}$)C(O)R$^8$, N(R$^{10}$)C(O)OR$^8$, N(R$^{10}$)C(O)NR$^8$R$^9$, S(O)$_n$R$^8$, S(O)$_n$OR$^8$, S(O)$_n$NR$^8$R$^9$, N(R$^{10}$)S(O)$_n$R$^8$, N(R$^{10}$)S(O)$_n$OR$^8$, or N(R$^{10}$)S(O)$_n$NR$^8$R$^9$, optionally substituted by one or more independent H, deuterium, halo, OH, CN, or NO$_2$;

R$^8$, R$^9$, or R$^{10}$ are each independently selected from H, deuterium, halo, CN, NO$_2$, alkyl, cycloalkyl or heterocycloalkyl, optionally substituted by one or more independent H, deuterium, halo, OH, CN, or NO$_2$;

n is 0, 1, or 2;

or a pharmaceutically acceptable salt thereof.

3. The compound of claim 1 of the formula (Ib):

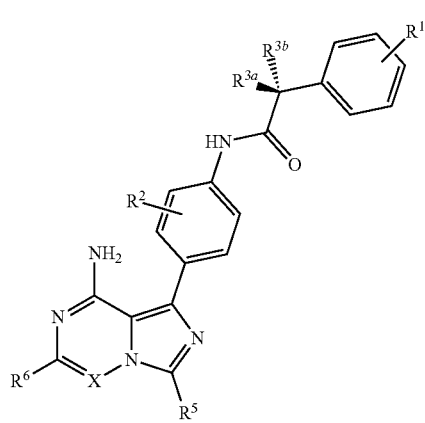

(Ib)

X is CR⁷ or N;

R¹ is one or more independent H, deuterium, halo, alkyl, cycloalkyl, $C_{0-6}$alkyl-O—$C_{1-12}$alkyl, $C_{0-6}$alkyl-OH, or $C_{0-6}$alkyl-O—$C_{3-12}$cycloalkyl, optionally substituted by one or more independent G¹ substituents;

R² is one or more independent H, deuterium, halo, alkyl, cycloalkyl, $C_{0-6}$alkyl-O—$C_{1-12}$alkyl, $C_{0-6}$alkyl-OH, or $C_{0-6}$alkyl-O—$C_{3-12}$cycloalkyl, optionally substituted by one or more independent G² substituents;

$R^{3a}$ is H or alkyl;

$R^{3b}$ is OR C or $NR^{3d}R^{3e}$;

$R^{3c}$, $R^{3d}$ and $R^{3e}$ are each independently H or alkyl, optionally substituted by one or more independent G³ substituents;

R⁵ is H, deuterium, halo, alkyl, cycloalkyl, or heterocycloalkyl, optionally substituted by one or more independent G⁴ substituents;

R⁶ is H, alkyl, CD₃, or CF₃;

R⁷ is H, deuterium, halo, CN, alkyl, cycloalkyl, heterocycloalkyl, aryl, or heteroaryl, optionally substituted by one or more independent H, deuterium or halo;

G¹, G², G³, or G are each independently H, deuterium, halo, CN, NO₂, $C_{1-12}$alkyl, $C_{0-12}$alkyl$C_{3-12}$cycloalkyl, $C_{0-12}$alkyl$C_{3-12}$heterocycloalkyl, OR⁸, NR⁸R⁹, C(O)R⁸, C(O)OR⁸, C(O)NR⁸R⁹, OC(O)R⁸, OC(O)OR⁸, OC(O)NR⁸R⁹, N(R¹⁰)C(O)R⁸, N(R¹⁰)C(O)OR⁸, N(R¹⁰)C(O)NR⁸R⁹, S(O)$_n$R⁸, S(O)$_n$OR⁸, S(O)$_n$NR⁸R⁹, N(R₁₀)S(O)$_n$R₈, N(R¹⁰)S(O)$_n$OR⁸, or N(R¹⁰)S(O)$_n$NR⁸R⁹, optionally substituted by one or more independent H, deuterium, halo, OH, CN, or NO₂;

R⁸, R⁹, or R¹⁰ are each independently selected from H, deuterium, halo, CN, NO₂, alkyl, cycloalkyl or heterocycloalkyl, optionally substituted by one or more independent H, deuterium, halo, OH, CN, or NO₂;

n is 0, 1, or 2;

or a pharmaceutically acceptable salt thereof.

4. The compound of claim 1 of the formula (Ic):

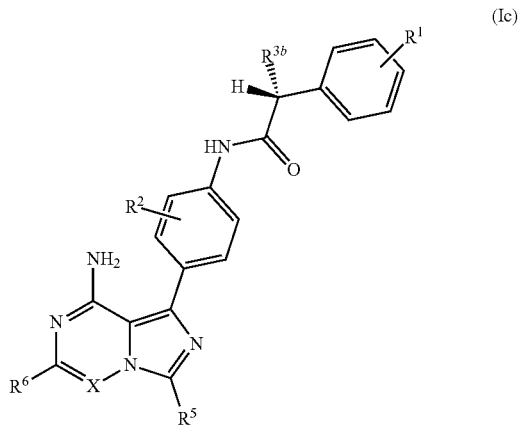

(Ic)

wherein:

X is CR⁷;

R¹ is one or more independent H, deuterium, halo, alkyl, $C_{0-6}$alkyl-OH, or $C_{0-6}$alkyl-O—$C_{1-12}$alkyl, optionally substituted by one or more independent G¹ substituents;

R² is one or more independent H, deuterium, halo, alkyl, $C_{0-6}$alkyl-OH, or $C_{0-6}$alkyl-O—$C_{1-12}$alkyl, optionally substituted by one or more independent G² substituents;

$R^{3b}$ is $OR^{3c}$;

$R^{3c}$ is H or alkyl, optionally substituted by one or more independent G³ substituents;

R⁵ is H, deuterium, halo, alkyl, cycloalkyl, or heterocycloalkyl, optionally substituted by one or more independent G⁴ substituents;

R⁶ is H, alkyl, CD₃, or CF₃;

R⁷ is H, deuterium, halo, heteroaryl or alkyl, optionally substituted by one or more independent H, deuterium or halo;

G¹, G², G³, or G are each independently H, deuterium, halo, CN, NO₂, $C_{1-12}$alkyl, $C_{0-12}$alkyl$C_{3-12}$cycloalkyl, $C_{0-12}$alkyl$C_{3-12}$heterocycloalkyl, OR⁸, NR⁸R⁹, C(O)R⁸, C(O)OR⁸, C(O)NR⁸R⁹, OC(O)R⁸, OC(O)OR⁸, OC(O)NR⁸R⁹, N(R¹⁰)C(O)R⁸, N(R¹⁰)C(O)OR⁸, N(R¹⁰)C(O)NR⁸R⁹, S(O)$_n$R⁸, S(O)$_n$OR⁸, S(O)$_n$NR⁸R⁹, N(R¹⁰)S(O)$_n$R⁸, N(R¹⁰)S(O)$_n$OR⁸, or N(R¹⁰)S(O)$_n$NR⁸R⁹, optionally substituted by one or more independent H, deuterium, halo, OH, CN, or NO₂;

R⁸, R⁹, or R¹⁰ are each independently selected from H, deuterium, halo, CN, NO₂, alkyl, cycloalkyl or heterocycloalkyl, optionally substituted by one or more independent H, deuterium, halo, OH, CN, or NO₂;

n is 0, 1, or 2;

or a pharmaceutically acceptable salt thereof.

5. The compound of claim 1 of the formula (Id):

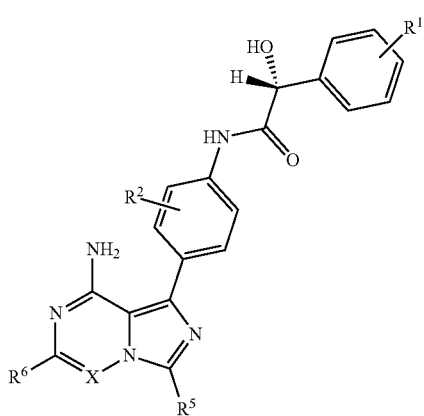
(Id)

X is CR⁷;
R¹ is one or more independent H, deuterium, halo, alkyl, $C_{0-6}$alkyl-OH, or $C_{0-6}$alkyl-O—$C_{1-12}$alkyl, optionally substituted by one or more independent H, deuterium, or halo;
R² is one or more independent H, deuterium, halo, alkyl, $C_{0-6}$alkyl-OH, or $C_{0-6}$alkyl-O—$C_{1-12}$alkyl, optionally substituted by one or more independent H, deuterium or halo;
R⁵ is H, deuterium, halo, alkyl, cycloalkyl, or heterocycloalkyl, optionally substituted by one or more independent H, deuterium, $C_{1-6}$alkyl, halo, OH, or CN;
R⁶ is H, alkyl, CD₃, or CF₃;
R⁷ is H, deuterium, halo, alkyl, heteroaryl or CD₃, wherein the alkyl may be optionally substituted by one or more halo substituents;
or a pharmaceutically acceptable salt thereof.

6. The compound of claim 1 of the formula (Ie):

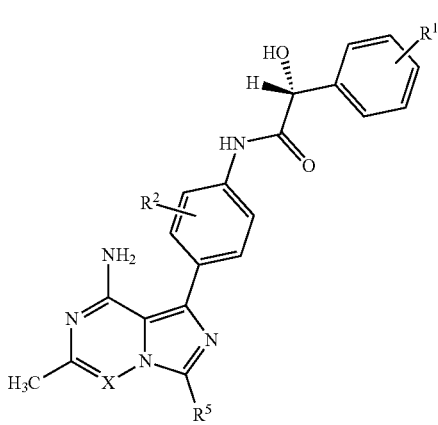
(Ie)

X is CH;
R¹ is one or more independent H, deuterium, halo, alkyl, $C_{0-6}$alkyl-OH, or $C_{0-6}$alkyl-O—$C_{1-12}$alkyl, optionally substituted by one or more independent H, deuterium, or halo;
R² is one or more independent H, deuterium, halo, alkyl, $C_{0-6}$alkyl-OH, or $C_{0-6}$alkyl-O—$C_{1-12}$alkyl, optionally substituted by one or more independent H, deuterium or halo;

R⁵ is H, deuterium, halo, methyl, ethyl, isopropyl

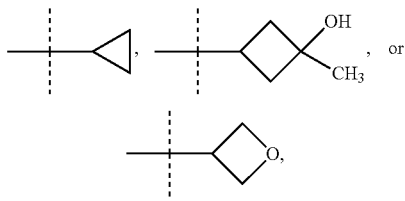

optionally substituted by one or more independent H, deuterium, halo, OH, or CN;
or a pharmaceutically acceptable salt thereof.

7. The compound of claim 1, wherein R⁷ is H, chloro, methyl, ethyl, heteroaryl, trifluoromethyl, or CD₃.

8. The compound of claim 1, wherein R¹, for each occurrence, is H, trifluoromethyl, trifluoromethoxy, methyl, ethyl, isopropyl, methoxy, ethoxy, propoxy, isopropoxy, deuterium, fluoro, or chloro.

9. The compound of claim 1, wherein R² is H, methyl, ethyl, propyl, isopropyl, methoxy, ethoxy, propoxy, isopropoxy, trifluoromethoxy, fluoro, chloro, CF₃, or OCF₃.

10. The compound of claim 1, wherein R⁵ is H, chloro, methyl, CD₃, ethyl, isopropyl,

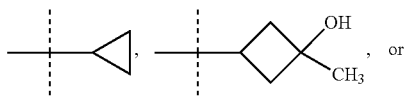, or

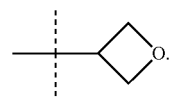.

11. The compound of claim 1, wherein R⁶ is H, methyl, ethyl, propyl, isopropyl, CD₃, or CF₃.

12. The compound of claim 1, wherein G¹, G², G³, or G⁴ are each independently H, deuterium, halo, CN, NO₂, $C_{1-6}$-alkyl, $C_{3-8}$cycloalkyl, $C_{3-8}$heterocycloalkyl, OR⁸, NR⁸R⁹, C(O)R⁸, C(O)OR⁸, C(O)NR⁸R⁹, OC(O)R⁸, OC(O)OR⁸, OC(O)NR⁸R⁹, N(R¹⁰)C(O)R⁸, N(R¹⁰)C(O)OR⁸, N(R¹⁰)C(O)NR⁸R⁹, S(O)ₙR⁸, S(O)ₙOR⁸, S(O)ₙNR⁸R⁹, N(R¹⁰)S(O)ₙR⁸, N(R¹⁰)S(O)ₙOR⁸, or N(R¹⁰)S(O)ₙNR⁸R⁹, optionally substituted by one or more independent H, deuterium, halo, OH, CN, or NO₂.

13. The compound of claim 1, wherein G¹, G², G³, or G⁴ are each independently H, deuterium, halo, CN, NO₂, $C_{1-3}$alkyl, $C_{3-6}$cycloalkyl, $C_{3-6}$heterocycloalkyl, OR⁸, NR⁸R⁹, C(O)R⁸, C(O)OR⁸, C(O)NR⁸R⁹, OC(O)R⁸, OC(O)OR⁸, OC(O)NR⁸R⁹, N(R¹⁰)C(O)R⁸, N(R¹⁰)C(O)OR⁸, N(R¹⁰)C(O)NR⁸R⁹, S(O)ₙR⁸, S(O)ₙOR⁸, S(O)ₙNR⁸R⁹, N(R¹⁰)S(O)ₙR⁸, N(R¹⁰)S(O)ₙOR⁸, or N(R¹⁰)S(O)ₙNR⁸R⁹, optionally substituted by one or more independent H, deuterium, halo, OH, CN, or NO₂.

14. The compound of claim 1, wherein Ar¹ is phenyl.

15. The compound of claim 1, wherein Ar² is phenyl or pyridyl.

16. The compound of claim 1 of the formula (If):

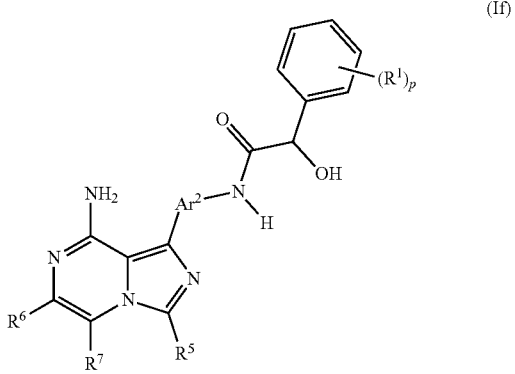

(If)

wherein:
Ar² is aryl or heteroaryl, optionally substituted by one or more independent R² substituents;
R¹ is each independently halo or alkyl, optionally substituted by one or more halogen substituents;
R² is each independently halo, alkyl, or $C_{0-6}$alkyl-O—$C_{1-12}$alkyl, optionally substituted by one or more halogen substituents;
R⁵ is alkyl or cycloalkyl, optionally substituted by one or more deuterium, hydroxyl or methyl substituents;
R⁶ is H or alkyl;
R⁷ is H, halo, or alkyl, optionally substituted by one or more halogen substituents; and
p is 1 or 2;
or a pharmaceutically acceptable salt thereof.

17. The compound of claim 16, wherein p is 1.
18. The compound of claim 17, wherein R¹ is chloro, fluoro, methyl, or trifluoromethyl.
19. The compound of claim 16, wherein p is 2.
20. The compound of claim 19, wherein R¹, for each occurrence, is fluoro, methyl, or trifluoromethyl.
21. The compound of claim 16, wherein Ar² is phenyl.
22. The compound of claim 16, wherein Ar² is phenyl, optionally substituted by one substituent selected from R².
23. The compound of claim 22, wherein R² is methyl, ethyl, fluoro, or trifluoromethoxy.
24. The compound of claim 16, wherein Ar² is phenyl, optionally substituted by two substituents each independently selected from R².
25. The compound of claim 24, wherein R², for each occurrence, is fluoro or methyl.
26. The compound of claim 16, wherein Ar² is pyridyl, optionally substituted by one substituent selected from R².
27. The compound of claim 26, wherein R² is methyl.
28. The compound of claim 16, wherein R⁵ is methyl, CD₃, or

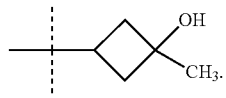

29. The compound of claim 16, wherein R⁶ is H or methyl.
30. The compound of claim 16, wherein R⁷ is H, chloro, methyl, or trifluoromethyl.

31. A compound selected from the group consisting of:
N-(4-(8-amino-3-methylimidazo[1,5-a]pyrazin-1-yl)-3-methylphenyl)-2-(3-fluorophenyl)-2-hydroxyacetamide;
(R)—N-(4-(8-amino-3-methylimidazo[1,5-a]pyrazin-1-yl)-3-methylphenyl)-2-(3-fluorophenyl)-2-hydroxyacetamide;
(S)—N-(4-(8-amino-3-methylimidazo[1,5-a]pyrazin-1-yl)-3-methylphenyl)-2-(3-fluorophenyl)-2-hydroxyacetamide;
N-(4-(8-amino-3,6-dimethylimidazo[1,5-a]pyrazin-1-yl)-3-methylphenyl)-2-(3-fluorophenyl)-2-hydroxyacetamide;
(R)—N-(4-(8-amino-3,6-dimethylimidazo[1,5-a]pyrazin-1-yl)-3-methylphenyl)-2-(3-fluorophenyl)-2-hydroxyacetamide;
(S)—N-(4-(8-amino-3,6-dimethylimidazo[1,5-a]pyrazin-1-yl)-3-methylphenyl)-2-(3-fluorophenyl)-2-hydroxyacetamide;
N-(4-(8-amino-6-methyl-3-(trideuteriomethyl)imidazo[1,5-a]pyrazin-1-yl)-3-methylphenyl)-2-(3-fluorophenyl)-2-hydroxyacetamide;
(R)—N-(4-(8-amino-6-methyl-3-(trideuteriomethyl)imidazo[1,5-a]pyrazin-1-yl)-3-methylphenyl)-2-(3-fluorophenyl)-2-hydroxyacetamide;
(S)—N-(4-(8-amino-6-methyl-3-(trideuteriomethyl)imidazo[1,5-a]pyrazin-1-yl)-3-methylphenyl)-2-(3-fluorophenyl)-2-hydroxyacetamide;
N-(4-(8-amino-3,5-dimethylimidazo[1,5-a]pyrazin-1-yl)-3-methylphenyl)-2-(3-fluorophenyl)-2-hydroxyacetamide;
(R)—N-(4-(8-amino-3,5-dimethylimidazo[1,5-a]pyrazin-1-yl)-3-methylphenyl)-2-(3-fluorophenyl)-2-hydroxyacetamide;
(S)—N-(4-(8-amino-3,5-dimethylimidazo[1,5-a]pyrazin-1-yl)-3-methylphenyl)-2-(3-fluorophenyl)-2-hydroxyacetamide;
N-(4-(8-amino-5-methyl-3-(trideuteriomethyl)imidazo[1,5-a]pyrazin-1-yl)-3-methylphenyl)-2-(3-fluorophenyl)-2-hydroxyacetamide;
(R)—N-(4-(8-amino-5-methyl-3-(trideuteriomethyl)imidazo[1,5-a]pyrazin-1-yl)-3-methylphenyl)-2-(3-fluorophenyl)-2-hydroxyacetamide;
(S)—N-(4-(8-amino-5-methyl-3-(trideuteriomethyl)imidazo[1,5-a]pyrazin-1-yl)-3-methylphenyl)-2-(3-fluorophenyl)-2-hydroxyacetamide;
N-(4-(8-amino-3,6-dimethylimidazo[1,5-a]pyrazin-1-yl)-3-methylphenyl)-2-(3-fluorophenyl)-2-hydroxyacetamide;
(R)—N-(4-(8-amino-3,6-dimethylimidazo[1,5-a]pyrazin-1-yl)-3-methylphenyl)-2-(3-fluorophenyl)-2-hydroxyacetamide;
(S)—N-(4-(8-amino-3,6-dimethylimidazo[1,5-a]pyrazin-1-yl)-3-methylphenyl)-2-(3-fluorophenyl)-2-hydroxyacetamide;
N-[4-[8-amino-6-methyl-3-(trideuteriomethyl)imidazo[1,5-a]pyrazin-1-yl]-3-methyl-phenyl]-2-hydroxy-2-[3-(trifluoromethyl)phenyl]acetamide;
(R)—N-[4-[8-amino-6-methyl-3-(trideuteriomethyl)imidazo[1,5-a]pyrazin-1-yl]-3-methyl-phenyl]-2-hydroxy-2-[3-(trifluoromethyl)phenyl]acetamide;
(S)—N-[4-[8-amino-6-methyl-3-(trideuteriomethyl)imidazo[1,5-a]pyrazin-1-yl]-3-methyl-phenyl]-2-hydroxy-2-[3-(trifluoromethyl)phenyl]acetamide;
N-[4-[8-amino-5-methyl-3-(trideuteriomethyl)imidazo[1,5-a]pyrazin-1-yl]-3-methyl-phenyl]-2-hydroxy-2-[3-(trifluoromethyl)phenyl]acetamide;

(R)—N-[4-[8-amino-5-methyl-3-(trideuteriomethyl)imidazo[1,5-a]pyrazin-1-yl]-3-methyl-phenyl]-2-hydroxy-2-[3-(trifluoromethyl)phenyl]acetamide;

(S)—N-[4-[8-amino-5-methyl-3-(trideuteriomethyl)imidazo[1,5-a]pyrazin-1-yl]-3-methyl-phenyl]-2-hydroxy-2-[3-(trifluoromethyl)phenyl]acetamide;

N-[4-[8-amino-5-chloro-3-(trideuteriomethyl)imidazo[1,5-a]pyrazin-1-yl]-3-methyl-phenyl]-2-hydroxy-2-[3-(trifluoromethyl)phenyl]acetamide;

(R)—N-[4-[8-amino-5-chloro-3-(trideuteriomethyl)imidazo[1,5-a]pyrazin-1-yl]-3-methyl-phenyl]-2-hydroxy-2-[3-(trifluoromethyl)phenyl]acetamide;

(S)—N-[4-[8-amino-5-chloro-3-(trideuteriomethyl)imidazo[1,5-a]pyrazin-1-yl]-3-methyl-phenyl]-2-hydroxy-2-[3-(trifluoromethyl)phenyl]acetamide;

N-[4-[8-amino-3-(trideuteriomethyl)-5-(trifluoromethyl)imidazo[1,5-a]pyrazin-1-yl]-3-methyl-phenyl]-2-hydroxy-2-[3-(trifluoromethyl)phenyl]acetamide;

(R)—N-[4-[8-amino-3-(trideuteriomethyl)-5-(trifluoromethyl)imidazo[1,5-a]pyrazin-1-yl]-3-methyl-phenyl]-2-hydroxy-2-[3-(trifluoromethyl)phenyl]acetamide;

(S)—N-[4-[8-amino-3-(trideuteriomethyl)-5-(trifluoromethyl)imidazo[1,5-a]pyrazin-1-yl]-3-methyl-phenyl]-2-hydroxy-2-[3-(trifluoromethyl)phenyl]acetamide;

N-(4-(8-amino-3,5,6-trimethylimidazo[1,5-a]pyrazin-1-yl)-3-methylphenyl)-2-(3-fluorophenyl)-2-hydroxyacetamide;

(R)—N-(4-(8-amino-3,5,6-trimethylimidazo[1,5-a]pyrazin-1-yl)-3-methylphenyl)-2-(3-fluorophenyl)-2-hydroxyacetamide;

(S)—N-(4-(8-amino-3,5,6-trimethylimidazo[1,5-a]pyrazin-1-yl)-3-methylphenyl)-2-(3-fluorophenyl)-2-hydroxyacetamide;

N-(4-(8-amino-3-(3-hydroxy-3-methylcyclobutyl)-6-methylimidazo[1,5-a]pyrazin-1-yl)-3-methylphenyl)-2-(3-fluorophenyl)-2-hydroxyacetamide;

(R)—N-(4-(8-amino-3-(3-hydroxy-3-methylcyclobutyl)-6-methylimidazo[1,5-a]pyrazin-1-yl)-3-methylphenyl)-2-(3-fluorophenyl)-2-hydroxyacetamide;

(S)—N-(4-(8-amino-3-(3-hydroxy-3-methylcyclobutyl)-6-methylimidazo[1,5-a]pyrazin-1-yl)-3-methylphenyl)-2-(3-fluorophenyl)-2-hydroxyacetamide;

N-(4-(8-amino-3-methyl-5-(trifluoromethyl)imidazo[1,5-a]pyrazin-1-yl)-3-methylphenyl)-2-(3-fluorophenyl)-2-hydroxyacetamide;

(R)—N-(4-(8-amino-3-methyl-5-(trifluoromethyl)imidazo[1,5-a]pyrazin-1-yl)-3-methylphenyl)-2-(3-fluorophenyl)-2-hydroxyacetamide;

(S)—N-(4-(8-amino-3-methyl-5-(trifluoromethyl)imidazo[1,5-a]pyrazin-1-yl)-3-methylphenyl)-2-(3-fluorophenyl)-2-hydroxyacetamide;

N-(4-(8-amino-5-chloro-3-methylimidazo[1,5-a]pyrazin-1-yl)-3-methylphenyl)-2-(3-fluorophenyl)-2-hydroxyacetamide;

(R)—N-(4-(8-amino-5-chloro-3-methylimidazo[1,5-a]pyrazin-1-yl)-3-methylphenyl)-2-(3-fluorophenyl)-2-hydroxyacetamide;

(S)—N-(4-(8-amino-5-chloro-3-methylimidazo[1,5-a]pyrazin-1-yl)-3-methylphenyl)-2-(3-fluorophenyl)-2-hydroxyacetamide;

N-[4-[8-amino-3-(trideuteriomethyl)-5-(trifluoromethyl)imidazo[1,5-a]pyrazin-1-yl]-3-methyl-phenyl]-2-(3-fluorophenyl)-2-hydroxy-acetamide;

(R)—N-[4-[8-amino-3-(trideuteriomethyl)-5-(trifluoromethyl)imidazo[1,5-a]pyrazin-1-yl]-3-methyl-phenyl]-2-(3-fluorophenyl)-2-hydroxy-acetamide;

(S)—N-[4-[8-amino-3-(trideuteriomethyl)-5-(trifluoromethyl)imidazo[1,5-a]pyrazin-1-yl]-3-methyl-phenyl]-2-(3-fluorophenyl)-2-hydroxy-acetamide;

N-[4-[8-amino-5-chloro-3-(trideuteriomethyl)imidazo[1,5-a]pyrazin-1-yl]-3-methyl-phenyl]-2-(3-fluorophenyl)-2-hydroxy-acetamide;

(R)—N-[4-[8-amino-5-chloro-3-(trideuteriomethyl)imidazo[1,5-a]pyrazin-1-yl]-3-methyl-phenyl]-2-(3-fluorophenyl)-2-hydroxy-acetamide;

(S)—N-[4-[8-amino-5-chloro-3-(trideuteriomethyl)imidazo[1,5-a]pyrazin-1-yl]-3-methyl-phenyl]-2-(3-fluorophenyl)-2-hydroxy-acetamide;

N-[4-[8-amino-6-methyl-3-(trideuteriomethyl)imidazo[1,5-a]pyrazin-1-yl]-3-methyl-phenyl]-2-(3-chlorophenyl)-2-hydroxy-acetamide;

(R)—N-[4-[8-amino-6-methyl-3-(trideuteriomethyl)imidazo[1,5-a]pyrazin-1-yl]-3-methyl-phenyl]-2-(3-chlorophenyl)-2-hydroxy-acetamide;

(S)—N-[4-[8-amino-6-methyl-3-(trideuteriomethyl)imidazo[1,5-a]pyrazin-1-yl]-3-methyl-phenyl]-2-(3-chlorophenyl)-2-hydroxy-acetamide;

N-[4-[8-amino-5-methyl-3-(trideuteriomethyl)imidazo[1,5-a]pyrazin-1-yl]-3-methyl-phenyl]-2-(3-chlorophenyl)-2-hydroxy-acetamide;

(R)—N-[4-[8-amino-5-methyl-3-(trideuteriomethyl)imidazo[1,5-a]pyrazin-1-yl]-3-methyl-phenyl]-2-(3-chlorophenyl)-2-hydroxy-acetamide;

(S)—N-[4-[8-amino-5-methyl-3-(trideuteriomethyl)imidazo[1,5-a]pyrazin-1-yl]-3-methyl-phenyl]-2-(3-chlorophenyl)-2-hydroxy-acetamide;

N-(4-(8-amino-3,5-dimethylimidazo[1,5-a]pyrazin-1-yl)-3-methylphenyl)-2-(3-chlorophenyl)-2-hydroxyacetamide;

(R)—N-(4-(8-amino-3,5-dimethylimidazo[1,5-a]pyrazin-1-yl)-3-methylphenyl)-2-(3-chlorophenyl)-2-hydroxyacetamide;

(S)—N-(4-(8-amino-3,5-dimethylimidazo[1,5-a]pyrazin-1-yl)-3-methylphenyl)-2-(3-chlorophenyl)-2-hydroxyacetamide;

N-[4-[8-amino-3-(trideuteriomethyl)-5-(trifluoromethyl)imidazo[1,5-a]pyrazin-1-yl]-3-methyl-phenyl]-2-(3-chlorophenyl)-2-hydroxy-acetamide;

(R)—N-[4-[8-amino-3-(trideuteriomethyl)-5-(trifluoromethyl)imidazo[1,5-a]pyrazin-1-yl]-3-methyl-phenyl]-2-(3-chlorophenyl)-2-hydroxy-acetamide;

(S)—N-[4-[8-amino-3-(trideuteriomethyl)-5-(trifluoromethyl)imidazo[1,5-a]pyrazin-1-yl]-3-methyl-phenyl]-2-(3-chlorophenyl)-2-hydroxy-acetamide;

N-[4-[8-amino-5-chloro-3-(trideuteriomethyl)imidazo[1,5-a]pyrazin-1-yl]-3-methyl-phenyl]-2-(3-chlorophenyl)-2-hydroxy-acetamide;

(R)—N-[4-[8-amino-5-chloro-3-(trideuteriomethyl)imidazo[1,5-a]pyrazin-1-yl]-3-methyl-phenyl]-2-(3-chlorophenyl)-2-hydroxy-acetamide;

(S)—N-[4-[8-amino-5-chloro-3-(trideuteriomethyl)imidazo[1,5-a]pyrazin-1-yl]-3-methyl-phenyl]-2-(3-chlorophenyl)-2-hydroxy-acetamide;

N-[4-[8-amino-6-methyl-3-(trideuteriomethyl)imidazo[1,5-a]pyrazin-1-yl]-3-methyl-phenyl]-2-(3,5-difluorophenyl)-2-hydroxy-acetamide;

(R)—N-[4-[8-amino-6-methyl-3-(trideuteriomethyl)imidazo[1,5-a]pyrazin-1-yl]-3-methyl-phenyl]-2-(3,5-difluorophenyl)-2-hydroxy-acetamide;

(S)—N-[4-[8-amino-6-methyl-3-(trideuteriomethyl)imidazo[1,5-a]pyrazin-1-yl]-3-methyl-phenyl]-2-(3,5-difluorophenyl)-2-hydroxy-acetamide;

N-[4-[8-amino-3-(trideuteriomethyl)-5-(trifluoromethyl)imidazo[1,5-a]pyrazin-1-yl]-3-methyl-phenyl]-2-(3,5-difluorophenyl)-2-hydroxy-acetamide;

(R)—N-[4-[8-amino-3-(trideuteriomethyl)-5-(trifluoromethyl)imidazo[1,5-a]pyrazin-1-yl]-3-methyl-phenyl]-2-(3,5-difluorophenyl)-2-hydroxy-acetamide;

(S)—N-[4-[8-amino-3-(trideuteriomethyl)-5-(trifluoromethyl)imidazo[1,5-a]pyrazin-1-yl]-3-methyl-phenyl]-2-(3,5-difluorophenyl)-2-hydroxy-acetamide;

N-[4-[8-amino-5-chloro-3-(trideuteriomethyl)imidazo[1,5-a]pyrazin-1-yl]-3-methyl-phenyl]-2-(3,5-difluorophenyl)-2-hydroxy-acetamide;

(R)—N-[4-[8-amino-5-chloro-3-(trideuteriomethyl)imidazo[1,5-a]pyrazin-1-yl]-3-methyl-phenyl]-2-(3,5-difluorophenyl)-2-hydroxy-acetamide;

(S)—N-[4-[8-amino-5-chloro-3-(trideuteriomethyl)imidazo[1,5-a]pyrazin-1-yl]-3-methyl-phenyl]-2-(3,5-difluorophenyl)-2-hydroxy-acetamide;

N-[4-[8-amino-5-methyl-3-(trideuteriomethyl)imidazo[1,5-a]pyrazin-1-yl]-3-methyl-phenyl]-2-(3,5-difluorophenyl)-2-hydroxy-acetamide;

(R)—N-[4-[8-amino-5-methyl-3-(trideuteriomethyl)imidazo[1,5-a]pyrazin-1-yl]-3-methyl-phenyl]-2-(3,5-difluorophenyl)-2-hydroxy-acetamide;

(S)—N-[4-[8-amino-5-methyl-3-(trideuteriomethyl)imidazo[1,5-a]pyrazin-1-yl]-3-methyl-phenyl]-2-(3,5-difluorophenyl)-2-hydroxy-acetamide;

N-[4-[8-amino-6-methyl-3-(trideuteriomethyl)imidazo[1,5-a]pyrazin-1-yl]-3-methyl-phenyl]-2-[3-fluoro-5-(trifluoromethyl)phenyl]-2-hydroxy-acetamide;

(R)—N-[4-[8-amino-6-methyl-3-(trideuteriomethyl)imidazo[1,5-a]pyrazin-1-yl]-3-methyl-phenyl]-2-[3-fluoro-5-(trifluoromethyl)phenyl]-2-hydroxy-acetamide;

(S)—N-[4-[8-amino-6-methyl-3-(trideuteriomethyl)imidazo[1,5-a]pyrazin-1-yl]-3-methyl-phenyl]-2-[3-fluoro-5-(trifluoromethyl)phenyl]-2-hydroxy-acetamide;

N-[4-[8-amino-5-methyl-3-(trideuteriomethyl)imidazo[1,5-a]pyrazin-1-yl]-3-methyl-phenyl]-2-[3-fluoro-5-(trifluoromethyl)phenyl]-2-hydroxy-acetamide;

(R)—N-[4-[8-amino-5-methyl-3-(trideuteriomethyl)imidazo[1,5-a]pyrazin-1-yl]-3-methyl-phenyl]-2-[3-fluoro-5-(trifluoromethyl)phenyl]-2-hydroxy-acetamide;

(S)—N-[4-[8-amino-5-methyl-3-(trideuteriomethyl)imidazo[1,5-a]pyrazin-1-yl]-3-methyl-phenyl]-2-[3-fluoro-5-(trifluoromethyl)phenyl]-2-hydroxy-acetamide;

N-[4-[8-amino-5-chloro-3-(trideuteriomethyl)imidazo[1,5-a]pyrazin-1-yl]-3-methyl-phenyl]-2-[3-fluoro-5-(trifluoromethyl)phenyl]-2-hydroxy-acetamide;

(R)—N-[4-[8-amino-5-chloro-3-(trideuteriomethyl)imidazo[1,5-a]pyrazin-1-yl]-3-methyl-phenyl]-2-[3-fluoro-5-(trifluoromethyl)phenyl]-2-hydroxy-acetamide;

(S)—N-[4-[8-amino-5-chloro-3-(trideuteriomethyl)imidazo[1,5-a]pyrazin-1-yl]-3-methyl-phenyl]-2-[3-fluoro-5-(trifluoromethyl)phenyl]-2-hydroxy-acetamide;

N-(4-(8-amino-3,5-dimethylimidazo[1,5-a]pyrazin-1-yl)-3-methylphenyl)-2-(3-fluoro-5-(trifluoromethyl)phenyl)-2-hydroxyacetamide;

(R)—N-(4-(8-amino-3,5-dimethylimidazo[1,5-a]pyrazin-1-yl)-3-methylphenyl)-2-(3-fluoro-5-(trifluoromethyl)phenyl)-2-hydroxyacetamide;

(S)—N-(4-(8-amino-3,5-dimethylimidazo[1,5-a]pyrazin-1-yl)-3-methylphenyl)-2-(3-fluoro-5-(trifluoromethyl)phenyl)-2-hydroxyacetamide;

N-[4-[8-amino-3-(trideuteriomethyl)-5-(trifluoromethyl)imidazo[1,5-a]pyrazin-1-yl]-3-methyl-phenyl]-2-[3-fluoro-5-(trifluoromethyl)phenyl]-2-hydroxy-acetamide;

(R)—N-[4-[8-amino-3-(trideuteriomethyl)-5-(trifluoromethyl)imidazo[1,5-a]pyrazin-1-yl]-3-methyl-phenyl]-2-[3-fluoro-5-(trifluoromethyl)phenyl]-2-hydroxy-acetamide;

(S)—N-[4-[8-amino-3-(trideuteriomethyl)-5-(trifluoromethyl)imidazo[1,5-a]pyrazin-1-yl]-3-methyl-phenyl]-2-[3-fluoro-5-(trifluoromethyl)phenyl]-2-hydroxy-acetamide;

N-(4-(8-amino-3,5-dimethylimidazo[1,5-a]pyrazin-1-yl)-3-methylphenyl)-2-(3-fluoro-5-methylphenyl)-2-hydroxyacetamide;

(R)—N-(4-(8-amino-3,5-dimethylimidazo[1,5-a]pyrazin-1-yl)-3-methylphenyl)-2-(3-fluoro-5-methylphenyl)-2-hydroxyacetamide;

(S)—N-(4-(8-amino-3,5-dimethylimidazo[1,5-a]pyrazin-1-yl)-3-methylphenyl)-2-(3-fluoro-5-methylphenyl)-2-hydroxyacetamide;

N-(4-(8-amino-3,5-dimethylimidazo[1,5-a]pyrazin-1-yl)-2-fluoro-5-methylphenyl)-2-(3-fluorophenyl)-2-hydroxyacetamide;

(R)—N-(4-(8-amino-3,5-dimethylimidazo[1,5-a]pyrazin-1-yl)-2-fluoro-5-methylphenyl)-2-(3-fluorophenyl)-2-hydroxyacetamide;

(S)—N-(4-(8-amino-3,5-dimethylimidazo[1,5-a]pyrazin-1-yl)-2-fluoro-5-methylphenyl)-2-(3-fluorophenyl)-2-hydroxyacetamide;

N-(4-(8-amino-3,5-dimethylimidazo[1,5-a]pyrazin-1-yl)-3-ethylphenyl)-2-(3-fluorophenyl)-2-hydroxyacetamide;

(R)—N-(4-(8-amino-3,5-dimethylimidazo[1,5-a]pyrazin-1-yl)-3-ethylphenyl)-2-(3-fluorophenyl)-2-hydroxyacetamide;

(S)—N-(4-(8-amino-3,5-dimethylimidazo[1,5-a]pyrazin-1-yl)-3-ethylphenyl)-2-(3-fluorophenyl)-2-hydroxyacetamide;

N-(4-(8-amino-3,5-dimethylimidazo[1,5-a]pyrazin-1-yl)phenyl)-2-(3-fluorophenyl)-2-hydroxyacetamide;

(R)—N-(4-(8-amino-3,5-dimethylimidazo[1,5-a]pyrazin-1-yl)phenyl)-2-(3-fluorophenyl)-2-hydroxyacetamide;

(S)—N-(4-(8-amino-3,5-dimethylimidazo[1,5-a]pyrazin-1-yl)phenyl)-2-(3-fluorophenyl)-2-hydroxyacetamide;

N-(4-(8-amino-3,5-dimethylimidazo[1,5-a]pyrazin-1-yl)-3-fluorophenyl)-2-(3-fluorophenyl)-2-hydroxyacetamide;

(R)—N-(4-(8-amino-3,5-dimethylimidazo[1,5-a]pyrazin-1-yl)-3-fluorophenyl)-2-(3-fluorophenyl)-2-hydroxyacetamide;

(S)—N-(4-(8-amino-3,5-dimethylimidazo[1,5-a]pyrazin-1-yl)-3-fluorophenyl)-2-(3-fluorophenyl)-2-hydroxyacetamide;

N-[4-[8-amino-5-methyl-3-(trideuteriomethyl)imidazo[1,5-a]pyrazin-1-yl]-3-fluoro-phenyl]-2-(3-fluorophenyl)-2-hydroxy-acetamide;

(R)—N-[4-[8-amino-5-methyl-3-(trideuteriomethyl)imidazo[1,5-a]pyrazin-1-yl]-3-fluoro-phenyl]-2-(3-fluorophenyl)-2-hydroxy-acetamide;

(S)—N-[4-[8-amino-5-methyl-3-(trideuteriomethyl)imidazo[1,5-a]pyrazin-1-yl]-3-fluoro-phenyl]-2-(3-fluorophenyl)-2-hydroxy-acetamide;

N-[4-[8-amino-5-chloro-3-(trideuteriomethyl)imidazo[1,5-a]pyrazin-1-yl]-3-fluoro-phenyl]-2-(3-fluorophenyl)-2-hydroxy-acetamide;
(R)—N-[4-[8-amino-5-chloro-3-(trideuteriomethyl)imidazo[1,5-a]pyrazin-1-yl]-3-fluoro-phenyl]-2-(3-fluorophenyl)-2-hydroxy-acetamide;
(S)—N-[4-[8-amino-5-chloro-3-(trideuteriomethyl)imidazo[1,5-a]pyrazin-1-yl]-3-fluoro-phenyl]-2-(3-fluorophenyl)-2-hydroxy-acetamide;
N-(4-(8-amino-3,5-dimethylimidazo[1,5-a]pyrazin-1-yl)-3-fluorophenyl)-2-(3-chlorophenyl)-2-hydroxyacetamide;
(R)—N-(4-(8-amino-3,5-dimethylimidazo[1,5-a]pyrazin-1-yl)-3-fluorophenyl)-2-(3-chlorophenyl)-2-hydroxy-acetamide;
(S)—N-(4-(8-amino-3,5-dimethylimidazo[1,5-a]pyrazin-1-yl)-3-fluorophenyl)-2-(3-chlorophenyl)-2-hydroxy-acetamide;
N-[4-[8-amino-6-methyl-3-(trideuteriomethyl)imidazo[1,5-a]pyrazin-1-yl]-3-fluoro-phenyl]-2-(3-chlorophenyl)-2-hydroxy-acetamide;
(R)—N-[4-[8-amino-6-methyl-3-(trideuteriomethyl)imidazo[1,5-a]pyrazin-1-yl]-3-fluoro-phenyl]-2-(3-chlorophenyl)-2-hydroxy-acetamide;
(S)—N-[4-[8-amino-6-methyl-3-(trideuteriomethyl)imidazo[1,5-a]pyrazin-1-yl]-3-fluoro-phenyl]-2-(3-chlorophenyl)-2-hydroxy-acetamide;
N-[4-[8-amino-3-(trideuteriomethyl)-5-(trifluoromethyl)imidazo[1,5-a]pyrazin-1-yl]-3-fluoro-phenyl]-2-(3-chlorophenyl)-2-hydroxy-acetamide;
(R)—N-[4-[8-amino-3-(trideuteriomethyl)-5-(trifluoromethyl)imidazo[1,5-a]pyrazin-1-yl]-3-fluoro-phenyl]-2-(3-chlorophenyl)-2-hydroxy-acetamide;
(S)—N-[4-[8-amino-3-(trideuteriomethyl)-5-(trifluoromethyl)imidazo[1,5-a]pyrazin-1-yl]-3-fluoro-phenyl]-2-(3-chlorophenyl)-2-hydroxy-acetamide;
N-[4-[8-amino-5-methyl-3-(trideuteriomethyl)imidazo[1,5-a]pyrazin-1-yl]-3-fluoro-phenyl]-2-(3-chlorophenyl)-2-hydroxy-acetamide;
(R)—N-[4-[8-amino-5-methyl-3-(trideuteriomethyl)imidazo[1,5-a]pyrazin-1-yl]-3-fluoro-phenyl]-2-(3-chlorophenyl)-2-hydroxy-acetamide;
(S)—N-[4-[8-amino-5-methyl-3-(trideuteriomethyl)imidazo[1,5-a]pyrazin-1-yl]-3-fluoro-phenyl]-2-(3-chlorophenyl)-2-hydroxy-acetamide;
N-[4-[8-amino-5-chloro-3-(trideuteriomethyl)imidazo[1,5-a]pyrazin-1-yl]-3-fluoro-phenyl]-2-(3-chlorophenyl)-2-hydroxy-acetamide;
(R)—N-[4-[8-amino-5-chloro-3-(trideuteriomethyl)imidazo[1,5-a]pyrazin-1-yl]-3-fluoro-phenyl]-2-(3-chlorophenyl)-2-hydroxy-acetamide;
(S)—N-[4-[8-amino-5-chloro-3-(trideuteriomethyl)imidazo[1,5-a]pyrazin-1-yl]-3-fluoro-phenyl]-2-(3-chlorophenyl)-2-hydroxy-acetamide;
N-(4-(8-amino-3,5-dimethylimidazo[1,5-a]pyrazin-1-yl)-3-fluorophenyl)-2-hydroxy-2-(m-tolyl) acetamide;
(R)—N-(4-(8-amino-3,5-dimethylimidazo[1,5-a]pyrazin-1-yl)-3-fluorophenyl)-2-hydroxy-2-(m-tolyl) acetamide;
(S)—N-(4-(8-amino-3,5-dimethylimidazo[1,5-a]pyrazin-1-yl)-3-fluorophenyl)-2-hydroxy-2-(m-tolyl) acetamide;
N-[4-[8-amino-5-methyl-3-(trideuteriomethyl)imidazo[1,5-a]pyrazin-1-yl]-3-fluoro-phenyl]-2-hydroxy-2-(m-tolyl) acetamide;
(R)—N-[4-[8-amino-5-methyl-3-(trideuteriomethyl)imidazo[1,5-a]pyrazin-1-yl]-3-fluoro-phenyl]-2-hydroxy-2-(m-tolyl) acetamide;
(S)—N-[4-[8-amino-5-methyl-3-(trideuteriomethyl)imidazo[1,5-a]pyrazin-1-yl]-3-fluoro-phenyl]-2-hydroxy-2-(m-tolyl) acetamide;
N-(4-(8-amino-3,5-dimethylimidazo[1,5-a]pyrazin-1-yl)-3-fluorophenyl)-2-hydroxy-2-(3-(trifluoromethyl)phenyl) acetamide;
(R)—N-(4-(8-amino-3,5-dimethylimidazo[1,5-a]pyrazin-1-yl)-3-fluorophenyl)-2-hydroxy-2-(3-(trifluoromethyl)phenyl) acetamide;
(S)—N-(4-(8-amino-3,5-dimethylimidazo[1,5-a]pyrazin-1-yl)-3-fluorophenyl)-2-hydroxy-2-(3-(trifluoromethyl)phenyl) acetamide;
N-[4-[8-amino-5-methyl-3-(trideuteriomethyl)imidazo[1,5-a]pyrazin-1-yl]-3-fluoro-phenyl]-2-hydroxy-2-[3-(trifluoromethyl)phenyl]acetamide;
(R)—N-[4-[8-amino-5-methyl-3-(trideuteriomethyl)imidazo[1,5-a]pyrazin-1-yl]-3-fluoro-phenyl]-2-hydroxy-2-[3-(trifluoromethyl)phenyl]acetamide;
(S)—N-[4-[8-amino-5-methyl-3-(trideuteriomethyl)imidazo[1,5-a]pyrazin-1-yl]-3-fluoro-phenyl]-2-hydroxy-2-[3-(trifluoromethyl)phenyl]acetamide;
N-[4-[8-amino-6-methyl-3-(trideuteriomethyl)imidazo[1,5-a]pyrazin-1-yl]-3-fluoro-phenyl]-2-hydroxy-2-[3-(trifluoromethyl)phenyl]acetamide;
(R)—N-[4-[8-amino-6-methyl-3-(trideuteriomethyl)imidazo[1,5-a]pyrazin-1-yl]-3-fluoro-phenyl]-2-hydroxy-2-[3-(trifluoromethyl)phenyl]acetamide;
(S)—N-[4-[8-amino-6-methyl-3-(trideuteriomethyl)imidazo[1,5-a]pyrazin-1-yl]-3-fluoro-phenyl]-2-hydroxy-2-[3-(trifluoromethyl)phenyl]acetamide;
N-[4-[8-amino-3-(trideuteriomethyl)-5-(trifluoromethyl)imidazo[1,5-a]pyrazin-1-yl]-3-fluoro-phenyl]-2-hydroxy-2-[3-(trifluoromethyl)phenyl]acetamide;
(R)—N-[4-[8-amino-3-(trideuteriomethyl)-5-(trifluoromethyl)imidazo[1,5-a]pyrazin-1-yl]-3-fluoro-phenyl]-2-hydroxy-2-[3-(trifluoromethyl)phenyl]acetamide;
(S)—N-[4-[8-amino-3-(trideuteriomethyl)-5-(trifluoromethyl)imidazo[1,5-a]pyrazin-1-yl]-3-fluoro-phenyl]-2-hydroxy-2-[3-(trifluoromethyl)phenyl]acetamide;
N-[4-[8-amino-5-chloro-3-(trideuteriomethyl)imidazo[1,5-a]pyrazin-1-yl]-3-fluoro-phenyl]-2-hydroxy-2-[3-(trifluoromethyl)phenyl]acetamide;
(R)—N-[4-[8-amino-5-chloro-3-(trideuteriomethyl)imidazo[1,5-a]pyrazin-1-yl]-3-fluoro-phenyl]-2-hydroxy-2-[3-(trifluoromethyl)phenyl]acetamide;
(S)—N-[4-[8-amino-5-chloro-3-(trideuteriomethyl)imidazo[1,5-a]pyrazin-1-yl]-3-fluoro-phenyl]-2-hydroxy-2-[3-(trifluoromethyl)phenyl]acetamide;
N-[4-[8-amino-6-methyl-3-(trideuteriomethyl)imidazo[1,5-a]pyrazin-1-yl]-3-fluoro-phenyl]-2-(3,5-difluorophenyl)-2-hydroxy-acetamide;
(R)—N-[4-[8-amino-6-methyl-3-(trideuteriomethyl)imidazo[1,5-a]pyrazin-1-yl]-3-fluoro-phenyl]-2-(3,5-difluorophenyl)-2-hydroxy-acetamide;
(S)—N-[4-[8-amino-6-methyl-3-(trideuteriomethyl)imidazo[1,5-a]pyrazin-1-yl]-3-fluoro-phenyl]-2-(3,5-difluorophenyl)-2-hydroxy-acetamide;
N-[4-[8-amino-5-methyl-3-(trideuteriomethyl)imidazo[1,5-a]pyrazin-1-yl]-3-fluoro-phenyl]-2-(3,5-difluorophenyl)-2-hydroxy-acetamide;
(R)—N-[4-[8-amino-5-methyl-3-(trideuteriomethyl)imidazo[1,5-a]pyrazin-1-yl]-3-fluoro-phenyl]-2-(3,5-difluorophenyl)-2-hydroxy-acetamide;

- (S)—N-[4-[8-amino-5-methyl-3-(trideuteriomethyl)imidazo[1,5-a]pyrazin-1-yl]-3-fluoro-phenyl]-2-(3,5-difluorophenyl)-2-hydroxy-acetamide;
- N-[4-[8-amino-3-(trideuteriomethyl)-5-(trifluoromethyl)imidazo[1,5-a]pyrazin-1-yl]-3-fluoro-phenyl]-2-(3,5-difluorophenyl)-2-hydroxy-acetamide;
- (R)—N-[4-[8-amino-3-(trideuteriomethyl)-5-(trifluoromethyl)imidazo[1,5-a]pyrazin-1-yl]-3-fluoro-phenyl]-2-(3,5-difluorophenyl)-2-hydroxy-acetamide;
- (S)—N-[4-[8-amino-3-(trideuteriomethyl)-5-(trifluoromethyl)imidazo[1,5-a]pyrazin-1-yl]-3-fluoro-phenyl]-2-(3,5-difluorophenyl)-2-hydroxy-acetamide;
- N-[4-[8-amino-5-chloro-3-(trideuteriomethyl)imidazo[1,5-a]pyrazin-1-yl]-3-fluoro-phenyl]-2-(3,5-difluorophenyl)-2-hydroxy-acetamide;
- (R)—N-[4-[8-amino-5-chloro-3-(trideuteriomethyl)imidazo[1,5-a]pyrazin-1-yl]-3-fluoro-phenyl]-2-(3,5-difluorophenyl)-2-hydroxy-acetamide;
- (S)—N-[4-[8-amino-5-chloro-3-(trideuteriomethyl)imidazo[1,5-a]pyrazin-1-yl]-3-fluoro-phenyl]-2-(3,5-difluorophenyl)-2-hydroxy-acetamide;
- N-[4-[8-amino-5-methyl-3-(trideuteriomethyl)imidazo[1,5-a]pyrazin-1-yl]-3-fluoro-phenyl]-2-[3-fluoro-5-(trifluoromethyl)phenyl]-2-hydroxy-acetamide;
- (R)—N-[4-[8-amino-5-methyl-3-(trideuteriomethyl)imidazo[1,5-a]pyrazin-1-yl]-3-fluoro-phenyl]-2-[3-fluoro-5-(trifluoromethyl)phenyl]-2-hydroxy-acetamide;
- (S)—N-[4-[8-amino-5-methyl-3-(trideuteriomethyl)imidazo[1,5-a]pyrazin-1-yl]-3-fluoro-phenyl]-2-[3-fluoro-5-(trifluoromethyl)phenyl]-2-hydroxy-acetamide;
- N-[4-[8-amino-3-(trideuteriomethyl)-5-(trifluoromethyl)imidazo[1,5-a]pyrazin-1-yl]-3-fluoro-phenyl]-2-[3-fluoro-5-(trifluoromethyl)phenyl]-2-hydroxy-acetamide;
- (R)—N-[4-[8-amino-3-(trideuteriomethyl)-5-(trifluoromethyl)imidazo[1,5-a]pyrazin-1-yl]-3-fluoro-phenyl]-2-[3-fluoro-5-(trifluoromethyl)phenyl]-2-hydroxy-acetamide;
- (S)—N-[4-[8-amino-3-(trideuteriomethyl)-5-(trifluoromethyl)imidazo[1,5-a]pyrazin-1-yl]-3-fluoro-phenyl]-2-[3-fluoro-5-(trifluoromethyl)phenyl]-2-hydroxy-acetamide;
- N-[4-[8-amino-5-chloro-3-(trideuteriomethyl)imidazo[1,5-a]pyrazin-1-yl]-3-fluoro-phenyl]-2-[3-fluoro-5-(trifluoromethyl)phenyl]-2-hydroxy-acetamide;
- (R)—N-[4-[8-amino-5-chloro-3-(trideuteriomethyl)imidazo[1,5-a]pyrazin-1-yl]-3-fluoro-phenyl]-2-[3-fluoro-5-(trifluoromethyl)phenyl]-2-hydroxy-acetamide;
- (S)—N-[4-[8-amino-5-chloro-3-(trideuteriomethyl)imidazo[1,5-a]pyrazin-1-yl]-3-fluoro-phenyl]-2-[3-fluoro-5-(trifluoromethyl)phenyl]-2-hydroxy-acetamide;
- N-[4-[8-amino-6-methyl-3-(trideuteriomethyl)imidazo[1,5-a]pyrazin-1-yl]-3-fluoro-phenyl]-2-[3-fluoro-5-(trifluoromethyl)phenyl]-2-hydroxy-acetamide;
- (R)—N-[4-[8-amino-6-methyl-3-(trideuteriomethyl)imidazo[1,5-a]pyrazin-1-yl]-3-fluoro-phenyl]-2-[3-fluoro-5-(trifluoromethyl)phenyl]-2-hydroxy-acetamide;
- (S)—N-[4-[8-amino-6-methyl-3-(trideuteriomethyl)imidazo[1,5-a]pyrazin-1-yl]-3-fluoro-phenyl]-2-[3-fluoro-5-(trifluoromethyl)phenyl]-2-hydroxy-acetamide;
- N-(4-(8-amino-3,6-dimethylimidazo[1,5-a]pyrazin-1-yl)-2-fluorophenyl)-2-(3-fluorophenyl)-2-hydroxyacetamide;
- (R)—N-(4-(8-amino-3,6-dimethylimidazo[1,5-a]pyrazin-1-yl)-2-fluorophenyl)-2-(3-fluorophenyl)-2-hydroxy-acetamide;
- (S)—N-(4-(8-amino-3,6-dimethylimidazo[1,5-a]pyrazin-1-yl)-2-fluorophenyl)-2-(3-fluorophenyl)-2-hydroxy-acetamide;
- N-[4-[8-amino-6-methyl-3-(trideuteriomethyl)imidazo[1,5-a]pyrazin-1-yl]-2-fluorophenyl]-2-(3-fluorophenyl)-2-hydroxy-acetamide;
- (R)—N-[4-[8-amino-6-methyl-3-(trideuteriomethyl)imidazo[1,5-a]pyrazin-1-yl]-2-fluorophenyl]-2-(3-fluorophenyl)-2-hydroxy-acetamide;
- (S)—N-[4-[8-amino-6-methyl-3-(trideuteriomethyl)imidazo[1,5-a]pyrazin-1-yl]-2-fluorophenyl]-2-(3-fluorophenyl)-2-hydroxy-acetamide;
- N-[4-[8-amino-5-methyl-3-(trideuteriomethyl)imidazo[1,5-a]pyrazin-1-yl]-2-fluoro-phenyl]-2-(3-fluorophenyl)-2-hydroxy-acetamide;
- (R)—N-[4-[8-amino-5-methyl-3-(trideuteriomethyl)imidazo[1,5-a]pyrazin-1-yl]-2-fluoro-phenyl]-2-(3-fluorophenyl)-2-hydroxy-acetamide;
- (S)—N-[4-[8-amino-5-methyl-3-(trideuteriomethyl)imidazo[1,5-a]pyrazin-1-yl]-2-fluoro-phenyl]-2-(3-fluorophenyl)-2-hydroxy-acetamide;
- N-(4-(8-amino-3,5-dimethylimidazo[1,5-a]pyrazin-1-yl)-2-fluorophenyl)-2-(3-fluorophenyl)-2-hydroxyacetamide;
- (R)—N-(4-(8-amino-3,5-dimethylimidazo[1,5-a]pyrazin-1-yl)-2-fluorophenyl)-2-(3-fluorophenyl)-2-hydroxy-acetamide;
- (S)—N-(4-(8-amino-3,5-dimethylimidazo[1,5-a]pyrazin-1-yl)-2-fluorophenyl)-2-(3-fluorophenyl)-2-hydroxy-acetamide;
- N-(4-(8-amino-3,5-dimethylimidazo[1,5-a]pyrazin-1-yl)-3-(trifluoromethoxy)phenyl)-2-(3-fluorophenyl)-2-hydroxyacetamide;
- (R)—N-(4-(8-amino-3,5-dimethylimidazo[1,5-a]pyrazin-1-yl)-3-(trifluoromethoxy)phenyl)-2-(3-fluorophenyl)-2-hydroxyacetamide;
- (S)—N-(4-(8-amino-3,5-dimethylimidazo[1,5-a]pyrazin-1-yl)-3-(trifluoromethoxy)phenyl)-2-(3-fluorophenyl)-2-hydroxyacetamide;
- N-(4-(8-amino-3,6-dimethylimidazo[1,5-a]pyrazin-1-yl)-2,3-difluorophenyl)-2-(3-fluorophenyl)-2-hydroxyacetamide;
- (R)—N-(4-(8-amino-3,6-dimethylimidazo[1,5-a]pyrazin-1-yl)-2,3-difluorophenyl)-2-(3-fluorophenyl)-2-hydroxyacetamide;
- (S)—N-(4-(8-amino-3,6-dimethylimidazo[1,5-a]pyrazin-1-yl)-2,3-difluorophenyl)-2-(3-fluorophenyl)-2-hydroxyacetamide;
- N-[4-[8-amino-6-methyl-3-(trideuteriomethyl)imidazo[1,5-a]pyrazin-1-yl]-2,3-difluoro-phenyl]-2-(3-fluorophenyl)-2-hydroxy-acetamide;
- (R)—N-[4-[8-amino-6-methyl-3-(trideuteriomethyl)imidazo[1,5-a]pyrazin-1-yl]-2,3-difluoro-phenyl]-2-(3-fluorophenyl)-2-hydroxy-acetamide;
- (S)—N-[4-[8-amino-6-methyl-3-(trideuteriomethyl)imidazo[1,5-a]pyrazin-1-yl]-2,3-difluoro-phenyl]-2-(3-fluorophenyl)-2-hydroxy-acetamide;
- N-[4-[8-amino-5-methyl-3-(trideuteriomethyl)imidazo[1,5-a]pyrazin-1-yl]-2,3-difluoro-phenyl]-2-(3-fluorophenyl)-2-hydroxy-acetamide;
- (R)—N-[4-[8-amino-5-methyl-3-(trideuteriomethyl)imidazo[1,5-a]pyrazin-1-yl]-2,3-difluoro-phenyl]-2-(3-fluorophenyl)-2-hydroxy-acetamide;
- (S)—N-[4-[8-amino-5-methyl-3-(trideuteriomethyl)imidazo[1,5-a]pyrazin-1-yl]-2,3-difluoro-phenyl]-2-(3-fluorophenyl)-2-hydroxy-acetamide;

N-[4-[8-amino-3-(trideuteriomethyl)-5-(trifluoromethyl)imidazo[1,5-a]pyrazin-1-yl]-2,3-difluoro-phenyl]-2-(3-fluorophenyl)-2-hydroxy-acetamide;

(R)—N-[4-[8-amino-3-(trideuteriomethyl)-5-(trifluoromethyl)imidazo[1,5-a]pyrazin-1-yl]-2,3-difluoro-phenyl]-2-(3-fluorophenyl)-2-hydroxy-acetamide;

(S)—N-[4-[8-amino-3-(trideuteriomethyl)-5-(trifluoromethyl)imidazo[1,5-a]pyrazin-1-yl]-2,3-difluoro-phenyl]-2-(3-fluorophenyl)-2-hydroxy-acetamide;

N-[4-[8-amino-5-chloro-3-(trideuteriomethyl)imidazo[1,5-a]pyrazin-1-yl]-2,3-difluoro-phenyl]-2-(3-fluorophenyl)-2-hydroxy-acetamide;

(R)—N-[4-[8-amino-5-chloro-3-(trideuteriomethyl)imidazo[1,5-a]pyrazin-1-yl]-2,3-difluoro-phenyl]-2-(3-fluorophenyl)-2-hydroxy-acetamide;

(S)—N-[4-[8-amino-5-chloro-3-(trideuteriomethyl)imidazo[1,5-a]pyrazin-1-yl]-2,3-difluoro-phenyl]-2-(3-fluorophenyl)-2-hydroxy-acetamide;

N-[4-[8-amino-5-methyl-3-(trideuteriomethyl)imidazo[1,5-a]pyrazin-1-yl]-2,3-difluoro-phenyl]-2-(3-chlorophenyl)-2-hydroxy-acetamide;

(R)—N-[4-[8-amino-5-methyl-3-(trideuteriomethyl)imidazo[1,5-a]pyrazin-1-yl]-2,3-difluoro-phenyl]-2-(3-chlorophenyl)-2-hydroxy-acetamide;

(S)—N-[4-[8-amino-5-methyl-3-(trideuteriomethyl)imidazo[1,5-a]pyrazin-1-yl]-2,3-difluoro-phenyl]-2-(3-chlorophenyl)-2-hydroxy-acetamide;

N-[4-[8-amino-6-methyl-3-(trideuteriomethyl)imidazo[1,5-a]pyrazin-1-yl]-2,3-difluoro-phenyl]-2-(3-chlorophenyl)-2-hydroxy-acetamide;

(R)—N-[4-[8-amino-6-methyl-3-(trideuteriomethyl)imidazo[1,5-a]pyrazin-1-yl]-2,3-difluoro-phenyl]-2-(3-chlorophenyl)-2-hydroxy-acetamide;

(S)—N-[4-[8-amino-6-methyl-3-(trideuteriomethyl)imidazo[1,5-a]pyrazin-1-yl]-2,3-difluoro-phenyl]-2-(3-chlorophenyl)-2-hydroxy-acetamide;

N-[4-[8-amino-3-(trideuteriomethyl)-5-(trifluoromethyl)imidazo[1,5-a]pyrazin-1-yl]-2,3-difluoro-phenyl]-2-(3-chlorophenyl)-2-hydroxy-acetamide;

(R)—N-[4-[8-amino-3-(trideuteriomethyl)-5-(trifluoromethyl)imidazo[1,5-a]pyrazin-1-yl]-2,3-difluoro-phenyl]-2-(3-chlorophenyl)-2-hydroxy-acetamide;

(S)—N-[4-[8-amino-3-(trideuteriomethyl)-5-(trifluoromethyl)imidazo[1,5-a]pyrazin-1-yl]-2,3-difluoro-phenyl]-2-(3-chlorophenyl)-2-hydroxy-acetamide;

N-[4-[8-amino-5-chloro-3-(trideuteriomethyl)imidazo[1,5-a]pyrazin-1-yl]-2,3-difluoro-phenyl]-2-(3-chlorophenyl)-2-hydroxy-acetamide;

(R)—N-[4-[8-amino-5-chloro-3-(trideuteriomethyl)imidazo[1,5-a]pyrazin-1-yl]-2,3-difluoro-phenyl]-2-(3-chlorophenyl)-2-hydroxy-acetamide;

(S)—N-[4-[8-amino-5-chloro-3-(trideuteriomethyl)imidazo[1,5-a]pyrazin-1-yl]-2,3-difluoro-phenyl]-2-(3-chlorophenyl)-2-hydroxy-acetamide;

N-[4-[8-amino-5-methyl-3-(trideuteriomethyl)imidazo[1,5-a]pyrazin-1-yl]-2,3-difluoro-phenyl]-2-hydroxy-2-[3-(trifluoromethyl)phenyl]acetamide;

(R)—N-[4-[8-amino-5-methyl-3-(trideuteriomethyl)imidazo[1,5-a]pyrazin-1-yl]-2,3-difluoro-phenyl]-2-hydroxy-2-[3-(trifluoromethyl)phenyl]acetamide;

(S)—N-[4-[8-amino-5-methyl-3-(trideuteriomethyl)imidazo[1,5-a]pyrazin-1-yl]-2,3-difluoro-phenyl]-2-hydroxy-2-[3-(trifluoromethyl)phenyl]acetamide;

N-[4-[8-amino-3-(trideuteriomethyl)-5-(trifluoromethyl)imidazo[1,5-a]pyrazin-1-yl]-2,3-difluoro-phenyl]-2-hydroxy-2-[3-(trifluoromethyl)phenyl]acetamide;

(R)—N-[4-[8-amino-3-(trideuteriomethyl)-5-(trifluoromethyl)imidazo[1,5-a]pyrazin-1-yl]-2,3-difluoro-phenyl]-2-hydroxy-2-[3-(trifluoromethyl)phenyl]acetamide;

(S)—N-[4-[8-amino-3-(trideuteriomethyl)-5-(trifluoromethyl)imidazo[1,5-a]pyrazin-1-yl]-2,3-difluoro-phenyl]-2-hydroxy-2-[3-(trifluoromethyl)phenyl]acetamide;

N-[4-[8-amino-6-methyl-3-(trideuteriomethyl)imidazo[1,5-a]pyrazin-1-yl]-2,3-difluoro-phenyl]-2-hydroxy-2-[3-(trifluoromethyl)phenyl]acetamide;

(R)—N-[4-[8-amino-6-methyl-3-(trideuteriomethyl)imidazo[1,5-a]pyrazin-1-yl]-2,3-difluoro-phenyl]-2-hydroxy-2-[3-(trifluoromethyl)phenyl]acetamide;

(S)—N-[4-[8-amino-6-methyl-3-(trideuteriomethyl)imidazo[1,5-a]pyrazin-1-yl]-2,3-difluoro-phenyl]-2-hydroxy-2-[3-(trifluoromethyl)phenyl]acetamide;

N-[4-[8-amino-5-chloro-3-(trideuteriomethyl)imidazo[1,5-a]pyrazin-1-yl]-2,3-difluoro-phenyl]-2-hydroxy-2-[3-(trifluoromethyl)phenyl]acetamide;

(R)—N-[4-[8-amino-5-chloro-3-(trideuteriomethyl)imidazo[1,5-a]pyrazin-1-yl]-2,3-difluoro-phenyl]-2-hydroxy-2-[3-(trifluoromethyl)phenyl]acetamide;

(S)—N-[4-[8-amino-5-chloro-3-(trideuteriomethyl)imidazo[1,5-a]pyrazin-1-yl]-2,3-difluoro-phenyl]-2-hydroxy-2-[3-(trifluoromethyl)phenyl]acetamide;

N-[4-[8-amino-5-methyl-3-(trideuteriomethyl)imidazo[1,5-a]pyrazin-1-yl]-2,3-difluoro-phenyl]-2-(3,5-difluorophenyl)-2-hydroxy-acetamide;

(R)—N-[4-[8-amino-5-methyl-3-(trideuteriomethyl)imidazo[1,5-a]pyrazin-1-yl]-2,3-difluoro-phenyl]-2-(3,5-difluorophenyl)-2-hydroxy-acetamide;

(S)—N-[4-[8-amino-5-methyl-3-(trideuteriomethyl)imidazo[1,5-a]pyrazin-1-yl]-2,3-difluoro-phenyl]-2-(3,5-difluorophenyl)-2-hydroxy-acetamide;

N-[4-[8-amino-5-chloro-3-(trideuteriomethyl)imidazo[1,5-a]pyrazin-1-yl]-2,3-difluoro-phenyl]-2-(3,5-difluorophenyl)-2-hydroxy-acetamide;

(R)—N-[4-[8-amino-5-chloro-3-(trideuteriomethyl)imidazo[1,5-a]pyrazin-1-yl]-2,3-difluoro-phenyl]-2-(3,5-difluorophenyl)-2-hydroxy-acetamide;

(S)—N-[4-[8-amino-5-chloro-3-(trideuteriomethyl)imidazo[1,5-a]pyrazin-1-yl]-2,3-difluoro-phenyl]-2-(3,5-difluorophenyl)-2-hydroxy-acetamide;

N-[4-[8-amino-5-methyl-3-(trideuteriomethyl)imidazo[1,5-a]pyrazin-1-yl]-2,3-difluoro-phenyl]-2-[3-fluoro-5-(trifluoromethyl)phenyl]-2-hydroxy-acetamide;

(R)—N-[4-[8-amino-5-methyl-3-(trideuteriomethyl)imidazo[1,5-a]pyrazin-1-yl]-2,3-difluoro-phenyl]-2-[3-fluoro-5-(trifluoromethyl)phenyl]-2-hydroxy-acetamide;

(S)—N-[4-[8-amino-5-methyl-3-(trideuteriomethyl)imidazo[1,5-a]pyrazin-1-yl]-2,3-difluoro-phenyl]-2-[3-fluoro-5-(trifluoromethyl)phenyl]-2-hydroxy-acetamide;

N-[4-[8-amino-3-(trideuteriomethyl)-5-(trifluoromethyl)imidazo[1,5-a]pyrazin-1-yl]-2,3-difluoro-phenyl]-2-[3-fluoro-5-(trifluoromethyl)phenyl]-2-hydroxy-acetamide;

(R)—N-[4-[8-amino-3-(trideuteriomethyl)-5-(trifluoromethyl)imidazo[1,5-a]pyrazin-1-yl]-2,3-difluoro-phenyl]-2-[3-fluoro-5-(trifluoromethyl)phenyl]-2-hydroxy-acetamide;

(S)—N-[4-[8-amino-3-(trideuteriomethyl)-5-(trifluoromethyl)imidazo[1,5-a]pyrazin-1-yl]-2,3-difluoro-phenyl]-2-[3-fluoro-5-(trifluoromethyl)phenyl]-2-hydroxy-acetamide;

N-[4-[8-amino-5-chloro-3-(trideuteriomethyl)imidazo[1,5-a]pyrazin-1-yl]-2,3-difluoro-phenyl]-2-[3-fluoro-5-(trifluoromethyl)phenyl]-2-hydroxy-acetamide;

(R)—N-[4-[8-amino-5-chloro-3-(trideuteriomethyl)imidazo[1,5-a]pyrazin-1-yl]-2,3-difluoro-phenyl]-2-[3-fluoro-5-(trifluoromethyl)phenyl]-2-hydroxy-acetamide;

(S)—N-[4-[8-amino-5-chloro-3-(trideuteriomethyl)imidazo[1,5-a]pyrazin-1-yl]-2,3-difluoro-phenyl]-2-[3-fluoro-5-(trifluoromethyl)phenyl]-2-hydroxy-acetamide;

N-[4-[8-amino-6-methyl-3-(trideuteriomethyl)imidazo[1,5-a]pyrazin-1-yl]-2,3-difluoro-phenyl]-2-[3-fluoro-5-(trifluoromethyl)phenyl]-2-hydroxy-acetamide;

(R)—N-[4-[8-amino-6-methyl-3-(trideuteriomethyl)imidazo[1,5-a]pyrazin-1-yl]-2,3-difluoro-phenyl]-2-[3-fluoro-5-(trifluoromethyl)phenyl]-2-hydroxy-acetamide;

(S)—N-[4-[8-amino-6-methyl-3-(trideuteriomethyl)imidazo[1,5-a]pyrazin-1-yl]-2,3-difluoro-phenyl]-2-[3-fluoro-5-(trifluoromethyl)phenyl]-2-hydroxy-acetamide;

N-(4-(8-amino-3,5-dimethylimidazo[1,5-a]pyrazin-1-yl)-2-fluoro-3-methylphenyl)-2-(3-fluorophenyl)-2-hydroxyacetamide;

(R)—N-(4-(8-amino-3,5-dimethylimidazo[1,5-a]pyrazin-1-yl)-2-fluoro-3-methylphenyl)-2-(3-fluorophenyl)-2-hydroxyacetamide;

(S)—N-(4-(8-amino-3,5-dimethylimidazo[1,5-a]pyrazin-1-yl)-2-fluoro-3-methylphenyl)-2-(3-fluorophenyl)-2-hydroxyacetamide;

N-[5-[8-amino-6-methyl-3-(trideuteriomethyl)imidazo[1,5-a]pyrazin-1-yl]-6-methyl-2-pyridyl]-2-(3-fluorophenyl)-2-hydroxy-acetamide;

(R)—N-[5-[8-amino-6-methyl-3-(trideuteriomethyl)imidazo[1,5-a]pyrazin-1-yl]-6-methyl-2-pyridyl]-2-(3-fluorophenyl)-2-hydroxy-acetamide;

(S)—N-[5-[8-amino-6-methyl-3-(trideuteriomethyl)imidazo[1,5-a]pyrazin-1-yl]-6-methyl-2-pyridyl]-2-(3-fluorophenyl)-2-hydroxy-acetamide;

N-[5-[8-amino-5-methyl-3-(trideuteriomethyl)imidazo[1,5-a]pyrazin-1-yl]-6-methyl-2-pyridyl]-2-(3-fluorophenyl)-2-hydroxy-acetamide;

(R)—N-[5-[8-amino-5-methyl-3-(trideuteriomethyl)imidazo[1,5-a]pyrazin-1-yl]-6-methyl-2-pyridyl]-2-(3-fluorophenyl)-2-hydroxy-acetamide;

(S)—N-[5-[8-amino-5-methyl-3-(trideuteriomethyl)imidazo[1,5-a]pyrazin-1-yl]-6-methyl-2-pyridyl]-2-(3-fluorophenyl)-2-hydroxy-acetamide;

N-[5-[8-amino-5-methyl-3-(trideuteriomethyl)imidazo[1,5-a]pyrazin-1-yl]-6-methyl-2-pyridyl]-2-hydroxy-2-[3-(trifluoromethyl)phenyl]acetamide;

(R)—N-[5-[8-amino-5-methyl-3-(trideuteriomethyl)imidazo[1,5-a]pyrazin-1-yl]-6-methyl-2-pyridyl]-2-hydroxy-2-[3-(trifluoromethyl)phenyl]acetamide;

(S)—N-[5-[8-amino-5-methyl-3-(trideuteriomethyl)imidazo[1,5-a]pyrazin-1-yl]-6-methyl-2-pyridyl]-2-hydroxy-2-[3-(trifluoromethyl)phenyl]acetamide;

N-[5-[8-amino-6-methyl-3-(trideuteriomethyl)imidazo[1,5-a]pyrazin-1-yl]-4-methyl-2-pyridyl]-2-(3-fluorophenyl)-2-hydroxy-acetamide;

(R)—N-[5-[8-amino-6-methyl-3-(trideuteriomethyl)imidazo[1,5-a]pyrazin-1-yl]-4-methyl-2-pyridyl]-2-(3-fluorophenyl)-2-hydroxy-acetamide;

(S)—N-[5-[8-amino-6-methyl-3-(trideuteriomethyl)imidazo[1,5-a]pyrazin-1-yl]-4-methyl-2-pyridyl]-2-(3-fluorophenyl)-2-hydroxy-acetamide;

N-[5-[8-amino-5-methyl-3-(trideuteriomethyl)imidazo[1,5-a]pyrazin-1-yl]-4-methyl-2-pyridyl]-2-(3-fluorophenyl)-2-hydroxy-acetamide;

(R)—N-[5-[8-amino-5-methyl-3-(trideuteriomethyl)imidazo[1,5-a]pyrazin-1-yl]-4-methyl-2-pyridyl]-2-(3-fluorophenyl)-2-hydroxy-acetamide;

(S)—N-[5-[8-amino-5-methyl-3-(trideuteriomethyl)imidazo[1,5-a]pyrazin-1-yl]-4-methyl-2-pyridyl]-2-(3-fluorophenyl)-2-hydroxy-acetamide;

or a pharmaceutically acceptable salt thereof.

32. A pharmaceutical composition, comprising a compound or a pharmaceutically acceptable salt thereof according to claim 1 with one or more pharmaceutically acceptable carriers, diluents, or excipients.

33. A method of treating cancer in a patient comprising administering to a patient in need thereof an effective amount of a compound of claim 1, or a pharmaceutically acceptable salt thereof.

34. A compound or pharmaceutically acceptable salt thereof according to claim 1 for use in therapy.

35. A compound or pharmaceutically acceptable salt thereof according to claim 1 for use in the treatment of cancer.

36. A method of treating a disease in a patient in need of such treatment, said method comprising administering a PERK kinase modulating compound of claim 1, or a pharmaceutically acceptable salt thereof, wherein the disease is cancer.

* * * * *